US010577666B2

(12) United States Patent
Forth et al.

(10) Patent No.: US 10,577,666 B2
(45) Date of Patent: Mar. 3, 2020

(54) COMPOSITIONS ASSOCIATED WITH SOYBEAN REPRODUCTIVE GROWTH AND METHODS OF USE

(71) Applicant: PIONEER HI-BRED INTERNATIONAL, INC., Johnston, IA (US)

(72) Inventors: Kathryn Anne Forth, Ohio, IL (US); David L. Hyten, Jr., Johnston, IA (US); Andrea Beth Kalvig, Waukee, IA (US); Keith Edward King, Johnston, IA (US); Leslie Charles Kuhlman, Lawrence, KS (US); Donald Kyle, Princeton, IL (US); Thai Lee, Johnston, IA (US); Jon M. Massman, Ankeny, IA (US); Edwin J. Mendez, West Des Moines, IA (US); Sally Anne Santiago-Parton, San Antonio, TX (US); Joshua Michael Shendelman, Ankeny, IA (US); Jordan Dustin Spear, Algona, IA (US); John Bryan Woodward, Ankeny, IA (US); Yanwen Xiong, Johnston, IA (US)

(73) Assignee: PIONEER HI-BRED INTERNATIONAL, INC. IA (US)

( * ) Notice: Subject to any disclaimer, the term of this patent is extended or adjusted under 35 U.S.C. 154(b) by 0 days.

(21) Appl. No.: 15/920,619

(22) Filed: Mar. 14, 2018

(65) Prior Publication Data
US 2018/0223378 A1 Aug. 9, 2018

Related U.S. Application Data

(62) Division of application No. 14/776,044, filed as application No. PCT/US2014/021517 on Mar. 7, 2014, now Pat. No. 9,951,391.

(60) Provisional application No. 61/781,826, filed on Mar. 14, 2013.

(51) Int. Cl.
*A01H 5/10* (2018.01)
*C12Q 1/6895* (2018.01)

(52) U.S. Cl.
CPC ....... *C12Q 1/6895* (2013.01); *C12Q 2600/13* (2013.01)

(58) Field of Classification Search
None
See application file for complete search history.

(56) References Cited

U.S. PATENT DOCUMENTS

| 6,455,758 B1 | 9/2002 | Johnson |
| 8,329,982 B2 | 12/2012 | Kyle et al. |
| 8,847,006 B2 | 9/2014 | Jenkinson et al. |
| 2008/0256660 A1 | 10/2008 | Jenkinson et al. |
| 2010/0122372 A1 | 5/2010 | Sebastian et al. |
| 2011/0191893 A1 | 8/2011 | Harada et al. |
| 2012/0324598 A1 | 12/2012 | Lu et al. |

OTHER PUBLICATIONS

Elroy Cober et al., A New Locus for Early Maturity in Soybeans, Crop Science, 2010, pp. 524-527, vol. 50.
P. B. Cregan et al., An Integrated Genetic Linkage Map of the Soybean Genome, Crop Science, 1999, pp. 1464-1490, vol. 39.
R. H. Ellis et al., Effects of Photoperiod and Maturity Genes on Plant Growth, Partitioning, Radiation Use Efficiency, and Yield in Soybeans [*Glycine max*(L.)Merrill] 'Clark', Annals of Botany, 2000, pp. 335-343, vol. 85.
Larry Heatherly, Soybean maturity group, planting date and development related, Delta Farm Press, Oct. 14, 2005.
Kunihikio Komatsu et al., Identification of QTL controlling post-flowering period in soybeans, Breeding Science, 2012, pp. 646-652, vol. 61.
Chad Lee et al., Predicting Soybean First Flowering Date, University of Kentucky—College of Agriculture, 2005, AGR-184, 2 pages.
Wenxin Li et al., QTL Mapping for Major Agronomic Traits across Two Years in Soybeans (*Glycine max* L. Merr.), J. Crop Sci. Biotech, Sep. 2008, pp. 171-190, vol. 11(3).
Wenxin Li et al., QTL identification flowering time at three different latitudes reveals homeologous genomic regions that control flowering in soybean, Theor Appl Genet, 2011, pp. 545-553, vol. 123.
L. M. Mansur et al., Interval mapping of quantitative trait loci for reproductive, morphological, and seed traits of soybean (*Glycine max* L.), Theor Appl Genet, 1993, pp. 907-913, vol. 86.
Hisakazu Matsumura et al., AFLP Mapping of Soybean Maturity Gene E4, Journal of Heredity, 2008, pp. 193-197, vol. 99(2).
D. A. McWilliams et al., Soybean Growth and Management Quick Guide A-1174, North Dakota State University, Jun. 1999, 8 pages.
C. D. Messina et al., A gene-Based Model to Simulate Soybean Development and Yield Responses to Environment, Crop Science, 2006, pp. 456-466, vol. 46.
Stephen J. Molnar et al., Simple sequence repeat (SSR) markers linked to E1, E3, E4, and E7 maturity genes in soybean, Genome, 2003, pp. 1024-1036, vol. 46.
Praveen K. Pallikonda, Impact of E-genes on Soybean (*Glycine max* L.[Merr]) Development, Senescence and Yield, 2006, University of Kentucky Master's Theses.
V. E. Rozenzweig et al., Prospects of exploiting of photoperiod sensitivity gene E7 in early soybean breeding and revealing of its sources with SSR-markers. Institute of Genetics and Cytology, National Acad. Sci. of Belarus; Soya-North Co. Ltd.
Jin Hee Shin et al., Molecular markers for the E2 and E3 genes controlling flowering and maturity in soybeans, Mol. Breeding, 2012, pp. 1793-1798, vol. 30.
I. M Tasma et al., Mapping genetic loci for flowering time, maturity, and photoperiod sensitivity in soybean, Molecular Breeding, 2001, pp. 25-35, vol. 8.

(Continued)

Primary Examiner — Bratislav Stankovic

(57) ABSTRACT

Molecular markers associated with soybean reproductive stage, methods of their use, and compositions having one or more marker loci are provided. Methods comprise detecting at least one marker locus, detecting a haplotype, and/or detecting a marker profile. Methods may further comprise crossing a selected soybean plant with a second soybean plant. Isolated polynucleotides, primers, probes, kits, systems, etc., are also provided.

9 Claims, No Drawings
Specification includes a Sequence Listing.

(56) References Cited

OTHER PUBLICATIONS

D. Wang et al., Identification of putative QTL that underlie yield in interspecific soybean backcross populations, Theor Appl Genet, 2004, pp. 458-467, vol. 108.

Satoshi Watanabe et al., Map-based cloning of the Gene Associated With the Soybean Maturity Locus E3, Genetics, Aug. 2009, pp. 1251-1262, vol. 182.

Satoshi Watanabe et al., Genetic and molecular bases of photoperiod responses of flowering in soybean, Breeding Science, 2012, pp. 531-543, vol. 61.

Zhengjun Xia et al., Positional cloning and characterization reveal the molecular basis for soybean maturity locus E1 that regulates photoperiodic flowering, PNAS, May 22, 2012, E2155-E2164.

Zhengjun Xia et al., Molecular identification of genes controlling flowering time, maturity, and photoperiod response in soybean, Plant Syst Evol, 2012, pp. 1217-1227, vol. 298.

Da-Wei Xin et al., Analysis of quantitative trait loci underlying the period of reproductive growth stages in soybean (*Glycine max* [L.]Merr.), Euphytica, 2008, pp. 155-165, vol. 162.

Tetsuya Yamada et al., Effects on flowering and seed yield of dominant alleles at maturity E2 and E3 in a Japanese cultivar, Enrei, Breeding Science, 2012, pp. 653-660, vol. 61.

Niaoki Yamanaka et al, An informative Linkage Map of Soybean Reveals QTL's for Flowering Time, Leaflet Morphology and Regions of Segregation Distortion, DNA Research, 2001, pp. 61-72, vol. 8.

U.S. Appl. No. 15/125738, filed Mar. 11, 2015, Status—Allowed.

International Search Report and Written opinion, International Application No. PCT/US2014/021517, dated Jun. 2, 2014.

COMPOSITIONS ASSOCIATED WITH SOYBEAN REPRODUCTIVE GROWTH AND METHODS OF USE

FIELD OF THE INVENTION

This invention relates to compositions associated with reproductive stage in soybean plants and methods of their use.

BACKGROUND

Soybeans (*Glycine max* L. Merr.) are a major cash crop and investment commodity in North America and elsewhere. Soybean is the world's primary source of seed oil and seed protein. Improving soybean adaptation for various growing regions and environmental conditions is crucial for maximizing yields.

There remains a need for means to identify genomic regions associated with reproductive stages in soybean plants. The compositions and methods provide important tools for use in plant breeding programs to optimize or maximize the reproductive growth stage, and/or to develop varieties adapted for various growing regions or environments.

SUMMARY

Molecular markers associated with soybean reproductive stages, methods of their use, and compositions having one or more marker loci are provided. Methods comprise detecting at least one marker locus, detecting a haplotype, and/or detecting a marker profile. Methods may further comprise crossing a selected soybean plant with a second soybean plant. Isolated polynucleotides, primers, probes, kits, systems, etc., are also provided.

SUMMARY OF SEQUENCES

SEQ ID NOs: 1-512 comprise nucleotide sequences of regions of the soybean genome, each capable of being used as a probe or primer, either alone or in combination, for the detection of a marker locus associated with reproductive growth in soybean. In certain examples, Primer1 and Primer2 are used as allele specific primers and Probe1 and Probe2 are used as allele probes. The SEQ ID NOs provided in the "Region" column of the table below are each a genomic DNA region encompassing the respective marker locus. In some examples, the primers and/or probes detect the polymorphism on based on a polynucleotide complementary to the genomic region provided here. It is to be understood that the sequences provided are sufficient for one of skill in the art to detect a locus associated with reproductive growth in soybean regardless of the orientation (forward, or reverse) of the strand used for detection.

| Locus | Primer1 SEQ ID NO: | Primer2 SEQ ID NO: | Probe1 SEQ ID NO: | Probe2 SEQ ID NO: | Region SEQ ID NO: |
|---|---|---|---|---|---|
| S01435-1 | 1 | 2 | 3 | 4 | 5 |
| S01239-1 | 6 | 7 | 8 | 9 | 10 |
| S00780-1 | 11 | 12 | 13 | 14 | 15 |
| S06925-1 | 16 | 17 | 18 | 19 | 20 |
| S09951-1 | 21 | 22 | 23 | 24 | 25 |
| S00170-1 | 26 | 27 | 28 | 29 | 30 |
| S04059-1 | 31 | 32 | 33 | 34 | 35 |
| S07851-1 | 36 | 37 | 38 | 39 | 40 |
| S11659-1 | 41 | 42 | 43 | 44 | 45 |
| S04279-1 | 46 | 47 | 48 | 49 | 50 |
| S02211-1 | 51 | 52 | 53 | 54 | 55 |
| S08942-1 | 56 | 57 | 58 | 59 | 60 |
| S05742-1 | 61 | 62 | 63 | 64 | 65 |
| S09155-1 | 66 | 67 | 68 | 69 | 70 |
| S02037-1 | 71 | 72 | 73 | 74 | 75 |
| S13136-1 | 76 | 77 | 78 | 79 | 80 |
| S17291-001 | — | 81 | 82 | 83 | 84 |
| S13139-1 | 85 | 86 | 87 | 88 | 89 |
| S17292-001 | — | 90 | 91 | 92 | 93 |
| S13146-1 | 94 | 95 | 96 | 97 | 98 |
| S17293-001 | — | 99 | 100 | 101 | 102 |
| S17294-001 | — | 103 | 104 | 105 | 106 |
| S17581-001 | 107 | 108 | 109 | 110 | 111 |
| S17691-001 | 112 | 113 | 114 | — | 115 |
| S17701-001 | 116 | 117 | 118 | 119 | 120 |
| S03703-1 | 121 | 122 | 123 | 124 | 125 |
| S17297-001 | — | 126 | 127 | 128 | 129 |
| S17298-001 | — | 130 | 131 | 132 | 133 |
| S17299-001 | — | 134 | 135 | 136 | 137 |
| S17300-001 | — | 138 | 139 | 140 | 141 |
| S17301-001 | — | 142 | 143 | 144 | 145 |
| S17306-001 | — | 146 | 147 | 148 | 149 |
| S17310-001 | — | 150 | 151 | 152 | 153 |
| S17311-001 | — | 154 | 155 | 156 | 157 |
| S17312-001 | — | 158 | 159 | 160 | 161 |
| S17313-001 | — | 162 | 163 | 164 | 165 |
| S17316-001 | — | 166 | 167 | 168 | 169 |
| S17317-001 | — | 170 | 171 | 172 | 173 |
| S17318-001 | — | 174 | 175 | 176 | 177 |
| S17322-001 | — | 178 | 179 | 180 | 181 |
| S17326-001 | — | 182 | 183 | 184 | 185 |
| S17327-001 | — | 186 | 187 | 188 | 189 |
| S17328-001 | — | 190 | 191 | 192 | 193 |
| S17329-001 | — | 194 | 195 | 196 | 197 |
| S10746-1 | 198 | 199 | 200 | 201 | 202 |
| S17331-001 | — | 203 | 204 | 205 | 206 |
| S17332-001 | — | 207 | 208 | 209 | 210 |
| S17337-001 | — | 211 | 212 | 213 | 214 |
| S13093-1 | 215 | 216 | 217 | 218 | 219 |
| S12211-1 | 220 | 221 | 222 | 223 | 224 |
| S04555-1 | 225 | 226 | 227 | 228 | 229 |
| S08519-1 | 230 | 231 | 232 | 233 | 234 |
| S12876-1 | 235 | 236 | 237 | 238 | 239 |
| S05937-1 | 240 | 241 | 242 | 243 | 244 |
| S08575-1 | 245 | 246 | 247 | 248 | 249 |
| S08669-1 | 250 | 251 | 252 | 253 | 254 |
| S11212-1 | 255 | 256 | 257 | 258 | 259 |
| S00543-1 | 260 | 261 | 262 | 263 | 264 |
| S01452-1 | 265 | 266 | 267 | 268 | 269 |
| S11993-1 | 270 | 271 | 272 | 273 | 274 |
| S13446-1 | 275 | 276 | 277 | 278 | 279 |
| S00252-1 | 280 | 281 | 282 | 283 | 284 |
| S04060-1 | 285 | 286 | 287 | 288 | 289 |
| S02664-1 | 290 | 291 | 292 | 293 | 294 |
| S00281-1 | 295 | 296 | 297 | 298 | 299 |
| S01109-1 | 300 | 301 | 302 | 303 | 304 |
| S13844-1 | 305 | 306 | 307 | 308 | 309 |
| S05058-1 | 310 | 311 | 312 | 313 | 314 |
| S04660-1 | 315 | 316 | 317 | 318 | 319 |
| S09955-1 | 320 | 321 | 322 | 323 | 324 |
| S08034-1 | 325 | 326 | 327 | 328 | 329 |
| S10293-1 | 330 | 331 | 332 | 333 | 334 |
| S03813-1 | 335 | 336 | 337 | 338 | 339 |
| S02042-1 | 340 | 341 | 342 | 343 | 344 |
| S16601-001 | 345 | 346 | 347 | 348 | 349 |
| S01481-1 | 350 | 351 | 352 | 353 | 354 |
| S11309-1 | 355 | 356 | 357 | 358 | 359 |
| S11320-1 | 360 | 361 | 362 | 363 | 364 |
| S04040-1 | 365 | 366 | 367 | 368 | 369 |
| S00863-1 | 370 | 371 | 372 | 373 | 374 |
| S17151-001 | — | 375 | 376 | 377 | 378 |
| S17153-001 | — | 379 | 380 | 381 | 382 |

-continued

| Locus | Primer1 SEQ ID NO: | Primer2 SEQ ID NO: | Probe1 SEQ ID NO: | Probe2 SEQ ID NO: | Region SEQ ID NO: |
|---|---|---|---|---|---|
| S17154-001 | — | 383 | 384 | 385 | 386 |
| S17156-001 | — | 387 | 388 | 389 | 390 |
| S17159-001 | — | 391 | 392 | 393 | 394 |
| S08590-1 | 395 | 396 | 397 | 398 | 399 |
| S17242-001 | — | 400 | 401 | 402 | 403 |
| S17166-001 | 404 | 405 | 406 | 407 | 408 |
| S17167-001 | 409 | 410 | 411 | 412 | 413 |
| S08539-1 | 414 | 415 | 416 | 417 | 418 |
| S17178-001 | — | 419 | 420 | 421 | 422 |
| S17179-001 | — | 423 | 424 | 425 | 426 |
| S17180-001 | — | 427 | 428 | 429 | 430 |
| S17181-001 | — | 431 | 432 | 433 | 434 |
| S17182-001 | — | 435 | 436 | 437 | 438 |
| S17183-001 | — | 439 | 440 | 441 | 442 |
| S02780-1 | 443 | 444 | 445 | 446 | 447 |
| S12107-1 | 448 | 449 | 450 | 451 | 452 |
| S03624-1 | 453 | 454 | 455 | 456 | 457 |
| S01953-1 | 458 | 459 | 460 | 461 | 462 |
| S00111-1 | 463 | 464 | 465 | 466 | 467 |
| S04180-1 | 468 | 469 | 470 | 471 | 472 |
| S01008-1 | 473 | 474 | 475 | 476 | 477 |
| S12862-1 | 478 | 479 | 480 | 481 | 482 |
| S12867-1 | 483 | 484 | 485 | 486 | 487 |
| S04966-1 | 488 | 489 | 490 | 491 | 492 |
| S10631-1 | 493 | 494 | 495 | 496 | 497 |
| S01574-1 | 498 | 499 | 500 | 501 | 502 |
| S16594-001 | 503 | 504 | 505 | 506 | 507 |
| S02777-1 | 508 | 509 | 510 | 511 | 512 |

DETAILED DESCRIPTION

The timing of soybean flowering and maturity are important agronomical traits that are associated with yield. These traits are largely affected by the genetic response to environmental signals such as day-length and temperature. Through selective breeding for flowering and maturity phenotypes, soybean varieties have been developed that are ideally suited for maximizing yield within a particular environment. Field testing for reproductive characteristics is laborious and challenging, and it cannot be accomplished until late in the plant life cycle. Having markers that can be used to select for reproductive growth expedite the introgression of desired alleles into elite cultivars.

Multiple genetic loci have been identified as containing genes that control the reproductive growth period of soybean. Relative maturity (RM) in soybean plays a significant role in determining final seed yield, and it is common for seed yield and the length of reproductive growth to have a positive correlation. Extending the reproductive period through manipulation of these loci is important for maximizing yield potential. However, it is important to evaluate soybean varieties in the correct environments. Utilizing markers associated with soybean reproductive growth that distinguish between early and late alleles, such as early and late alleles for initiation of flowering, provides the ability to segregate soybean populations into the correct testing environment, without having to conduct a preliminary progeny test on the line to identify an appropriate environment. It is also desirable to increase genetic diversity by crossing soybeans line with disparate reproductive habits, such as late flowering by early flowering crosses. This process has been utilized with limited success in the past due to the low frequency of desirable segregates that have a specific reproductive periods for the target area of adaptation environment. By utilizing molecular markers associated with reproductive growth, a breeder can identify plants in early generations which likely will have reproductive characteristics for the target environment, rather than having to phenotype and select a preferred reproductive growth phenotype in a previous growing season, therefore saving time and other resources. For example, a parent with relative maturity (RM) of 3.1 crossed with a second parent with RM 1.7 will produce progeny with an expected RM range from about 1.5 to about 3.5. If the breeder is only interested in testing the lines from this population that are <2.0 RM, the breeder would have to grow out a large number of progeny and select only those that mature as <2.0 RM. But, using molecular markers associated with reproductive growth, single plants can be selected having a <2.0 RM by selecting preferred locus, allele, haplotype, and/or marker profile. It is also desirable to increase the amount of time a soybean plant is in the reproductive growth stage. For example, one could select for an earlier flowering date without affecting the pod maturity.

Nucleotide polymorphisms, including SNPs as well as insertions/deletions (INDELs) have been identified that are closely linked to and in linkage disequilibrium (LD) with the reproductive growth loci in soybean. These polymorphisms allow for marker-assisted selection (MAS) of these loci, expediting the creation and precise selection soybean plants with a desired reproductive growth phenotype. This will allow for more precision in developing varieties tailored to a particular environment.

At least eight loci affecting flowering and maturity, known as E genes (E1-E8), have been identified (see, e.g., Cober et al. (1996) Crop Sci 36:601-605; Cober et al. (1996) Crop Sci 36:606-610; Asumadu et al. (1998) Ann Bot 82:773-778; Cober et al. (2001) Crop Sci 41:721-727; Abe et al. (2003) Crop Sci 43:1300-1304; Tasma & Shoemaker (2003) Crop Sci 41:319-328; Cober & Voldeng (2001) Crop Sci 41:698-701; Cober & Voldeng (2001) Crop Sci 41:1823-1926; and, Cober et al. (2010) Crop Sci 50:524-527). The E1, E2, and E3 loci have been recently cloned and found to encode a nuclear localized E1 protein (Xia et al. (2012) Proc Natl Acad Sci USA doi/10.1073/pnas.1117982109 E2155-E2164), a GIGANTEA homolog (Watanabe et al. (2011) Genetics 188:395-407), and a phytochrome A homolog respectively (Watanabe et al. (2009) Genetics 182:1251-1262). Recessive loss-of-function mutant alleles at these three loci can independently condition earlier flowering phenotypes.

A method for identifying a soybean plant or germplasm having a trait locus associated with reproductive growth, the method comprising detecting at least one allele of one or more marker loci associated with reproductive growth in soybean is provided. In some examples, a trait locus associated with reproductive growth is a locus associated with reproductive development, time to initiation of flowering (R1), time from planting to initiation of flowering (R1), time from emergence (VE) to initiation of flowering (R1), early flowering, length of reproductive growth, time from initiation of flowering (R1) to pod fill, length of flowering, time from initiation of flowering (R1) to beginning maturity (R7), time to full bloom (R2), time from first trifoliate (V1) to pre-flowering (V6), and the like.

In some examples, the method involves detecting at least one marker locus associated with reproductive growth in soybean. In some examples the method comprises detecting at least one polymorphism within 30 cM of a marker locus on LG A1 (ch 5), LG A2 (ch 8), LG B1 (ch 11), LG B2 (ch 14), LG C1 (ch 4), LG C2 (ch 6), LG D1a (ch 1), LG D1b (ch 2), LG D2 (ch 17), LG E (ch 15), LG F (ch 13), LG G (ch 18), LGH (ch 12) LG I (ch 20), LG J (ch 16), LGL (ch 19), LGM (ch 7), LGN (ch 3), and/or LG O (ch 10), or any combination thereof. In some examples the method comprises detecting at least one polymorphism within about 0-25 cM, 0-20 cM, 0-15 cM, 0-10 cM, 0-5 cM, or about 0-2.5 cM on LG A1 (ch 5), LG A2 (ch 8), LG B1 (ch 11), LG B2 (ch 14), LG C1 (ch 4), LG C2 (ch 6), LG D1a (ch 1), LG D1b (ch 2), LG D2 (ch 17), LG E (ch 15), LG F (ch 13), LG G (ch 18), LG H (ch 12) LG I (ch 20), LG J (ch 16), LG L (ch 19), LG M (ch 7), LG N (ch 3), and/or LG O (ch 10), or any combination thereof.

In some examples the method comprises detecting at least one polymorphism within about 0-50 kb, 0-100 kb, 0-200 kb, 0-500 kb, 0-750 kb, or about 0-1000 kb on LG A1 (ch 5), LG A2 (ch 8), LG B1 (ch 11), LG B2 (ch 14), LG C1 (ch 4), LG C2 (ch 6), LG D1a (ch 1), LG D1b (ch 2), LG D2 (ch 17), LGE (ch 15), LG F (ch 13), LG G (ch 18), LGH (12), LG I (ch 20), LG J (ch 16), LGL (ch 19), LGM (ch 7), LG N (ch 3), and/or LG O (ch 10), or any combination thereof.

In some examples the method comprises detecting at least one polymorphism linked to a marker locus selected from the group consisting of S01435-1 on LG A1 (ch 5), S01239-1 and/or S00780-1 on LG A2 (ch 8), S06925-1, S09951-1, and/or S00170-1 on LG B1 (ch 11), S04059-1 and/or S07851-1 on LG B2 (ch 14), S11659-1, S04279-1, S02211-1, and/or S08942-1 on LG C1 (ch 4), S05742-1, S09155-1, S02037-1, S13136-1, S17291-001, S13139-1, S17292-001, S13146-1, S17293-001, S17294-001, S17581-001, S17691-001, S17701-001, S03703-1, S17297-001, S17298-001, S17299-001, S17300-001, S17306-001, S17310-001, S17311-001, S17312-001, S17312-001, S17316-001, S17317-001, S17318-001, S17322-001, S17326-001, S17327-001, S17328-001, S17329-001, S10746-1, S17331-001, S17332-001, S17337-001, S13093-1, S12211-1, S04555-1, and/or S17301-001 on LG C2 (ch 6), S08519-1 on LG D1a (ch 1), S12876-1, S05937-1, S08575-1, S08669-1, S11212-1, and/or S00543-1 on LG D1b (ch 2), S01452-1 and/or S11993-1 on LG D2 (ch 17), S13446-1 on LG E (ch 15), S00252-1, S04060-1, S02664-1, and/or S00281-1 on LG F (ch 13), S01109-1, S13844-1, S05058-1 and/or S04660-1 on LG G (ch 18), S09955-1 on LGH (ch 12), S08034-1 and/or S10293-1 on LG I (ch 20), S03813-1 and/or S02042-1 on LG J (ch 16), S16601-001, S01481-1, S11309-1, S11320-1 and/or S04040-1 on LGL (ch 19), S00863-1, S17151-001, S17153-001, S17154-001, S17156-001, S17159-001, S08590-1, S17242-001, S17166-001, S17167-001, S08539-1, S17178-001, S17179-001, S17180-001, S17181-001, S17182-001, S17183-001, S02780-1, S12107-1, S03624-1, S01953-1, S00111-1, S04180-1, and/or S01008-1 on LGM (ch 7), S12861-1, S04966-1, and/or S12867-1 on LGN (ch 3), and S10631-1, S01574-1, S16594-001, and/or S02777-1 on LG O (ch 10), or any combination thereof.

In some examples the method comprises detecting at least one polymorphism within about 0-25 cM, 0-20 cM, 0-15 cM, 0-10 cM, 0-5 cM, or about 0-2.5 cM of a marker locus selected from the group consisting of S01435-1 on LG A1 (ch 5), S01239-1 and/or S00780-1 on LG A2 (ch 8), S06925-1, S09951-1, and/or S00170-1 on LG B1 (ch 11), S04059-1 and/or S07851-1 on LG B2 (ch 14), S11659-1, S04279-1, S02211-1, and/or S08942-1 on LG C1 (ch 4), S05742-1, S09155-1, S02037-1, S13136-1, S17291-001, S13139-1, S17292-001, S13146-1, S17293-001, S17294-001, S17581-001, S17691-001, S17701-001, S03703-1, S17297-001, S17298-001, S17299-001, S17300-001, S17306-001, S17310-001, S17311-001, S17312-001, S17312-001, S17316-001, S17317-001, S17318-001, S17322-001, S17326-001, S17327-001, S17328-001, S17329-001, S10746-1, S17331-001, S17332-001, S17337-001, S13093-1, S12211-1, S04555-1, and/or S17301-001 on LG C2 (ch 6), S08519-1 on LG D1a (ch 1), S12876-1, S05937-1, S08575-1, S08669-1, S11212-1, and/or S00543-1 on LG D1b (ch 2), S01452-1 and/or S11993-1 on LG D2 (ch 17), S13446-1 on LGE (ch 15), S00252-1, S04060-1, S02664-1, and/or S00281-1 on LG F (ch 13), S01109-1, S13844-1, S05058-1 and/or S04660-1 on LG G (ch 18), S09955-1 on LGH (ch 12), S08034-1 and/or S10293-1 on LG I (ch 20), S03813-1 and/or S02042-1 on LG J (ch 16), S16601-001, S01481-1, S11309-1, S11320-1, and/or S04040-1 on LGL (ch 19), S00863-1, S17151-001, S17153-001, S17154-001, S17156-001, S17159-001, S08590-1, S17242-001, S17166-001, S17167-001, S08539-1, S17178-001, S17179-001, S17180-001, S17181-001, S17182-001, S17183-001, S02780-1, S12107-1, S03624-1, S01953-1, S00111-1, S04180-1, and/or S01008-1 on LGM (ch 7), S12861-1, S04966-1, and/or S12867-1 on LGN (ch 3), and S10631-1, S01574-1, S16594-001, and/or S02777-1 on LG O (ch 10), or any combination thereof.

In some examples the method comprises detecting at least one polymorphism within about 0-50 kb, 0-100 kb, 0-200 kb, 0-500 kb, 0-750 kb, or about 0-1000 kb of a marker locus selected from the group consisting of S01435-1 on LG A1 (ch 5), S01239-1 and/or S00780-1 on LG A2 (ch 8), S06925-1, S09951-1, and/or S00170-1 on LG B1 (ch 11), S04059-1 and/or S07851-1 on LG B2 (ch 14), S11659-1, S04279-1, S02211-1, and/or S08942-1 on LG C1 (ch 4), S05742-1, S09155-1, S02037-1, S13136-1, S17291-001, S13139-1, S17292-001, S13146-1, S17293-001, S17294-001, S17581-001, S17691-001, S17701-001, S03703-1, S17297-001, S17298-001, S17299-001, S17300-001, S17306-001, S17310-001, S17311-001, S17312-001, S17312-001, S17316-001, S17317-001, S17318-001, S17322-001, S17326-001, S17327-001, S17328-001, S17329-001, S10746-1, S17331-001, S17332-001, S17337-001, S13093-1, S12211-1, S04555-1, and/or S17301-001 on LG C2 (ch 6), S08519-1 on LG D1a (ch 1), S12876-1, S05937-1, S08575-1, S08669-1, S11212-1, and/or S00543-1 on LG D1b (ch 2), S01452-1 and/or S11993-1 on LG D2 (ch 17), S13446-1 on LGE (ch 15), S00252-1, S04060-1, S02664-1, and/or S00281-1 on LG F (ch 13), S01109-1, S13844-1, S05058-1 and/or S04660-1 on LG G (ch 18), S09955-1 on LGH (ch 12), S08034-1 and/or S10293-1 on LG I (ch 20), S03813-1 and/or S02042-1 on LG J (ch 16), S16601-001, S01481-1, S11309-1, S11320-1, and/or S04040-1 on LGL (ch 19), S00863-1, S17151-001, S17153-001, S17154-001, S17156-001, S17159-001, S08590-1, S17242-001, S17166-001, S17167-001, S08539-1, S17178-001, S17179-001, S17180-001, S17181-001, S17182-001, S17183-001, S02780-1, S12107-1, S03624-1, S01953-1, S00111-1, S04180-1, and/or S01008-1 on LGM (ch 7), S12861-1, S04966-1, and/or S12867-1 on LGN (ch 3), and S10631-1, S01574-1, S16594-001, and/or S02777-1 on LG O (ch 10), or any combination thereof.

In some examples the method comprises detecting at least one polymorphism closely linked to a marker locus selected from the group consisting of S01435-1 on LG A1 (ch 5), S01239-1 and/or S00780-1 on LG A2 (ch 8), S06925-1, S09951-1, and/or S00170-1 on LG B1 (ch 11), S04059-1 and/or S07851-1 on LG B2 (ch 14), S11659-1, S04279-1, S02211-1, and/or S08942-1 on LG C1 (ch 4), S05742-1, S09155-1, S02037-1, S13136-1, S17291-001, S13139-1, S17292-001, S13146-1, S17293-001, S17294-001, S17581-001, S17691-001, S17701-001, S03703-1, S17297-001, S17298-001, S17299-001, S17300-001, S17306-001, S17310-001, S17311-001, S17312-001, S17312-001, S17316-001, S17317-001, S17318-001, S17322-001, S17326-001, S17327-001, S17328-001, S17329-001, S10746-1, S17331-001, S17332-001, S17337-001, S13093-1, S12211-1, S04555-1, and/or S17301-001 on LG C2 (ch 6), S08519-1 on LG D1a (ch 1), S12876-1, S05937-1, S08575-1, S08669-1, S11212-1, and/or S00543-1 on LG D1b (ch 2), S01452-1 and/or S11993-1 on LG D2 (ch 17), S13446-1 on LGE (ch 15), S00252-1, S04060-1, S02664-1, and/or S00281-1 on LGF (ch 13), S01109-1, S13844-1, S05058-1 and/or S04660-1 on LG G (ch 18), S09955-1 on LGH (ch 12), S08034-1 and/or S10293-1 on LG I (ch 20), S03813-1 and/or S02042-1 on LG J (ch 16), S16601-001, S01481-1, S11309-1, S11320-1, and/or S04040-1 on LGL (ch 19), S00863-1, S17151-001, S17153-001, S17154-001, S17156-001, S17159-001, S08590-1, S17242-001, S17166-001, S17167-001, S08539-1, S17178-001, S17179-001, S17180-001, S17181-001, S17182-001, S17183-001, S02780-1, S12107-1, S03624-1, S01953-1, S00111-1, S04180-1, and/or S01008-1 on LGM (ch 7), S12861-1, S04966-1, and/or S12867-1 on LGN (ch 3), and S10631-1, S01574-1, S16594-001, and/or S02777-1 on LG O (ch 10), or any combination thereof.

In some examples, the method comprises detecting at least one polymorphism in a marker locus selected from the group consisting of S01435-1 on LG A1 (ch 5), S01239-1 and/or S00780-1 on LG A2 (ch 8), S06925-1, S09951-1, and/or S00170-1 on LG B1 (ch 11), S04059-1 and/or S07851-1 on LG B2 (ch 14), S11659-1, S04279-1, S02211-1, and/or S08942-1 on LG C1 (ch 4), S05742-1, S09155-1, S02037-1, S13136-1, S17291-001, S13139-1, S17292-001, S13146-1, S17293-001, S17294-001, S17581-001, S17691-001, S17701-001, S03703-1, S17297-001, S17298-001, S17299-001, S17300-001, S17306-001, S17310-001, S17311-001, S17312-001, S17312-001, S17316-001, S17317-001, S17318-001, S17322-001, S17326-001, S17327-001, S17328-001, S17329-001, S10746-1, S17331-001, S17332-001, S17337-001, S13093-1, S12211-1, S04555-1, and/or S17301-001 on LG C2 (ch 6), S08519-1 on LG D1a (ch 1), S12876-1, S05937-1, S08575-1, S08669-1, S11212-1, and/or S00543-1 on LG D1b (ch 2), S01452-1 and/or S11993-1 on LG D2 (ch 17), S13446-1 on LGE (ch 15), S00252-1, S04060-1, S02664-1, and/or S00281-1 on LG F (ch 13), S01109-1, S13844-1, S05058-1 and/or S04660-1 on LG G (ch 18), S09955-1 on LGH (ch 12), S08034-1 and/or S10293-1 on LG I (ch 20), S03813-1 and/or S02042-1 on LG J (ch 16), S16601-001, S01481-1, S11309-1, S11320-1, and/or S04040-1 on LGL (ch 19), S00863-1, S17151-001, S17153-001, S17154-001, S17156-001, S17159-001, S08590-1, S17242-001, S17166-001, S17167-001, S08539-1, S17178-001, S17179-001, S17180-001, S17181-001, S17182-001, S17183-001, S02780-1, S12107-1, S03624-1, S01953-1, S00111-1, S04180-1, and/or S01008-1 on LGM (ch 7), S12861-1, S04966-1, and/or S12867-1 on LGN (ch 3), and S10631-1, S01574-1, S16594-001, and/or S02777-1 on LG O (ch 10), or any combination thereof.

In some examples, the method comprises detecting a polymorphism using at least one marker selected from the group consisting of a marker selected from the group consisting of S01435-1-001 on LG A1 (ch 5), S01239-1-A and/or S00780-1-A on LG A2 (ch 8), S06925-1-Q1, S09951-1-Q1, and/or S00170-1-A on LG B1 (ch 11), S04059-1-A and/or S07851-1-Q1 on LG B2 (ch 14), S11659-1-Q1, S04279-1-A, S02211-1-A, and/or S08942-1-Q1 on LG C1 (ch 4), S05742-1-Q1, S09155-1-Q1, S02037-1-A, S13136-1-Q1, S17291-001-K001, S13139-1-Q1, S17292-001-K001, S13146-1-Q1, S17293-001-K001, S17294-001-K001, S17581-001-Q008, S17691-001-Q001, S17701-001-Q001, S03703-1-Q1, S17297-001-K001, S17298-001-K001, S17299-001-K001, S17300-001-K001, S17306-001-K001, S17310-001-K001, S17311-001-K001, S17312-001-K001, S17312-001-K001, S17316-001-K001, S17317-001-K001, S17318-001-K001, S17322-001-K001, S17326-001-K001, S17327-001-K001, S17328-001-K001, S17329-001-K001, S10746-1-Q1, S17331-001-K001, S17332-001-K001, S17337-001-K001, S13093-1-Q1, S12211-1-Q1, S04555-1-Q1, and/or S17301-001-K001 on LG C2 (ch 6), S08519-1-Q1 on LG D1a (ch 1), S12876-1-Q1, S05937-1-Q1, S08575-1-Q1, S08669-1-Q1, S11212-1-Q1, and/or S00543-1-A on LG D1b (ch 2), S01452-1-A and/or S11993-1-Q2 on LG D2 (ch 17), S13446-1-Q1 on LGE (ch 15), S00252-1-A, S04060-1-A, S02664-1-A, and/or S00281-1-A on LGF (ch 13), S01109-1-Q002, S13844-1-Q1, S05058-1-Q1 and/or S04660-1-A on LG G (ch 18), S09955-1-Q1 on LGH (ch 12), S08034-1-Q1 and/or S10293-1-Q1 on LG I (ch 20), S03813-1-A and/or S02042-1-A on LG J (ch 16), S16601-001-Q001, S01481-1-A, S11309-1-Q1, S11320-1-Q1, and/or S04040-1-A on LGL (ch 19), S00863-1-A, S17151-001-K001, S17153-001-K001, S17154-001-K001, S17156-001-K001, S17159-001-K001, S08590-1-Q1, S17242-001-K001, S17166-001-Q006, S17167-001-Q007, S08539-1-Q1, S17178-001-K001, S17179-001-K001, S17180-001-K001, S17181-001-K001, S17182-001-K001, S17183-001-K001, S02780-1-Q1, S12107-1-Q1, S03624-1-Q001, S01953-1-A, S00111-1-A, S04180-1-A, and/or S01008-1-B on LGM (ch 7), S12861-1-Q1, S04966-1-Q1, and/or S12867-1-Q002 on LGN (ch 3), and S10631-1-Q1, S01574-1-A, S16594-001-Q10, and/or S02777-1-A on LG O (ch 10), or any combination thereof.

In other examples, the method involves detecting a haplotype comprising two or more marker loci, for example, 2, 3, 4, 5, 6, 7, 8, 9, 10, 11, 12, 13, 14, 15, 16, 17, 18, 19, 20, 21, 22, 23, 24, 25, 26, 27, 28, 29, 30, or 31 marker loci, or more. In certain examples, the haplotype comprises two or more markers selected from the group consisting of S01435-1-001 on LG A1 (ch 5), S01239-1-A and/or S00780-1-A on LG A2 (ch 8), S06925-1-Q1, S09951-1-Q1, and/or S00170-1-A on LG B1 (ch 11), S04059-1-A and/or S07851-1-Q1 on LG B2 (ch 14), S11659-1-Q1, S04279-1-A, S02211-1-A, and/or S08942-1-Q1 on LG C1 (ch 4), S05742-1-Q1, S09155-1-Q1, S02037-1-A, S13136-1-Q1, S17291-001-K001, S13139-1-Q1, S17292-001-K001, S13146-1-Q1, S17293-001-K001, S17294-001-K001, S17581-001-Q008, S17691-001-Q001, S17701-001-Q001, S03703-1-Q1, S17297-001-K001, S17298-001-K001, S17299-001-K001, S17300-001-K001, S17306-001-K001, S17310-001-K001, S17311-001-K001, S17312-001-K001, S17312-001-K001, S17316-001-K001, S17317-001-K001, S17318-001-K001, S17322-001-K001, S17326-001-K001, S17327-001-K001, S17328-001-K001, S17329-001-K001, S10746-1-Q1, S17331-001-K001, S17332-001-K001, S17337-001-K001, S13093-1-Q1, S12211-1-Q1, S04555-1-Q1, and/or S17301-001-K001 on LG C2 (ch 6), S08519-1-Q1 on LG D1a (ch 1), S12876-1-Q1, S05937-1-Q1, S08575-1-Q1, S08669-1-Q1, S11212-1-Q1, and/or S00543-1-A on LG D1b (ch 2), S01452-1-A and/or S11993-1-Q2 on LG D2 (ch 17), S13446-1-Q1 on LGE (ch 15), S00252-1-A, S04060-1-A, S02664-1-A, and/or S00281-1-A on LGF (ch 13), S01109-1-Q002, S13844-1-Q1, S05058-1-Q1 and/or S04660-1-A on LG G (ch 18), S09955-1-Q1 on LGH (ch 12), S08034-1-Q1 and/or S10293-1-Q1 on LG I (ch 20), S03813-1-A and/or S02042-1-A on LG J (ch 16), S16601-001-Q001, S01481-1-A, S11309-1-Q1, S11320-1-Q1, and/or S04040-1-A on LGL (ch 19), S00863-1-A, S17151-001-K001, S17153-001-K001, S17154-001-K001, S17156-001-K001, S17159-001-

K001, S08590-1-Q1, S17242-001-K001, S17166-001-Q006, S17167-001-Q007, S08539-1-Q1, S17178-001-K001, S17179-001-K001, S17180-001-K001, S17181-001-K001, S17182-001-K001, S17183-001-K001, S02780-1-Q1, S12107-1-Q1, S03624-1-Q001, S01953-1-A, S00111-1-A, S04180-1-A, and/or S01008-1-B on LG M (ch 7), S12861-1-Q1, S04966-1-Q1, and/or S12867-1-Q002 on LGN (ch 3), and S10631-1-Q1, S01574-1-A, S16594-001-Q10, and/or S02777-1-A on LG O (ch 10), or any combination thereof. In further examples, the haplotype comprises markers from the set of markers described in Tables 26-46.

In other examples, the method involves detecting a marker profile comprising two or more marker loci, for example, 2, 3, 4, 5, 6, 7, 8, 9, 10, 11, 12, 13, 14, 15, 16, 17, 18, 19, 20, 21, 22, 23, 24, 25, 26, 27, 28, 29, 30, or 31 marker loci, or more. In some examples the method uses marker assisted selection to stack two or more loci in a soybean plant, cell, seed, or germplasm. In some examples the method uses a marker profile to produce a soybean plant, cell, seed, or germplasm having a desired predicted flowering time. In some examples the desired predicted flowering time, is a desired flowering time for a specific adapted growing zones or area of adaptability, including but not limited to day length, latitude, environmental class, management zone, maturity group and/or relative maturity. In some examples, the area of adaptability may include using soybean to produce a second crop during a growing season. Second crops are commonly planted in areas with longer growing seasons, however the selected crop may need different reproductive characteristics to be adapted for the second growing cycle in the season than it would for the first growing cycle of the season. Any method of environmental classification can be used, including but not limited to those described in U.S. Pat. No. 8,032,389, and Loeffler et al. (2005) Crop Sci 45:1708-1716, each of which is herein incorporated by reference in its entirety. In certain examples, the marker profile comprises two or more markers selected from the group consisting of S01435-1-001 on LG A1 (ch 5), S01239-1-A and/or S00780-1-A on LG A2 (ch 8), S06925-1-Q1, S09951-1-Q1, and/or S00170-1-A on LG B1 (ch 11), S04059-1-A and/or S07851-1-Q1 on LG B2 (ch 14), S11659-1-Q1, S04279-1-A, S02211-1-A, and/or S08942-1-Q1 on LG Cl (ch 4), S05742-1-Q1, S09155-1-Q1, S02037-1-A, S13136-1-Q1, S17291-001-K001, S13139-1-Q1, S17292-001-K001, S13146-1-Q1, S17293-001-K001, S17294-001-K001, S17581-001-Q008, S17691-001-Q001, S17701-001-Q001, S03703-1-Q1, S17297-001-K001, S17298-001-K001, S17299-001-K001, S17300-001-K001, S17306-001-K001, S17310-001-K001, S17311-001-K001, S17312-001-K001, S17312-001-K001, S17316-001-K001, S17317-001-K001, S17318-001-K001, S17322-001-K001, S17326-001-K001, S17327-001-K001, S17328-001-K001, S17329-001-K001, S10746-1-Q1, S17331-001-K001, S17332-001-K001, S17337-001-K001, S13093-1-Q1, S12211-1-Q1, S04555-1-Q1, and/or S17301-001-K001 on LG C2 (ch 6), S08519-1-Q1 on LG D1a (ch 1), S12876-1-Q1, S05937-1-Q1, S08575-1-Q1, S08669-1-Q1, S11212-1-Q1, and/or S00543-1-A on LG D1b (ch 2), S01452-1-A and/or S11993-1-Q2 on LG D2 (ch 17), S13446-1-Q1 on LGE (ch 15), S00252-1-A, S04060-1-A, S02664-1-A, and/or S00281-1-A on LGF (ch 13), S01109-1-Q002, S13844-1-Q1, S05058-1-Q1 and/or S04660-1-A on LG G (ch 18), S09955-1-Q1 on LG H (ch 12), S08034-1-Q1 and/or S10293-1-Q1 on LG I (ch 20), S03813-1-A and/or S02042-1-A on LG J (ch 16), S16601-001-Q001, S01481-1-A, S11309-1-Q1, S11320-1-Q1, and/or S04040-1-A on LGL (ch 19), S00863-1-A, S17151-001-K001, S17153-001-K001, S17154-001-K001, S17156-001-K001, S17159-001-K001, S08590-1-Q1, S17242-001-K001, S17166-001-Q006, S17167-001-Q007, S08539-1-Q1, S17178-001-K001, S17179-001-K001, S17180-001-K001, S17181-001-K001, S17182-001-K001, S17183-001-K001, S02780-1-Q1, S12107-1-Q1, S03624-1-Q001, S01953-1-A, S00111-1-A, S04180-1-A, and/or S01008-1-B on LG M (ch 7), S12861-1-Q1, S04966-1-Q1, and/or S12867-1-Q002 on LGN (ch 3), and S10631-1-Q1, S01574-1-A, S16594-001-Q10, and/or S02777-1-A on LG O (ch 10), or any combination thereof. In further examples, the marker profile comprises markers from the set of markers described in Tables 26-46.

In other examples, the one or more marker locus detected comprises one or more markers within a chromosome interval selected from the group consisting of an interval on linkage group A1 flanked by and including Satt364 and BARC-020479-04637, an interval on linkage group A2 flanked by and including S01239-1 and S00780-1, an interval on linkage group B1 flanked by and including S06925-1 and S00170-1, an interval on linkage group B2 flanked by and including S04059-1-A and S07851-1-Q1, an interval on linkage group B2 flanked by and including BARC-052789-11619 and BARC-013273-00464, an interval on linkage group C1 flanked by and including S11659-1 and S02211-1, an interval on linkage group C1 flanked by and including BARC-042189-08197 and BARC-019093-0331, an interval on linkage group C1 flanked by and including S02211-1 and S08942-1, an interval on linkage group C2 flanked by and including S05742-1 and BARCSOYSSR_06_0283, an interval on linkage group C2 flanked by and including S05742-1 and BARC-035239-07157, an interval on linkage group C2 flanked by and including BARC-0299-06757 and Satt322, an interval on linkage group C2 flanked by and including S13136-1 and S17294-001, an interval on linkage group C2 flanked by and including S17297-001 and S17317-001, an interval on linkage group C2 flanked by and including S17318-001 and S17331-001, an interval on linkage group D1a flanked by and including BARC-024147-04784 and BARC-045297-08928, an interval on linkage group D1b flanked by and including BARC-029753-06334 and BARC-013995-01298, an interval on linkage group D1b flanked by and including S12876-1 and S08575-1, an interval on linkage group D1b flanked by and including S08669-1 and S11212-1, an interval on linkage group D1b flanked by and including S08575-1 and S08669-1, an interval on linkage group D2 flanked by and including Satt389 and BARC-040583-007786, an interval on linkage group D2 flanked by and including S01452-1 and S11993-1, an interval on linkage group E flanked by and including BARC-020425-04614 and Satt231, an interval on linkage group F flanked by and including S00252-1 and Sat 039, an interval on linkage group F flanked by and including S04060-1 and S00281-1, an interval on linkage group G flanked by and including BARC-020027-04405 and Satt309, an interval on linkage group G flanked by and including S13844-1 and BARC-013305-00475, an interval on linkage group G flanked by and including Sat 064 and BARC-013305-00475, an interval on linkage group H flanked by and including BARC-018437-03181 and Satt629, an interval on linkage group I flanked by and including S08034-1 and S10293-1, an interval on linkage group I flanked by and including S10293-1 and Satt299, an interval on linkage group J flanked by and including Sct_046 and Satt693, an interval on linkage group J flanked by and including Satt547 and BARC-030817-06946, an interval on linkage group M flanked by and including S00863-1 and S17167-001, an interval on linkage group M flanked by and including BARC-SOYSSR_07_0017 and S08590-1, an interval on linkage group M flanked by and including S08590-1 and S17167-001, an interval on linkage group M flanked by and including S00111-1 and Sat_121, an interval on linkage group M flanked by and including S00111-1 and, and/or S01008-1, an interval on linkage group N flanked by and including Sat_236 and Satt339, an interval on linkage group N flanked by and including S12862-1 and S12867-1, an interval on linkage group N flanked by and including Sat_125 and BARC-039729-07559, and an interval on linkage group O flanked by and including S02777-1 and BARC-029629-06265, or any interval provided in Tables 28-46.

In further examples, the one or more marker locus detected comprises one or more markers within one or more of the genomic DNA regions of SEQ ID NOs: 1-512. In other examples, the one or more marker locus detected comprises one or more markers within one or more of the genomic regions of SEQ ID NOs:5, 10, 15, 20, 25, 30, 35, 40, 45, 50, 55, 60, 65, 70, 75, 80, 84, 89, 93, 98, 102, 106, 111, 115, 120, 125, 129, 133, 137, 141, 145, 149, 153, 157, 161, 165, 169, 173, 177, 181, 185, 189, 193, 197, 202, 206, 210, 214, 219, 224, 229, 234, 239, 244, 249, 254, 259, 264, 269, 274, 279, 284, 289, 294, 299, 304, 309, 314, 319, 324, 329, 334, 339, 344, 349, 354, 359, 364, 369, 374, 378, 382, 386, 390, 394, 399, 403, 408, 413, 418, 422, 426, 430, 434, 438, 442, 447, 452, 457, 462, 467, 472, 477, 482, 487, 492, 497, 502, 507, or, 512. In some examples, the one or more polymorphism detected may be less than 1 cM, 1 cM, 5 cM, 10 cM, 15 cM, 20 cM, or 30 cM from SEQ ID NOs: 1-512. In further examples, the one or more marker locus detected comprises one or more markers within a chromosome interval described in Tables 28-46.

In some examples, the method comprises detecting one or more polymorphisms linked to one or more loci, said loci comprising a polymorphism selected from the group consisting of Gm05:30568085, Gm08:7464336, Gm08:15841570, Gm11:4674824, Gm11:5231500, Gm11:7847341, Gm14:46138053, Gm14:47331319, Gm04:5754268, Gm04:8295779, Gm04:39691731, Gm04:44725098, Gm06:410442, Gm06:11659627, Gm06:15457913, Gm06:16391391, Gm06:16499786, Gm06:16593381, Gm06:16670047, Gm06:16804435, Gm06:17498270, Gm06:18203964, Gm06:19743496, Gm06:19986645, Gm06:20007173, Gm06:20084642, Gm06:20501491, Gm06:21197184, Gm06:21500085, Gm06:22501610, Gm06:25700006, Gm06:28501458, Gm06:28671736, Gm06:29499523, Gm06:30203054, Gm06:31694650, Gm06:32503141, Gm06:33196184, Gm06:35509548, Gm06:37712913, Gm06:38467854, Gm06:39168136, Gm06:39533730, Gm06:40766974, Gm06:41476201, Gm06:42450296, Gm06:47500976, Gm06:47521797, Gm06:48475049, Gm06:49978151, Gm06:22700011, Gm01:759365, Gm02:4893148, Gm02:9714426, Gm02:11502780, Gm02:15446229, Gm02:33158449, Gm02:45776142, Gm17:16136646, Gm17:39804515, Gm15:50237460, Gm13:235439, Gm13:20365663, Gm13:20744030, Gm13:35174140, Gm18:305113, Gm18:58086324, Gm18:61591142, Gm18:61831970, Gm12:11512115, Gm20:39051858, Gm20:41216234, Gm16:4678569, Gm16:36524407, Gm19:47535046, Gm19:47826727, Gm19:48252040, Gm19:48638646, Gm19:50222676, Gm07:1141099, Gm07:1830296, Gm07:1923026, Gm07:2179883, Gm07:2310058, Gm07:2679749, Gm07:3009018, Gm07:4282676, Gm07:4319368, Gm07:4342479, Gm07:5576650, Gm07:6288899, Gm07:6340656, Gm07:6347675, Gm07:6614649, Gm07:6616695, Gm07:6623333, Gm07:6671535, Gm07:7096376, Gm07:7774056, Gm07:8674220, Gm07:35590550, Gm07:36459825, Gm07:36638366, Gm03:38491492, Gm03:39583405, Gm03:46209939, Gm10:43974548, Gm10:44725777, Gm10:44732850, Gm10:50495033, or any combination thereof.

In some examples, the method comprises detecting a haplotype or a marker profile comprising two or more of the polymorphisms linked to marker loci, said loci comprising a polymorphism selected from the group consisting of Gm05:30568085, Gm08:7464336, Gm08:15841570, Gm11:4674824, Gm11:5231500, Gm11:7847341, Gm14:46138053, Gm14:47331319, Gm04:5754268, Gm04:8295779, Gm04:39691731, Gm04:44725098, Gm06:410442, Gm06:11659627, Gm06:15457913, Gm06:16391391, Gm06:16499786, Gm06:16593381, Gm06:16670047, Gm06:16804435, Gm06:17498270, Gm06:18203964, Gm06:19743496, Gm06:19986645, Gm06:20007173, Gm06:20084642, Gm06:20501491, Gm06:21197184, Gm06:21500085, Gm06:22501610, Gm06:25700006, Gm06:28501458, Gm06:28671736, Gm06:29499523, Gm06:30203054, Gm06:31694650, Gm06:32503141, Gm06:33196184, Gm06:35509548, Gm06:37712913, Gm06:38467854, Gm06:39168136, Gm06:39533730, Gm06:40766974, Gm06:41476201, Gm06:42450296, Gm06:47500976, Gm06:47521797, Gm06:48475049, Gm06:49978151, Gm06:22700011, Gm01:759365, Gm02:4893148, Gm02:9714426, Gm02:11502780, Gm02:15446229, Gm02:33158449, Gm02:45776142, Gm17:16136646, Gm17:39804515, Gm15:50237460, Gm13:235439, Gm13:20365663, Gm13:20744030, Gm13:35174140, Gm18:305113, Gm18:58086324, Gm18:61591142, Gm18:61831970, Gm12:11512115, Gm20:39051858, Gm20:41216234, Gm16:4678569, Gm16:36524407, Gm19:47535046, Gm19:47826727, Gm19:48252040, Gm19:48638646, Gm19:50222676, Gm07:1141099, Gm07:1830296, Gm07:1923026, Gm07:2179883, Gm07:2310058, Gm07:2679749, Gm07:3009018, Gm07:4282676, Gm07:4319368, Gm07:4342479, Gm07:5576650, Gm07:6288899, Gm07:6340656, Gm07:6347675, Gm07:6614649, Gm07:6616695, Gm07:6623333, Gm07:6671535, Gm07:7096376, Gm07:7774056, Gm07:8674220, Gm07:35590550, Gm07:36459825, Gm07:36638366, Gm03:38491492, Gm03:39583405, Gm03:46209939, Gm10:43974548, Gm10:44725777, Gm10:44732850, Gm10:50495033, or any combination thereof. In other examples, the haplotype or marker profile comprises two or more polymorphisms described in Tables 26-46. In some examples, the haplotype or the marker profile may comprise a combination of early alleles and late alleles.

In some examples, the at least one favorable allele of one or more marker loci is selected from the group consisting of an allele of a marker provided in Table 24. In some examples, the at least one favorable allele of one or more marker loci is selected from the group consisting of an early allele of a marker provided in Table 25, or any combination thereof.

Detecting may comprise isolating nucleic acids, amplifying the marker locus or a portion of the marker locus and detecting the resulting amplified marker amplicon. In particular examples, the amplifying comprises admixing an amplification primer or amplification primer pair and, optionally at least one nucleic acid probe, with a nucleic acid isolated from the first soybean plant or germplasm, wherein the primer or primer pair and optional probe is complementary or partially complementary to at least a portion of the marker locus and is capable of initiating DNA polymerization by a DNA polymerase using the soybean nucleic acid as a template; and, extending the primer or primer pair in a DNA polymerization reaction comprising a DNA polymerase and a template nucleic acid to generate at least one amplicon. In particular examples, the detection comprises real time PCR analysis.

In still further aspects, the information disclosed herein regarding marker alleles, haplotypes, and/or marker profiles can be used to aid in the creation and/or selection of breeding plants, lines, and populations for a preferred reproductive growth phenotype, including but not limited to at least one or more of a preferred time to initiation of flowering, early flowering, relative maturity, and/or length of reproductive growth. Further, the marker alleles, haplotypes, and/or marker profiles can be used for use in introgression into elite soybean germplasm, exotic soybean germplasm, or any other soybean germplasm. In some examples the marker alleles, haplotypes, and/or marker profiles can be used to aid in the creation and/or selection of breeding plants, lines, and populations for a preferred reproductive growth phenotype for a specific area of adaptation or target environment. Also provided is a method for introgressing a soybean QTL, marker, haplotype, and/or marker profile associated with at least a preferred time or length of at least one reproductive stage into soybean germplasm. Methods are provided wherein one or more loci, markers, haplotypes and/or marker profiles are used to create and/or select soybean plants having at a preferred time or length of at least one reproductive stage. Plants so created and selected can be used in a soybean breeding program. Through the process of introgression, the QTL, marker, haplotype, and/or marker profile associated with a preferred time or length of at least one reproductive stage, such as a preferred time to initiation of flowering, early flowering, and/or length of reproductive growth, is introduced from plants identified using marker-assisted selection (MAS) to other plants. According to the method, agronomically desirable plants and seeds can be produced containing the QTL, marker, haplotype, and/or marker profile associated with a preferred time or length of at least one reproductive stage from germplasm containing the QTL, marker, haplotype, and/or marker profile.

Also provided herein is a method for producing a soybean plant adapted for a preferred reproductive growth phenotype. First, donor soybean plants for a parental line containing at least one preferred reproductive growth QTL, marker, haplotype and/or marker profile are selected. According to the method, selection can be accomplished via MAS as explained herein. Selected plant material may represent, among others, an inbred line, a hybrid line, a heterogeneous population of soybean plants, or an individual plant. According to techniques well known in the art of plant breeding, this donor parental line is crossed with a second parental line. In some examples, the second parental line is a high yielding line. This cross produces a segregating plant population composed of genetically heterogeneous plants. Plants of the segregating plant population are screened for the tolerance QTL, marker, or haplotype. Further breeding may include, among other techniques, additional crosses with other lines, hybrids, backcrossing, or self-crossing. The result is a line of soybean plants that has a preferred reproductive growth phenotype and optionally also has other desirable traits from one or more other soybean lines.

Also provided is a method of soybean plant breeding comprising crossing at least two different soybean parent plants, wherein the parent soybean plants differ in time to R1 reproductive stage, obtaining a population of progeny soybean seed from said cross, genotyping the progeny soybean seed with at least one genetic marker, and, selecting a subpopulation comprising at least one soybean seed possessing a genotype for altered time to R1 reproductive stage, wherein the mean time to R1 reproductive stage of the selected subpopulation is altered as compared to the mean time to R1 reproductive stage of the non-selected progeny. In some examples the mean time to R1 reproductive stage of the selected subpopulation of progeny is at least 3-7 days different, or at least 1, 2, 3, 4, 5, 6, 7, 8, 9, 10, 11, 12, 13, 14, 15, 16, 17, 18, 19, 20, 21, 22, 23, 24, 25, 26, 27, 28, 29, or more days different than the mean time to R1 reproductive stage of the non-selected progeny. In other examples the mean time to R1 reproductive stage of the selected subpopulation of progeny is at least 2, 3, 4, 5, 6, 7, or 8 days different than the mean time to R1 reproductive stage of the non-selected progeny. In some examples, the two different soybean parent plants also differ by maturity. The maturity groups of the parent plants may differ by one or more maturity subgroups, by one or more maturity groups, or by 1 or more days to maturity. In some examples the parents differ in maturity by at least 10 days, between 10 days-20 days, between 10 days-30 days, by at least 0.1, 0.2, 0.3. 0.4, 0.5, 0.6, 0.7, 0.8, or 0.9 maturity subgroups, by at least 1, 2, 3. 4, 5, 6, 7, 8, 9, 10, 11, or 12 maturity groups. In some examples one parent is adapted for a northern growing region, and the second parent is not adapted for a northern growing region. In some examples the parent adapted for a northern growing region comprises a better reproductive growth phenotype for a northern growing region than the parent not adapted for a northern growing region. In some examples, the method further comprises obtaining progeny better adapted for a northern growing region.

In some examples the methods include identifying trait loci in a mixed defined plant population comprising multiple plant families (see, e.g., U.S. Pat. No. 6,399,855, herein incorporated by reference in its entirety). The method comprises quantifying a phenotypic trait across lines sampled from the population, identifying at least one genetic marker associated with the phenotypic trait by screening a set of markers and identifying the quantitative trait loci based on the association of the phenotypic trait and the genetic marker(s). In some examples the plant population consists of diploid plants, either hybrid or inbred. The phenotypic traits associated with the locus are quantitative such that a numerical value can be ascribed to the trait, and the association of the genetic loci and the phenotypic trait is determined through specified statistical models. In some examples the statistical models are linear models with fixed effects and random effects. In a other examples the statistical model is a mixed effects model.

Soybean plants, seeds, tissue cultures, variants and mutants having a preferred reproductive growth phenotype produced by the foregoing methods are also provided. Soybean plants, seeds, tissue cultures, variants and mutants comprising one or more of the marker loci, one or more of the favorable alleles, and/or one or more of the haplotypes and having a preferred reproductive growth phenotype are provided. Also provided are isolated nucleic acids, kits, and systems useful for the identification, prediction, and/or selection methods disclosed herein.

In some examples, the soybean plant, germplasm, plant part, or seed having a preferred reproductive growth phenotype further comprises one or more other traits of interest including but not limited to improved resistance to one or more ALS-inhibiting herbicides, a hydroxyphenylpyruvate-dioxygenase inhibitor, a phosphanoglycine (including but not limited to a glyphosate), a sulfonamide, an imidazolinone, a bialaphos, a phosphinothricin, a metribuzin, a mesotrione, an isoxaflutole, an azafenidin, a butafenacil, a sulfosate, a glufosinate, a dicamba, a 2,4-D, and a protox inhibitor. In some examples, resistance to the herbicidal formulation is conferred by a transgene. In some examples, the plant or germplasm further comprises a trait selected from the group consisting of drought tolerance, stress tolerance, disease resistance, herbicide resistance, enhanced yield, modified oil, modified protein, tolerance to chlorotic conditions, and insect resistance, or any combination thereof. In some examples, the trait is selected from the group consisting of brown stem rot resistance, charcoal rot drought complex resistance, *Fusarium* resistance, *Phytophthora* resistance, stem canker resistance, sudden death syndrome resistance, *Sclerotinia* resistance, *Cercospora* resistance, anthracnose resistance, target spot resistance, frogeye leaf spot resistance, soybean cyst nematode resistance, root knot nematode resistance, rust resistance, high oleic content, low linolenic content, aphid resistance, stink bug resistance, and iron chlorosis deficiency tolerance, or any combination thereof. In some examples, one or more of the traits is conferred by one or more transgenes, by one or more native loci, or any combination thereof.

In another example a method of producing a cleaned soybean seed is provided, the method comprising cleaning a soybean seed having at least one locus conferred a preferred reproductive growth phenotype is provided. In some examples, the cleaned soybean seed has enhanced yield characteristics when compared to a soybean seed which has not been cleaned. Cleaned soybean seed produced by the methods are also provided.

In another example a method of producing a treated soybean seed is provided, the method comprising treating a soybean seed having at least one locus conferred a preferred reproductive growth phenotype is provided. In some examples, the seed treatment comprises a fungicide, an insecticide, or any combination thereof. In some examples the seed treatment comprises trifloxystrobin, metalaxyl, imidacloprid, *Bacillus* spp., and any combination thereof. In some examples the seed treatment comprises picoxystrobin, penthiopyrad, cyantraniliprole, chlorantraniliprole, and any combination thereof. In some examples, the seed treatment improves seed germination under normal and/or stress environments, early stand count, vigor, yield, root formation, nodulation, and any combination thereof when compared to a soybean seed which has not been treated. In some examples seed treatment reduces seed dust levels, insect damage, pathogen establishment and/or damage, plant virus infection and/or damage, and any combination thereof. Treated soybean seed produced by the methods are also provided.

It is to be understood that this invention is not limited to particular embodiments, which can, of course, vary. It is also to be understood that the terminology used herein is for the purpose of describing particular embodiments only, and is not intended to be limiting. Further, all publications referred to herein are incorporated by reference for the purpose cited to the same extent as if each was specifically and individually indicated to be incorporated by reference herein.

As used in this specification and the appended claims, terms in the singular and the singular forms "a," "an," and "the," for example, include plural referents unless the content clearly dictates otherwise. Thus, for example, reference to "plant," "the plant," or "a plant" also includes a plurality of plants; also, depending on the context, use of the term "plant" can also include genetically similar or identical progeny of that plant; use of the term "a nucleic acid" optionally includes, as a practical matter, many copies of that nucleic acid molecule; similarly, the term "probe" optionally (and typically) encompasses many similar or identical probe molecules.

Additionally, as used herein, "comprising" is to be interpreted as specifying the presence of the stated features, integers, steps, or components as referred to, but does not preclude the presence or addition of one or more features, integers, steps, or components, or groups thereof. Thus, for example, a kit comprising one pair of oligonucleotide primers may have two or more pairs of oligonucleotide primers. Additionally, the term "comprising" is intended to include examples encompassed by the terms "consisting essentially of" and "consisting of." Similarly, the term "consisting essentially of" is intended to include examples encompassed by the term "consisting of."

Certain definitions used in the specification and claims are provided below. In order to provide a clear and consistent understanding of the specification and claims, including the scope to be given such terms, the following definitions are provided:

"Allele" means any of one or more alternative forms of a genetic sequence. In a diploid cell or organism, the two alleles of a given sequence typically occupy corresponding loci on a pair of homologous chromosomes. With regard to a SNP marker, allele refers to the specific nucleotide base present at that SNP locus in that individual plant.

The term "amplifying" in the context of nucleic acid amplification is any process whereby additional copies of a selected nucleic acid (or a transcribed form thereof) are produced. An "amplicon" is an amplified nucleic acid, e.g., a nucleic acid that is produced by amplifying a template nucleic acid by any available amplification method.

"Backcrossing" is a process in which a breeder crosses a progeny variety back to one of the parental genotypes one or more times.

The term "chromosome segment" designates a contiguous linear span of genomic DNA that resides in planta on a single chromosome. "Chromosome interval" refers to a chromosome segment defined by specific flanking marker loci.

"Cultivar" and "variety" are used synonymously and mean a group of plants within a species (e.g., *Glycine max*) that share certain genetic traits that separate them from other possible varieties within that species. Soybean cultivars are inbred lines produced after several generations of self-pollinations. Individuals within a soybean cultivar are homogeneous, nearly genetically identical, with most loci in the homozygous state.

An "elite line" is an agronomically superior line that has resulted from many cycles of breeding and selection for superior agronomic performance. Numerous elite lines are available and known to those of skill in the art of soybean breeding.

An "elite population" is an assortment of elite individuals or lines that can be used to represent the state of the art in terms of agronomically superior genotypes of a given crop species, such as soybean.

An "exotic soybean strain" or an "exotic soybean germplasm" is a strain or germplasm derived from a soybean not belonging to an available elite soybean line or strain of germplasm. In the context of a cross between two soybean plants or strains of germplasm, an exotic germplasm is not closely related by descent to the elite germplasm with which it is crossed. Most commonly, the exotic germplasm is not derived from any known elite line of soybean, but rather is selected to introduce novel genetic elements (typically novel alleles) into a breeding program.

A "genetic map" is a description of genetic association or linkage relationships among loci on one or more chromosomes (or linkage groups) within a given species, generally depicted in a diagrammatic or tabular form.

"Genotype" refers to the genetic constitution of a cell or organism.

"Germplasm" means the genetic material that comprises the physical foundation of the hereditary qualities of an organism. As used herein, germplasm includes seeds and living tissue from which new plants may be grown; or, another plant part, such as leaf, stem, pollen, or cells, that may be cultured into a whole plant. Germplasm resources provide sources of genetic traits used by plant breeders to improve commercial cultivars.

An individual is "homozygous" if the individual has only one type of allele at a given locus (e.g., a diploid individual has a copy of the same allele at a locus for each of two homologous chromosomes). An individual is "heterozygous" if more than one allele type is present at a given locus (e.g., a diploid individual with one copy each of two different alleles). The term "homogeneity" indicates that members of a group have the same genotype at one or more specific loci. In contrast, the term "heterogeneity" is used to indicate that individuals within the group differ in genotype at one or more specific loci.

"Introgression" means the entry or introduction of a gene, QTL, marker, haplotype, marker profile, trait, or trait locus from the genome of one plant into the genome of another plant.

The terms "label" and "detectable label" refer to a molecule capable of detection. A detectable label can also include a combination of a reporter and a quencher, such as are employed in FRET probes or TAQMAN® probes. The term "reporter" refers to a substance or a portion thereof that is capable of exhibiting a detectable signal, which signal can be suppressed by a quencher. The detectable signal of the reporter is, e.g., fluorescence in the detectable range. The term "quencher" refers to a substance or portion thereof that is capable of suppressing, reducing, inhibiting, etc., the detectable signal produced by the reporter. As used herein, the terms "quenching" and "fluorescence energy transfer" refer to the process whereby, when a reporter and a quencher are in close proximity, and the reporter is excited by an energy source, a substantial portion of the energy of the excited state nonradiatively transfers to the quencher where it either dissipates nonradiatively or is emitted at a different emission wavelength than that of the reporter.

A "line" or "strain" is a group of individuals of identical parentage that are generally inbred to some degree and that are generally homozygous and homogeneous at most loci (isogenic or near isogenic). A "subline" refers to an inbred subset of descendents that are genetically distinct from other similarly inbred subsets descended from the same progenitor. Traditionally, a subline has been derived by inbreeding the seed from an individual soybean plant selected at the F3 to F5 generation until the residual segregating loci are "fixed" or homozygous across most or all loci. Commercial soybean varieties (or lines) are typically produced by aggregating ("bulking") the self-pollinated progeny of a single F3 to F5 plant from a controlled cross between two genetically different parents. While the variety typically appears uniform, the self-pollinating variety derived from the selected plant eventually (e.g., F8) becomes a mixture of homozygous plants that can vary in genotype at any locus that was heterozygous in the originally selected F3 to F5 plant. Marker-based sublines that differ from each other based on qualitative polymorphism at the DNA level at one or more specific marker loci are derived by genotyping a sample of seed derived from individual self-pollinated progeny derived from a selected F3-F5 plant. The seed sample can be genotyped directly as seed, or as plant tissue grown from such a seed sample. Optionally, seed sharing a common genotype at the specified locus (or loci) are bulked providing a subline that is genetically homogenous at identified loci important for a trait of interest (e.g., yield, tolerance, etc.).

"Linkage" refers to the tendency for alleles to segregate together more often than expected by chance if their transmission was independent. Typically, linkage refers to alleles on the same chromosome. Genetic recombination occurs with an assumed random frequency over the entire genome. Genetic maps are constructed by measuring the frequency of recombination between pairs of traits or markers, the lower the frequency of recombination, the greater the degree of linkage.

"Linkage disequilibrium" is a non-random association of 2 or more alleles wherein the 2 or more alleles occur together at a greater frequency than expected from their individual frequencies.

"Linkage group" refers to traits or markers that co-segregate. A linkage group generally corresponds to a chromosomal region containing genetic material that encodes the traits or markers.

"Locus" is a defined segment of DNA.

A "management zone" is any specific area within a field that responds to management practices in a similar way. There are various criteria and ways to create management zones, including but not limited to using soil data, climate information, geographic data, and/or crop information in conjunction with an algorithm to identify areas of a field that are most similar. The computer can take thousands of numbers and find areas that are alike, cluster them together, and generate a map. Different zones can be defined by using different data inputs, but weighting inputs differently, by assigning different criteria, or by identifying different management practices of interest. For example a management zone for irrigation is probably not identical to a management zone for weed management for the same field in the same year.

Management zones may also use the same inputs and criteria and yet differ across years.

A "map location," a "map position," or a "relative map position" is an assigned location on a genetic map relative to linked genetic markers where a specified marker can be found within a given species. Map positions are generally provided in centimorgans (cM), unless otherwise indicated, genetic positions provided are based on the *Glycine max* consensus map v 4.0 as provided by Hyten et al. (2010) Crop Sci 50:960-968. A "physical position" or "physical location" is the position, typically in nucleotide bases, of a particular nucleotide, such as a SNP nucleotide, on the chromosome. Unless otherwise indicated, the physical position within the soybean genome provided is based on the Glyma 1.0 genome sequence described in Schmutz et al. (2010) Nature 463:178-183, available from the Phytozome website (phytozome-dot-net/soybean).

"Mapping" is the process of defining the association and relationships of loci through the use of genetic markers, populations segregating for the markers, and standard genetic principles of recombination frequency.

"Marker" or "molecular marker" is a term used to denote a nucleic acid or amino acid sequence that is sufficiently unique to characterize a specific locus on the genome. Any detectible polymorphic trait can be used as a marker so long as it is inherited differentially and exhibits non-random association with a phenotypic trait of interest.

"Marker assisted selection" refers to the process of selecting a desired trait or traits in a plant or plants by detecting one or more nucleic acids from the plant, where the nucleic acid is associated with or linked to the desired trait, and then selecting the plant or germplasm possessing those one or more nucleic acids.

"Maturity Group" is an agreed-on industry division of groups of varieties, based on the zones in which they are adapted primarily according to day length and/or latitude. Soybean varieties are grouped into 13 maturity groups, depending on the climate and latitude for which they are adapted. Soybean maturities are divided into relative maturity groups (denoted as 000, 00, 0, I, II, III, IV, V, VI, VII, VIII, IX, X, or 000, 00, 0, 1, 2, 3, 4, 5, 6, 7, 8, 9, 10). These maturity groups are given numbers, with numbers 000, 00, 0 and 1 typically being adapted to Canada and the northern United States, groups VII, VIII and IX being grown in the southern regions, and Group X is tropical. Within a maturity group are sub-groups. A sub-group is a tenth of a relative maturity group (for example 1.3 would indicate a group 1 and subgroup 3). Within narrow comparisons, the difference of a tenth of a relative maturity group equates very roughly to a day difference in maturity at harvest.

A "mixed defined plant population" refers to a plant population containing many different families and lines of plants. Typically, the defined plant population exhibits a quantitative variability for a phenotype that is of interest. "Multiple plant families" refers to different families of related plants within a population.

"Haplotype" refers to a combination of particular alleles present within a particular plant's genome at two or more linked marker loci, for instance at two or more loci on a particular linkage group. For instance, in one example, two specific marker loci on LG A1 are used to define a haplotype for a particular plant. In still further examples, 3, 4, 5, 6, 7, 8, 9, 10, 11, 12, 13, 14, 15, 16, 17, 18, 19, 20, or more linked marker loci are used to define a haplotype for a particular plant.

As used herein, a "marker profile" means a combination of particular alleles present within a particular plant's genome at two or more marker loci which are not linked, for instance two or more loci on two or more different linkage groups or two or more chromosomes. For instance, in one example, one marker locus on LG A1 and a marker locus on another linkage group are used to define a marker profile for a particular plant. In certain other examples a plant's marker profile comprises one or more haplotypes. In some examples, the marker profile encompasses two or more loci for the same trait, such as time to first flower. In other examples, the marker profile encompasses two or more loci associated with two or more traits of interest, such as time to first flower and a second trait of interest.

The term "plant" includes reference to an immature or mature whole plant, including a plant from which seed or grain or anthers have been removed. Seed or embryo that will produce the plant is also considered to be the plant.

"Plant parts" means any portion or piece of a plant, including leaves, stems, buds, roots, root tips, anthers, seed, grain, embryo, pollen, ovules, flowers, cotyledons, hypocotyls, pods, flowers, shoots, stalks, tissues, tissue cultures, cells, and the like.

"Polymorphism" means a change or difference between two related nucleic acids. A "nucleotide polymorphism" refers to a nucleotide that is different in one sequence when compared to a related sequence when the two nucleic acids are aligned for maximal correspondence.

"Polynucleotide," "polynucleotide sequence," "nucleic acid sequence," "nucleic acid fragment," and "oligonucleotide" are used interchangeably herein to indicate a polymer of nucleotides that is single- or multi-stranded, that optionally contains synthetic, non-natural, or altered RNA or DNA nucleotide bases. A DNA polynucleotide may be comprised of one or more strands of cDNA, genomic DNA, synthetic DNA, or mixtures thereof.

"Primer" refers to an oligonucleotide which is capable of acting as a point of initiation of nucleic acid synthesis or replication along a complementary strand when placed under conditions in which synthesis of a complementary strand is catalyzed by a polymerase. Typically, primers are about 10 to 30 nucleotides in length, but longer or shorter sequences can be employed. Primers may be provided in double-stranded form, though the single-stranded form is more typically used. A primer can further contain a detectable label, for example a 5' end label.

"Probe" refers to an oligonucleotide that is complementary (though not necessarily fully complementary) to a polynucleotide of interest and forms a duplexed structure by hybridization with at least one strand of the polynucleotide of interest. Typically, probes are oligonucleotides from 10 to 50 nucleotides in length, but longer or shorter sequences can be employed. A probe can further contain a detectable label.

"Quantitative trait loci" or "QTL" refer to the genetic elements controlling a quantitative trait.

"Recombination frequency" is the frequency of a crossing over event (recombination) between two genetic loci. Recombination frequency can be observed by following the segregation of markers and/or traits during meiosis.

"Reproductive stage" is a description of the characteristics associated with various phases of reproductive growth.

"R1" is the first reproductive stage when soybean begins to bloom by producing the first flower.

"Time to R1 reproductive stage" is measured in days unless otherwise stated.

"Tolerance" and "improved tolerance" are used interchangeably herein and refer to any type of" increase in resistance or tolerance to, or any type of decrease in susceptibility. A "tolerant plant" or "tolerant plant variety" need not possess absolute or complete tolerance. Instead, a "tolerant plant," "tolerant plant variety," or a plant or plant variety with "improved tolerance" will have a level of resistance or tolerance which is higher than that of a comparable susceptible plant or variety.

"Self-crossing" or "self-pollination" or "selfing" is a process through which a breeder crosses a plant with itself; for example, a second-generation hybrid F2 with itself to yield progeny designated F2:3.

"SNP" or "single nucleotide polymorphism" means a sequence variation that occurs when a single nucleotide (A, T, C, or G) in the genome sequence is altered or variable. "SNP markers" exist when SNPs are mapped to sites on the soybean genome.

The term "yield" refers to the productivity per unit area of a particular plant product of commercial value. For example, yield of soybean is commonly measured in bushels of seed per acre or metric tons of seed per hectare per season. Yield is affected by both genetic and environmental factors.

An "isolated" or "purified" polynucleotide or polypeptide, or biologically active portion thereof, is substantially or essentially free from components that normally accompany or interact with the polynucleotide or polypeptide as found in its naturally occurring environment. Typically, an "isolated" polynucleotide is free of sequences (optimally protein encoding sequences) that naturally flank the polynucleotide (i.e., sequences located at the 5' and 3' ends of the polynucleotide) in the genomic DNA of the organism from which the polynucleotide is derived. For example, the isolated polynucleotide can contain less than about 5 kb, 4 kb, 3 kb, 2 kb, 1 kb, 0.5 kb, or 0.1 kb of nucleotide sequence that naturally flank the polynucleotide in genomic DNA of the cell from which the polynucleotide is derived. A polypeptide that is substantially free of cellular material includes preparations of polypeptides having less than about 30%, 20%, 10%, 5%, or 1% (by dry weight) of contaminating protein, culture media, or other chemical components.

Standard recombinant DNA and molecular cloning techniques used herein are well known in the art and are described more fully in Sambrook et al. *Molecular Cloning: A Laboratory Manual*; Cold Spring Harbor Laboratory Press: Cold Spring Harbor, 1989 (hereinafter "Sambrook").

Soybean is a short-day crop and its development is largely determined by variety-specific day length requirements that initiate floral development. In other words, as the days grow shorter soybean will flower and enter into reproductive development stages. Due to this photoperiod requirement, days from planting until maturity cannot be accurately estimated for soybean due to variation in planting date and other environmental variations. After flowering, temperature drives development and the days until maturity can be estimated. The number of days from floral initiation (R1) until physiological maturity (R7) is usually independent of variety, but will vary slightly from year to year due to temperature differences between years. Although most sensitive to day length, soybean flowering will be delayed to some extent with later planting dates. However, later planted soybean initiates flowering during a warmer time of the year; therefore, post-flower development speeds up. The precise number of days from full flower (R2) until R7 cannot be predicted, but fairly reliable estimates can be derived from historical information (see, e.g., Holshouser (2010) "Days to Soybean Physiological Maturity," Virginia Cooperative Extension, Bulletin 3009-1459; and, Heatherly (2005) "Soybean maturity group, planting date and development related," Delta Farm Press, Oct. 14, 2005).

Soybean growth is often characterized as comprising two stages: vegetative growth and reproductive growth. The vegetative (V) stages are numbered according to how many fully-developed trifoliate leaves are present. The reproductive (R) stages begin at flowering and include pod development, seed development, and plant maturation. Soybean yield is impacted by genetics and environment, and various management practices can impact crop growth and yield in the context of the genetics of the crop. These stages are well-characterized and known (see, e.g., McWilliams et al. (1999) Soybean Growth & Management Quick Guide, A-1174, NDSU Extension Service), and summarized in the table below.

| Vegetative Stages | | | Reproductive Stages | |
|---|---|---|---|---|
| VE | Emergence | R1 | beginning bloom, 1$^{st}$ flower | |
| VC | Cotyledon Stage | R2 | full bloom, flower in top 2 nodes | |
| V1 | 1st trifoliate leaf | R3 | beginning pod, $^{3}/_{16}$" pod in top 4 nodes | |
| V2 | 2$^{nd}$ trifoliate | R4 | full pod, $^{3}/_{4}$" pod in top 4 nodes | |
| V3 | 3$^{rd}$ trifoliate | R5 | $^{1}/_{8}$" seed in top 4 nodes | |
| Vn | nth trifoliate | R6 | full size seed in top 4 nodes | |
| V6 | flowering should start soon | R7 | beginning maturity, one mature pod | |
| | | R8 | full maturity, 95% of pods are mature | |

The advent of molecular genetic markers has facilitated mapping and selection of agriculturally important traits in soybean. Markers tightly linked to tolerance genes are an asset in the rapid identification of tolerant soybean lines on the basis of genotype by the use of marker assisted selection (MAS). Introgressing tolerance genes into a desired cultivar would also be facilitated by using suitable markers.

Soybean cultivar development for preferred reproductive growth phenotype can be performed using classical breeding methods or by using marker assisted selection (MAS). Genetic markers for maturity or flowering time have been identified.

Provided are markers, haplotypes, and/or marker profiles associated with a preferred reproductive growth phenotype, as well as related primers and/or probes and methods for the use of any of the foregoing for identifying and/or selecting soybean plants with preferred time to floral initiation. A method for determining the presence or absence of at least one allele of a particular marker or haplotype associated with floral initiation comprises analyzing genomic DNA from a soybean plant or germplasm to determine if at least one, or a plurality, of such markers is present or absent and if present, determining the allelic form of the marker(s). If a plurality of markers on a single linkage group are investigated, this information regarding the markers present in the particular plant or germplasm can be used to determine a haplotype for that plant/germplasm.

In certain examples, plants or germplasm are identified that have at least one favorable allele, marker, and/or haplotype that positively correlate a preferred reproductive growth phenotype. However, in other examples, it is useful to identify alleles, markers, and/or haplotypes that negatively correlate with a preferred reproductive growth phenotype, for example to eliminate such plants or germplasm from subsequent rounds of breeding, or to use as controls or check. Soybean plants, cells, seed, varieties, and/or germplasm having preferred reproductive growth phenotype are provided.

Any marker associated with a preferred reproductive growth phenotype locus or QTL is useful. Further, any suitable type of marker can be used, including Restriction Fragment Length Polymorphisms (RFLPs), Single Sequence Repeats (SSRs), Target Region Amplification Polymorphisms (TRAPs), Isozyme Electrophoresis, Randomly Amplified Polymorphic DNAs (RAPDs), Arbitrarily Primed Polymerase Chain Reaction (AP-PCR), DNA Amplification Fingerprinting (DAF), Sequence Characterized Amplified Regions (SCARs), Amplified Fragment Length Polymorphisms (AFLPs), and Single Nucleotide Polymorphisms (SNPs). Additionally, other types of molecular markers known in the art or phenotypic traits may also be used as markers in the methods.

Markers that map closer to a QTL are generally used over markers that map farther from such a QTL. Marker loci are especially useful when they are closely linked to a locus associated with a preferred reproductive growth phenotype. Thus, in one example, marker loci display an inter-locus cross-over frequency of about 10% or less, about 9% or less, about 8% or less, about 7% or less, about 6% or less, about 5% or less, about 4% or less, about 3% or less, about 2% or less, about 1% or less, about 0.75% or less, about 0.5% or less, or about 0.25% or less with a QTL to which they are linked. Thus, the loci are separated from the QTL to which they are linked by about 10 cM, 9 cM, 8 cM, 7 cM, 6 cM, 5 cM, 4 cM, 3 cM, 2 cM, 1 cM, 0.75 cM, 0.5 cM, or 0.25 cM or less.

In certain examples, multiple marker loci that collectively make up a haplotype and/or a marker profile are investigated, for instance 2, 3, 4, 5, 6, 7, 8, 9, 10, 11, 12, 13, 14, 15, 16, 17, 18, 19, 20, 21, 22, 23, 24, 25, 26, 27, 28, 29, 30, or more marker loci.

In addition to the markers discussed herein, information regarding useful soybean markers can be found, for example, on the USDA's Soybase website, available at soybase.org. A number of soybean markers have been mapped and linkage groups created, as described in Cregan et al. (1999) Crop Sci 39:1464-90, Choi et al. (2007) Genetics 176:685-96, and Hyten, et al. (2010) Crop Sci 50:960-968, each of which is herein incorporated by reference in its entirety, including any supplemental materials associated with the publication. Many soybean markers are publicly available at the USDA affiliated soybase website (at soybase-dot-org). One of skill in the art will recognize that the identification of favorable marker alleles may be germplasm-specific. One of skill will also recognize that methods for identifying the favorable alleles are routine and well known in the art, and furthermore, that the identification and use of such favorable alleles is well within the scope of the invention.

The use of marker assisted selection (MAS) to select a soybean plant or germplasm based upon detection of a particular marker or haplotype of interest is provided. For instance, in certain examples, a soybean plant or germplasm possessing a certain predetermined favorable marker allele or haplotype will be selected via MAS. Using MAS, soybean plants or germplasm can be selected for markers or marker alleles that positively correlate with tolerance, without actually raising soybean and measuring for tolerance (or, contrawise, soybean plants can be selected against if they possess markers that negatively correlate with tolerance). MAS is a powerful tool to select for desired phenotypes and for introgressing desired traits into cultivars of soybean (e.g., introgressing desired traits into elite lines). MAS is easily adapted to high throughput molecular analysis methods that can quickly screen large numbers of plant or germplasm genetic material for the markers of interest and is much more cost effective than raising and observing plants for visible traits.

In some examples, molecular markers are detected using a suitable amplification-based detection method. Typical amplification methods include various polymerase based replication methods, including the polymerase chain reaction (PCR), ligase mediated methods, such as the ligase chain reaction (LCR), and RNA polymerase based amplification (e.g., by transcription) methods. In these types of methods, nucleic acid primers are typically hybridized to the conserved regions flanking the polymorphic marker region. In certain methods, nucleic acid probes that bind to the amplified region are also employed. In general, synthetic methods for making oligonucleotides, including primers and probes, are well known in the art. For example, oligonucleotides can be synthesized chemically according to the solid phase phosphoramidite triester method described by Beaucage & Caruthers (1981) Tetrahedron Letts 22:1859-1862, e.g., using a commercially available automated synthesizer, e.g., as described in Needham-VanDevanter et al. (1984) Nucl Acids Res 12:6159-6168. Oligonucleotides, including modified oligonucleotides, can also be ordered from a variety of commercial sources known to persons of skill in the art.

It will be appreciated that suitable primers and probes to be used can be designed using any suitable method. It is not intended that the invention be limited to any particular primer, primer pair, or probe. For example, primers can be designed using any suitable software program, such as LASERGENE® or Primer3.

The primers are not limited to generating an amplicon of any particular size. For example, the primers used to amplify the marker loci and alleles herein are not limited to amplifying the entire region of the relevant locus. In some examples, marker amplification produces an amplicon at least 20 nucleotides in length, or alternatively, at least S0 nucleotides in length, or alternatively, at least 100 nucleotides in length, or alternatively, at least 200 nucleotides in length, or alternatively, at least 300 nucleotides in length, or alternatively, at least 400 nucleotides in length, or alternatively, at least S00 nucleotides in length, or alternatively, at least 1000 nucleotides in length, or alternatively, at least 2000 nucleotides in length or more.

PCR, RT-PCR, and LCR are common amplification and amplification-detection methods for amplifying nucleic acids of interest (e.g., those comprising marker loci), facilitating detection of the markers. Details regarding the use of these and other amplification methods are well known in the art and can be found in any of a variety of standard texts. Details for these techniques can also be found in numerous references, such as Mullis et al. (1987) U.S. Pat. No. 4,683,202; Arnheim & Levinson (1990) C&EN 36-47; Kwoh et al. (1989) Proc Natl Acad Sci USA 86:1173; Guatelli et al. (1990) Proc Natl Acad Sci USA 87:1874; Lomell et al. (1989) J Clin Chem 35:1826; Landegren et al. (1988) Science 241:1077-1080; Van Brunt (1990) Biotechnology 8:291-294; Wu & Wallace (1989) Gene 4:560; Barringer et al. (1990) Gene 89:117; and Sooknanan & Malek (1995) Biotechnology 13:563-564.

Such nucleic acid amplification techniques can be applied to amplify and/or detect nucleic acids of interest, such as nucleic acids comprising marker loci.

Amplification primers for amplifying useful marker loci and suitable probes to detect useful marker loci or to genotype alleles, such as SNP alleles, are provided. For example, exemplary primers and probes are provided in Table 26. However, one of skill will immediately recognize that other primer and probe sequences could also be used. For instance, primers to either side of the given primers can be used in place of the given primers, so long as the primers can amplify a region that includes the allele to be detected, as can primers and probes directed to other marker loci. Further, it will be appreciated that the precise probe to be used for detection can vary, e.g., any probe that can identify the region of a marker amplicon to be detected can be substituted for those examples provided herein. Further, the configuration of the amplification primers and detection probes can, of course, vary. Thus, the compositions and methods are not limited to the primers and probes specifically recited herein.

In certain examples, probes will possess a detectable label. Any suitable label can be used with a probe. Detectable labels suitable for use with nucleic acid probes include, for example, any composition detectable by spectroscopic, radioisotopic, photochemical, biochemical, immunochemical, electrical, optical, or chemical means. Useful labels include biotin for staining with labeled streptavidin conjugate, magnetic beads, fluorescent dyes, radiolabels, enzymes, and colorimetric labels. Other labels include ligands, which bind to antibodies labeled with fluorophores, chemiluminescent agents, and enzymes. A probe can also constitute radiolabelled PCR primers that are used to generate a radiolabelled amplicon. Labeling strategies for labeling nucleic acids and their corresponding detection strategies can be found, e.g., in Haugland (1996) *Handbook of Fluorescent Probes and Research Chemicals Sixth Edition* by Molecular Probes, Inc. (Eugene, Oreg.); or Haugland (2001) *Handbook of Fluorescent Probes and Research Chemicals Eighth Edition* by Molecular Probes, Inc. (Eugene, Oreg.).

Detectable labels may also include reporter-quencher pairs, such as are employed in Molecular Beacon and TAQMAN® probes. The reporter may be a fluorescent organic dye modified with a suitable linking group for attachment to the oligonucleotide, such as to the terminal 3' carbon or terminal 5' carbon. The quencher may also be an organic dye, which may or may not be fluorescent. Generally, whether the quencher is fluorescent or simply releases the transferred energy from the reporter by nonradiative decay, the absorption band of the quencher should at least substantially overlap the fluorescent emission band of the reporter to optimize the quenching. Non-fluorescent quenchers or dark quenchers typically function by absorbing energy from excited reporters, but do not release the energy radiatively.

Selection of appropriate reporter-quencher pairs for particular probes may be undertaken in accordance with known techniques. Fluorescent and dark quenchers and their relevant optical properties from which exemplary reporter-quencher pairs may be selected are listed and described, for example, in Berlman, *Handbook of Fluorescence Spectra of Aromatic Molecules*, 2nd ed., Academic Press, New York, 1971, the content of which is incorporated herein by reference. Examples of modifying reporters and quenchers for covalent attachment via common reactive groups that can be added to an oligonucleotide in the present invention may be found, for example, in Haugland (2001) *Handbook of Fluorescent Probes and Research Chemicals Eighth Edition* by Molecular Probes, Inc. (Eugene, Oreg.), the content of which is incorporated herein by reference.

In certain examples, reporter-quencher pairs are selected from xanthene dyes including fluorescein and rhodamine dyes. Many suitable forms of these compounds are available commercially with substituents on the phenyl groups, which can be used as the site for bonding or as the bonding functionality for attachment to an oligonucleotide. Another useful group of fluorescent compounds for use as reporters is the naphthylamines, having an amino group in the alpha or beta position. Included among such naphthylamino compounds are 1-dimethylaminonaphthyl-5 sulfonate, 1-anilino-8-naphthalene sulfonate and 2-p-touidinyl-6-naphthalene sulfonate. Other dyes include 3-phenyl-7-isocyanatocoumarin; acridines such as 9-isothiocyanatoacridine; N-(p-(2-benzoxazolyl)phenyl)maleimide; benzoxadiazoles; stilbenes; pyrenes and the like. In certain other examples, the reporters and quenchers are selected from fluorescein and rhodamine dyes. These dyes and appropriate linking methodologies for attachment to oligonucleotides are well known in the art.

Suitable examples of reporters may be selected from dyes such as SYBR green, 5-carboxyfluorescein (5-FAM™ available from Applied Biosystems of Foster City, Calif.), 6-carboxyfluorescein (6-FAM), tetrachloro-6-carboxyfluorescein (TET), 2,7-dimethoxy-4,5-dichloro-6-carboxyfluorescein, hexachloro-6-carboxyfluorescein (HEX), 6-carboxy-2',4,7,7'-tetrachlorofluorescein (6-TET™ available from Applied Biosystems), carboxy-X-rhodamine (ROX), 6-carboxy-4',5'-dichloro-2',7'-dimethoxyfluorescein (6-JOE™ available from Applied Biosystems), VIC™ dye products available from Molecular Probes, Inc., NED™ dye products available from available from Applied Biosystems, and the like.

Suitable examples of quenchers may be selected from 6-carboxy-tetramethyl-rhodamine, 4-(4-dimethylaminophenylazo) benzoic acid (DABYL), tetramethylrhodamine (TAMRA), BHQ-0™, BHQ-1™, BHQ-2™, and BHQ-3™, each of which are available from Biosearch Technologies, Inc. of Novato, Calif., QSY-7™, QSY-9™, QSY-21™ and QSY-35™, each of which are available from Molecular Probes, Inc., and the like.

In one aspect, real time PCR or LCR is performed on the amplification mixtures described herein, e.g., using molecular beacons or TAQMAN® probes. A molecular beacon (MB) is an oligonucleotide that, under appropriate hybridization conditions, self-hybridizes to form a stem and loop structure. The MB has a label and a quencher at the termini of the oligonucleotide; thus, under conditions that permit intra-molecular hybridization, the label is typically quenched (or at least altered in its fluorescence) by the quencher. Under conditions where the MB does not display intra-molecular hybridization (e.g., when bound to a target nucleic acid, such as to a region of an amplicon during amplification), the MB label is unquenched. Details regarding standard methods of making and using MBs are well established in the literature and MBs are available from a number of commercial reagent sources. See also, e.g., Leone et al. (1995) Nucl Acids Res 26:2150-2155; Tyagi & Kramer (1996) Nat Biotechnol 14:303-308; Blok & Kramer (1997) Mol Cell Probes 11:187-194; Hsuih et al. (1997) J Clin Microbiol 34:501-507; Kostrikis et al. (1998) Science 279: 1228-1229; Sokol et al. (1998) Proc Natl Acad Sci USA 95:11538-11543; Tyagi et al. (1998) Nat Biotechnol 16:49-53; Bonnet et al. (1999) Proc Natl Acad Sci USA 96:6171-6176; Fang et al. (1999) J Am Chem Soc 121:2921-2922; Marras et al. (1999) Genet Anal Biomol Eng 14:151-156; and, Vet et al. (1999) Proc Natl Acad Sci USA 96:6394-6399. Additional details regarding MB construction and use are also found in the patent literature, e.g., U.S. Pat. Nos. 5,925,517; 6,150,097; and 6,037,130.

Another real-time detection method is the 5'-exonuclease detection method, also called the TAQMAN® assay, as set forth in U.S. Pat. Nos. 5,804,375; 5,538,848; 5,487,972; and 5,210,015, each of which is hereby incorporated by reference in its entirety. In the TAQMAN® assay, a modified probe, typically 10-30 nucleotides in length, is employed during PCR which binds intermediate to or between the two members of the amplification primer pair. The modified probe possesses a reporter and a quencher and is designed to generate a detectable signal to indicate that it has hybridized with the target nucleic acid sequence during PCR. As long as both the reporter and the quencher are on the probe, the quencher stops the reporter from emitting a detectable signal. However, as the polymerase extends the primer during amplification, the intrinsic 5' to 3' nuclease activity of the polymerase degrades the probe, separating the reporter from the quencher, and enabling the detectable signal to be emitted. Generally, the amount of detectable signal generated during the amplification cycle is proportional to the amount of product generated in each cycle.

It is well known that the efficiency of quenching is a strong function of the proximity of the reporter and the quencher, i.e., as the two molecules get closer, the quenching efficiency increases. As quenching is strongly dependent on the physical proximity of the reporter and quencher, the reporter and the quencher are typically attached to the probe within a few nucleotides of one another, usually within 30 nucleotides of one another, or within 6 to 16 nucleotides. Typically, this separation is achieved by attaching one member of a reporter-quencher pair to the 5' end of the probe and the other member to a nucleotide about 6 to 16 nucleotides away, in some cases at the 3' end of the probe.

Separate detection probes can also be omitted in amplification/detection methods, e.g., by performing a real time amplification reaction that detects product formation by modification of the relevant amplification primer upon incorporation into a product, incorporation of labeled nucleotides into an amplicon, or by monitoring changes in molecular rotation properties of amplicons as compared to unamplified precursors (e.g., by fluorescence polarization).

One example of a suitable real-time detection technique that does not use a separate probe that binds intermediate to the two primers is the KASPar detection system/method, which is well known in the art. In KASPar, two allele specific primers are designed such that the 3' nucleotide of each primer hybridizes to the polymorphic base. For example, if the SNP is an A/C polymorphism, one of the primers would have an "A" in the 3' position, while the other primer would have a "C" in the 3' position. Each of these two allele specific primers also has a unique tail sequence on the 5' end of the primer. A common reverse primer is employed that amplifies in conjunction with either of the two allele specific primers. Two 5' fluor-labeled reporter oligos are also included in the reaction mix, one designed to interact with each of the unique tail sequences of the allele-specific primers. Lastly, one quencher oligo is included for each of the two reporter oligos, the quencher oligo being complementary to the reporter oligo and being able to quench the fluor signal when bound to the reporter oligo. During PCR, the allele-specific primers and reverse primers bind to complementary DNA, allowing amplification of the amplicon to take place. During a subsequent cycle, a complementary nucleic acid strand containing a sequence complementary to the unique tail sequence of the allele-specific primer is created. In a further cycle, the reporter oligo interacts with this complementary tail sequence, acting as a labeled primer. Thus, the product created from this cycle of PCR is a fluorescently-labeled nucleic acid strand. Because the label incorporated into this amplification product is specific to the allele specific primer that resulted in the amplification, detecting the specific fluor presenting a signal can be used to determine the SNP allele that was present in the sample.

Further, it will be appreciated that amplification is not a requirement for marker detection—for example, one can directly detect unamplified genomic DNA simply by performing a Southern blot on a sample of genomic DNA. Procedures for performing Southern blotting, amplification e.g., (PCR, LCR, or the like), and many other nucleic acid detection methods are well established and are taught, e.g., in Sambrook et al. *Molecular Cloning—A Laboratory Manual* (3d ed.) Vol. 1-3, Cold Spring Harbor Laboratory, Cold Spring Harbor, N.Y., 2000 ("Sambrook"); *Current Protocols in Molecular Biology*, F. M. Ausubel et al., eds., Current Protocols, a joint venture between Greene Publishing Associates, Inc. and John Wiley & Sons, Inc., (supplemented through 2002) ("Ausubel"); and, *PCR Protocols A Guide to Methods and Applications* (Innis et al., eds) Academic Press Inc. San Diego, Calif. (1990) ("Innis"). Additional details regarding detection of nucleic acids in plants can also be found, e.g., in *Plant Molecular Biology* (1993) Croy (ed.) BIOS Scientific Publishers, Inc.

Other techniques for detecting SNPs can also be employed, such as allele specific hybridization (ASH) or nucleic acid sequencing techniques. ASH technology is based on the stable annealing of a short, single-stranded, oligonucleotide probe to a completely complementary single-stranded target nucleic acid. Detection is via an isotopic or non-isotopic label attached to the probe. For each polymorphism, two or more different ASH probes are designed to have identical DNA sequences except at the polymorphic nucleotides. Each probe will have exact homology with one allele sequence so that the range of probes can distinguish all the known alternative allele sequences. Each probe is hybridized to the target DNA. With appropriate probe design and hybridization conditions, a single-base mismatch between the probe and target DNA will prevent hybridization.

Isolated polynucleotide or fragments thereof are capable of specifically hybridizing to other nucleic acid molecules under appropriate conditions. In one example, the nucleic acid molecules comprise any of SEQ ID NOs: 1-512, complements thereof and fragments thereof. In another aspect, the nucleic acid molecules of the present invention include nucleic acid molecules that hybridize, for example, under high or low stringency, substantially homologous sequences, or that have both to these molecules. Conventional stringency conditions are described by Sambrook et al. In: Molecular Cloning, A Laboratory Manual, 2nd Edition, Cold Spring Harbor Press, Cold Spring Harbor, N.Y. (1989)), and by Haymes et al. In: Nucleic Acid Hybridization, A Practical Approach, IRL Press, Washington, D.C. (1985). Departures from complete complementarity are therefore permissible, as long as such departures do not completely preclude the capacity of the molecules to form a double-stranded structure. In order for a nucleic acid molecule to serve as a primer or probe it need only be sufficiently complementary in sequence to be able to form a stable double-stranded structure under the particular solvent and salt concentrations employed. Appropriate stringency conditions that promote DNA hybridization are, for example, 6.0× sodium chloride/sodium citrate (SSC) at about 45° C., followed by a wash of 2.0×SSC at 50° C., are known to those skilled in the art or can be found in Current Protocols in Molecular Biology, John Wiley & Sons, N.Y., 1989, 6.3.1-6.3.6. For example, the salt concentration in the wash step can be selected from a low stringency of about 2.0×SSC at 50° C. to a high stringency of about 0.2×SSC at 50° C. In addition, the temperature in the wash step can be increased from low stringency conditions at room temperature, about 22° C., to high stringency conditions at about 65° C. Both temperature and salt may be varied, or either the temperature or the salt concentration may be held constant while the other variable is changed.

In some examples, an a marker locus will specifically hybridize to one or more of the nucleic acid molecules set forth in SEQ ID NOs: 1-512 or complements thereof or fragments of either under moderately stringent conditions, for example at about 2.0×SSC and about 65° C. In an aspect, a nucleic acid of the present invention will specifically hybridize to one or more SEQ ID NOs: 1-512 or complements or fragments of either under high stringency conditions.

In some examples, a marker associated with a preferred reproductive growth phenotype comprises any one of SEQ ID NOs: 1-512 or complements or fragments thereof. In other examples, a marker has between 80%, 85%, 90%, 91%, 92%, 93%, 94%, 95%, 96%, 97%, 98%, 99%, or 100% sequence identity to any one of SEQ ID NOs: 1-512 or complements or fragments thereof. Unless otherwise stated, percent sequence identity is determined using the GAP program is default parameters for nucleic acid alignment (Accelrys, San Diego, Calif., USA).

Traits or markers are considered herein to be linked if they generally co-segregate. A $1/100$ probability of recombination per generation is defined as a map distance of 1.0 centiMorgan (1.0 cM). The genetic elements or genes located on a single chromosome segment are physically linked. In some embodiments, the two loci are located in close proximity such that recombination between homologous chromosome pairs does not occur between the two loci during meiosis with high frequency, e.g., such that linked loci co-segregate at least about 90% of the time, e.g., 91%, 92%, 93%, 94%, 95%, 96%, 97%, 98%, 99%, 99.5%, 99.75%, or more of the time. The genetic elements located within a chromosome segment are also genetically linked, typically within a genetic recombination distance of less than or equal to 50 centimorgans (cM), e.g., about 49, 40, 30, 20, 10, 9, 8, 7, 6, 5, 4, 3, 2, 1, 0.75, 0.5, or 0.25 cM or less. That is, two genetic elements within a single chromosome segment undergo recombination during meiosis with each other at a frequency of less than or equal to about 50%, e.g., about 49%, 40%, 30%, 20%, 10%, 9%, 8%, 7%, 6%, 5%, 4%, 3%, 2%, 1%, 0.75%, 0.5%, or 0.25% or less. Closely linked markers display a cross over frequency with a given marker of about 10% or less (the given marker is within about 10 cM of a closely linked marker). Put another way, closely linked loci co-segregate at least about 90% of the time. With regard to physical position on a chromosome, closely linked markers can be separated, for example, by about 1 megabase (Mb; 1 million nucleotides), about 500 kilobases (Kb; 1000 nucleotides), about 400 Kb, about 300 Kb, about 200 Kb, about 100 Kb, about 50 Kb, about 25 Kb, about 10 Kb, about 5 Kb, about 4 Kb, about 3 Kb, about 2 Kb, about 1 Kb, about 500 nucleotides, about 250 nucleotides, or less.

When referring to the relationship between two genetic elements, such as a genetic element contributing to tolerance and a proximal marker, "coupling" phase linkage indicates the state where the "favorable" allele at the tolerance locus is physically associated on the same chromosome strand as the "favorable" allele of the respective linked marker locus. In coupling phase, both favorable alleles are inherited together by progeny that inherit that chromosome strand. In "repulsion" phase linkage, the "favorable" allele at the locus of interest (e.g., a QTL for tolerance) is physically linked with an "unfavorable" allele at the proximal marker locus, and the two "favorable" alleles are not inherited together (i.e., the two loci are "out of phase" with each other).

Markers are used to define a specific locus on the soybean genome. Each marker is therefore an indicator of a specific segment of DNA, having a unique nucleotide sequence. Map positions provide a measure of the relative positions of particular markers with respect to one another. When a trait is stated to be linked to a given marker it will be understood that the actual DNA segment whose sequence affects the trait generally co-segregates with the marker. More precise and definite localization of a trait can be obtained if markers are identified on both sides of the trait. By measuring the appearance of the marker(s) in progeny of crosses, the existence of the trait can be detected by relatively simple molecular tests without actually evaluating the appearance of the trait itself, which can be difficult and time-consuming because the actual evaluation of the trait requires growing plants to a stage and/or under environmental conditions where the trait can be expressed. Molecular markers have been widely used to determine genetic composition in soybeans.

Favorable genotypes associated with at least trait of interest may be identified by one or more methodologies. In some examples one or more markers are used, including but not limited to AFLPs, RFLPs, ASH, SSRs, SNPs, indels, padlock probes, molecular inversion probes, microarrays, sequencing, and the like. In some methods, a target nucleic acid is amplified prior to hybridization with a probe. In other cases, the target nucleic acid is not amplified prior to hybridization, such as methods using molecular inversion probes (see, for example Hardenbol et al. (2003) Nat Biotech 21:673-678). In some examples, the genotype related to a specific trait is monitored, while in other examples, a genome-wide evaluation including but not limited to one or more of marker panels, library screens, association studies, microarrays, gene chips, expression studies, or sequencing such as whole-genome resequencing and genotyping-by-sequencing (GBS) may be used. In some examples, no target-specific probe is needed, for example by using sequencing technologies, including but not limited to next-generation sequencing methods (see, for example, Metzker (2010) Nat Rev Genet 11:31-46; and, Egan et al. (2012) Am J Bot 99:175-185) such as sequencing by synthesis (e.g., Roche 454 pyrosequencing, Illumina Genome Analyzer, and Ion Torrent PGM or Proton systems), sequencing by ligation (e.g., SOLiD from Applied Biosystems, and Polnator system from Azco Biotech), and single molecule sequencing (SMS or third-generation sequencing) which eliminate template amplification (e.g., Helicos system, and PacBio RS system from Pacific BioSciences). Further technologies include optical sequencing systems (e.g., Starlight from Life Technologies), and nanopore sequencing (e.g., GridION from Oxford Nanopore Technologies). Each of these may be coupled with one or more enrichment strategies for organellar or nuclear genomes in order to reduce the complexity of the genome under investigation via PCR, hybridization, restriction enzyme (see, e.g., Elshire et al. (2011) PLoS ONE 6:e19379), and expression methods. In some examples, no reference genome sequence is needed in order to complete the analysis.

In some examples, markers within 1 cM, 5 cM, 10 cM, 15 cM, or 30 cM of SEQ ID NO: 1-512 are provided. Similarly, one or more markers mapped within 1, 5, 10, 20 and 30 cM or less from the markers provided can be used for the selection or introgression of the region associated with a preferred reproductive growth phenotype. In other examples, any marker that is linked with SEQ ID NOs: 1-512 and associated with a preferred reproductive growth phenotype is provided. In other examples, markers provided include a substantially a nucleic acid molecule within 5 kb, 10 kb, 20 kb, 30 kb, 100 kb, 500 kb, 1,000 kb, 10,000 kb, 25,000 kb, or 50,000 kb of a marker selected from the group consisting of SEQ ID NOs: 1-512.

Real-time amplification assays, including MB or TAQMAN® based assays, are especially useful for detecting SNP alleles. In such cases, probes are typically designed to bind to the amplicon region that includes the SNP locus, with one allele-specific probe being designed for each possible SNP allele. For instance, if there are two known SNP alleles for a particular SNP locus, "A" or "C," then one probe is designed with an "A" at the SNP position, while a separate probe is designed with a "C" at the SNP position. While the probes are typically identical to one another other than at the SNP position, they need not be. For instance, the two allele-specific probes could be shifted upstream or downstream relative to one another by one or more bases. However, if the probes are not otherwise identical, they should be designed such that they bind with approximately equal efficiencies, which can be accomplished by designing under a strict set of parameters that restrict the chemical properties of the probes. Further, a different detectable label, for instance a different reporter-quencher pair, is typically employed on each different allele-specific probe to permit differential detection of each probe. In certain examples, each allele-specific probe for a certain SNP locus is 13-18 nucleotides in length, dual-labeled with a florescence quencher at the 3' end and either the 6-FAM (6-carboxy-fluorescein) or VIC (4,7,2'-trichloro-7'-phenyl-6-carboxy-fluorescein) fluorophore at the 5' end.

To effectuate SNP allele detection, a real-time PCR reaction can be performed using primers that amplify the region including the SNP locus, the reaction being performed in the presence of all allele-specific probes for the given SNP locus. By then detecting signal for each detectable label employed and determining which detectable label(s) demonstrated an increased signal, a determination can be made of which allele-specific probe(s) bound to the amplicon and, thus, which SNP allele(s) the amplicon possessed. For instance, when 6-FAM- and VIC-labeled probes are employed, the distinct emission wavelengths of 6-FAM (518 nm) and VIC (554 nm) can be captured. A sample that is homozygous for one allele will have fluorescence from only the respective 6-FAM or VIC fluorophore, while a sample that is heterozygous at the analyzed locus will have both 6-FAM and VIC fluorescence.

Introgression of a preferred reproductive growth phenotype into a soybean germplasm having an undesired or less preferred reproductive growth phenotype is provided. Any method for introgressing a QTL or marker into soybean plants known to one of skill in the art can be used. Typically, a first soybean germplasm that contains a preferred reproductive growth phenotype derived from a particular marker or haplotype and a second soybean germplasm that lacks such a reproductive growth phenotype derived from the marker or haplotype are provided. The first soybean germplasm may be crossed with the second soybean germplasm to provide progeny soybean germplasm. These progeny germplasm are screened to determine the presence a preferred reproductive growth phenotype derived from the marker or haplotype, and progeny that tests positive for the presence of tolerance derived from the marker or haplotype are selected as being soybean germplasm into which the marker or haplotype has been introgressed. Methods for performing such screening are well known in the art and any suitable method can be used.

One application of MAS is to use the tolerance markers or haplotypes to increase the efficiency of an introgression or backcrossing effort aimed at introducing a tolerance trait into a desired (typically high yielding) background. In marker assisted backcrossing of specific markers from a donor source, e.g., to an elite genetic background, one selects among backcross progeny for the donor trait and then uses repeated backcrossing to the elite line to reconstitute as much of the elite background's genome as possible.

Thus, the markers and methods can be utilized to guide marker assisted selection or breeding of soybean varieties with the desired complement (set) of allelic forms of chromosome segments associated with superior agronomic performance (tolerance, along with any other available markers for yield, disease tolerance, etc.). Any of the disclosed marker alleles or haplotypes can be introduced into a soybean line via introgression, by traditional breeding (or introduced via transformation, or both) to yield a soybean plant with superior agronomic performance. The number of alleles associated with tolerance that can be introduced or be present in a soybean plant ranges from 1 to the number of alleles disclosed herein, each integer of which is incorporated herein as if explicitly recited.

This also provides a method of making a progeny soybean plant and these progeny soybean plants, per se. The method comprises crossing a first parent soybean plant with a second soybean plant and growing the female soybean plant under plant growth conditions to yield soybean plant progeny. Methods of crossing and growing soybean plants are well within the ability of those of ordinary skill in the art. Such soybean plant progeny can be assayed for alleles associated with tolerance and, thereby, the desired progeny selected. Such progeny plants or seed can be sold commercially for soybean production, used for food, processed to obtain a desired constituent of the soybean, or further utilized in subsequent rounds of breeding. At least one of the first or second soybean plants is a soybean plant that comprises at least one of the markers or haplotypes associated with tolerance, such that the progeny are capable of inheriting the marker or haplotype.

Often, a method is applied to at least one related soybean plant such as from progenitor or descendant lines in the subject soybean plants pedigree such that inheritance of the desired tolerance can be traced. The number of generations separating the soybean plants being subject to the methods will generally be from 1 to 20, commonly 1 to 5, and typically 1, 2, or 3 generations of separation, and quite often a direct descendant or parent of the soybean plant will be subject to the method (i.e., 1 generation of separation).

Genetic diversity is important for long-term genetic gain in any breeding program. With limited diversity, genetic gain will eventually plateau when all of the favorable alleles have been fixed within the elite population. One objective is to incorporate diversity into an elite pool without losing the genetic gain that has already been made and with the minimum possible investment. MAS provides an indication of which genomic regions and which favorable alleles from the original ancestors have been selected for and conserved over time, facilitating efforts to incorporate favorable variation from exotic germplasm sources (parents that are unrelated to the elite gene pool) in the hopes of finding favorable alleles that do not currently exist in the elite gene pool.

For example, the markers, haplotypes, primers, and probes can be used for MAS involving crosses of elite lines to exotic soybean lines (elite X exotic) by subjecting the segregating progeny to MAS to maintain major yield alleles, along with the tolerance marker alleles herein.

As an alternative to standard breeding methods of introducing traits of interest into soybean (e.g., introgression), transgenic approaches can also be used to create transgenic plants with the desired traits. In these methods, exogenous nucleic acids that encode a desired QTL, marker, or haplotype are introduced into target plants or germplasm. For example, a nucleic acid that codes for a preferred reproductive growth trait is cloned, e.g., via positional cloning, and introduced into a target plant or germplasm.

Experienced plant breeders can recognize the time to R1 reproductive stage trait for soybean plants in the field, and can select the individuals or populations for breeding purposes or for propagation with the desired phenotype. In this context, the plant breeder recognizes "preferred" soybean plants. However, time to R1 is a phenotypic spectrum consisting of extremes in timing, as well as a continuum of intermediate phenotypes. Evaluation of these intermediate phenotypes using reproducible assays are of value to scientists who seek to identify genetic loci that impart a specific time to R1 stage, to conduct marker assisted selection for populations, and to use introgression techniques to breed a specific R1 trait into an elite soybean line, for example.

In some examples, a kit for detecting markers or haplotypes, and/or for correlating the markers or haplotypes with a desired phenotype (e.g., a preferred reproductive growth phenotype), are provided. Thus, a typical kit can include a set of marker probes and/or primers configured to detect at least one favorable allele of one or more marker locus associated with a preferred reproductive growth phenotype. These probes or primers can be configured, for example, to detect the marker alleles noted in the tables and examples herein, e.g., using any available allele detection format, such as solid or liquid phase array based detection, microfluidic-based sample detection, etc. The kits can further include packaging materials for packaging the probes, primers, or instructions; controls, such as control amplification reactions that include probes, primers, and/or template nucleic acids for amplifications; molecular size markers; or the like.

System or kit instructions that describe how to use the system or kit and/or that correlate the presence or absence of the allele with the predicted preferred or non-preferred phenotype are also provided. For example, the instructions can include at least one look-up table that includes a correlation between the presence or absence of the favorable allele(s) and the predicted time to floral initiation. The precise form of the instructions can vary depending on the components of the system, e.g., they can be present as system software in one or more integrated unit of the system (e.g., a microprocessor, computer or computer readable medium), or can be present in one or more units (e.g., computers or computer readable media) operably coupled to the detector.

Isolated nucleic acids comprising a nucleic acid sequence coding for a preferred reproductive growth phenotype, or capable of detecting such a phenotypic trait, or sequences complementary thereto, are also included. In certain examples, the isolated nucleic acids are capable of hybridizing under stringent conditions to nucleic acids of a soybean cultivar phenotyped for a preferred reproductive growth phenotype, to detect loci associated with a preferred reproductive growth phenotype, including one or more of S01435-1, S01239-1, S00780-1, S06925-1, S09951-1, S00170-1, S04059-1, S07851-1, S11659-1, S04279-1, S02211-1, S08942-1, S05742-1, S09155-1, S02037-1, S13136-1, S17291-001, S13139-1, S17292-001, S13146-1, S17293-001, S17294-001, S17581-001, S17691-001, S17701-001, S03703-1, S17297-001, S17298-001, S17299-001, S17300-001, S17306-001, S17310-001, S17311-001, S17312-001, S17312-001, S17316-001, S17317-001, S17318-001, S17322-001, S17326-001, S17327-001, S17328-001, S17329-001, S10746-1, S17331-001, S17332-001, S17337-001, S13093-1, S12211-1, S04555-1, S17301-001, S08519-1, S12876-1, S05937-1, S08575-1, S08669-1, S11212-1, S00543-1, S01452-1, S11993-1, S13446-1, S00252-1, S04060-1, S02664-1, S00281-1, S01109-1, S13844-1, S05058-1, S04660-1, S09955-1, S08034-1, S10293-1, S03813-1, S02042-1, S16601-001, S01481-1, S11309-1, S11320-1, S04040-1, S00863-1, S17151-001, S17153-001, S17154-001, S17156-001, S17159-001, S08590-1, S17242-001, S17166-001, S17167-001, S08539-1, S17178-001, S17179-001, S17180-001, S17181-001, S17182-001, S17183-001, S02780-1, S12107-1, S03624-1, S01953-1, S00111-1, S04180-1, S01008-1, S12861-1, S04966-1, S12867-1, S10631-1-Q1, S01574-1, S16594-001, S02777-1, Gm05:30568085, Gm08:7464336, Gm08: 15841570, Gm11:4674824, Gm11:5231500, Gm11: 7847341, Gm14:46138053, Gm14:47331319, Gm04: 5754268, Gm04:8295779, Gm04:39691731, Gm04: 44725098, Gm06:410442, Gm06:11659627, Gm06: 15457913, Gm06:16391391, Gm06:16499786, Gm06: 16593381, Gm06:16670047, Gm06:16804435, Gm06: 17498270, Gm06:18203964, Gm06:19743496, Gm06: 19986645, Gm06:20007173, Gm06:20084642, Gm06: 20501491, Gm06:21197184, Gm06:21500085, Gm06: 22501610, Gm06:25700006, Gm06:28501458, Gm06: 28671736, Gm06:29499523, Gm06:30203054, Gm06: 31694650, Gm06:32503141, Gm06:33196184, Gm06: 35509548, Gm06:37712913, Gm06:38467854, Gm06: 39168136, Gm06:39533730, Gm06:40766974, Gm06: 41476201, Gm06:42450296, Gm06:47500976, Gm06: 47521797, Gm06:48475049, Gm06:49978151, Gm06: 22700011, Gm01:759365, Gm02:4893148, Gm02:9714426, Gm02:11502780, Gm02:15446229, Gm02:33158449, Gm02:45776142, Gm17:16136646, Gm17:39804515, Gm15:50237460, Gm13:235439, Gm13:20365663, Gm13: 20744030, Gm13:35174140, Gm18:305113, Gm18: 58086324, Gm18:61591142, Gm18:61831970, Gm12: 11512115, Gm20:39051858, Gm20:41216234, Gm16: 4678569, Gm16:36524407, Gm19:47535046, Gm19: 47826727, Gm19:48252040, Gm19:48638646, Gm19: 50222676, Gm07:1141099, Gm07:1830296, Gm07: 1923026, Gm07:2179883, Gm07:2310058, Gm07:2679749, Gm07:3009018, Gm07:4282676, Gm07:4319368, Gm07: 4342479, Gm07:5576650, Gm07:6288899, Gm07:6340656, Gm07:6347675, Gm07:6614649, Gm07:6616695, Gm07: 6623333, Gm07:6671535, Gm07:7096376, Gm07:7774056, Gm07:8674220, Gm07:35590550, Gm07:36459825, Gm07: 36638366, Gm03:38491492, Gm03:39583405, Gm03: 46209939, Gm10:43974548, Gm10:44725777, Gm10: 44732850, Gm10:50495033, and any combination thereof.

In some examples the isolated nucleic acids are markers, for example markers selected from the group consisting of S01435-1-001, S01239-1-A, S00780-1-A, S06925-1-Q1, S09951-1-Q1, S00170-1-A, S04059-1-A, S07851-1, S11659-1-Q1, S04279-1-A, S02211-1-A, S08942-1-Q1, S05742-1-Q1, S09155-1-Q1, S02037-1-A, S13136-1-Q1, S17291-001-K001, S13139-1-Q1, S17292-001-K001, S13146-1-Q1, S17293-001-K001, S17294-001-K001, S07518-001-Q008, S17691-001-Q001, S17701-001-Q001, S03703-1-Q1, S17297-001-K001, S17298-001-K001, S17299-001-K001, S17300-001-K001, S17306-001-K001, S17310-001-K001, S17311-001-K001, S17312-001-K001, S17312-001-K001, S17316-001-K001, S17317-001-K001, S17318-001-K001, S17322-001-K001, S17326-001-K001, S17327-001-K001, S17328-001-K001, S17329-001-K001, S10746-1-Q1, S17331-001-K001, S17332-001-K001, S17337-001-K001, S13093-1-Q1, S12211-1-Q1, S04555-1-Q1, S17301-001-K001, S08519-1-Q1, S12876-1-Q1, S05937-1-Q1, S08575-1-Q1, S08669-1-Q1, S11212-1-Q1, S00543-1-A, S01452-1-A, S11993-1-Q2, S13446-1-Q1, S00252-1-A, S04060-1-A, S02664-1-A, S00281-1-A, S01109-1-Q002, S13844-1-Q1, S05058-1-Q1, S04660-1-A, S09955-1-Q1, S08034-1-Q1, S10293-1-Q1, S03813-1-A, S02042-1-A, S16601-001-Q001, S01481-1-A, S11309-1-Q1, S11320-1-Q1, S04040-1-A, S00863-1-A, S17151-001-K001, S17153-001-K001, S17154-001-K001, S17156-001-K001, S17159-001-K001, S08590-1-Q1, S17242-001-K001, S17166-001-Q006, S17167-001-Q007, S08539-1-Q1, S17178-001-K001, S17179-001-K001, S17180-001-K001, S17181-001-K001, S17182-001-K001, S17183-001-K001, S02780-1-Q1, S12107-1-Q1, S03624-1-Q001, S01953-1-A, S00111-1-A, S04180-1-A, S01008-1-B, S12861-1-Q1, S04966-1-Q1, S12867-1-Q002, S10631-1-Q1, S01574-1-A, S16594-001-Q10, and S02777-1-A. In some examples the nucleic acid is one of more polynucleotides selected from the group consisting of SEQ ID NOs: 1-512. Vectors comprising one or more of such nucleic acids, expression products of such vectors expressed in a host compatible therewith, antibodies to the expression product (both polyclonal and monoclonal), and antisense nucleic acids are also included. In some examples, one or more of these nucleic acids is provided in a kit.

As the parental line having a preferred reproductive growth phenotype, any line known to the art or disclosed herein may be used. Also included are soybean plants produced by any of the foregoing methods. Seed of a soybean germplasm produced by crossing a soybean variety having a marker or haplotype associated with time to R1 reproductive stage with a soybean variety lacking such marker or haplotype, and progeny thereof, is also included.

A soybean plant, germplasm, plant part, or seed further comprising resistance to at least one herbicidal formulation is provided. For example, the herbicidal formulation can comprise a compound selected from the group consisting of an ALS-inhibiting herbicide, a glyphosate, a hydroxyphenylpyruvatedioxygenase (HPPD) inhibitor, a sulfonamide, an imidazolinone, a bialaphos, a phosphinothricin, a metribuzin, a mesotrione, an isoxaflutole, an azafenidin, a butafenacil, a sulfosate, a glufosinate, a dicamba, a 2,4-D, and a protox inhibitor. In some examples, resistance to the herbicidal formulation is conferred by a transgene.

Glyphosate resistance can be conferred from genes including but not limited to EPSPS, GAT, GOX, and the like, such as described in U.S. Pat. Nos. 6,248,876; 5,627,061; 5,804,425; 5,633,435; 5,145,783; 4,971,908; 5,312,910; 5,188,642; 4,940,835; 5,866,775; 6,225,114; 6,130,366; 5,310,667; 4,535,060; 4,769,061; 5,633,448; 5,510,471; RE36,449; RE37,287 E; 5,491,288; 5,776,760; 5,463,175; 8,044,261; 7,527,955; 7,666,643; 7,998,703; 7,951,995; 7,968,770; 8,088,972, 7,863,503; and US20030083480; WO 97/04103; WO 00/66746; WO 01/66704; and WO 00/66747, which are each incorporated herein by reference in their entireties for all purposes. Additionally, glyphosate tolerant plants can be generated through the selection of naturally occurring mutations that impart tolerance to glyphosate.

HPPD resistance can be conferred by genes including exemplary sequences disclosed in U.S. Pat. Nos. 6,245,968; 6,268,549; and 6,069,115; and WO 99/23886, which are each incorporated herein by reference in their entireties for all purposes. Mutant hydroxyphenylpyruvatedioxygenases having this activity are also known. For further examples see US20110185444 and US20110185445.

Resistance to auxins, such as 2,4-D or dicamba, can be provided by polynucleotides as described, for example, in WO2005/107437, US20070220629, and U.S. Pat. No. 7,838,733 and in Herman et al. (2005) J. Biol. Chem. 280:24759-24767, each which is herein incorporated by reference.

Resistance to PPO-inhibiting herbicides can be provided as described in U.S. Pat. Nos. 6,288,306; 6,282,837; and 5,767,373; and WO 01/12825, each of which is herein incorporated by reference. Plants containing such polynucleotides can exhibit improved tolerance to any of a variety of herbicides which target the protox enzyme. Resistance can also be conferred as described in US20100186131; US20110185444; US20100024080, each of which is herein incorporated by reference.

The development of plants containing an exogenous phosphinothricin acetyltransferase which confers resistance to glufosinate, bialaphos, or phosphinothricin is described, for example, in U.S. Pat. Nos. 5,969,213; 5,489,520; 5,550,318; 5,874,265; 5,919,675; 5,561,236; 5,648,477; 5,646,024; 6,177,616; and 5,879,903, which are each incorporated herein by reference in their entireties for all purposes. Mutant phosphinothricin acetyltransferase having this activity are also known in the art.

In some examples, the plant or germplasm further comprises a trait selected from the group consisting of drought tolerance, stress tolerance, disease resistance, herbicide resistance, enhanced yield, modified oil, modified protein, tolerance to chlorotic conditions, and insect resistance, or any combination thereof. In some examples, the trait is selected from the group consisting of brown stem rot resistance, charcoal rot drought complex resistance, *Fusarium* resistance, *Phytophthora* resistance, stem canker resistance, sudden death syndrome resistance, *Sclerotinia* resistance, *Cercospora* resistance, anthracnose resistance, target spot resistance, frogeye leaf spot resistance, soybean cyst nematode resistance, root knot nematode resistance, rust resistance, high oleic content, low linolenic content, aphid resistance, stink bug resistance, and iron chlorosis deficiency tolerance, or any combination thereof. In some examples, one or more of the traits is conferred by one or more transgenes, by one or more native loci, or any combination thereof. Examples of markers and loci conferring improved iron chlorosis deficiency tolerance are disclosed in US20110258743, U.S. Pat. Nos. 7,582,806, and 7,977,533, each of which is herein incorporated by reference. Various disease resistance loci and markers are disclosed, for example, in WO1999031964, U.S. Pat. Nos. 5,948,953, 5,689,035, US20090170112, US20090172829, US20090172830, US20110271409, US20110145953, U.S. Pat. Nos. 7,642,403, 7,919,675, US20110131677, U.S. Pat. Nos. 7,767,882, 7,910,799, US20080263720, U.S. Pat. No. 7,507,874, US20040034890, US20110055960, US20110185448, US20110191893, US20120017339, U.S. Pat. Nos. 7,250,552, 7,595,432, 7,790,949, 7,956,239, 7,968,763, each of which is herein incorporated by reference. Markers and loci conferring improved yield are provided, for example, in U.S. Pat. No. 7,973,212 and WO2000018963, each of which is herein incorporated by reference. Markers and loci conferring improved resistance to insects are disclosed in, for example, US20090049565, U.S. Pat. No. 7,781,648, US20100263085, U.S. Pat. Nos. 7,928,286, 7,994,389, and WO2011116131, each of which is herein incorporated by reference. Markers and loci for modified soybean oil content or composition are disclosed in, for example, US20120028255 and US20110277173, each of which is herein incorporated by reference. Methods and compositions to modified soybean oil content are described in, for example, WO2008147935, U.S. Pat. Nos. 8,119,860; 8,119,784; 8,101,189; 8,058,517; 8,049,062; 8,124,845, 7,790,959, 7,531,718, 7,504,563, and 6,949,698, each of which is herein incorporated by reference. Markers and loci conferring tolerance to nematodes are disclosed in, for example, US20090064354, US20090100537, US20110083234, US20060225150, US20110083224, U.S. Pat. Nos. 5,491,081, 6,162,967, 6,538,175, 7,872,171, 6,096,944, and 6,300,541, each of which is herein incorporated by reference. Resistance to nematodes may be conferred using a transgenic approach as described, for example, in U.S. Pat. Nos. 6,284,948 and 6,228,992, each of which is herein incorporated by reference. Plant phenotypes can be modified using isopentyl transferase polynucleotides as described, for example, in U.S. Pat. Nos. 7,553,951 and 7,893,236, each of which is herein incorporated by reference.

Soybean seeds, plants, and plant parts comprising a preferred reproductive growth phenotype may be cleaned and/or treated. The resulting seeds, plants, or plant parts produced by the cleaning and/or treating process(es) may exhibit enhanced yield characteristics. Enhanced yield characteristics can include one or more of the following:

increased germination efficiency under normal and/or stress conditions, improved plant physiology, growth and/or development, such as water use efficiency, water retention efficiency, improved nitrogen use, enhanced carbon assimilation, improved photosynthesis, and accelerated maturation, and improved disease and/or pathogen tolerance. Yield characteristics can furthermore include enhanced plant architecture (under stress and non-stress conditions), including but not limited to early flowering, flowering control for hybrid seed production, seedling vigor, plant size, internode number and distance, root growth, seed size, fruit size, pod size, pod or ear number, seed number per pod or ear, seed mass, enhanced seed filling, reduced seed dispersal, reduced pod dehiscence and lodging resistance. Further yield characteristics include seed composition, such as carbohydrate content, protein content, oil content and composition, nutritional value, reduction in anti-nutritional compounds, improved processability and better storage stability.

Cleaning a seed or seed cleaning refers to the removal of impurities and debris material from the harvested seed. Material to be removed from the seed includes but is not limited to soil, and plant waste, pebbles, weed seeds, broken soybean seeds, fungi, bacteria, insect material, including insect eggs, larvae, and parts thereof, and any other pests that exist with the harvested crop. The terms cleaning a seed or seed cleaning also refer to the removal of any debris or low quality, infested, or infected seeds and seeds of different species that are foreign to the sample.

Treating a seed or applying a treatment to a seed refers to the application of a composition to a seed as a coating or otherwise. The composition may be applied to the seed in a seed treatment at any time from harvesting of the seed to sowing of the seed. The composition may be applied using methods including but not limited to mixing in a container, mechanical application, tumbling, spraying, misting, and immersion. Thus, the composition may be applied as a powder, a crystalline, a ready-to-use, a slurry, a mist, and/or a soak. For a general discussion of techniques used to apply fungicides to seeds, see "Seed Treatment," 2d ed., (1986), edited by K A Jeffs (chapter 9), herein incorporated by reference in its entirety. The composition to be used as a seed treatment can comprise one or more of a pesticide, a fungicide, an insecticide, a nematicide, an antimicrobial, an inoculant, a growth promoter, a polymer, a flow agent, a coating, or any combination thereof. General classes or family of seed treatment agents include triazoles, anilides, pyrazoles, carboxamides, succinate dehydrogenase inhibitors (SDHI), triazolinthiones, strobilurins, amides, and anthranilic diamides. In some examples, the seed treatment comprises trifloxystrobin, azoxystrobin, metalaxyl, metalaxyl-m, mefenoxam, fludioxinil, imidacloprid, thiamethoxam, thiabendazole, ipconazole, penflufen, sedaxane, prothioconazole, picoxystrobin, penthiopyrad, pyraclastrobin, xemium, *Rhizobia* spp., *Bradyrhizobium* spp. (e.g., *B. japonicum*), *Bacillus* spp. (e.g., *B. firmus, B. pumilus, B. subtilus*), lipochitooligosaccharide, clothianidin, cyantraniliprole, chlorantraniliprole, abamectin, and any combination thereof. In some examples the seed treatment comprises trifloxystrobin, metalaxyl, imidacloprid, *Bacillus* spp., and any combination thereof. In some examples the seed treatment comprises picoxystrobin, penthiopyrad, cyantraniliprole, chlorantraniliprole, and any combination thereof. In some examples, the seed treatment improves seed germination under normal and/or stress environments, early stand count, vigor, yield, root formation, nodulation, and any combination thereof. In some examples seed treatment reduces seed dust levels, insect damage, pathogen establishment and/or damage, plant virus infection and/or damage, and any combination thereof.

The present invention is illustrated by the following examples. The foregoing and following description of the present invention and the various examples are not intended to be limiting of the invention but rather are illustrative thereof. Hence, it will be understood that the invention is not limited to the specific details of these examples.

EXAMPLES

Example 1

An F5 mapping population from a cross of 90Y50 and 90Y41 was used to identify loci associated with reproductive stage traits in soybean. The population consisted of 340 progeny phenotyped for physiological maturity. A set of 141 markers expected to be polymorphic were selected across all 20 chromosomes, and the samples were genotyped. Eighty-three markers showed monomorphism in this population and were removed from analysis. A further 35 markers were removed based on severe segregation distortion ($p<0.001$). The remaining 22 markers were used to construct a linkage map and perform QTL analysis using Map Manager QTX.b20 (Manly et al. (2001) Mammalian Genome 12:930-932; available online at mapmanager.org). The initial parameters were set at: Linkage Evaluation: Intercross; search criteria: $p=1e^{-5}$; map function: Kosambi; and, cross type: line cross. A 1000 permutation test was used to establish the threshold for statistical significance (LOD ratio statistic—LRS). The maternal alleles were assigned as "A", and the paternal alleles as "B", and the heterozygous as "H", and the "Low Signal" and "Equivocal" as "-" (missing). Chi-square test was used for goodness of fit test. One marker, S00281-1-A on LG F (Gm13:35174140, 73.16 cM) showed significant association in the QTL analysis.

Genomic DNA was extracted from leaf tissue of each progeny using a modification of the CTAB (cetyltriethylammonium bromide, Sigma H5882) method described by Stacey & Isaac (Methods in Molecular Biology, Vol. 28: Protocols for Nucleic Acid Analysis by Nonradioactive Probes, Ed: Isaac, Humana Press Inc, Totowa, N.J. 1994, Ch 2, pp. 9-15). Approximately 100-200 mg of tissue was ground into powder in liquid nitrogen and homogenised in 1 ml of CTAB extraction buffer (2% CTAB, 0.02 M EDTA, 0.1 M Tris-Cl pH 8, 1.4 M NaCl, 25 mM DTT) for 30 min at 65° C. Homogenised samples were cooled at room temperature for 15 min before a single protein extraction with approximately 1 ml 24:1 v/v chloroform:octanol was done. Samples were centrifuged for 7 min at 13,000 rpm and the upper layer of supernatant was collected using wide-mouthed pipette tips. DNA was precipitated from the supernatant by incubation in 95% ethanol on ice for 1 h. DNA threads are spooled onto a glass hook, washed in 75% ethanol containing 0.2 M sodium acetate for 10 min, air-dried for 5 min and resuspended in TE buffer. Five µl RNAse A was added to the samples and incubated at 37° C. for 1 hour.

Example 2

An F2 mapping population from a cross of 90A01 and 90Y41 comprising 227 progeny that were segregating for flowering date and for maturity date was used to identify loci associated with the R1 reproductive stage trait in soybean. A set of 197 markers was used to genotype the samples. The F2 plant samples were genotyped, and 1-4 F3 plants were phenotyped for each F2 genotyped plant. Flowering date and maturity date were recorded, and converted to sequential numbering with the earliest date assigned to equal 1. The replicates were averaged to produce one phenotypic score/genotyped plant.

Genomic DNA was extracted essentially as described by Truett et al. (2000 BioTechniques 29:52-54). The samples are prepared for extraction by adding 400 µl Extraction Buffer (25 mM NaOH, 0.2 mM disodium EDTA (pH not adjusted, ~pH 12)) to sample racks containing 1-2 leaf punches and a stainless steel bb for grinding in each well. Each plate is heat-sealed, and ground in a Genogrinder. After grinding, the plate is heated at 94° C. for 70 minutes. The seal is removed and 400 µl of Neutralization Buffer is added (40 mM Tris-HCl (pH not adjusted, ~pH 5)). The plate is sealed with a new foil seal and shaken to mix the solutions. The sealed plate is centrifuged for 10 minutes. The final DNA extract contains 20 mM Tris-HCl, pH 8.1, and 0.1 mM EDTA and is ready for use in various assays.

Map Manager QTX.b20 (Manly et al. (2001) Mammalian Genome 12:930-932; available online at mapmanager.org) was used to construct the linkage map using the following settings: Linkage Evaluation: Intercross; search criteria: $p=1e^{-5}$; map function: Kosambi; and, cross type: line cross.

Single marker analysis (SMA), composite interval mapping (CIM), and multiple interval mapping (MIM) were executed using QTL Cartographer 2.5 (Wang et al. (2011) Windows QTL Cartographer 2.5; Dept. of Statistics, North Carolina State University, Raleigh, N.C. Available online at statgen.ncsu.edu/qticart/WQTLCart.htm). The standard CIM model and forward and backward regression method was used, and the LRS threshold for statistical significance to declare QTLs was determined by a 500 permutation test. The initial MIM model was determined using the CIM results and the threshold found by permutation test. The default criteria were used to optimize QTL positions, verify QTL significance, and search for interactions.

While evaluating the genotype data, 27 markers were removed from the analysis for failing one or more criteria. Markers were evaluated for segregation distortion via distribution of chi test results, from this 11 markers were identified as severely distorted (p<0.0001), but were retained in the analysis. Genotypic data across each progeny indicated no selfed plants within the population, and all progeny had greater than 70% data return.

Phenotype data for the population was also evaluated, 7 progeny with high standard deviation between replications of phenotypic scores and one progeny that was an extreme outlier for maturity were removed from the analysis. The remaining 219 progeny showed a relatively normal distribution for maturity, and a skewed distribution for flowering (skewed left).

Linkage groups were created using 159 non-distorted markers, resulting in 28 linkage groups with 7 markers remaining unlinked. Three distorted markers formed an additional linkage group and the remaining 8 distorted markers could not be distributed.

Single marker analysis of the flowering time phenotypic dataset found highly significant associations on LG C2 (ch 6) in an interval flanked by and including S02037-1-A and S13093-1-Q1 at 89.19-113.11 cM. Table 1 summarizes data for markers found with an F test statistic (pr(F))<0.05 level of significance.

TABLE 1

| Marker | LG (ch) | Position (cM) | QTL Effect | Pr(F) | R2 |
|---|---|---|---|---|---|
| S09155-1-Q1 | C2 (6) | 69.29 | 90Y41 | 0.02132 | 0.0236 |
| S02037-1-A | C2 (6) | 89.19 | 90Y41 | 0.00000 | 0.2749 |
| S13136-1-Q1 | C2 (6) | 96.04 | 90Y41 | 0.00000 | 0.3702 |
| S13146-1-Q1 | C2 (6) | 98.23 | 90Y41 | 0.00000 | 0.3749 |
| S10746-1-Q1 | C2 (6) | 104.94 | 90Y41 | 0.00000 | 0.3108 |
| S13093-1-Q1 | C2 (6) | 113.11 | 90Y41 | 0.00002 | 0.0752 |
| S12211-1-Q1 | C2 (6) | 116.04 | 90Y41 | 0.00088 | 0.0477 |
| S04555-1-Q1 | C2 (6) | 132.43 | 90Y41 | 0.02968 | 0.0194 |
| S08539-1-Q1 | M (7) | 36.74 | 90Y41 | 0.00578 | 0.0416 |
| S08590-1-Q1 | M (7) | 19.96 | 90A01 | 0.02616 | 0.0224 |
| S01239-1-A | A2 (8) | 40.49 | 90A01 | 004836 | 0.0188 |
| S08669-1-Q1 | D1b (2) | 76.53 | 90A01 | 0.02989 | 0.0215 |
| S11212-1-Q1 | D1b (2) | 83.28 | 90A01 | 0.01806 | 0.0244 |
| S03813-1-A | J (16) | 30.57 | 90Y41 | 0.01707 | 0.0259 |
| S02042-1-A | J (16) | 85.53 | 90Y41 | 0.04332 | 0.0187 |
| S12862-1-Q1 | N (3) | 53.56 | 90Y41 | 0.01687 | 0.023 |
| S12867-1-Q002 | N (3) | 58.35 | 90Y41 | 0.02117 | 0.0242 |
| S04966-1-Q1 | N (3) | 92.16 | 90Y41 | 0.02070 | 0.0213 |

Single marker analysis of the maturity time phenotypic dataset found highly significant associations on LG C2 (ch 6) in an interval flanked by and including S02037-1-A and S13093-1-Q1 at 89.19-113.11 cM. Additional significant associations were found on LG D1b (ch 2) in an interval at about 29.48-34.18 cM which included S12876-1-Q1, LG F (ch 13) at marker S00252-1-A (~0 cM), LG L (ch 19) at marker S04040-1-A (~100.89 cM), and LG M (ch 7) at S08539-1-Q1 at about 36.74 cM. Table 2 summarizes data for these markers with an F test statistic (pr(F))<0.05 level of significance.

TABLE 2

| Marker | LG (ch) | Position (cM) | QTL Effect | Pr(F) | R2 |
|---|---|---|---|---|---|
| S05742-1-Q1 | C2 (6) | 4.88 | 90Y41 | 0.01338 | 0.0279 |
| S09155-1-Q1 | C2 (6) | 69.29 | 90Y41 | 0.01271 | 0.0273 |
| S02037-1-A | C2 (6) | 89.19 | 90Y41 | 0.00000 | 0.2741 |
| S13136-1-Q1 | C2 (6) | 94.84 | 90Y41 | 0.00000 | 0.3837 |
| S13146-1-Q1 | C2 (6) | 98.23 | 90Y41 | 0.00000 | 0.4036 |
| S10746-1-Q1 | C2 (6) | 104.94 | 90Y41 | 0.00000 | 0.3463 |
| S13093-1-Q1 | C2 (6) | 113.11 | 90Y41 | 0.00005 | 0.0692 |
| S12211-1-Q1 | C2 (6) | 116.04 | 90Y41 | 0.00026 | 0.0614 |
| S04555-1-Q1 | C2 (6) | 132.43 | 90Y41 | 0.00801 | 0.0292 |
| S08590-1-Q1 | M (7) | 19.96 | 90A01 | 0.00108 | 0.0487 |
| S12107-1-Q1 | M (7) | 43.16 | 90A01 | 0.02162 | 0.0187 |
| S08539-1-Q1 | M (7) | 36.74 | 90A01 | 0.00218 | 0.0558 |
| S12876-1-Q1 | D1b (2) | 29.48 | 90Y41 | 0.00014 | 0.0645 |
| S08669-1-Q1 | D1b (2) | 76.53 | 90Y41 | 0.02810 | 0.022 |
| S00252-1-A | F (13) | 0 | 90Y41 | 0.00606 | 0.046 |
| S04060-1-A | F (13) | 36.9 | 90Y41 | 0.01496 | 0.0372 |
| S02664-1-A | F (13) | 36.96 | 90Y41 | 0.03657 | 0.0223 |
| S11309-1-Q1 | L (19) | 91.1 | 90A01 | 0.01827 | 0.0231 |
| S04040-1-A | L (19) | 100.89 | 90A01 | 0.00543 | 0.0351 |
| S05058-1-Q1 | G (18) | 105.85 | 90Y41 | 0.01395 | 0.0275 |
| S01435-1-Q001 | A1 (5) | 33.61 | 90Y41 | 0.04597 | 0.0182 |
| S00780-1-A | A2 (8) | 76.47 | 90A01 | 0.04270 | 0.017 |
| S11659-1-Q1 | C1 (4) | 29.24 | 90Y41 | 0.01646 | 0.0253 |
| S04279-1-A | C1 (4) | 45.75 | 90Y41 | 0.03048 | 0.0275 |
| S02211-1-A | C1 (4) | 54.48 | 90Y41 | 0.02204 | 0.0242 |

Composite interval mapping also identified the markers on LG C2 associated with flowering date and with maturity date, as well as the markers on LG D1b and LG M associated with maturity date. Four QTLs were identified on LG C2 for flowering date using a 1-LOD interval. The peak markers spanned 69.29 cM to 104.94 cM, and percent variation explained ranged from 22.6% to 66%. The QTL effect was from 90Y41 for all four QTLs. Table 3 summarizes the CIM analysis for flowering date associations on LG C2.

TABLE 3

| Marker | LG (ch) | Position (cM) | LOD | R2 |
|---|---|---|---|---|
| S09155-1-Q1 | C2 (6) | 69.29 | 21.1 | 0.461 |
| S02037-1-A | C2 (6) | 89.19 | 16.0 | 0.226 |
| S13146-1-Q1 | C2 (6) | 98.23 | 40.5 | 0.660 |
| S10746-1-Q1 | C2 (6) | 104.94 | 22.0 | 0.414 |

QTLs for maturity were identified on LG C2, D1b, and M. The QTL identified in this analysis on LG C2 was in about the same region as the loci found for flowering date, with a peak position at S13146-1-Q1 (98.23 cM). The percent variation explained was 44.9% and the effect was from 90Y41. QTLs were identified on LG D1b, including a peak at S05937-1-Q1 (48.44 cM). The percent variation explained was 4.6% and the effects were from 90A01. A QTL was also found on LG M with a peak at S08590-1-Q1 (19.96 cM), which explained about 4.8% of the phenotypic variation and the effect was from 90A01. Table 4 summarizes the CIM analysis for maturity date associations on these linkage groups.

TABLE 4

| Marker | LG (ch) | Position (cM) | LOD | R2 |
|---|---|---|---|---|
| S13146-1-Q1 | C2 (6) | 98.23 | 31.5 | 0.449 |
| S05937-1-Q1 | D1b (2) | 48.44 | 4.6 | 0.058 |
| S08590-1-Q1 | M (7) | 19.96 | 4.2 | 0.048 |

Multiple interval mapping (MIM) was performed to better estimate the percent variation explained by each QTL and to test for QTL interactions for flowering date. MIM results indicated three QTLs on LG C2, explaining a total of 87.1% of the phenotypic variation for flowering date (Table 5). Three epistatic interactions (A=Additive; D=Dominance; AA=Additive by Additive; AD=Additive by Dominance) were also identified, accounting for an additional 9.2% of the variation (Table 6). Combined, 96.3% of the phenotypic variation was explained by this model.

TABLE 5

| Marker | LG (ch) | Position (cM) | R2 |
|---|---|---|---|
| S09155-1-Q1 | C2 (6) | 69.29 | −0.071 |
| S02037-1-A | C2 (6) | 89.19 | 0.109 |
| S13146-1-Q1 | C2 (6) | 98.23 | 0.833 |

TABLE 6

| QTL1 | QTL2 | Type | Effect | R2 |
|---|---|---|---|---|
| 1 | 2 | AA | −1.503 | 0.050 |
| 1 | 2 | AD | 0.477 | −0.080 |
| 1 | 3 | AD | 0.066 | 0.123 |

Multiple interval mapping (MIM) was performed to better estimate the percent variation explained by each QTL and to test for QTL interactions for maturity date. The four QTLs identified in the CIM analysis explained a total of about 67.7% of the phenotypic variation using MIM. One dominant by dominant (DD) epistatic interaction was identified between S13146-1-Q1 on LG C2 and S05837-1-Q1 on LG D1b, explaining an additional 2% of the variation. Results are summarized in Table 7.

TABLE 7

| Marker | LG (ch) | Position (cM) | R2 |
|---|---|---|---|
| S13146-1-Q1 | C2 (6) | 98.23 | 0.479 |
| S12876-1-Q1 | D1b (2) | 29.48 | 0.105 |
| S05937-1-Q1 | D1b (2) | 48.44 | 0.049 |
| S08590-1-Q1 | M (7) | 19.96 | 0.044 |

Example 3

Genome-wide analysis indicated a reproductive stage QTL related to maturity on LG M in 8 different biparental crosses. KASPar markers were designed across the putative region and used to fine map the locus. Three F3 populations were selected, two populations from 92Y91 X 92Y60 (designated as JB5341 and JB5386 respectively), and one population from 92Y80 X 92Y60 (JB5333). A total of 33 KASPar markers were designed and used to assay all populations in a region between 1.83 Mbps and 6.63 Mbps on LGM. Phenotype data comprised maturity scores.

Map Manager QTX.b20 (Manly et al. (2001) Mammalian Genome 12:930-932; available online at mapmanager.org) was used to construct the linkage map using the following settings: Linkage Evaluation: Intercross; search criteria: $p=1e^{-5}$; map function: Kosambi; and, cross type: line cross.

Single marker analysis (SMA) and composite interval mapping (CIM) were done using QTL Cartographer 2.5 (Wang et al. (2011) Windows QTL Cartographer 2.5; Dept. of Statistics, North Carolina State University, Raleigh, N.C. Available online at statgen.ncsu.edu/qticart/WQTLCart.htm). The standard CIM model and forward and backward regression method was used, and the default LRS threshold of 11.5 was used to declare QTLs statistically significant.

Genotyping results indicated that 9 KASPar markers were polymorphic for JB5341, 14 KASPar markers were polymorphic for JB5386, and 13 KASPar markers were polymorphic for JB5333. Six markers from previous genome wide analysis were added to each job. A chi test was performed to identify segregation distortion, and indicated that 5 markers were severely distorted in JB5341, 12 in JB5386, and 2 in JB5333. A total of 48 progeny were missing phenotypic scores and another three were missing more than 30% data for JB5341. Likewise, one progeny was missing a phenotypic score and two were missing more than 30% data for JB5386. These 54 progeny were removed from the analysis. The phenotypic distribution for each population was essentially normal for each population, though some distortion was observed in JB5341 as noted earlier.

Linkage groups were created for each population, with 6 linkage groups formed and 5 unlinked markers for JB5386, 4 linkage groups and 1 unlinked marker for JB5341, and two linkage groups and 1 unlinked marker for JB5333.

Single marker analysis indicated minor significance on LG M in JB5341 and JB5386, with the highest associations at S17179-001-K001 (40.83 cM) (PVE=5.7%) and S17159-001-K001 (18.14 cM) (PVE=2.2%), respectively. Highly significant markers were found in JB5333 between S00863-1 (8.09 cM) and S01953-1 (48.13 cM). The peak marker was S17167-001-K001 at 31.99 cM, with an R2 value of 37.7%. Table 8 summarizes all markers on LG M significant by single marker analysis at a pr(F)<0.05 level.

TABLE 8

| Marker | Position | JB5341 | | JB5386 | | JB5333 | |
|---|---|---|---|---|---|---|---|
| | | Pr(F) | R2 | Pr(F) | R2 | Pr(F) | R2 |
| S00863-1 | 8.09 | — | — | — | — | 0.00000 | 0.075 |
| S17151-001-K001 | 11.64 | 0.02341 | 0.029 | — | — | 0.00000 | 0.110 |
| S17153-001-K001 | 12.12 | 0.00452 | 0.051 | 0.03158 | 0.021 | 0.00000 | 0.147 |
| S17154-001-K001 | 13.97 | 0.02816 | 0.033 | — | — | 0.00000 | 0.138 |
| S17156-001-K001 | 15.53 | 0.01732 | 0.037 | 0.03859 | 0.021 | 0.00000 | 0.147 |
| S17159-001-K001 | 18.14 | 0.00873 | 0.044 | 0.03687 | 0.022 | 0.00000 | 0.125 |
| S17166-001-K001 | 31.87 | — | — | — | — | 0.00000 | 0.345 |
| S17167-001-K001 | 31.99 | — | — | — | — | 0.00000 | 0.377 |
| S17178-001-K001 | 40.59 | — | — | — | — | 0.00000 | 0.154 |
| S17179-001-K001 | 40.83 | 0.00285 | 0.057 | — | — | 0.00000 | 0.166 |
| S17180-001-K001 | 40.85 | — | — | — | — | 0.00000 | 0.152 |
| S17181-001-K001 | 41.66 | 0.00285 | 0.052 | — | — | 0.00000 | 0.141 |
| S17182-001-K001 | 41.66 | — | — | — | — | 0.00000 | 0.145 |
| S17183-001-K001 | 41.69 | 0.00285 | 0.057 | — | — | 0.00000 | 0.144 |
| S03624-1 | 45.02 | 0.00203 | 0.054 | — | — | — | — |
| S00111-1 | 79.14 | 0.03238 | 0.029 | — | — | — | — |
| S02780-1 | 41.85 | — | — | — | — | 0.00000 | 0.125 |
| S01953-1 | 48.13 | — | — | — | — | 0.00000 | 0.068 |
| S04180-1 | 86.05 | — | — | — | — | 0.00878 | 0.020 |

Composite interval mapping analysis did not find any QTL for populations JB5341 or JB5386, however a QTL was found for population JB5333. The peak for the region was near S17167-001-K001 (31.99 cM) on LG M, with LOD=35.1. This locus explained 37.8% of the phenotypic variation. The additive effect indicated that early maturity was from parent 92Y60.

Example 4

Additional markers targeting a region on LG C2 were developed to probe the F2 population from 90A01/90Y41 (Example 3) and to fine map one or more loci associated with flowering data or maturity. Additional markers were developed based on KASPar technology and used to saturate the region to further refine the locus.

Forty-seven KASPar markers were developed to target a region on LG C2 spanning 16.5 Mbps to 47.5 Mbps. The genotypic data from these markers was combined with the results from 13 markers on LG C2 from previous analysis.

Map Manager QTX.b20 (Manly et al. (2001) Mammalian Genome 12:930-932; available online at mapmanager.org) was used to construct the linkage map using the following settings: Linkage Evaluation: Intercross; search criteria: p=1e$^{-5}$; map function: Kosambi; and, cross type: line cross.

Single marker analysis (SMA), composite interval mapping (CIM), and multiple interval mapping (MIM) were done using QTL Cartographer 2.5 (Wang et al. (2011) Windows QTL Cartographer 2.5; Dept. of Statistics, North Carolina State University, Raleigh, N.C. Available online at statgen.ncsu.edu/qticart/WQTLCart.htm). The standard CIM model and forward and backward regression method was used, and the default LRS threshold for statistical significance was used to declare QTLs statistically significant. Window size and walk speed parameters were adjusted to narrow the QTL peak. The initial MIM model was determined using the MIM forward search method. The default criteria were used to optimize QTL positions, verify QTL significance, and search for interactions.

Preliminary analysis of the marker genotype data indicated 11 markers were missing more than 30% data, nine markers were monomorphic, and 2 failed. There was also one progeny that was removed from analysis based on missing more than 30% data.

Reviewing phenotype data showed seven progeny with exceptionally high standard deviations between phenotype score replicants, additionally one progeny was an extreme outlier for maturity. These progeny were removed from the analysis and the phenotypic distributions for flowering time and for maturity of the remaining 218 progeny evaluated. The phenotypic distribution for maturity was essentially normal, while the distribution for flowering time had some skewing to the left. Linkage analysis was done and one linkage group was formed comprising all 38 markers.

Single marker analysis of the flowering time data set showed highly significant associations in an interval flanked by and comprising S02037-1-A (89.19 cM) and S13093-1-Q1 (113.11 cM) on LG C2, with R2 values ranging from 7.5% to 44.5%. The peak marker in this region was S17297-001-K001 at 102.43 cM. Table 9 summarizes all markers associated with flowering time at a pr(F)<10$^{-5}$ level of significance.

TABLE 9

| Marker | Position (cM) | QTL Donor | Pr(F) | R2 |
|---|---|---|---|---|
| S02037-1-A | 89.19 | 90Y41 | 0.00000 | 0.274 |
| S13136-1-Q1 | 94.84 | 90Y41 | 0.00000 | 0.369 |
| S17291-001-K001 | 96.04 | 90Y41 | 0.00000 | 0.369 |
| S17292-001-K001 | 97.84 | 90Y41 | 0.00000 | 0.353 |
| S13146-1-Q1 | 98.23 | 90Y41 | 0.00000 | 0.374 |
| S17293-001-K001 | 100.29 | 90Y41 | 0.00000 | 0.405 |
| S17294-001-K001 | 101.72 | 90Y41 | 0.00000 | 0.413 |
| S17297-001-K001 | 102.43 | 90Y41 | 0.00000 | 0.445 |
| S17298-001-K001 | 102.71 | 90Y41 | 0.00000 | 0.426 |
| S17299-001-K001 | 102.83 | 90Y41 | 0.00000 | 0.418 |
| S17300-001-K001 | 102.93 | 90Y41 | 0.00000 | 0.410 |
| S17301-001-K001 | 102.97 | 90Y41 | 0.00000 | 0.412 |
| S17306-001-K001 | 103.29 | 90Y41 | 0.00000 | 0.419 |
| S17310-001-K001 | 103.3 | 90Y41 | 0.00000 | 0.421 |
| S17311-001-K001 | 103.3 | 90Y41 | 0.00000 | 0.378 |
| S17312-001-K001 | 103.3 | 90Y41 | 0.00000 | 0.377 |
| S17313-001-K001 | 103.31 | 90Y41 | 0.00000 | 0.399 |
| S17316-001-K001 | 103.31 | 90Y41 | 0.00000 | 0.389 |
| S17317-001-K001 | 103.31 | 90Y41 | 0.00000 | 0.203 |
| S17318-001-K001 | 103.32 | 90Y41 | 0.00000 | 0.405 |
| S17322-001-K001 | 103.37 | 90Y41 | 0.00000 | 0.378 |
| S17326-001-K001 | 103.79 | 90Y41 | 0.00000 | 0.372 |
| S17327-001-K001 | 104 | 90Y41 | 0.00000 | 0.376 |
| S17328-001-K001 | 104.25 | 90Y41 | 0.00000 | 0.349 |
| S17329-001-K001 | 104.38 | 90Y41 | 0.00000 | 0.324 |
| S10746-1-Q1 | 104.94 | 90Y41 | 0.00000 | 0.310 |

TABLE 9-continued

| Marker | Position (cM) | QTL Donor | Pr(F) | R2 |
|---|---|---|---|---|
| S17331-001-K001 | 105.8 | 90Y41 | 0.00000 | 0.347 |
| S17332-001-K001 | 106.19 | 90Y41 | 0.00000 | 0.347 |
| S17337-001-K001 | 113.1 | 90Y41 | 0.00001 | 0.080 |
| S13093-1-Q1 | 113.11 | 90Y41 | 0.00001 | 0.075 |

Single marker analysis of the maturity data set showed highly significant associations in an interval flanked by and comprising S02037-1-A (89.19 cM) and S13093-1-Q1 (113.11 cM) on LG C2, with R2 values ranging from 7.0% to 49.7%. The peak marker in this region was S17297-001-K001 at 102.43 cM. Table 10 summarizes all markers associated with maturity at a pr(F)<$10^{-5}$ level of significance.

TABLE 10

| Marker | Position (cM) | QTL Donor | Pr(F) | R2 |
|---|---|---|---|---|
| S02037-1-A | 89.19 | 90Y41 | 0.00000 | 0.243 |
| S13136-1-Q1 | 94.84 | 90Y41 | 0.00000 | 0.379 |
| S17291-001-K001 | 96.04 | 90Y41 | 0.00000 | 0.379 |
| S17292-001-K001 | 97.84 | 90Y41 | 0.00000 | 0.367 |
| S13146-1-Q1 | 98.23 | 90Y41 | 0.00000 | 0.399 |
| S17293-001-K001 | 100.29 | 90Y41 | 0.00000 | 0.449 |
| S17294-001-K001 | 101.72 | 90Y41 | 0.00000 | 0.470 |
| S17297-001-K001 | 102.43 | 90Y41 | 0.00000 | 0.497 |
| S17298-001-K001 | 102.71 | 90Y41 | 0.00000 | 0.494 |
| S17299-001-K001 | 102.83 | 90Y41 | 0.00000 | 0.484 |
| S17300-001-K001 | 102.93 | 90Y41 | 0.00000 | 0.475 |
| S17301-001-K001 | 102.97 | 90Y41 | 0.00000 | 0.481 |
| S17306-001-K001 | 103.29 | 90Y41 | 0.00000 | 0.488 |
| S17310-001-K001 | 103.3 | 90Y41 | 0.00000 | 0.474 |
| S17311-001-K001 | 103.3 | 90Y41 | 0.00000 | 0.449 |
| S17312-001-K001 | 103.3 | 90Y41 | 0.00000 | 0.433 |
| S17313-001-K001 | 103.31 | 90Y41 | 0.00000 | 0.452 |
| S17316-001-K001 | 103.31 | 90Y41 | 0.00000 | 0.430 |
| S17317-001-K001 | 103.31 | 90Y41 | 0.00000 | 0.356 |
| S17318-001-K001 | 103.32 | 90Y41 | 0.00000 | 0.453 |
| S17322-001-K001 | 103.37 | 90Y41 | 0.00000 | 0.428 |
| S17326-001-K001 | 103.79 | 90Y41 | 0.00000 | 0.426 |
| S17327-001-K001 | 104 | 90Y41 | 0.00000 | 0.425 |
| S17328-001-K001 | 104.25 | 90Y41 | 0.00000 | 0.384 |
| S17329-001-K001 | 104.38 | 90Y41 | 0.00000 | 0.372 |
| S10746-1-Q1 | 104.94 | 90Y41 | 0.00000 | 0.342 |
| S17331-001-K001 | 105.8 | 90Y41 | 0.00000 | 0.345 |
| S17332-001-K001 | 106.19 | 90Y41 | 0.00000 | 0.345 |
| S17337-001-K001 | 113.1 | 90Y41 | 0.00003 | 0.083 |
| S13093-1-Q1 | 113.11 | 90Y41 | 0.00003 | 0.070 |

The initial composite interval mapping results for flowering date using the default settings showed 4 QTLs on LG C2 between about 89.19 cM and 104.38 cM. In further analyses the window size was adjusted to 5 cM, and then to 1 cM, to narrow down the probable location of the locus. The final results indicate a QTL peak at marker S17297-001-K001 explaining 26.4% of the phenotypic variation for flowering time. Early flowering date was from parent 90A01. Table 11 summarizes the results of CIM analysis on LG C2.

TABLE 11

| Window | Peak | Position | LRS | R2 |
|---|---|---|---|---|
| 10 cM | S13146-1-Q1 | 98.23 | 161.0 | 0.526 |
| 5 cM | S17297-001-K001 | 102.43 | 102.9 | 0.264 |
| 1 cM | S17297-001-K001 | 102.43 | 102.9 | 0.264 |

The initial composite interval mapping results for maturity using the default settings showed 2 QTLs on LG C2. In further analyses the window size was adjusted to 5 cM, and then to 1 cM, which resulted in a single QTL. The final results indicate a QTL peak at marker S17297-001-K001 explaining 49.7% of the phenotypic variation for maturity. Early maturity date was from parent 90A01. Table 12 summarizes the results of CIM analysis on LG C2.

TABLE 12

| Window | Peak | Position | LRS | R2 |
|---|---|---|---|---|
| 10 cM | S17297-001-K001 | 102.43 | 150.4 | 0.497 |
| 5 cM | S17297-001-K001 | 102.43 | 150.4 | 0.497 |
| 1 cM | S17297-001-K001 | 102.43 | 150.4 | 0.497 |

Multiple interval mapping (MIM) was used to corroborate the results obtained from composite interval mapping. MIM results indicated a single QTL on LG C2 with a peak near S17297-001-K001 for both flowering date and for maturity. In the MIM analysis 54.4% of the phenotypic variation in flowering time, and 49.9% of the phenotypic variation in maturity was explained by this model.

Example 5

Populations were developed by crossing lines from maturity groups (MG) 0 or 1 with lines from maturity groups 3 or 4, specifically 90Y20/94Y22, 90Y90/93Y82, and 91Y20/93Y82. Plants from F2 seed and check lines were leaf punched and genotyped with markers S01574-1-A (E2) and S01481-1-A (E3), these markers are in high linkage disequilibrium (LD) with the causative mutation at each respective locus. The polymorphism detected by marker S01574-1-A has allele C associated with early flowering and allele A associated with late flowering. The polymorphism detected by marker S01481-1-A polymorphism has allele T associated with early flowering and allele G associated with late flowering.

F3 seed were harvested from selected plants from each population, planted in randomized plots, and phenotyped for flowering time and maturity during the growing season. The genotyping and phenotyping data sample information is summarized in Table 13.

TABLE 13

| Population | 90Y20/94Y22 | 90Y90/93Y82 | 91Y20/93Y82 |
|---|---|---|---|
| F2 plants genotyped | 552 | 736 | 1104 |
| F3 plants phenotyped | 91 | 184 | 265 |

Genotyping data was grouped into one of eight classes depending on the allele identified by each marker, and whether both loci are considered in the analysis, and then phenotypic data aggregated and analyzed accordingly. The data is summarized in Table 14.

TABLE 14

| Genotype Class (E2/E3) | Pedigree | #F2:3 progeny | Avg. #days to flowering | Avg. #days planting to maturity | Avg. #days flowering to maturity | Note |
|---|---|---|---|---|---|---|
| Late/late | 94Y22 | — | 49 | NA | NA | Check |
| Early/Early | 90Y20/94Y22 | 22 | 34 | 100 | 66 | Progeny |
| Early/Late | 90Y20/94Y22 | 24 | 38 | 106 | 68 | Progeny |
| Late/Early | 90Y20/94Y22 | 21 | 43 | 113 | 70 | Progeny |
| Late/Late | 90Y20/94Y22 | 24 | 46 | 115 | 69 | Progeny |
| Early/— | 90Y20/94Y22 | 46 | 36 | 103 | 67 | Progeny |
| —/Early | 90Y20/94Y22 | 43 | 38 | 106 | 68 | Progeny |
| —/Late | 90Y20/94Y22 | 48 | 42 | 110 | 68 | Progeny |
| Late/— | 90Y20/94Y22 | 45 | 45 | 114 | 69 | Progeny |
| Early/Early | 90Y90 | — | 35 | 97 | 62 | Check |
| Late/Late | 93Y82 | — | 47 | NA | NA | Check |
| Early/Early | 90Y90/93Y82 | 49 | 37 | 100 | 63 | Progeny |
| Early/Late | 90Y90/93Y82 | 44 | 39 | 104 | 65 | Progeny |
| Late/Early | 90Y90/93Y82 | 37 | 42 | 111 | 69 | Progeny |
| Late/Late | 90Y90/93Y82 | 54 | 47 | 115 | 68 | Progeny |
| Early/— | 90Y90/93Y82 | 93 | 38 | 102 | 64 | Progeny |
| —/Early | 90Y90/93Y82 | 86 | 39 | 105 | 66 | Progeny |
| —/Late | 90Y90/93Y82 | 98 | 43 | 110 | 67 | Progeny |
| Late/— | 90Y90/93Y82 | 91 | 45 | 113 | 68 | Progeny |
| Early/Early | 91Y20 | — | 35 | 97 | 62 | Check |
| Late/Late | 93Y82 | — | 47 | NA | NA | Check |
| Early/Early | 91Y20/93Y82 | 69 | 37 | 101 | 65 | Progeny |
| Early/Late | 91Y20/93Y82 | 63 | 39 | 107 | 68 | Progeny |
| Late/Early | 91Y20/93Y82 | 65 | 42 | 113 | 71 | Progeny |
| Late/Late | 91Y20/93Y82 | 68 | 46 | 116 | 70 | Progeny |
| Early/— | 91Y20/93Y82 | 132 | 38 | 104 | 66 | Progeny |
| —/Early | 91Y20/93Y82 | 134 | 39 | 107 | 68 | Progeny |
| —/Late | 91Y20/93Y82 | 131 | 43 | 112 | 69 | Progeny |
| Late/— | 91Y20/93Y82 | 133 | 44 | 114 | 70 | Progeny |
| Early/Early | 91Y40 | — | 37 | 101 | 64 | Check |
| Early/Early | 91Y62 | — | 36 | 101 | 65 | Check |
| Late/Early | 91Y81 | — | 37 | 106 | 69 | Check |
| Early/Late | 91Y92 | — | 34 | 109 | 75 | Check |
| Late/Early | 92Y11 | — | 38 | 107 | 69 | Check |
| Late/Early | 92Y31 | — | 39 | 112 | 73 | Check |
| Late/Early | 92Y53 | — | 39 | 110 | 71 | Check |
| Late/Early | 92Y60 | — | 41 | 115 | 74 | Check |
| Late/Early | 92Y74 | — | 39 | 113 | 74 | Check |
| Late/Early | 92Y83 | — | 40 | 115 | 75 | Check |
| Late/Early | 92Y91 | — | 39 | 114 | 75 | Check |
| Late/Late | 93Y22 | — | 45 | NA | NA | Check |
| Late/Late | 93Y82 | — | 47 | NA | NA | Check |
| Late/Late | 94Y22 | — | 49 | NA | NA | Check |

Example 6

Several segregating populations in one or more locations were genotyped using one or more markers, which in some cases included markers associated with reproductive growth, as well as phenotyped for one or more reproductive stages. Initiation of flowering was measured both as days after planting (DAP), and as day of the year (DOY), which helps account for different planting dates across locations where relevant. Marker data and phenotypic data associations were analyzed using a partial least squares (PLS) methodology. Tables 15-23 summarize these studies, Tables 20-23 show single location results which are also aggregated for analysis and presentation in Table 19.

TABLE 15

| Pop (♀/♂) (n) | Locs | Locus (ch) | Position (cM) | SNP ♀ | SNP ♂ | μFLDATE (DAP) ♀ | μFLDATE (DAP) ♂ | Allelic Sub (DAP) |
|---|---|---|---|---|---|---|---|---|
| 92Y75/92Y22 (319) | 1 | S09951-1 (11) | 32.04 | G_G | T_T | 41.7 | 39.6 | 2.0 |
| | | S00170-1 (11) | 45.37 | A_A | T_T | 41.6 | 39.7 | 2.0 |
| | | S08519-1 (1) | 8.96 | C_C | G_G | 41.2 | 40.4 | 0.8 |
| | | S08942-1 (4) | 80.59 | G_G | C_C | 40.3 | 41.5 | 1.2 |
| | | S02780-1 (7) | 41.85 | G_G | A_A | 40.6 | 40.4 | 0.2 |

TABLE 15-continued

| Pop (♀/♂) (n) | Locs | Locus (ch) | Position (cM) | SNP ♀ | SNP ♂ | μFLDATE (DAP) ♀ | μFLDATE (DAP) ♂ | Allelic Sub (DAP) |
|---|---|---|---|---|---|---|---|---|
| | | S02777-1 (10) | 129.25 | T_T | C_C | 40.0 | 40.9 | 0.9 |
| | | S04059-1 (14) | 75.42 | G_G | A_A | 40.5 | 41.4 | 0.9 |
| Variance (DAP or DOY) | | | | | 11.0 | | | |
| Mean (DAP) | | | | | 40.8 | | | |
| Mean (DOY) | | | | | 181.8 | | | |

TABLE 16

| Pop (♀/♂) (n) | Locs | Locus (ch) | Position (cM) | SNP ♀ | SNP ♂ | μFLDATE (DAP) ♀ | μFLDATE (DAP) ♂ | Allelic Sub (DAP) |
|---|---|---|---|---|---|---|---|---|
| 92Y75/92Y80 (304) | 1 | S08575-1 (2) | 58.78 | A_A | G_G | 65.1 | 66.3 | 1.1 |
| | | S08942-1 (4) | 80.59 | G_G | C_C | 65.1 | 66.2 | 1.1 |
| | | S13139-1 (6) | 97.08 | C_C | T_T | 64.9 | 66.3 | 1.4 |
| | | S06925-1 (11) | 28.92 | G_G | A_A | 66.5 | 65.1 | 1.3 |
| | | S13446-1 (15) | 92.65 | T_T | C_C | 65.4 | 66.3 | 0.9 |
| | | S01452-1 (17) | 73.34 | C_C | T_T | 66.2 | 64.9 | 1.2 |
| | | S01109-1 (18) | 0.92 | T_T | G_G | 66.2 | 64.9 | 1.3 |
| | | S10293-1 (20) | 85.1 | A_A | G_G | 66.7 | 64.7 | 2.0 |
| Variance (DAP or DOY) | | | | | 8.2 | | | |
| Mean (DAP) | | | | | 65.7 | | | |
| Mean (DOY) | | | | | 176.7 | | | |

TABLE 17

| Pop (♀/♂) (n) | Locs | Locus (ch) | Position (cM) | SNP ♀ | SNP ♂ | μFLDATE (DAP) ♀ | μFLDATE (DAP) ♂ | Allelic Sub (DAP) |
|---|---|---|---|---|---|---|---|---|
| 93Y30/92Y22 (136) | 1 | S01481-1 (19) | 89.53 | G_G | T_T | 50.3 | 45.9 | 4.4 |
| Variance (DAP or DOY) | | | | | 8.2 | | | |
| Mean (DAP) | | | | | 47.4 | | | |
| Mean (DOY) | | | | | 189.4 | | | |

TABLE 18

| Pop (♀/♂) (n) | Locs | Locus (ch) | Position (cM) | SNP ♀ | SNP ♂ | μFLDATE (DAP) ♀ | μFLDATE (DAP) ♂ | Allelic Sub (DAP) |
|---|---|---|---|---|---|---|---|---|
| 92Y60/92Y32 (174) | 1 | S01008-1 (7) | 87.09 | C_C | G_G | 42.9 | 41.8 | 1.1 |
| | | S09955-1 (12) | 58.82 | C_C | T_T | 41.6 | 43.2 | 1.6 |
| | | S07851-1 (14) | 83.76 | A_A | G_G | 43.6 | 42.2 | 1.4 |

TABLE 18-continued

| Pop (♀/♂) (n) | Locs | Locus (ch) | Position (cM) | SNP ♀ | SNP ♂ | μFLDATE (DAP) ♀ | μFLDATE (DAP) ♂ | Allelic Sub (DAP) |
|---|---|---|---|---|---|---|---|---|
| | | S11993-1 (17) | 99.75 | A_A | G_G | 42.1 | 42.1 | 0.1 |
| | | S13844-1 (18) | 85.55 | T_T | G_G | 43.6 | 41.7 | 1.8 |
| | | S08034-1 (20) | 71.47 | C_C | G_G | 41.8 | 42.8 | 1.0 |
| Variance (DAP or DOY) | | | | | | 10.3 | | |
| Mean (DAP) | | | | | | 42.6 | | |
| Mean (DOY) | | | | | | 183.6 | | |

15

TABLE 19

| Pop (♀/♂) (n) | Locs | Locus (ch) | Position (cM) | SNP ♀ | SNP ♂ | μFLDATE (DAP; DOY) ♀ | μFLDATE (DAP; DOY) ♂ | Allelic Sub (DAP; DOY) |
|---|---|---|---|---|---|---|---|---|
| 91Y90/92Y22 (1253) | 4 | S08942-1 (4) | 80.59 | G_G | C_C | 46.1; 178.8 | 50.4; 177.7 | 4.3; 1.1 |
| | | S10631-1 (10) | 94.2 | T_T | C_C | 44.8; 175.5 | 50.1; 180.4 | 5.3; 4.9 |
| | | S01574-1 (10) | 99.5 | C_C | A_A | 44.6; 174.7 | 50.1; 180.5 | 5.5; 5.7 |
| | | S04660-1 (18) | 106.5 | T_T | C_C | 48.1; 180.1 | 48.1; 176.7 | 0.0; 3.4 |
| | | S01481-1 (19) | 89.53 | G_G | T_T | 49.3; 180.8 | 46.9; 176.4 | 2.4; 4.4 |
| | | S11320-1 (19) | 92.18 | A_A | T_T | 49.5; 180.6 | 46.9; 176.7 | 2.6; 3.9 |
| Variance (DAP; DOY) | | | | | | 60.3; 51.1 | | |
| Mean (DAP) | | | | | | 48.4 | | |
| Mean (DOY) | | | | | | 178.1 | | |

TABLE 20

| Pop (♀/♂) (n) | Locs | Locus (ch) | Position (cM) | SNP ♀ | SNP ♂ | μFLDATE (DAP) ♀ | μFLDATE (DAP) ♂ | Allelic Sub (DAP) |
|---|---|---|---|---|---|---|---|---|
| 91Y90/92Y22 (254) | 1 | S08942-1 (4) | 80.59 | G_G | C_C | 41.0 | 41.9 | 0.8 |
| | | S10631-1 (10) | 94.2 | T_T | C_C | 38.5 | 43.3 | 4.8 |
| | | S01574-1 (10) | 99.5 | C_C | A_A | 37.9 | 43.2 | 5.2 |
| | | S04660-1 (18) | 106.5 | T_T | C_C | 41.6 | 40.9 | 0.7 |
| | | S01481-1 (19) | 89.53 | G_G | T_T | 43.2 | 39.3 | 3.9 |
| | | S11320-1 (19) | 92.18 | A_A | T_T | 43.0 | 39.9 | 3.2 |
| Variance (DAP or DOY) | | | | | | 18.3 | | |
| Mean (DAP) | | | | | | 41.2 | | |
| Mean (DOY) | | | | | | 182.2 | | |

TABLE 21

| Pop (♀/♂) (n) | Locs | Locus (ch) | Position (cM) | SNP ♀ | SNP ♂ | µFLDATE (DAP) ♀ | µFLDATE (DAP) ♂ | Allelic Sub (DAP) |
|---|---|---|---|---|---|---|---|---|
| 91Y90/92Y22 (337) | 1 | S08942-1 (4) | 80.59 | G_G | C_C | 44.3 | 48.1 | 3.8 |
| | | S10631-1 (10) | 94.2 | T_T | C_C | 41.3 | 48.4 | 7.1 |
| | | S01574-1 (10) | 99.5 | C_C | A_A | 40.8 | 48.6 | 7.8 |
| | | S04660-1 (18) | 106.5 | T_T | C_C | 48.1 | 44.3 | 3.8 |
| | | S01481-1 (19) | 89.53 | G_G | T_T | 48.4 | 43.6 | 4.8 |
| | | S11320-1 (19) | 92.18 | A_A | T_T | 48.4 | 43.8 | 4.6 |
| Variance (DAP or DOY) | | | | | | 28.3 | | |
| Mean (DAP) | | | | | | 46.1 | | |
| Mean (DOY) | | | | | | 178.1 | | |

20

TABLE 22

| Pop (♀/♂) (n) | Locs | Locus (ch) | Position (cM) | SNP ♀ | SNP ♂ | µFLDATE (DAP) ♀ | µFLDATE (DAP) ♂ | Allelic Sub (DAP) |
|---|---|---|---|---|---|---|---|---|
| 91Y90/92Y22 (334) | 1 | S08942-1 (4) | 80.59 | G_G | C_C | 59.6 | 58.2 | 1.4 |
| | | S10631-1 (10) | 94.2 | T_T | C_C | 56.8 | 59.7 | 2.9 |
| | | S01574-1 (10) | 99.5 | C_C | A_A | 56.6 | 59.9 | 3.2 |
| | | S04660-1 (18) | 106.5 | T_T | C_C | 59.8 | 57.8 | 2.0 |
| | | S01481-1 (19) | 89.53 | G_G | T_T | 59.1 | 58.2 | 1.0 |
| | | S11320-1 (19) | 92.18 | A_A | T_T | 59.6 | 57.9 | 1.7 |
| Variance (DAP or DOY) | | | | | | 6.5 | | |
| Mean (DAP) | | | | | | 58.5 | | |
| Mean (DOY) | | | | | | 169.5 | | |

TABLE 23

| Pop (♀/♂) (n) | Locs | Locus (ch) | Position (cM) | SNP ♀ | SNP ♂ | µFLDATE (DAP) ♀ | µFLDATE (DAP) ♂ | Allelic Sub (DAP) |
|---|---|---|---|---|---|---|---|---|
| 91Y90/92Y22 (328) | 1 | S08942-1 (4) | 80.59 | G_G | C_C | 45.3 | 46.8 | 1.4 |
| | | S10631-1 (10) | 94.2 | T_T | C_C | 42.4 | 48.6 | 6.2 |
| | | S01574-1 (10) | 99.5 | C_C | A_A | 41.8 | 48.6 | 6.8 |
| | | S04660-1 (18) | 106.5 | T_T | C_C | 46.1 | 45.6 | 0.4 |
| | | S01481-1 (19) | 89.53 | G_G | T_T | 48.1 | 44.3 | 3.7 |
| | | S11320-1 (19) | 92.18 | A_A | T_T | 47.9 | 44.6 | 3.3 |
| Variance (DAP or DOY) | | | | | | 24.0 | | |
| Mean (DAP) | | | | | | 45.9 | | |
| Mean (DOY) | | | | | | 183.9 | | |

Example 7

From the analyses of marker loci associated with reproductive stage in soybean populations and varieties, several markers were developed, tested, and confirmed, as summarized in preceding tables. Any methodology can be deployed to use this information, including but not limited to any one or more of sequencing or marker methods.

In one example, sample tissue, including tissue from soybean leaves or seeds can be screened with the markers using a TAQMAN® PCR assay system (Life Technologies, Grand Island, N.Y., USA).

TAQMAN® Assay Conditions
Reaction Mixture (Total Volume=5 µl):

| | |
|---|---|
| Genomic DNA (dried) | 16 ng |
| DDH20 | 2.42 µl |
| Klearkall Mastermix | 2.5 µl |
| Forward primer (100 µM) | 0.0375 µl |
| Reverse primer (100 µM) | 0.0375 µl |
| Probe 1 (100 µM) | 0.005 µl |
| Probe 2 (100 µM) | 0.005 µl |

Reaction Conditions:

| | |
|---|---|
| 94° C. | 10 min 1 cycle |
| 40 cycles of the following: | |
| 94° C. | 30 sec |
| 60° C. | 60 sec |

Klearkall Mastermix is available from KBioscience Ltd. (Hoddesdon, UK).

A summary of the alleles for markers associated with reproductive growth phenotype in soybean is provided in Table 24. Marker S17691-001-Q001 detects a deletion event, as reported in the tables "D" represents the deletion.

TABLE 24

| Marker | Genetic (cM) | Physical (bp) | Allele polymorphism |
|---|---|---|---|
| S01435-1-Q001 | 33.61 | Gm05:30568085 | A/T |
| S01239-1-A | 40.49 | Gm08:7464336 | A/G |
| S00780-1-A | 76.47 | Gm08:15841570 | A/G |
| S06925-1-Q1 | 28.92 | Gm11:4674824 | C/T |
| S09951-1-Q1 | 32.04 | Gm11:5231500 | G/T |
| S00170-1-A | 45.37 | Gm11:7847341 | A/T |
| S04059-1-A | 75.42 | Gm14:46138053 | A/G |
| S07851-1-Q1 | 83.76 | Gm14:47331319 | A/G |
| S11659-1-Q1 | 29.24 | Gm04:5754268 | C/T |
| S04279-1-A | 45.75 | Gm04:8295779 | A/T |
| S02211-1-A | 54.48 | Gm04:39691731 | A/G |
| S08942-1-Q1 | 80.59 | Gm04:44725098 | C/G |
| S05742-1-Q1 | 4.88 | Gm06:410442 | G/T |
| S09155-1-Q1 | 69.29 | Gm06:11659627 | A/G |
| S02037-1-A | 89.19 | Gm06:15457913 | A/G |
| S13136-1-Q1 | 94.84 | Gm06:16391391 | A/G |
| S17291-001-K001 | 96.04 | Gm06:16499786 | C/T |
| S13139-1-Q1 | 97.08 | Gm06:16593381 | C/T |
| S17292-001-K001 | 97.84 | Gm06:16670047 | A/G |
| S13146-1-Q1 | 98.23 | Gm06:16804435 | A/G |
| S17293-001-K001 | 100.29 | Gm06:17498270 | A/G |
| S17294-001-K001 | 101.72 | Gm06:18203964 | C/T |
| S17581-001-Q008 | 102.13 | Gm06:19743496 | G/A |
| S17691-001-Q001 | 102.2 | Gm06:19986645 | D/I |
| S17701-001-Q001 | 102.2 | Gm06:20007173 | G/C |
| S03703-1-Q1 | 102.26 | Gm06:20084642 | C/T |
| S17297-001-K001 | 102.43 | Gm06:20501491 | A/T |
| S17298-001-K001 | 102.71 | Gm06:21197184 | A/C |
| S17299-001-K001 | 102.83 | Gm06:21500085 | C/T |

TABLE 24-continued

| Marker | Genetic (cM) | Physical (bp) | Allele polymorphism |
|---|---|---|---|
| S17300-001-K001 | 102.93 | Gm06:22501610 | C/T |
| S17301-001-K001 | 102.97 | Gm06:22700011 | A/G |
| S17306-001-K001 | 103.29 | Gm06:25700006 | A/G |
| S17310-001-K001 | 103.3 | Gm06:28501458 | G/T |
| S17311-001-K001 | 103.3 | Gm06:28671736 | C/T |
| S17312-001-K001 | 103.3 | Gm06:29499523 | G/T |
| S17313-001-K001 | 103.31 | Gm06:30203054 | C/G |
| S17316-001-K001 | 103.31 | Gm06:31694650 | A/G |
| S17317-001-K001 | 103.31 | Gm06:32503141 | A/C |
| S17318-001-K001 | 103.32 | Gm06:33196184 | C/T |
| S17322-001-K001 | 103.37 | Gm06:35509548 | C/G |
| S17326-001-K001 | 103.79 | Gm06:37712913 | A/C |
| S17327-001-K001 | 104 | Gm06:38467854 | C/T |
| S17328-001-K001 | 104.25 | Gm06:39168136 | C/T |
| S17329-001-K001 | 104.38 | Gm06:39533730 | G/T |
| S10746-1-Q1 | 104.94 | Gm06:40766974 | A/G |
| S17331-001-K001 | 105.8 | Gm06:41476201 | C/T |
| S17332-001-K001 | 106.19 | Gm06:42450296 | A/T |
| S17337-001-K001 | 113.1 | Gm06:47500976 | C/T |
| S13093-1-Q1 | 113.11 | Gm06:47521797 | C/T |
| S12211-1-Q1 | 116.04 | Gm06:48475049 | C/T |
| S04555-1-Q1 | 132.43 | Gm06:49978151 | A/G |
| S08519-1-Q1 | 8.96 | Gm01:759365 | C/G |
| S12876-1-Q1 | 29.48 | Gm02:4893148 | C/G |
| S05937-1-Q1 | 48.44 | Gm02:9714426 | A/C |
| S08575-1-Q1 | 58.78 | Gm02:11502780 | A/G |
| S08669-1-Q1 | 76.53 | Gm02:15446229 | C/T |
| S11212-1-Q1 | 83.28 | Gm02:33158449 | G/T |
| S00543-1-A | 103.71 | Gm02:45776142 | G/T |
| S01452-1-A | 73.34 | Gm17:16136646 | C/T |
| S11993-1-Q2 | 99.75 | Gm17:39804515 | C/T |
| S13446-1-Q1 | 92.65 | Gm15:50237460 | C/T |
| S00252-1-A | 0 | Gm13:235439 | A/T |
| S04060-1-A | 36.9 | Gm13:20365663 | C/G |
| S02664-1-A | 36.96 | Gm13:20744030 | A/G |
| S00281-1-A | 73.16 | Gm13:35174140 | C/T |
| S01109-1-Q002 | 0.92 | Gm18:305113 | A/C |
| S13844-1-Q1 | 85.55 | Gm18:58086324 | G/T |
| S05058-1-Q1 | 105.85 | Gm18:61591142 | A/G |
| S04660-1-A | 106.5 | Gm18:61831970 | C/T |
| S09955-1-Q1 | 58.82 | Gm12:11512115 | C/T |
| S08034-1-Q1 | 71.47 | Gm20:39051858 | C/G |
| S10293-1-Q1 | 85.1 | Gm20:41216234 | A/G |
| S03813-1-A | 30.57 | Gm16:4678569 | A/G |
| S02042-1-A | 85.53 | Gm16:36524407 | A/G |
| S16601-001-Q001 | 87.73 | Gm19:47535046 | A/C |
| S01481-1-A | 89.53 | Gm19:47826727 | G/T |
| S11309-1-Q1 | 91.1 | Gm19:48252040 | A/T |
| S11320-1-Q1 | 92.18 | Gm19:48638646 | A/G |
| S04040-1-A | 100.89 | Gm19:50222676 | G/T |
| S00863-1-A | 8.09 | Gm07:1141099 | A/T |
| S17151-001-K001 | 11.64 | Gm07:1830296 | A/G |
| S17153-001-K001 | 12.12 | Gm07:1923026 | A/C |
| S17154-001-K001 | 13.97 | Gm07:2179883 | C/T |
| S17156-001-K001 | 15.53 | Gm07:2310058 | A/G |
| S17159-001-K001 | 18.14 | Gm07:2679749 | A/G |
| S08590-1-Q1 | 19.96 | Gm07:3009018 | A/G |
| S17242-001-K001 | 31.68 | Gm07:4282676 | A/C |
| S17166-001-Q006 | 31.87 | Gm07:4319368 | C/T |
| S17167-001-Q007 | 31.99 | Gm07:4342479 | A/G |
| S08539-1-Q1 | 36.74 | Gm07:5576650 | A/G |
| S17178-001-K001 | 40.59 | Gm07:6288899 | C/T |
| S17179-001-K001 | 40.83 | Gm07:6340656 | A/G |
| S17180-001-K001 | 40.85 | Gm07:6347675 | A/C |
| S17181-001-K001 | 41.66 | Gm07:6614649 | C/G |
| S17182-001-K001 | 41.66 | Gm07:6616695 | A/T |
| S17183-001-K001 | 41.69 | Gm07:6623333 | G/T |
| S02780-1-Q1 | 41.85 | Gm07:6671535 | A/G |
| S12107-1-Q1 | 43.16 | Gm07:7096376 | G/T |
| S03624-1-Q001 | 45.02 | Gm07:7774056 | A/G |
| S01953-1-A | 48.13 | Gm07:8674220 | C/T |
| S00111-1-A | 79.14 | Gm07:35590550 | A/G |
| S04180-1-A | 86.05 | Gm07:36459825 | A/G |
| S01008-1-B | 87.09 | Gm07:36638366 | C/G |
| S12862-1-Q1 | 53.56 | Gm03:38491492 | C/T |
| S12867-1-Q002 | 58.35 | Gm03:39583405 | A/G |
| S04966-1-Q1 | 92.16 | Gm03:46209939 | A/T |

TABLE 24-continued

| Marker | Genetic (cM) | Physical (bp) | Allele polymorphism |
|---|---|---|---|
| S10631-1-Q1 | 94.2 | Gm10:43974548 | C/T |
| S01574-1-A | 99.5 | Gm10:44725777 | A/C |
| S16594-001-Q010 | 99.55 | Gm10:44732850 | A/T |
| S02777-1-A | 129.25 | Gm10:50495033 | A/G |

Table 25 summarizes exemplary allele polymorphisms and further associates them with early or late phenotype for time to flowering and/or maturity. In some instances, the allele polymorphisms in Table 25 represent the complement of calls provided in Table 24.

TABLE 25

| Marker | Genetic (cM) | Physical (bp) | Allele polymorphism (Early/Late) |
|---|---|---|---|
| S17581-001-Q008 | 102.13 | Gm06:19743496 | T/C |
| S17691-001-Q001 | 102.2 | Gm06:19986645 | D/I |
| S03703-1-Q1 | 102.26 | Gm06:20084642 | T/C |
| S16601-001-Q001 | 87.73 | Gm19:47535046 | C/A |
| S01481-1-A | 89.53 | Gm19:47826727 | T/G |
| S17166-001-Q006 | 31.87 | Gm07:4319368 | T/C |
| S17167-001-Q007 | 31.99 | Gm07:4342479 | A/G |
| S01574-1-A | 99.5 | Gm10:44725777 | A/C |
| S16594-001-Q010 | 99.55 | Gm10:44732850 | A/T |

A summary of exemplary marker sequences is provided in Tables 26 and 27.

TABLE 26

| Locus | Primers (FW/REV) | SEQ ID | Probes | SEQ ID | Region SEQ ID NO: |
|---|---|---|---|---|---|
| S01435-1 | GCCTCTACTAGAA TCCGTGCATAC | 1 | 6FAM-cagtacTttcgtcaataa | 3 | 5 |
|  | GGAAGTGCTCTTG GAACACAAT | 2 | VIC-cagtacAttcgtcaataa | 4 |  |
| S01239-1 | tgagaattgatgctcatttagg aa | 6 | 6FAM-acttgttaAcagcattc | 8 | 10 |
|  | ccctagtacattttccctct | 7 | VIC-ttgttaGcagcattc | 9 |  |
| S00780-1 | TGTAGTCCCATTG CCATATGAGGC | 11 | 6FAM- CTCGTTTTAAaCCTTCT | 13 | 15 |
|  | CATTAGGGGTTTC ACCACTGTCCA | 12 | VIC- CTCGTTTTAAgCCTTC | 14 |  |
| S06925-1 | tgaggggaaattaagaaattg g | 16 | 6FAM-caccgTgatgctatt | 18 | 20 |
|  | tgaggggaaattaagaaattg g | 17 | VIC-catcattttcaccgCgat | 19 |  |
| S09951-1 | tgccgtaagtaacacacacaa a | 21 | 6FAM-cacttgattAaattcctgt | 23 | 25 |
|  | caagagcacaccatcacctg | 22 | VIC-cttgattCaattcct | 24 |  |
| S00170-1 | GCTGATACCGTTT TGGTGTTTCCA | 26 | 6FAM- TGCATCTGCaGACGT | 28 | 30 |
|  | TGCAACATCCCGT GAAAGGATT | 27 | VIC- TGCATCTGCtGACGTG | 29 |  |
| S04059-1 | caccatcagcaagctttgag | 31 | 6FAM-cctctgagttAgcctt | 33 | 35 |
|  | gaagggcacttcaacagagc | 32 | VIC-ctctgagttGgcctt | 34 |  |
| S07851-1 | cttttccttggacggtacga | 36 | 6FAM-CactgTacaaatcaa | 38 | 40 |
|  | cgtgtgaatggaagaaagca | 37 | VIC-cactgCacaaatc | 39 |  |
| S11659-1 | tctgtcccaatgctcaatca | 41 | 6FAM-catgatgAcaacctc | 43 | 45 |
|  | cttggaggggaaggtctagc | 42 | VIC-atgatgGcaacctcta | 44 |  |
| S04279-1 | aacaactccctctggtgtcc | 46 | 6FAM-atctccttcTcttcctt | 48 | 50 |
|  | catagggagtagattatatg gcttt | 47 | VIC-tctccttcActtcct | 49 |  |
| S02211-1 | cctctctcattctcgttcacgat gtaa | 51 | 6FAM-caatttaTcgtaacatcag | 53 | 55 |
|  | cttaggttcatttaaattccattt gct | 52 | VIC-caatttaCcgtaacatc | 54 |  |
| S08942-1 | cgtgatcctacgcctctctt | 56 | 6FAM-tcacgatcgCagtct | 58 | 60 |
|  | aggtcatgtccacgacgaa | 57 | VIC-tcacgatcgGagtct | 59 |  |
| S05742-1 | acgacgtcaagaagttcctac | 61 | 6FAM-tccgaaatcAtaatc | 63 | 65 |
|  | ggccgaactcggttctaatc | 62 | VIC-ccgaaatcCtaatcc | 64 |  |
| S09155-1 | ctattgccgagaagctcgat | 66 | 6FAM-caacgtaTgtcatca | 68 | 70 |
|  | tcatcctccgtgagatagcc | 67 | VIC-caacgtaCgtcatca | 69 |  |

TABLE 26-continued

| Locus | Primers (FW/REV) | SEQ ID | Probes | SEQ ID | Region SEQ ID NO: |
|---|---|---|---|---|---|
| S02037-1 | tccatcaacaaagccca<br>aaaatatctagttgagttggaccaaga | 71<br>72 | 6FAM-aatgcttcAagatca<br>VIC-atgcttcGagatcaa | 73<br>74 | 75 |
| S13136-1 | cgtgcgccctatcagtctat<br>gagttgttgcttgcattgga | 76<br>77 | 6FAM-accaccaTgtcgc<br>VIC-accaccaCgtcgc | 78<br>79 | 80 |
| S17291-001 | N/A<br><br>AGGGCAATAGTTTGAAGATTTGGGATGAA | —<br><br>81 | GAAGGTGACCAAGTTCATGCTTTTCCTTTTGCTATTTTTGACTCGG<br>GAAGGTCGGAGTCAACGGATTAACTTTTCCTTTTGCTATTTTTGACTCGA | 82<br><br>83 | 84 |
| S13139-1 | aatctaccccgtacttgg<br>ttgcagaggcaaatagagctt | 85<br>86 | 6FAM-agatcccAttcatg<br>VIC-tatatagatcccGttcatg | 87<br>88 | 89 |
| S17292-001 | N/A<br><br>CRGGACACATTTTTAGCTTACGTAGTTAAA | —<br><br>90 | GAAGGTGACCAAGTTCATGCTCAATGTAATCATTTAAGTACATTATCCCACA<br>GAAGGTCGGAGTCAACGGATTAATGTAATCATTTAAGTACATTATCCCACG | 91<br><br>92 | 93 |
| S13146-1 | gtcatcatagccgcaatcaa<br>tccaaatctttgttgagtcgtg | 94<br>95 | 6FAM-aagttcatcAaagccat<br>VIC-aagttcatcGaagcca | 96<br>97 | 98 |
| S17293-001 | N/A<br><br>GCCTAAAGACCAACAATTTGTAAGAGTAAA | —<br><br>99 | GAAGGTGACCAAGTTCATGCTGTGTTTTAACTCACTCAGTTTCGAATGT<br>GAAGGTCGGAGTCAACGGATTGTTTTAACTCACTCAGTTTCGAATGC | 100<br><br>101 | 102 |
| S17294-001 | N/A<br><br>CACACAGGAGACAAATCAYGTCGATAA | —<br><br>103 | GAAGGTGACCAAGTTCATGCTAGAAAGTAAGGAAAATTTCTAATTTTCATTGC<br>GAAGGTCGGAGTCAACGGATTGAGAAAGTAAGGAAAATTTCTAATTTTCATTGT | 104<br><br>105 | 106 |
| S17581-001 | ACGAATGCAAAATTGGAAATG<br>TCTTCCTTCGTCCGTGTCA | 107<br>108 | 6FAM-ttgaggacgtgtagTtg<br>VIC-ttgaggacgtgtagCtgt | 109<br>110 | 111 |
| S17691-001 | CCTCTTTTCCTTGGCTATGTGAT<br>CAATCTTAACATGGTTCCAAAACA | 112<br>113 | VIC-cttctcatcattgtggac<br>N/A | 114<br>— | 115 |
| S17701-001 | GACCCTATTCATCTCTTCCAACA<br>GATGTCCTAAAGTTAGAGGCTTCG | 116<br>117 | 6FAM-tggatacCtcttctt<br>VIC-atggtggatttcGtc | 118<br>119 | 120 |
| S03703-1 | cccaaggactaaccaggattc<br>tttattaaatggagtgagaaggtgtc | 121<br>122 | 6FAM-acacaagTcgctacc<br>VIC-cacaagCcgctacc | 123<br>124 | 125 |
| S17297-001 | N/A<br><br>GTAAGAAAGTTTTTTTGTGTGTAAACTGAT | -<br><br>126 | GAAGGTGACCAAGTTCATGCTCACAACACTATTTAATTTATTTCTGAAAAGCAA<br>GAAGGTCGGAGTCAACGGATTCACAACACTATTTAATTTATTTCTGAAAAGCAT | 127<br><br>128 | 129 |

TABLE 26-continued

| Locus | Primers (FW/REV) | SEQ ID | Probes | SEQ ID | Region SEQ ID NO: |
|---|---|---|---|---|---|
| S17298-001 | N/A | - | GAAGGTGACCAAGTTC ATGCTCTCGCTTAGAG GAAGAACGTGTA | 131 | 133 |
|  | CTCGCGCTTGAAG GCATCAATCTT | 130 | GAAGGTCGGAGTCAAC GGATTCTCGCTTAGAG GAAGAACGTGTC | 132 |  |
| S17299-001 | N/A | - | GAAGGTGACCAAGTTC ATGCTGACTACCACCA CGCGTCATAG | 135 | 137 |
|  | GGCCTTTTACATC GGTTCTAATGACT TTT | 134 | GAAGGTCGGAGTCAAC GGATTGGACTACCACC ACGCGTCATAA | 136 |  |
| S17300-001 | N/A | - | GAAGGTGACCAAGTTC ATGCTCATATAAGTAG AGATGTCAAATTTTCG AC | 139 | 141 |
|  | TTGTGAAGGACAC TCAACTATTCCAC TA | 138 | GAAGGTCGGAGTCAAC GGATTAATCATATAAG TAGAGATGTCAAATTT TCGAT | 140 |  |
| S17301-001 | N/A | - | GAAGGTGACCAAGTTC ATGCTATACTTTATCCT GAGTATTTCTCATGAT CT | 143 | 145 |
|  | CCCTATCACCTGT CATATACCCCTT | 142 | GAAGGTCGGAGTCAAC GGATTCTTTATCCTGA GTATTTCTCATGATCC GAAGGTGACCAAGTTC | 144 |  |
| S17306-001 | N/A | - | ATGCTATTTTTAAGAA ACATGTTTTAGGAAA CTATA | 147 | 149 |
|  | CCCTCATCCTTCT CCATGGGATTTT | 146 | GAAGGTCGGAGTCAAC GGATTATTTTAAGAA ACATGTTTTAGGAAA CTATG | 148 |  |
| S17310-001 | N/A | - | GAAGGTGACCAAGTTC ATGCTGAAAATACGCA AGGAGCTCTGTTC | 151 | 153 |
|  | TCATTGATGGTGC CTCTTTATTGCAC TTT | 150 | GAAGGTCGGAGTCAAC GGATTCGAAAATACGC AAGGAGCTCTGTTA | 152 |  |
| S17311-001 | N/A | - | GAAGGTGACCAAGTTC ATGCTAAGTATCCTAT TACAACCATCAACGG | 155 | 157 |
|  | CGCAGGAGTCATG GATCTTGTCAAT | 154 | GAAGGTCGGAGTCAAC GGATTGATAAGTATCC TATTACAACCATCAAC GA | 156 |  |
| S17312-001 | N/A | - | GAAGGTGACCAAGTTC ATGCTAAGAAAGAAAA TCACGCAACATAAATG TTG | 159 | 161 |
|  | GAAGACCAACGC GTTCTCTACTTGT T | 158 | GAAGGTCGGAGTCAAC GGATTAAAAAGAAAG AAAATCACGCAACATA AATGTTT | 160 |  |
| S17313-001 | N/A | - | GAAGGTGACCAAGTTC ATGCTGGTACGGCCTC GATCACACC | 163 | 165 |
|  | AGTCCTTTGAAGA GGAGGACGTGTA | 162 | GAAGGTCGGAGTCAAC GGATTGGTACGGCCTC GATCACACG | 164 |  |
| S17316-001 | N/A | - | GAAGGTGACCAAGTTC ATGCTAAGAGCTTCCA TTTTCGATTACGAA | 167 | 169 |
|  | TCGGATGTTCGAT TGTGTCCCATAAT ATA | 166 | GAAGGTCGGAGTCAAC GGATTAAGAGCTTCCA TTTTCGATTACGAG | 168 |  |

TABLE 26-continued

| Locus | Primers (FW/REV) | SEQ ID | Probes | SEQ ID | Region SEQ ID NO: |
|---|---|---|---|---|---|
| S17317-001 | N/A | - | GAAGGTGACCAAGTTC ATGCTTGAGAAAATCC CTCCTCCATTTTA | 171 | 173 |
|  | GAGTTGGTGAACT AATTTTCCCTGTT GAT | 170 | GAAGGTCGGAGTCAAC GGATTCTTGAGAAAAT CCCTCCTCCATTTTC | 172 | |
| S17318-001 | N/A | - | GAAGGTGACCAAGTTC ATGCTAACAGGAAGGG AAAACAAAGTGTCG | 175 | 177 |
|  | CCTTGATGCTCTA TTTCTTTTCTCCCA A | 174 | GAAGGTCGGAGTCAAC GGATTGAACAGGAAGG GAAAACAAAGTGTCA GAAGGTGACCAAGTTC | 176 | |
| S17322-001 | N/A | - | ATGCTATTTTGGGTTTT TTTTTGTAAAAACAGA AAGTC | 179 | 181 |
|  | ATGTTGTTTGTGT AGATTAACATCGG CTTT | 178 | GAAGGTCGGAGTCAAC GGATTTGGGTTTTTTT TTGTAAAAACAGAAAG TG | 180 | |
| S17326-001 | N/A | - | GAAGGTGACCAAGTTC ATGCTAAAATAGCTGA AATTGCATTTATGGTG CAA | 183 | 185 |
|  | CACAACACTGCTT ACAGCAAATTGCA TAA | 182 | GAAGGTCGGAGTCAAC GGATTATAGCTGAAAT TGCATTTATGGTGCAC | 184 | |
| S17327-001 | N/A | - | GAAGGTGACCAAGTTC ATGCTAAGTAGCAGTT AAAGAGGACTGGTC | 187 | 189 |
|  | GACCTCATATGAA AGAATATGTCCAA TCTT | 186 | GAAGGTCGGAGTCAAC GGATTAAAAGTAGCAG TTAAAGAGGACTGGTT | 188 | |
| S17328-001 | N/A | - | GAAGGTGACCAAGTTC ATGCTATCCACCTTGCT TTACAATGCATCC | 191 | 193 |
|  | TTCTACAAGGCGA AGGACCATTTTAT CAT | 190 | GAAGGTCGGAGTCAAC GGATTCATCCACCTTG CTTTACAATGCATCT | 192 | |
| S17329-001 | N/A | - | GAAGGTGACCAAGTTC ATGCTCCTTTGCTTCTT GAAGATCATGGC | 195 | 197 |
|  | CTCCAATCATCTT TCTTCCTTCTCCAT TT | 194 | GAAGGTCGGAGTCAAC GGATTGTCCTTTGCTTC TTGAAGATCATGGA | 196 | |
| S10746-1 | attgggatcctgatcaacca cccaggcattggtgtttaag | 198 199 | 6FAM-caacaaTgagcctaat VIC-caacaaCgagcctaa | 200 201 | 202 |
| S17331-001 | N/A | - | GAAGGTGACCAAGTTC ATGCTGGGAAATGAAG ACAATTAATAACATCG TG | 204 | 206 |
|  | CGGTTGTCTCTGS TCTTCTCAGATT | 203 | GAAGGTCGGAGTCAAC GGATTGGGAAATGAAG ACAATTAATAACATCG TA | 205 | |
| S17332-001 | N/A | - | GAAGGTGACCAAGTTC ATGCTCAAACCTTAGG ATAGATGACTTCTTGTT | 208 | 210 |
|  | AACCTTACCCTAA CAACATACAACTA AGAA | 207 | GAAGGTCGGAGTCAAC GGATTCAAACCTTAGG ATAGATGACTTCTTGT A | 209 | |
| S17337-001 | N/A | - | GAAGGTGACCAAGTTC ATGCTTGATTGATAAT TTTTTTTATTATGTACA TGAC | 212 | 214 |

TABLE 26-continued

| Locus | Primers (FW/REV) | SEQ ID | Probes | SEQ ID | Region SEQ ID NO: |
|---|---|---|---|---|---|
| | CCTATTGACCGTG ATATTAATTAAGA CTTT | 211 | GAAGGTCGGAGTCAAC GGATTGATTGATAATT TTTTTTATTATGTACAT GAT | 213 | |
| S13093-1 | catcgagtctccagcaagtg | 215 | 6FAM-attggcacttTtaac | 217 | 219 |
| | tgagattcacgaagtgggttc | 216 | VIC-cacttCtaacatcaatg | 218 | |
| S12211-1 | gaccagaggtagtagattcca aaagt | 220 | 6FAM-ctgcaaTgccatact | 222 | 224 |
| | tgcattaagctcactcagttat gtatta | 221 | VIC-ctgcaaCgccatac | 223 | |
| S04555-1 | AAATCGCCACTAG GCTTGC | 225 | 6FAM-cagcacTggatctt | 227 | 229 |
| | CTAGGGTTCTGCA GTTCATCG | 226 | VIC-cagcacCggatct | 228 | |
| S08519-1 | acagttcattggccttgaca | 230 | 6FAM-tcagctctgCcaatag | 232 | 234 |
| | ggcttcacacttgaggaggt | 231 | VIC-tcagctctgGcaatag | 233 | |
| S12876-1 | cccgccacaactcttgttat | 235 | 6FAM-cacgcttcCaatct | 237 | 239 |
| | gggaggtgtttggcaatatc | 236 | VIC-aagcacgcttcGaat | 238 | |
| S05937-1 | gcaaaattaaggagaggacc ttg | 240 | 6FAM-catcAgctatgaccatg | 242 | 244 |
| | ctctcttgcaaaatgcacca | 241 | VIC-catcCgctatgacc | 243 | |
| S08575-1 | aactatgcacttatgctcatgg taa | 245 | 6FAM-acttcttgcTgaatct | 247 | 249 |
| | tggatccaaacatgcgtcta | 246 | VIC-aacttcttgcCgaatc | 248 | |
| S08669-1 | gtggtgggttggttttgac | 250 | 6FAM-tcttatgggacatTtc | 252 | 254 |
| | tccaatattctcagcctcttcag | 251 | VIC-tcttatgggacatCtc | 253 | |
| S11212-1 | ctccaagaccttgccttcct | 255 | 6FAM-ccccgTttacttcc | 257 | 259 |
| | gatcccaaatgagattaggag act | 256 | VIC-cccgGttacttcc | 258 | |
| S00543-1 | GCATGCAATATGA ACAACTTGACAAC | 260 | 6FAM-CACTTATCCAtTGGTTC | 262 | 264 |
| | CCCTTTTCACATG AGTATGCATGTC | 261 | VIC-CACTTATCCAgTGGTTC | 263 | |
| S01452-1 | caaacaatgaatgatgaatcc aa | 265 | 6FAM-aagcaaTtgg-tcacaac | 267 | 269 |
| | gcattttgagagccaccaata | 266 | VIC-aagcaaCtggtcacaa | 268 | |
| S11993-1 | atttgtgagtgctgcggatt | 270 | 6FAM-ccagcacaatTgat | 272 | 274 |
| | tgaacatgaacgtgctaaacg | 271 | VIC-ccagcacaatCga | 273 | |
| S13446-1 | atcccaggcttctaatgtgg | 275 | 6FAM-cccaccacActca | 277 | 279 |
| | ggctgcgctactttcgtact | 276 | VIC-cccaccacGctc | 278 | |
| S00252-1 | ATGCATGCAGCTG GCAATAAT | 280 | 6FAM-CGGTCTCtTGGTACTAT | 282 | 284 |
| | GATGCCACCGATG AAGAAGCAC | 281 | VIC-CGGTCTCaTGGTACTAT | 283 | |
| S04060-1 | ctcttgcagcggattcagtc | 285 | 6FAM-cgacttcaCtcacc | 287 | 289 |
| | ctcgccgatttcctcatct | 286 | VIC-acttcaGtcaccgagat | 288 | |
| S02664-1 | GTTTTGGTTTCCTT AGGATGAACT | 290 | 6FAM-CTTTCCATCTTaTTCG | 292 | 294 |
| | ATGTGCAGAGGTC CCATTCT | 291 | VIC-CTTTCCATCTTgTTCG | 293 | |
| S00281-1 | GGCCGAGCAAAC AACAAGAAAA | 295 | 6FAM-CATAGTGaACCTCTC | 297 | 299 |
| | TCCAAACTCCTCA CAAGCCTTCA | 296 | VIC-CCATAGTGgACCTCT | 298 | |
| S01109-1 | AGTAGTACTTCAT CCCTGACACCA | 300 | 6FAM-ccaccacCtctgaaa | 302 | 304 |
| | AGGAGTATAACCT TGGTTTAAAGCTG | 301 | VIC-accaccGctgaaaa | 303 | |

TABLE 26-continued

| Locus | Primers (FW/REV) | SEQ ID | Probes | SEQ ID | Region SEQ ID NO: |
|---|---|---|---|---|---|
| S13844-1 | tgatggaaagccgaaaaaga | 305 | 6FAM-tcccttaAgtagtcta | 307 | 309 |
| | ctgagcagccctcatatgta | 306 | VIC-atcccttaCgtagtctt | 308 | |
| S05058-1 | aaatgatacgcaattttgactcag | 310 | 6FAM-atagcAgttcattgtac | 312 | 314 |
| | tgtgttatgcctaccaatcaaact | 311 | VIC-atagcGgttcattgta | 313 | |
| S04660-1 | tcggccttcgtcatagaagt | 315 | 6FAM-catctacAtccttcc | 317 | 319 |
| | tccttcaatttccccatatcc | 316 | VIC-catctacGtccttcc | 318 | |
| S09955-1 | gatcgggatgaggaa | 320 | 6FAM-cacacttgaTactcca | 322 | 324 |
| | cttttcatgatccaaccagaca | 321 | VIC-cacacttgaCactcca | 323 | |
| S08034-1 | tcctactaaaccctgctgtg | 325 | 6FAM-caatccaCaggagcat | 327 | 329 |
| | ttggtctctacttagtacatctca | 326 | VIC-caatccaGaggagcat | 328 | |
| S10293-1 | gggcatccagactttatctatga | 330 | 6FAM-tacTacagtcgatctc | 332 | 334 |
| | acgatttaatgcacgacgagt | 331 | VIC-ttcCacagtcgatc | 333 | |
| S03813-1 | atttagcgtacatgtcaactaacga | 335 | 6FAM-cctaacTagaatac | 337 | 339 |
| | tgcaaatgctttgaatctgg | 336 | VIC-cctaacCagaata | 338 | |
| S02042-1 | gccatatccatactgcaacc | 340 | 6FAM-ctccttgaggTtac | 342 | 344 |
| | agaagcgttggctatgcacgag | 341 | VIC-ctccttgaggCta | 343 | |
| S16601-001 | TTCACACATGTACTAGGCTTTGG | 345 | 6FAM-cagcttcaAaacatt | 347 | 349 |
| | CCACCTTTCACACAGCTTGA | 346 | VIC-cagcttcaCaacatt | 348 | |
| S01481-1 | tacaggctggctgtactt | 350 | 6FAM-cagtcacTttatggtcc | 352 | 354 |
| | actctgggtgccaaagtcaa | 351 | VIC-cagtcacGttatggtc | 353 | |
| S11309-1 | gaccggtctgggacaatg | 355 | 6FAM-atttcAtggttctcg | 357 | 359 |
| | cacttaatcaagttgcccaagaa | 356 | VIC-caatttcTtggttctc | 358 | |
| S11320-1 | gcccaaagttcaaaagcaat | 360 | 6FAM-aaacaAacgatctcaac | 362 | 364 |
| | tcggatgcgaatatgaagtg | 361 | VIC-aaacaTacgatctcaac | 363 | |
| S04040-1 | cccagctgctgaggagaa | 365 | 6FAM-aaggtacccTctagtg | 367 | 369 |
| | ggattgaaaaacaattggagga | 366 | VIC-aaggtttcccGctagt | 368 | |
| S00863-1 | CAGCATCACACACGCTATAAGACCA | 370 | 6FAM-TCAACACTCACAaGAT | 372 | 374 |
| | CATGACTTTTCATACTAAGTTGGACACCA | 371 | VIC-TCAACACTCACAtGAT | 373 | |
| S17151-001 | N/A | - | GAAGGTGACCAAGTTCATGCTGGAAAAAGAAGAAAAAATTCCACTAATGTGA | 376 | 378 |
| | CRAGTCTCAGTCAATCTGTGACTCTTT | 375 | GAAGGTCGGAGTCAACGGATTGAAAAAGAAGAAAAAAATTCCACTAATGTGG | 377 | |
| S17153-001 | N/A | - | GAAGGTGACCAAGTTCATGCTGCCCTTAATTGCTCAAATTTCCACTA | 380 | 382 |
| | CTGACGTGGAGTGTGACAATGCAAT | 379 | GAAGGTCGGAGTCAACGGATTGCCCTTAATTGCTCAAATTTCCACTC | 381 | |
| S17154-001 | N/A | - | GAAGGTGACCAAGTTCATGCTAAATGTTTTTCTCGTGCTTGATTGC | 384 | 386 |
| | GAACCACATTTCTAAGTTAAAGCGACTTAA | 383 | GAAGGTCGGAGTCAACGGATTMTAAATGTTTTTCTCGTGCTTGATTGT | 385 | |

TABLE 26-continued

| Locus | Primers (FW/REV) | SEQ ID | Probes | SEQ ID | Region SEQ ID NO: |
|---|---|---|---|---|---|
| S17156-001 | N/A | - | GAAGGTGACCAAGTTC ATGCTCAACAACTAAT TGACCCTGCAGG | 388 | 390 |
|  | CCCTTCCAATGAA ATAAAGCACTTGG AT | 387 | GAAGGTCGGAGTCAAC GGATTAACAACTAATT GACCCTGCAGG | 389 |  |
| S17159-001 | N/A | - | GAAGGTGACCAAGTTC ATGCTGGAAGACACGT GGTCCACCT | 392 | 394 |
|  | TYCAGCCCAACAA ATCTCAAATGGGA T | 391 | GAAGGTCGGAGTCAAC GGATTGGAAGACACGT GGTCCACCC | 393 |  |
| S08590-1 | cccttgaaagacgaccaaaa | 395 | 6FAM-cagatcAgttgtcattt | 397 | 399 |
|  | acttatccgcagccgtacac | 396 | VIC-cagatcGgttgtcatt | 398 |  |
| S17242-001 | N/A | - | GAAGGTGACCAAGTTC ATGCTTGGGGAATAAA CATCGTGCTTTATAATT A | 401 | 403 |
|  | CAGAGTGCCTTGA CGTAGTGACATA | 400 | GAAGGTCGGAGTCAAC GGATTGGGGAATAAAC ATCGTGCTTTATAATTC | 402 |  |
| S17166-001 | CCGCAAACTGTAG TACAAATCAA | 404 | 6FAM-caagacaTgcagcaga | 406 | 408 |
|  | GGGTTGTAGAAA GTAACTTGGGAAG | 405 | VIC-caagacaCgcagcag | 407 |  |
| S17167-001 | GTTTTCACATGTA ATTTTCAAAACAA A | 409 | 6FAM-taactgtgcttttttaaaa | 411 | 413 |
|  | TGTCAGTGATGGT GAAAATGATAG | 410 | VIC-taactgtgctCttttaa | 412 |  |
| S08539-1 | cacttctgtaaagagtcaaca agagg | 414 | 6FAM-agagattgaagaAtt | 416 | 418 |
|  | tgaatacaccttgagtccaaa gaa | 415 | VIC-tagagattgaagaGttt | 417 |  |
| S17178-001 | N/A | - | GAAGGTGACCAAGTTC ATGCTACCACCATTCG GCTAAAGTCAATC | 420 | 422 |
|  | GAATTGATATTTC AACCATGGATGCA TCAT | 419 | GAAGGTCGGAGTCAAC GGATTCACCACCATTC GGCTAAAGTCAATT | 421 |  |
| S17179-001 | N/A | - | GAAGGTGACCAAGTTC ATGCTAAAAATATTTT CTAACTCTAAAAGCAA ACTGGA | 424 | 426 |
|  | CCAGTTTACTTAG TTAGGTGCCCAAA TTA | 423 | GAAGGTCGGAGTCAAC GGATTAATATTTTCTA ACTCTAAAAGCAAACT GGG | 425 |  |
| S17180-001 | N/A | - | GAAGGTGACCAAGTTC ATGCTGAAATGATAAA ACCTAGTAAGCTTTCA GTT | 428 | 430 |
|  | CAGTGCATTTCCC ATAGAAAGTTATT TGTT | 427 | GAAGGTCGGAGTCAAC GGATTAAATGATAAAA CCTAGTAAGCTTTCAG TG | 429 |  |
| S17181-001 | N/A | - | GAAGGTGACCAAGTTC ATGCTGTAATCACTAA AATTACACACTTAAAT TAC | 432 | 434 |
|  | GGGCCAATTTTGT ATTACATCTTTCC AGAA | 431 | GAAGGTCGGAGTCAAC GGATTGTAATCACTAA AATTACACACTTAAAT TAG | 433 |  |

TABLE 26-continued

| Locus | Primers (FW/REV) | SEQ ID | Probes | SEQ ID | Region SEQ ID NO: |
|---|---|---|---|---|---|
| S17182-001 | N/A | - | GAAGGTGACCAAGTTC ATGCTGTAATAGGTCA TAAATGTTGATGGAAT ATTCT | 436 | 438 |
|  | CTCAGATATACAT AGATGAGAGGTG ACAA | 435 | GAAGGTCGGAGTCAAC GGATTGTAATAGGTCA TAAATGTTGATGGAAT ATTCA | 437 |  |
| S17183-001 | N/A | - | GAAGGTGACCAAGTTC ATGCTGATCGTGCGGT GGATGTGAAG | 440 | 442 |
|  | ATRCGTGGCCACC ATTTACCTGTATT A | 439 | GAAGGTCGGAGTCAAC GGATTTGATCGTGCGG TGGATGTGAAT | 441 |  |
| S02780-1 | attttccagactattgcctttac ctt | 443 | 6FAM-actctggAtaacctg | 445 | 447 |
|  | agaatacttgactgtataggat gcaaac | 444 | VIC-actctggGtaacctg | 446 |  |
| S12107-1 | cctcctcctcaaactgttgc | 448 | 6FAM-caatcggctccAtc | 450 | 452 |
|  | gtggcaaagtgcgaacaata | 449 | VIC-caatcggctccCtc | 451 |  |
| S03624-1 | TAGAATAATCACT ACAATAACAGAT GATCTTG | 453 | 6FAM-agcatcattagtgTcacat | 455 | 457 |
|  | CATTACATGCATA ACCTCTCATCA | 454 | VIC-agcatcattagtgCcacat | 456 |  |
| S01953-1 | GGAGTGTACTTCT TTATGAAAAACGG TGA | 458 | 6FAM-ttccttctTcacttgat | 460 | 462 |
|  | GTGTCGGGCCACT AATTTTGGAGCCT TT | 459 | VIC-tccttctCcacttgat | 461 |  |
| S00111-1 | ACTGATTCAAGAT ACGATCAAGTTTC CTTATCATTT | 463 | 6FAM-CCTAATTgCGTTTACC | 465 | 467 |
|  | TTGGTTTTGGTGA ATAACTGGAAAA GTGTGT | 464 | VIC-CCTAATTaCGTTTACCC | 466 |  |
| S04180-1 | cattcaccatttatgaattttgat cc | 468 | 6FAM-cattgacActgttcct | 470 | 472 |
|  | aaatgaaaacccagaataatg tgc | 469 | VIC-cattgacGctgttcc | 471 |  |
| S01008-1 | atcccttgctttaactagattgtt attcatgt | 473 | 6FAM-caattCctctgtaagtc | 475 | 477 |
|  | atgcactggattgtgaagaga atataagc | 474 | VIC-caattGctctgtaagtc | 476 |  |
| S12862-1 | ggttcgagggttgtgtatcc | 478 | 6FAM-catttatcAgattcgatc | 480 | 482 |
|  | gattgcacccatatcgacct | 479 | VIC-acatttatcGgattcga | 481 |  |
| S12867-1 | CACACGTTAAAAC TCTTGTTCAGC | 483 | 6FAM-accacatgtaactAtt | 485 | 487 |
|  | TCCTAGAATAAAT ATGATCCCTTCTC AT | 484 | VIC-accacatgtaactGtt | 486 |  |
| S04966-1 | atacccagcagcagtcacca | 488 | 6FAM-catttgggtatgcTgtg | 490 | 492 |
|  | ttgtgtggccttacctttca | 489 | VIC-catttgggtatgcAgtg | 491 |  |
| S10631-1 | tttgatgcaagatctgtcgaa | 493 | 6FAM-ccaactcAgatctt | 495 | 497 |
|  | agccggtttacttggaatgtt | 494 | VIC-ccaactcGgatctt | 496 |  |
| S01574-1 | tgaagcaactaggaaagctg aa | 498 | 6FAM-aaggcatcTttatctc | 500 | 502 |
|  | acgacccaatttgcttgtct | 499 | VIC-aaggcatcGttatctc | 501 |  |
| S16594-001 | CACTACAGCCTCC CGTGCT | 503 | 6FAM-catgtcttatgTaaatat | 505 | 507 |
|  | CCTCTGAAGAATA GCTTCCACTG | 504 | VIC-catgtcttatgAaaata | 506 |  |

TABLE 26-continued

| Locus | Primers (FW/REV) | SEQ ID | Probes | SEQ ID | Region SEQ ID NO: |
|---|---|---|---|---|---|
| S02777-1 | acatatcgaagtgcaaatacg | 508 | 6FAM-ttgttatcttccActttag | 510 | 512 |
| | tcgacttgaaatggaaactgaa | 509 | VIC-ttgttatcttccGcttta | 511 | |

TABLE 27 provides the genomic region comprising the polymorphism associated with a reproductive growth phenotype in soybean.

| Locus | Genomic region | SEQ ID |
|---|---|---|
| S01435-1 | TGTTGATGAGGGGGCCATATACCATCAGGAACATGCCAATGC<br>TTATTAGAGAATGGAAACYTGATTTTAACCTGAAGCAAGACA<br>TGCTACGGACTCTTCCTATTTGGGTACAACTCCCTCAACTGCC<br>ATTGCATTTATGGGGTGGAAAAAGCCTAGGCAAAATTGGAAG<br>TGCTCTTGGAACACAATTGGTTATTGACGAA[A/T]GTACTGCA<br>AATAAACTTCGGGTCTCGTATGCACDGATTCTAGTAGAGGCA<br>GATGTCACGCCAGAACTGAGAAACGAAATTACTATAAAGGAC<br>AATGAGGGGCGGAGGATCACTCAAAAAKTCGAATATGAGTG<br>GAAACCAATGTTTTGTGATAAGTGCCAAAAGTTTGGCCAYAA<br>ATGTGGTGAAGTAAAGCCAAGGAAG | 5 |
| S01239-1 | ATTTTTATAGTTATATTTCTCAAAATTATATTCAAGAATCAGA<br>AAACAGAAAAATAATGTTATAAATTTSATGCATATCTTCCATT<br>AAAACAGGTTAGATCCATAGTTGTTGCTAGTCAATAACCTTAT<br>GGTTAGCAGTGCCATCCCTTDCAACAATGAGAATTGATGCTC<br>ATTTAGGAAGTCAACACTTGTACTTGTTA[A/G]CAGCATTCYG<br>GAAAGAAACAAGAGGGAAATGAAACAAAGGGTGTTTTTCA<br>AAAAATATTGGCTGATCATGATTTTTTGATCATGATTTTTACR<br>TGTTCTGTTAAGACTAAAGTACATTAATTTCACTGTGTTGGCA<br>CCTGAATAGTTATTGAGCATTATGTGAGGTGGCAATTAAGTA<br>TACAGTTTTGTCAYGACTTTT | 10 |
| S00780-1 | ACAATGAAGAAGGAAGTACTTTGCAGGTATTGCAATAAGAAG<br>TTCAGTTGTTACCAAGCCTTGGGTGGACATCATAATTCTCACA<br>AGGCGGAAAGAGCAGCAGAAATACATAGCAAGGCTTCTGCTT<br>GTTACAAAACATATGGTTATGGGTTTTGTGGCAAAACATTAG<br>GGGTTTCACCACTGTCCATGACTCGTTTTAA[A/G]CCTTCTATT<br>ATTGTTGGCCTCATATGGCAATGGGACTACATGACTGACTATC<br>ATCATGTTGCATGGCCAAGGCACCAGATTTTGAATCCTCCTCA<br>ACCCACCATGTATCAATTCATGGCTGAAGGGAGTGGATCTCA<br>CCAACACCACAAATTATATTARCCTTTGAGTTCTTCTATAGTC<br>AGAGGAGGACCAACAAATTC | 15 |
| S06925-1 | AGTCCATTGAACATTCCTCATATTGTTCCATGCACTTTGTGTG<br>AAACTGCAGTGGCACCGGTTCTTTTGGGGGAAGTAGATCAGC<br>TTCAAAGATTGCAGCTTTTCATTTTGCTTATTTTCCATATTTTA<br>TGAGGGGAAATTAAGAAATTGGTTGTTAAATAGAGAAACAA<br>AGATTTGTCTCCACTGCATCATTTTCACCG[C/T]GATGCTATTG<br>CTATATCTTGTTCCATATTAGCTGTGAATCCTTGTCACTTATG<br>GGGGATATTAGGCTTACCCGGGTAGAGCAAGGTCAAACAAA<br>GATTAGAAATGTTCCAATTGCTGTCACCCCTGAAGGATTTTGG<br>TGTTGCCMTACTCCTGTTGGGTTTCAGAAAAGCCTCAAACCTC<br>AAAACCCTTTGAATAAACTC | 20 |
| S09951-1 | CGAGCCCTTGCTATAAAAACGGGACTGAAGCTCATTTCAACG<br>GGGAAAATTCCCAAATCTGTTTTAGCTCGCCCCAACTGGCCAT<br>ACACGTTGCTCCCACAGCTCAAGAGCACACCATCACCTGATA<br>TAGCATATAGTAAAAAACTTAAGTTTTGAAAACGCATGCATA<br>CATCTTAATGATCTAACTTGCTACAGGAATT[G/T]AATCAAGT<br>GTTTGGTGTTTGTGTGTGTTACTTACGGCAAAGAATACAGAGA<br>GTGATCAAGGCCACACGCAATGTCCAGAACATGAACACCGTG<br>TAATTCTTCGACCAAGCGGGYTCCCATACTATTGGCATGTTA<br>TTCTCCTGYTCCATTCCTTGCAAGACTCTCTTTTCAGCAGCTT<br>AWGGTCCKCGAGAGCTGTGAG | 25 |
| S00170-1 | TSACGAGTAGAATTTCNANTAGAATTTCAAGTAATTTTCGGAC<br>TGAATCAAATAATCCAAACCAAAGAGTAGATTACAAGCCAGG<br>TAAATTTTCAAGGATCCAAATGTGGTAGGACCAGGTCACTGG<br>GATACACAATGCATCATATATATATGTACGTGCAACATCCCG<br>TGAAAGGATTTTGCCTAGGTCGTTGCMCGTC[A/T]GCAGATGC<br>ATTTTATTTGTACCTAAGAATAATACACTCGAGTACACAGCTA | 30 |

TABLE 27-continued provides the genomic region comprising the polymorphism associated with a reproductive growth phenotype in soybean.

| Locus | Genomic region | SEQ ID |
|---|---|---|
|  | TTTATTTCAGTCTTGAGCACTTGAAAACATCATGTTAAGTCCA<br>CATAAATTCATTAAAGACATTGGAAACACCAAAACGGTATCA<br>GCAACTGAGGCTATCCAAAGCCAGAGATCCAAAATTACAAAG<br>GCAAAATGATAAAATACGGAAT |  |
| S04059-1 | AAATTCCAAACGATTATTATTCTGGGAAGAGTCGAAGCACAA<br>TACTCATTAACAAGAAAATTCGGTTGTACCCATAAAATACCG<br>ATTCCTACCCGCACTTAGATTGATCAGTACTTGTAGTCCTCAA<br>CATGGAGGCTCTCTGAGGCACCATCAGCAAGCTTTGAGTTAC<br>CCTTGTAGGTTCCCAGAGTTGCCTCTGAGTT[A/G]GCCTTGGCT<br>CTTACCAAAAGGGCTTCCTGAGCCTTCTTCACATTCTCCTCTT<br>TTCCACTCCATGCCTTAAGGGTGCTCTGTTGAAGTGCCCTTCC<br>AAAGGAGAAAGAGAGTGACCATGGCTTCTTTCCATTGACCTG<br>GTTAATGGCATTGAGGTTAACGGATGCCTCCTCCTCACTCTGC<br>CCACCAGACAAGAAAACGAT | 35 |
| S07851-1 | TGTAAAAGGTTTACGTAACCATACTGCAATTTRCAACCACAT<br>GCTGCAGTCGTATCAGCTATATTTTCTTGTAACTGWGATTAAT<br>TATAATCGCAATCTAAATTCATTATTAGAGATAAATGACCAC<br>CATGCATCCTGATTTATGCGTGTGAATGGAAGAAAGCATATA<br>CAGATGTTGACATATCCAAGCATTGATTTGT[A/G]CAGTGATC<br>TCCAAATATTTCGTACCGTCCAAGGAAAAGATCAGGCTCTAG<br>CCACATATCTTCCGAGCCACATACATGAACTGAGCTTGAATC<br>ATATACCATAATTAGCATAAAAGGGATGAATTAATGCAGAGG<br>AGTTTAATTATAAAGCTTTATTTTTCGCTTCARAGTTTCAGCA<br>AGATTTTATATATATATATAT | 40 |
| S11659-1 | TAAAAATGATTTAATTATTATTAATTTAACTRTAGTTGAATGA<br>TTGAATCTTGAACTAATACCTTCTTCTTCATTGATTGAATGGA<br>AAATCTAATTTTATAAACATTGATTWGCCTCATTTGTCGAGGS<br>CCACTAATGAAATGTGAGATTTCCTTGGAGGGGAAGGTCTWG<br>CTCTAAAAAGCCCAGCTAGCTAGAGGTTG[C/T]CATCATGTAC<br>GCAATCTTAAATGATTGAGCATTGGGACAGAGCTTGCCATGT<br>ACTTTACTACCAATGCTCATATTTCCCMTGTTGATTGTGTCTC<br>CCTTTCTATCTTTATATCAACTTTCCAAGTTGTTGACCATGTCC<br>ATGTACAAAGGATCATAGCTGCTCTTTTCTTTTTTCTTTCTGTT<br>GTGCTTCTCACCTTACC | 45 |
| S04279-1 | TAGATTAACTGCAAGGAGACACATTTCATCTTGAATTTTCTAT<br>GTAACTTTGTATTACAACAAAGCCTTGTCCCGCTAGGTGAGGT<br>CAGTTATATGGATCACACGATGCCATTTGACTTGGTTGAAGG<br>CCAAATCTTAWGAGATATATTTACCATGAGATCCCTCTTAA<br>CAACTCCCTCTGGTGTCCTTGATCTCCTTC[A/T]CTTCCTTTTCA<br>CAAAACTAAAAGCCATATAATCTACTCCCCTATGTAGCAGTG<br>TAATACATCCTGGATTTTCTGTGAAAAGTTATACATTTTTTCA<br>GAAAATTGAAGGTCCTATTTATTTTCATAATGGCCACATGTCT<br>ATATGACACYCTTAGCCCATGTATATATAAAAAATATGGG<br>CTGGGAAAGAAATGGCACA | 50 |
| S02211-1 | GAGCTCTGCAAACAGATCTAGGAGGAGAGAGAGCGCACYGA<br>GTTTCGTCTTCTTCAGGAGAAAGCTAGCCTCGTTTCGTAATTT<br>CCCCTTTCCNATTCAATTTTATTTTTTAGGGTTTTCAATTTGT<br>ACTGTAGTGTAAGTGAATTTGGAAAGATGCTTTTGGTTCATTT<br>AAATTCCATTTGCTCGAACTGATGTTACG[A/G]TAAATTGCTTT<br>TCTTTTTTACATCGTGAACGAGAATGAGAGAGGAATGGYGTG<br>GCGACGTTGGCGTCACAGAGAAGGAAGAAGAAGAAGTGACG<br>TTGATGAAGAAGAAGAGTAAGAGAAATGAGAGGGTTGGTGC<br>CGCAAAGAAGGAATATGAAGAAGAATAAGAGAACGAAGAGG<br>GAGCGGTGGTGCTCCACTGTGCAT | 55 |
| S08942-1 | TTAAATAATTTTGTTAGATCTCTCTTATTTTTAAATATTTTATT<br>TAAATATTTATTAAATTAATATAATTATGTAAATATTCGGTTT<br>CTCTCCTTGTTTTTTTTCTTCTATTTTTTATTTTTTTTTACTTCC<br>CTCTCCCGTGATCCTACGCCTCTCTTCTTTCTTTTTCCTCCTTTT<br>TTCTTTCCCTCCATCACGATCG[C/G]AGTCTCCTTTCACCTTCC<br>CCTTCGTCGTGGACATGACCTCCCTCCCCCTTCCTTTCCGTCA<br>CGGCCTCCTCCCCATTCTCCTCCGTCGCGAGCCCCCTTTACTC<br>CTTCCGAAACTCTATCACGACCTCCTTCCCCATGTGTCAATAT<br>GTATATTTTGTTTTTATGGTTTGTTTTTATTTGTTTCTTTTTAAT<br>CATTCCAT | 60 |
| S05742-1 | GAGAGGACTCCCAGGTTTGGGCTGGGACGATTTTCTGGGCTT<br>CCAAACGCAGATAACTCTCTTTGGCAACAACTCCGCCACGGT<br>CTTCCCGAAAACGGCGTCGTCCTGATGGATCAGATGCTCCCC<br>CAGCTGTTCCTCCAGGTACTTGTCGAATTCGGGAGGGTCCTCG | 65 |

TABLE 27-continued provides the genomic region comprising the polymorphism associated with a reproductive growth phenotype in soybean.

| Locus | Genomic region | SEQ ID |
|---|---|---|
|  | TGGCCGAACTCGGTTCTAATCTCCAGGATTA[G/T]GATTTCGG ACTGCGTGTCGGAAAGGAACTTCTTGACGTCGTTGAGGACGA GGTCAACGCCGTAGGTGAGGAGGATACCGTGGCAGACGCGG CGGTGTTCTTGGACGCGGATGTCGAGGACGCGGGTGCCGAGG GAGAGCTGGCGGTAGATGGAGAGGGATTGGCACTGGGCGAA GGGGCGAGTGAGGAGAGGGATGCCAA |  |
| S09155-1 | TACTCATGGATCTTGTCCTAAACCTGATATGAATGATTCAAGC CCAACACGGGYGACAAGACTGATTTCGAGAGTGTGGACTGTA GCCAAACAGGAAGTGTTTGGTCWTGAACTTCCTATGGTTCAT ACTCATTTTTCATGCAATCTGCAATACGATCATCCTCCGTGAG ATAGCCAGGCAGAACAACAGGATTGATGAC[A/G]AAACGTTG CAATTTATGCGCCTTGATCACTGGTTCGACATGCWGTCGTCA GTGAAGGTAGTTTGAATCATCGAGCTTCTCGGCAATAGTGTTT GGGAACAACTGAGATACAGGATTCGAAGGTACGGAAGCCAT GGATACACAGATCTTGAATGATAACTACAAAGGATAGGCTCT CGATACCATATTTGATAAAACTGA | 70 |
| S02037-1 | GAAGGATAGCCCTGAYAGGAAGGGTGTCTTTACACGCTTTCC AAATCATGTTTTTGGCCTAGGGGATTGCTTTTGTTTTCCACAT CRCCTTTCAAAAGCTCCTGGAATTTCCATTRGACAAGGCATAG GAAGAATTATCCATCAACAAAGCCCTTTTATACCCAGATTTG ACAACATACCTTCCATGTTGTGAATGCTTC[A/G]AGATCAAAT CATTACTAGTCTTGGTCCAACTCAACTAGATATTTTGAATAAT TTGAGAGATATGTTATAGGAATAAAGAGTTTATGGAAGTGTT GTTCCAAGATTTGGACCCTGGCTCAATAAGGTCCTTAACCTTC AAAATAGGATCCATTGTAGAACCATTTGGAGGATCGAGAKAG TGCCTYGCCAGATTTAGAATY | 75 |
| S13136-1 | TTAACTTTGGTGGATTTTTAATTTTTTAATTTGCTTTTCAAAT TCCAATTTGTGATATTCCAATTTGTATGTGTGAGGTTGCTTGT GTTTGATTGTGTTGAATTGAGTTGTYGCTTGCATTGGATGCAG TTGATAGGATGGTGAAGTGTGAGAAGTTGGATTCGGGATGATG AAKATCACTTGGAGGGGTCTAAGGCGAC[A/G]TGGTGGTTGA ATAGACTGATAGGGCGCACGAAGAAAGTAACTGTTGACTGGC CATTCCCGTTTTCTGAGGGGAAGCTTTTTGTTCTTACTGTTAGT GCTGGGCTGGAGGGGTATCRTGTTTCTGTTGATGGGAGGCAT GTGACCTCTTTTCCTTATGGCACTGTAAGTKATATATATCTTT CTCCTCGAAGTTGCTAACC | 80 |
| S17291-001 | AAGACCCTTATGCACACCTAGCAACCTACATTGAGATTGTAA TACAACCAAGATTTCCGGTGTGCCAGAGGATGCAATTAGGTT GAGTTTGTTTTCATTTTCACTGTCTGGAGAAGCTAAGAGATGG CTACTCTCATTTAAGGGCAATAGTTTGAAGATTTGGGATGAA GTTATTGAAAAATTCTTGAAGAAATATTTC[C/T]CGAGTCAA AAATAGCAAAAGGAAAAGTTGTCATCTCTTTTTTTCACCAATT CCTAGATGAATCCTTGAGTGAAGTTCTAGAAAGATTCCGTAG CTTGCTACGAAAAACTCTGACTCATGGATTCCCAGAGCCGAT TCAACTTAATATCTTTATTGATGGGTTAAGGTCAYAGTCAAAG CAGTTTCTTGATGCTTCTGCTT | 84 |
| S13139-1 | GCTGAATGATATGATTCTAATAACTGTGGTTTAGACTTTACAC TTTGTTCTATTTCCATTTACTATTGTTTTTTTGTTCAAATCAGT TCCGAATTAGTGGATGCTGTCAAAGGTAGTGGTGATGCCATA CACAAAAAGGAAGAGACTCATAGAATKGCAGAGGCAAATAG AGCTTTTGCACATTTTCATTAATTCATGAA[C/T]GGGATCTATA TAGACAGACCCATATAGAGAGTATTTTGAAAATTGTAATCTG ACAATTAATCTATTACCCTATTACTTCCAAGAAACGGGGAAA GATTTGCCTTGTTTGGTACTTACACCATAAATATCTTTTTAGG AAAAATTCTGCTTTGGTTCTTTTACATCTGAGAAGTGGATATT TGTGTTTTTTGACAATATTT | 89 |
| S17292-001 | TATAAATTTTCTTGTATCATGTTCAATTCTTATTGATAAAAAA AAATACCTCTCATCTCTATTTACCATABCCAAGTTGAAGTAW GGGGCTGTGCTAAATCTTATTTMTAGAGAATCAAGTATGTAT TAATTGAATCAACTATCCATCAATAATTTCTTACCGTCTTTAA CAATGTAATCATTTAAGTACATTATCCCAC[A/G]TTCTTTATTC AAATCATTTCATTCTTTTTCACATAACTACTTAATTATCCTATT TAACTACGTAAGCTAAAAATGTGTCCYGTCAAATAATCATTTT CATTATTATGGTTATTGGTTAAGACACCGACACAACACAGGG TTTAAATCTAGTTATGCAAAAAATAAAAATATTATTATTGCTT CACTCTTAAACTGACTTC | 93 |
| S13146-1 | TGCTGCTAGTTATGTTAAATAGGTGATTAGGAAGTATTTGGA GAAAAGGACTCAAAAATAGGCCAAAAAYTGATGAAGTTGG | 98 |

TABLE 27-continued provides the genomic region comprising the polymorphism associated with a reproductive growth phenotype in soybean.

| Locus | Genomic region | SEQ ID |
|---|---|---|
| | ACTCTAACTATTCATCATGGCTATGATGAGTCATCATAGCCGC<br>AATCAAACATAGGCATCATCAAAGTCGTGATCCTTTAATCAT<br>AGCCCAATGACAGAAAAGTTATGAAGTTCATC[A/G]AAGCCA<br>TGATCTTTTGATCACGACTCAACAAAGATTTGGATTTGAAGG<br>ATCATCATGAMTTTGATGAATCCATCCTAGCCGTGATGAGGA<br>CACGTTGGCAGTCACGTAACATATTTATATAAATAGCCTTTTT<br>TAGACCCTAGGTTTCTAGTCTTTTATTCTTTTKCAGTTTTGAGA<br>AGTTCTGGGAGGCAAGAGTGCTA | |
| S17293-<br>001 | TAGAAAACACATGACCAAATAAAACCATTAACCCTAATTCCT<br>AAACAATATCTCTAATATATAAAGACCAACGATTTATAAAAG<br>TAAAAATAACATTCAAAATTAGGTGAATAAAAACAATTTAAT<br>ATAAAATTTAAATTATTAAACCTTAAACAATATCTCTAAAGCC<br>TAAAGACCAACAATTTGTAAGAGTAAAAACA[A/G]CATTCGA<br>AACTGAGTGAGTTAAAACACATGAACAAATAAAACCAATTTA<br>ATATAAAATTTAAATGATTAAAACCTAAACCCTAAATCTTAA<br>AACTTAATCTTAGCATAAAATCACTTAAATCAATTATTAAAAT<br>CTAACCCTAACTCCCTAAAAAACGTGTTTGATGATTGGGTGA<br>AGCCACCCAATTTGGCGCCACCAA | 102 |
| S17294-<br>001 | AAAAATAAAACATAAAAAAGGATATATAATAAGTTGAAAAG<br>TTAATAAGATAAAAAAATAAACACACTTGCTAAAGTTAAATC<br>AACAACACATAATAATAATAATAATAATAATAAYAATAA<br>TAATAATAATAAAATAAATTAATTAATTAATTAAATACAAAA<br>AGAGAAAGTAAGGAAAATTTCTAATTTTCATTG[C/T]ATTATC<br>GACRTGATTTGTCTCYTGTGTGAATCTCAGCATTAAAGTTGAT<br>AGAGTATTTTCAATTACAATAAATAAAANAATTCAGAGTATA<br>ATTTGWTTTCACCCATAAATATAAARAGAAATAACTAAAATA<br>CACAGAARATCAGAAATATATTATGTAAATAAAAATGCADGA<br>AGCAATCAVCAAGATAAAAATARAA | 106 |
| S17581-<br>001 | AACAAACAAATACAAATCCTATTTAAAAACATTTTTTAAAAC<br>ATAAATAACAAATTTTGCAAAAAAAAAATTAAAAACGTTCAT<br>ACAKAGGAAGTTACATTACGGATGAACTTCACCAGTACRAA<br>TGCAAAATTGGAAATGCGCAAATGCCATTAACGGAGACGTGA<br>AGCTTACCTCGACGRTGGAAGACCAAAKCACA[A/G]CTACAC<br>GTCCTCAATGCCTATGGTGAATCACCCTATGTGACACGGACG<br>AAGGAAGAAGAAGCTCGATCGGYGAYGAGAGGAGAAGAAG<br>RAGGAGGTCGAAGGCGCTGCGGAAGGAAGAAGGAAGYGTAT<br>GAAAATAAGCTGGTGCGCGASTTTTAAATTTTAAGTGAAGGG<br>AATTTTCGCCCATTCACTTAAAATGTTGG | 111 |
| S17691-<br>001 | TACATTGGTTTAGACATTTGTGACTCTAGCTATGATCATTGTG<br>TGATTGATTTGTACACAAGTTGAATAGTTAGCATGATCTTCCT<br>TGCTAGTGATTTCACTGACATTAGTCATGCATATTTGTGAAGA<br>TTTGAGCTTGAACAATAAGGTTTTATTACACTATATATCTATG<br>[CCTCTTTTCCTTGGCTATGTGATTAAGCTTCTCATCATTGTGGA<br>CTCTAGAATTTGTTTTGGAACCATGTTAAGATTG]TGTACTAGT<br>TTGCATTAATGAAGATGATCAAGGCACATAGGAAAATTCTTT<br>CTGGCCCTTGAATTAGTTGAGAGYTGTTGCCCCTTATTAGCCA<br>AATTTGAGCCTAACACTCTTGTTATTTGGTACCTTTGCATTTGT<br>TGAAATATTATAT | 115 |
| S17701-<br>001 | GCCTTCACTTCCATTTCACAAATACACAAAAAAAAAAAAAAA<br>TGCTAGTAGTGWAAACACTCAAAACACTCAAATTAAGCCCTT<br>TCAACCTTTCTTTCTTATGAGTTTACAATCTCAAAGCCCATCA<br>AAGTTCACGACCCTATTCATCTCTTCCAACATGAGCAACCCTT<br>CAGATGAAAGGGAGCAGTGTCAAAAGAAGA[C/G]GAAATCCA<br>CCATATGCGAAGCCTCTAACTTTAGGACATCAAGGAGAAGAT<br>TCTGCAGCAACAACAAAAATGAAGAGGAGATGAACAATAAG<br>GGAGTTTCAACAACACTGAAGCTTTACGATGATCCTTGGAAG<br>ATCAAGAAGACGCTAACCGATAGCGATTTGGGAATCCTAAGT<br>AGACTCTTGCTGGCTGCAGATTTGG | 120 |
| S03703-1 | GTTGGAGGATCATAAACCACTTTTTTTTGCTAACAATGGTATT<br>GGTACAAAGAAGCCCTGCCMGAAGCGGTGACTAATCTTCGTC<br>RAAGACTATGAGCATACAAKAGATGAGTGTACGTATTCCCCT<br>CCCAACRTGATTTATTCATACCCAAGGACTAACCAGGATTCA<br>AACYATGAATCATTTGATTAAGCGACAMAAG[C/T]CGCTACC<br>ACTTGTGTCAACCGTTGTTRGTATCATAAACCACATTTATAAG<br>CTTAATTAGACACCTTCTCACTCCATTTAATAAATTATTTTGA<br>ATATTACTTTTTATTAATATGTTGGTGTGAAATAAGTCAATT<br>GGTCAGTCGTGTCATCTTATTACCAACAAGTGATTTCCTTTAG<br>GCGACTAACTCAAGAAAGAAA | 125 |

TABLE 27-continued provides the genomic region comprising the polymorphism associated with a reproductive growth phenotype in soybean.

| Locus | Genomic region | SEQ ID |
|---|---|---|
| S17297-001 | AKAGTACCAAACCATTTTTTTATACTTTCAAATGTTTCTTAAT GCTYAAATATATTAATTCAACAAAATAAAAAATAATTATTAW TAAGTAATAATTTTACAACAATATTTAATTTATTATTATACAG ATATAACATATACAABTRAAAAGAAATAAATTAATAATTTCA CAACACTATTTAATTTATTTCTGAAAAGCA[A/T]TAAACAACA TTTTCACAACAATATTTAATTTATAATATTAAACATATCAGTT TACACACAAAAAAACTTTCTTACATATGTATTTGATAGTTACA ATATAATATTTTTTTCTAAAAAAAACTTACTTTATTATTAGTT GTATTTGCTAAACAAATATTTGAATCACGTAACTAAAAAGAA AAGAATTTGTATCTGTCGC | 129 |
| S17298-001 | AGTTCTTGTTGCTATATATTCGTTATCCTTAATTAACCACATA CGTGAAATTTAAAGATGCCATCACAAGCAGAGCTAAGCATGA TGGATTACAAGCCCTACAGCTACTCHACACTGCTGAAATCAT TTTTAGATCAAACTGAAACTGATCAGACCTACAAGCTTGAAG AGTTCCTCTCTCGCTTAGAGGAAGAACGTGT[A/C]AAGATTGA TGCCTTCAAGCGCGAGCTTCCTCTCTGCATGCAACTCCTCACC AACGGTACAAGTTTCAATCAATCATCATCATGGTTTCACCAA AGAAACATATCAAACGTAGTTGATGATATTCCAAATTCCAAT GAACCAATTAAAACATGGAATGTCCTAAACCCTAAAGTTTCA TCAATACCCCATGATGAAAATAT | 133 |
| S17299-001 | CACTATAACAAAATTGACTTGTTTTTTTTTAAATAACAAAAC TGACTTATACTAAGTAGGTTATATTTTGCTTATAAARAGAAGT AGCTTATATTTTAATCTTTCAACACATAAAACATTGTCAATAA ATAGTAGAGGTGRCTTACACTACTAAAAAAAAAGGCCTTTTA CATCGGTTCTAATGACTTTTCTACATCAA[C/T]TATGACGCGTG GTGGTAGTCCAATGTTGTCVAATAACGACATCGGTTGAAGGA CCGTCTTTGAAGAACATTGRTACGAAGACGAGCATGGTACCA AACTCTTCTTAGAATGGGAATTGTTCTATATCGGTTGTGTAGG TACAACAAATGTAGAATGTTAGTTTTCTACATCGGTTCTKAGG GTGAAACCGATGTAGAATG | 137 |
| S17300-001 | GTCGGATGCTCTTATTTTACTCTTATTATTTTCCAGTATTTCGT TTCTGGCTATCCATATCAAGGAGATGCTAAATTTTAGAAGAA TAGATATTGATATTATTAGTAATTATACTGGATGGTTATTTGG CTGATGAAATAGTCGGATACCCCTCCTTGATTAAAAAATAA TCATATAAGTAGAGATGTCAAATTTTCGA[C/T]TAGTGGAATA GTTGAGTGTCCTTCACAACCCACTAAAAGACAATCTCAGACA TCTAGCCACCAGAGTGTCTGAATACTTCCTAGAACATAAATG TCAGAYGGCAAGACAAATATAGACCTTGACCTTTTGGTTGGT CGGATGCCCGGATATGCATTTGGCCACCCGAATAATCAAATA CTCAATAAAGAGTAAACTCGAC | 141 |
| S17301-001 | AATAGTATGCTATTCAAAAGTAGGTTATCGAAATGTGTTTGA ATGACTCATGTTCGCAAGGAAAATATCAGTACAAAAGACCTC AATTTACCATACAATTTGATAAGGGGAACAACTTAYAGAAAA CATTATCGGACAAGAAAATTTGGATTAGTAAAGAATAACCCT ATCACCTGTCATATACCCCTTTATAGATAGCA[A/G]GATCATG AGAAATACTCRGGATAAAGTATAGTCTAAGGAAACAACTTTA TCTCTTAGCTTGGCAATATCTAACTATTTAACTATGCTATTTGT AACTAAATTGTGCCCTAACGRATCTCAAGGTCTTGACATTTCT CTCAACAATGTYGTCTCGAACTAATCCATACATAGCCTTAAA CTACTCACCATTTRAGGTGTCT | 145 |
| S17306-001 | GGATAAAGAAAATAAAAACATTTTTTTTTCTTTCTTTCTCTTTC TTTTCATTAAAGGCTATGTTTGACAACTAGCCGGAAAGCTAG CTAGAAATTAATGTTTTAAGAAAATGTAACTTCAAACAAAGT TACTAAAAAAGTTAAAACTTAATTTTTCATGTTTGATATGTAT TTTTAAGAAACATGTTTTTAGGAAACTAT[A/G]AAACTATGAT TCTTAGGAATAATTTTTAACTCACATTCTTGCAAAAACAAAAA ATCCCATGGAGAAGGATGAGGGGTAGAATCTTACTTTTTAAA GTTTAATTTTTTGCTTCACTATAATAAAAACAGGTGCTACTCT TATTAAGTTATTCAATGTGGTAAATTTTAAAGTTATTGATAAA AATATCACGTAAATTTTTT | 149 |
| S17310-001 | CGATGATCGCAAAGTTTGGCTACGACAATAGCTTGAGTGAGG GAAGGTGGTTGGAAGGCCAGTACCTCATGGCGCAATTCTGGT GTAAGGCCGGAAATGGAGCAACTCATCAGGAATGTTGGAGC AAGGCCCACAATGCGATTAGCCAGTGTTCGAATTCCGTGAG GTATTCATTGATGGTGCCTCTTTATTGCACTTT[G/T]AACAGAG CTCCTTGCGTATTTTCGTAGAAGGACGAGGAAAACTGAGACT CTAAGGCCTAAAGCATAGTTGACCATGACATGAAGAAGCCGT | 153 |

TABLE 27-continued provides the genomic region comprising the polymorphism associated with a reproductive growth phenotype in soybean.

| Locus | Genomic region | SEQ ID |
|---|---|---|
| | TGCGGGACATCCATGGGTACCACGAGAACGTTGGGCCCTCCA<br>TGTAAAAGGAGGCCACGGTCAAGYGTTCATGGTTCAAGAGAC<br>CCTAATAATCAAAGAATTGTGATAT | |
| S17311-<br>001 | AAAATTTGAATTCATCGTGGATTGGAAAGTATCTAGGGTATT<br>CACAAGACCAAATGGAGTCGTGAAGTGCTCATAATGACCTTC<br>GTKAGTGTGAAAGGAAATTTTGGGAATGTTAGATTCCCTTAT<br>GCGGATCTGATGAAATCTAGATTTTAAATCAAGCTTCGAGTA<br>GACGCAGGAGTMATGGATCTTGTCAATGAGCC[C/T]CGTTGAT<br>GGTTGTAATAGGATACTTATCTAGGACAAGGACCTTATTGAG<br>GGCCCTAAAGTCCACACATATCCTTTATGATTCATCTTTCTTC<br>ACTAAGATGATAGGGCTCGAAAATGGACTAATTGAGTGACGG<br>ATGATGTCCTTTGTGAGAAGCTCTTGCACTTGTCGCTTAATCT<br>CGTCCTTGTGATGGTAAGCATTT | 157 |
| S17312-<br>001 | TTGTTTGCAGYCGACAAGTGTACTGGATCGCACAAGTAGTAT<br>AAAACGATAAGAACCAAGTATCAAACTCTTGGGGAACTTGTG<br>TTATCTATCAAGCTATTTCGRTAAATAGGTGTCTGGTATGAAA<br>AGATGATTGTGGTTATGAACAAGTATGTAAACTATCTATGCA<br>AAAAGAAAGAAAATCACGCAACATAAATGTT[G/T]TGTAAAA<br>ACAAGTAGAGAACGCGTTGGTCTTCCTAATWGGTTCCTGATG<br>CTAAAACGGATGTTCTCTATCTAACAATGCTCATGTATTCCTA<br>TGTTGTCTCCTGGACTGTTAGACCCCGATTCCTCATGATAGCC<br>TAGCGTAATCCTGATCAAGTCTCATCCGCAGATTCCTCTTGTA<br>AGACTAAACTCATTCAGGACCG | 161 |
| S17313-<br>001 | AATATTAGTAGTTTYGTATTCCATTTTATTTGTTCTTCTCTTTA<br>ATTACCAAACAACCAACCCCCCCCCCCMYCGTTACTGTTACT<br>GCAAGTATATTATGAACATTTGGCTTGTCACTGCTCGTTGGGA<br>AACGACCTAGGATCACTTCCTAGTTACTGCATTTTCATGTTTA<br>TTTGATTCGGGTACGGCCTCGATCACAC[C/G]CCCTCGCCTTC<br>AGAGGACTACACGTCCTCCTCTTCAAAGGACTATACGTCCTCT<br>TCTTCAGAGGACCACACRTCCTCCCCTTCAGAGGACTTCACGT<br>CCTTGCCATCAGAGGACTACAYGTCCTCACCTTCAGAGGGAT<br>ACACATCCTCACCTTCATAGGATTACACGTCCTCCCCTTCASA<br>GGGCTGCACGCCCTCGCC | 165 |
| S17316-<br>001 | TTCTRTTTTCAATAACGAGCGTCTCGATATATTACGVGACTCA<br>ATCGGAGATCYGTGTAAAAAGTTATTGTCGTTTGATTTTTCTC<br>AGAGCTTCAGTTTTCAATTCCGAGCGTCTCGATATACTACGGG<br>ACACAATCRGACATCCGASTTAAAATTTATTGTCGTTTGATAT<br>TTCTAAGAGCTTCCATTTTCGATTACGA[A/G]GATTTTGATATA<br>TTAYGGGACACAATCGAACATCCGAGTAAAAAGTTATTCGT<br>TTGATTTTTCTCAGAGCTTCAGTTTTCWATTTCGAGCGTCTCG<br>ATATACCACGGGACACMATCARACATMCKAGTCAAAAGTTA<br>TTGTCGTTYRAATTTGCTAAGAGCTTCTGTTTTCAATTACGAG<br>CRCCAGCCCCACGTCATNN | 169 |
| S17317-<br>001 | TCAATTATTTCAGCATGAAATACAAAARGATCTTCAGATGGG<br>TGTTTCATAGCATCAAGAATATTAAAATGAACAGTTATATCA<br>CCAAACTCCATAGATAGTGTGCCTGCATATACATCTATCTTAG<br>TTCTAGCAGTTTTCATAAAAGGTCTGCCTAGAATGATGGGAA<br>CTGATCCTTGAGAAAATCCCTCCTCCATTTT[A/C]AAAATATA<br>AAAATCAACAGGGAAAATTAGTTCACCAACTCTAACTAAGAC<br>ATCCTCTATGAAACCAGCAGGATAGGCAACACTTCTATTAGC<br>TAAATGAATTACCACATCAGTTGRCTGCAAAGGACCAAGAGA<br>TAGAGAATTAAAAATAGACAGAGGCATAACACTAACAGAAG<br>CTCCTAAATCYAGCATGGCATTGTC | 173 |
| S17318-<br>001 | AATCTTAAATAGATAGTTAGAGTTTTACATCAAGAGTGCTCA<br>GTGGAAAAATTCTCTAACAATGAAGTGTTTAGCCCTCCATTA<br>GCARGGAGGGCTCAATACAAGGTTGAAACAAGATAGAAATT<br>GAGTGGTGAAGTGAATGTGTGAAGAAAGTAGCTTCCTTCAGC<br>CTTGATGCTCTATTTCTTTTCTCCCAACCTGC[C/T]GACACTTT<br>GTTTTCCCTTCCTGTTCTATTTTAATGACTTTTGGGATTCTCG<br>GATTATGAATGCGCACTCAGCCAGCATGTCTCGCTGAGTGAG<br>AGTTAGTGATTAGGCTCTTAGCGAGCTTTGACACGCTAAGCG<br>CGAGAAGCGACAAAGGCTTCGCTGGGCGGGCTGGTTGCGTGC<br>TTAGCACGTTGCTCTCTGAATT | 177 |
| S17322-<br>001 | TTGAATATTAATTATTGATAGTTATTAATAAATTATTTATTCA<br>TAGTTATCAATTGATTTTTTACAATTGATAGTTTACTAGCTAG<br>CTTTCTGCTAAAAACTGTTTGAAAGCAAAATGCAAATGCTAT<br>ATGCTGTGTTGTGTGGTCTGATTTGAAATTTACAGGTTAAATT<br>TTGGGTTTTTTTTTGTAAAAACAGAAAGT[C/G]TATTTAAAAA | 181 |

TABLE 27-continued provides the genomic region comprising the polymorphism associated with a reproductive growth phenotype in soybean.

| Locus | Genomic region | SEQ ID |
|---|---|---|
| | AAATCCTAATAACAACATCGATTTTTTTATAAAAAAAAGCCG<br>ATGTTAATCTACACAAACAACATTGGTTTTTTGGAAAAATCG<br>ATGTTAATATCCAAAARCGTTAACATCGRTTTCTGTGAAAAAC<br>CGATGTTAACATAGAAAATGTTAACATCGGTTTTCTATAGTTC<br>ACATCGGTTTTTGACTGAAA | |
| S17326-001 | GGGCAYGGTAAACAGCTGGTTAGTGAACTAGATTCTTGTTCT<br>TTCTTTTCAAAGTGTTTCAAGATATCCTGAACTAAYGTAATTT<br>GATGCTCCCTGTAACTCCCGTAGTCCCGCTGTATGBTGTGTTG<br>AATTGCTTGCTCAGGCAGCTTGAAGGAGCACATTGCTAAGGT<br>TAAAATAGCTGAAATTGCATTTATGGTGCA[A/C]TTATGCAAT<br>TTGCTGTAAGCAGTGTTGTGGTAGTAATGTTCTAAATCTTGAA<br>AGTGTTGTTTCCTAGGTTTATAGCATCTATTTAAGGACTCATG<br>AGAAATCCCAGTTTATTGGAACATGTTTGTCTCGCTGACATCT<br>ATCTGCTGTAGCATTCAACTAGTCTGTGTTTTGGTAACTGTGT<br>GGACATGCCATTCAATCCC | 185 |
| S17327-001 | ATAGTGGATGTAACTAGAGTCTAACAGAGAGACTATGGTGGT<br>TATAGGCAGTCTTCTTCNGCCATGTAAAGATAATACCAGTCTA<br>ATTGCTCCATAGTGAAGATGAGTGTATCCTTGGTGTTGCTAAC<br>TTCTGATCAGTTGTTTAGGAATCTCAATATTAACATATTGCTC<br>CTCAAAAGTAGCAGTTAAAGAGGACTGGT[C/T]CATTCTTAAA<br>GATTGGACATATTCTTTCATATGAGGTCTTCTAGTGGTGATCA<br>AGTTGGTAATAGATCTTAAAGAGTAACGATGTCTTTTAAATAT<br>ATGGTAAGGGCTCAACAAGGGATTTAGTGACTGAGAGATTTG<br>AGCATCTTCTGGAATATATGAATATTCTACAAGATTCTCTATT<br>TTTCTGAAAGAGTTTTGGA | 189 |
| S17328-001 | RTCTCTACCAAGAGATTCAGCAAGATCCACGTGTTTTGGAGTC<br>CATAGATTCAATCHCATTTGTTGAAACTCCTTTGCATGTTGCT<br>GCATCTCTTGGTCATTTTGAGTTTGCTAYTRAGATCATGACAC<br>TGAAACCTTMACTTGCTGTGAAACTAAATCCAGAAGGCTTCA<br>CTCCCATCMACCTTGCTTTACAATGCATC[C/T]ATGATAAAAT<br>GGTCCTTCRCCTTGTAGAAATGARCAAAGATCTCGTCCGAGTC<br>AAAGGGAGTGAAGGCTTCACTCCACTGCATTTTGCAAGTCAA<br>CAAWGTAAAACTGAGCTTTTKGATAAGTTCCTCAAGGCTTGT<br>CCAGATTCCATTGAGGATGTGACTACCAGAAGTGARACCGCA<br>CTACATATTGCAGTGAAACAT | 193 |
| S17329-001 | ATCATTTGAGAATTATACTTCMAAGTTCAGACCTCATTTGAG<br>GCACAAAATTTCKTGCTCCTTCTCTCCYTCTCCCTCCACTCAT<br>CTTCYCCTTCCTTCRAGCTCTTATCCAYGGCTTCCTGTGGTGG<br>TGAGCTTYTTCTTGACTCATCTTCTCCTTGAAGTGGCRTCTCC<br>AATCATCTTTCTTCCTTCTCCATTTYGCT[G/T]CCATGATCTTC<br>AAGAAGCAAAGGACTCCATTGATGAAGAAGATCCAAGGCCT<br>ACAAGCTCCACATAGAGCTACATCACTTAGCAACTCTCCAAT<br>GGTCAATACCTGGATTACTCTAATATCTTCCTAACATTCCAAC<br>TRCAAAAGCAATGCCAGACCTTGTGCATACTTGAGCATACAT<br>AAGGCTTCCAACAACTAAAGC | 197 |
| S10746-1 | TGGTTGATTCGAAGAACAATTGGTTTTGATTAAYGTGATGA<br>AGGTGTTTGCTAAGTTGGCTCCCTTGGAACCTAGGTTGGGGA<br>AGATTGTTGAGCCTGTTTGTGACCADATGAGGCGCTCTGGGG<br>CCCAGGCATTGGTGTTTAAGTGTGTTAGGACTGTGCTCACTAG<br>CTTGAGTGATTATCATTYTGCTATTAGGCTC[A/G]TTGTTGAGA<br>AGGCTAGGGATTTGTTGGTTGATCAGGATCCCAATCTTAGAT<br>ATCTTGGTCTGTAGGCGCTTTTGGTTGCCACTCATAAGCACTT<br>GTGGGTGGTGATAGAGAATAKGGAAGTGGTGGTTAAGTCGTT<br>GAGTGATGATGATTTGACTATCAAGATCYTGTYAGTRCGATT<br>KTTGATGGGCATATATGGTGTC | 202 |
| S17331-001 | TTCATTGGAATGGAATATAACAAAGTAATTAGATTAGATAAG<br>AARAATAGTTGGAAATGAGACGTTAGTGTGGTGTGCGAGGCG<br>AGGCCATGTGCTCCAATGCGGCGGTTATTTAAATATGTCGTAT<br>TGTTTAGKTACACACATTAACGTCAAAGTTTCAAACTATATGC<br>GGTTGTCTCYGSTCTTCTCAGATTCTCTCC[C/T]ACGATGTTAT<br>TAATTGTCTTCATTTCCCATCTCTATTCTCTATTTGATCACACC<br>GTTAACATGTTCCCATTCCATCTCATTGACAATACAAAATAAA<br>TTATTTATGCACTGAAATTAATATCTTAACACACATTTTTATTT<br>TTTTGGTAACGTCACACATTTTTATTTTCATTGTAAATTATCAG<br>GTGTAATAAATTTAWT | 206 |
| S17332-001 | TCCAAAATTTTAAYAGTTACGATGAACARACTAAGCGCAACA<br>GGCGCGYTTAGCACGTTCATCGCTATTTCCAAACAAAACCAC<br>AGGGGTYTTCACCCGTTTTAGCCACATGGCCCCTAATGGGCTT | 210 |

TABLE 27-continued provides the genomic region comprising the polymorphism associated with a reproductive growth phenotype in soybean.

| Locus | Genomic region | SEQ ID |
|---|---|---|
| | CTAAGTTACCTAAAATCCTATATTGACTAACCCTAAAACTAAT<br>AACCTTACCCTAACAACATACAACTAAGAA[A/T]ACAAGAAG<br>TCATCTATCCTAAGGTTTGAAGAATGAAAAATGGAAATAGAA<br>AAGTACTCACTTACTTGGATTGTTCTTGAAATGAAGCAAAGA<br>AGATGYAGACAAGCAGTACACACACAGCAAAAATACACACT<br>TGCTYAGGGTTCACAAATGTAGAAGCTGAAGGTATTTGGGGT<br>AACACCCAAGATCCTTAGCCTTTGT | |
| S17337-001 | TAGTCTTGTTATTTTTTAATTGAGACAATTTATTYCCAATTTTA<br>AAAAGTTTATAATTTTARTCTCCTATTTTTTAAATTAGACGTTT<br>CGTCTTTCACTTTTAAAAAAATCAATAATTTTAATCTTTATGT<br>CCAATTTCAAACGTTGATCTATACACTTTTGTAAATGTTGATT<br>GATAATTTTTTTATTATGTACATGA[C/T]AAATATTTTTTTAT<br>AATTATTTAATTGTTATCAAGCTTAATTTATTAAAAGAATTAA<br>AAAAAGTCTTAATTAATATCACGGTCAATAGGTTTTAAATTG<br>ATCAAGGAGATTAAAATTATAAATTTTTTTTAAAAATAGAG<br>GACGAAATGTTACAATTAAAAAAAAATAAGGAGACTAAAATT<br>GTATATTTTTTWAAATG | 214 |
| S13093-1 | TAAACACATGAATTTTTTTATCGACAAATATTAATCATTAAT<br>TTGTTAGTAAGAGGATMGAACTGCGCSATATTTTTCTTGTTCC<br>GTTAAATTANACACATGAATTAATATGAAGGGAAAATTAAAC<br>AACAACATGATACATACCTCAGCATGCACAACATGAAGCATC<br>GAGTCTCCAGMARGTGAGGAATTGGCACTT[C/T]TAACATCAA<br>TGTTCTCTTCATGCAGCATTCGAATGATCTCAGAGAAAATGA<br>ACTGGTGGTCTAATCCACAAGTAAGAACAACTTGTAAAGAAG<br>AACCCACTTCGTGAATCTCAAGTTGTGGCGATTTTGGGAAAC<br>CTGCAGAAGTTGCAGCAAAATTGGTACTATTATTGGAGAAGC<br>AATCACGGGATCTCTTTCTAATT | 219 |
| S12211-1 | TACTAGACACTCACTCATTGGATTATGAGTATTGGTATTAAAT<br>GTGACCATCACTTACAACATTTAAACTTATGATAGTATTAAAT<br>GTGACCACCACTTTCCTTGGTCTTGATGATTTGTCCTATATTTC<br>TTATATATAGGACCAGAGGTAGTAGATTCCAAAAGTTTATGC<br>TACCACAATATTACTTGTAAAGCTGCAA[C/T]GCCATACTAAA<br>CCATAATACATAACTGAGTGAGCTTAATGCAAATTGCTTGTTC<br>ACCAGAAATAAATAGAAGATTCAGGCACGCGGTACAACAGG<br>ATAATGGAGTCAAAACACAAAACTAAAGTTATTTATAGACTA<br>CCATGTATTTTATTAAATGACCACTAATTTGTGATATAGGCCA<br>TTAAAAAACAATTTCATCAA | 224 |
| S04555-1 | CTTCAATGGCATGGCCGTGGAAAGAAACAGAGCTTAGATTCT<br>CTGTTTTTAATTCTCCAACGAGGAAGCTCCGATTCGAAAATTG<br>CCTCCGCTAGGGTTCTGCAGTTCATCGCCGTGGACGCGGATG<br>CGAAGATYTCAATCGYCGAGAAGCAAGGCGTGGTGGCCGAG<br>TTGCTGAAATCGGCCGCACCAGAGAAAGATCC[A/G]GTGCTG<br>ATCGAGGCCGCGCTGGCAAGCCTAGTGGMGATTTCGGTGCCG<br>AAGCGGAACAAACTGAAGMTGGTGAACCTCGGAGCGGTGAA<br>GGCGATGAAGAGGCTGTTGAAGGAGGCGAATTTGGGCGCGG<br>TGGAGAAGGTGCTGAAAGAGAATGAGAATGGAAGAGTGGAC<br>GACAATGAGAATGGAAAACTGAGGGTAGA | 229 |
| S08519-1 | TTTGAAAGAARAAAGAAAGTGCTCACTGCTACCAATATACTA<br>ATACCGAACCATCCAACCAAATTATCTTTCGTCTATACTTTTT<br>AGGCTTCACACTTGAGGAGGTGTGAACTGTATGGCCAAATTC<br>TATCAACAGACCAATCAAATATTAACCCATAAATGGCTCACC<br>ATGTCCAATCAGGCTCATGGCTGATCTATTG[C/G]CAGAGCTG<br>ACTCAATGTCAAGGCCAATGAACTGTTGTGCACTGATAGCAG<br>GAAGCACTAGAGCTGTGAAGAATTGGCAGGCCAACTAGTCT<br>TGGCGGCCCAACDTAACAGTCTCTTGATCCTTCTCATGGATCT<br>AGCTAAAGTGTCATTGGCCAGAACAGTTAAAGAATGGCACAC<br>TTGTTAAATAGGTGTGACTAGTC | 234 |
| S12876-1 | GAAAGGTCTTCCCCTGGTTCATTTCCTTGCTTCTTGGCTGACT<br>CACGAGGACTTCAATCGTTTTCTGCGAAGCTCTTAGGGTCGTG<br>GCTCGAATTGGGATCAGGGGATTCTCTCTTTCTCCGATGATCT<br>CCAAAATTGGAACCGGGAGGTGTTTGGCAATATCTTCCGAAA<br>TAGGGTCTCCTTAAGCAAATTCAGAGATT[C/G]GAAGCGTGCT<br>TGGGCTCCTCCTTTTCTGATGATCTCGTTTACAGATAACAAGA<br>GTTGTGGCGGGAATAGGAGCAAGTGCTGATACAGGAGGAAC<br>TATTATGGTTACAAAAATCTTTTTGTTACAGCAGGGGATTTCG<br>TCCATTTCTATTTATCTAACTCTTTCCCTGAGTTGGACATGTTG<br>GCTGCCAGGCCAGCTTGGT | 239 |

TABLE 27-continued provides the genomic region comprising the polymorphism associated with a reproductive growth phenotype in soybean.

| Locus | Genomic region | SEQ ID |
|---|---|---|
| S05937-1 | GAAGGGGGCTGGGTTGGAGTAACACAAGGGGAACTCATAGT<br>CAGGCTTGATAGACCATGCCCAAAGGAGTAAGGAGAAGAAT<br>TAGAATYCAWGTAGAGGAAATTATTGAGAAGCAAACAGGAA<br>ATGGCAACAATTGAATTGTTCCCATGTCCCAATGGGCAAAGT<br>CCAGCAAAATTAAGGAGAGGACCTTGATAATCATC[A/C]GCT<br>ATGACCATGTGCACTGGTGCATTTTGCAAGAGAGCCAACTCA<br>GCCAAGGGATCTTCACAATATAACCATAAAGGCTCTAATGCT<br>CTGTTTCATGACGAACTGGAGTCGGAGGTGGGCTGCAGGGTA<br>AGTTTGAGTTAAGTCACCAACAATACCATGAAAAACAAAGGC<br>GCTAGGGGAGCAAGGGCGTTCACATGCTT | 244 |
| S08575-1 | GCAATTTGAGTATAATTAGCTGCTTCTTTGGACATATGTTTGT<br>ACTGTGTGTTTAGTAGTGCTTTCACCAGGTCCAATGTGCATCA<br>AAACAGAAGCAACTAAAACTAGCTTCCACATTTTTTTAGATG<br>ATATGAGGTGATTTAAGCTTCAAACATGCATATTTGGAGTGG<br>ATCCAAACATGCGTCTAGTCTAAGAGATTC[A/G]GCAAGAAGT<br>TCAAAGAGATGAAGCTCTAAATTTATTATTTTTGTAATATTCA<br>GAAATTAAGCTTATTACCATGAGCATAAGTGCATAGTTACAA<br>CAATTTACTGAGACCTCTTTCATTATGGTTGCTCATAAATGGA<br>ATAACATTTTCATTTTTAATTATATCATGTTATTCTCWACATC<br>TTCCGATTGCTTAGTTTGAA | 249 |
| S08669-1 | CCTCCATTCATCTAGATAAAMAGTTGAAGTTTAGCACAAGGT<br>ATGTTATGCTTGTACATTGTCCACACTTCAAGCCCAAAACGTC<br>TTGCATGAGGTGGTGGGTTGGTTTTTGACATATCATAATATGT<br>GTATCTTGTGCTAACTGATCAGAAACTTCATTACATTATCTGT<br>TTTTTCTGGGTCATTTTCTTATGGGACAT[C/T]TCCTCTAKGTC<br>CTCAGATCTGAAGAGGCTGAGAATATTGGATATGTGATTCCT<br>ACAACTGTTGTATCTCATTTTTTGACCGATTATGAAAGGAATG<br>GCAGGTATACTGGTAAGAAACTCTTCTAGAATATGGTTATATT<br>TGATAGATTTGGCATGTCACTATGTCTTATTTGAGTAAGCACA<br>CTGGATTGTGTATTTTTT | 254 |
| S11212-1 | TAGTCTTATAAGAACTTCAAGACTTGTTTCTTTAAGGTGACAA<br>TAAAKTCGATTACTGGGAATAACTTATTCTTTGATTCAAAGAA<br>ATCCTTGTTTCCTTTATATAGGCTKCCATATCTGTGTYAGTAT<br>GATGAATACCTTAAGGATTTTTTTTASCAAAAGGAGCTCCAAG<br>ACCTTGCCTTCCTCGAGACCCTCCCCCG[G/T]TTACTTCCTGTT<br>AAACAAATATTTTCCCTCCTTAAGTCTCCTAATCTCATTTGGG<br>ATCTTGAGGGTTAGTTGTTTTTCTTTTGTGCACATBTCATTTTT<br>TGCCCAAACTTTCTGATTTATTATTTTTGACTTGTTTCAGGTAT<br>AACGACTCAAGCACGCGCCAACATGACTGCTTTCTAACTTGC<br>CCACAAAAACTGTAT | 259 |
| S00543-1 | CTTCAATTGATAAAGCATTTGCAAGCTGTGAATTGAAGTTGC<br>AAAACCACAACTTCATGGAAATCCTTCAAGAAAATAAACTAG<br>AAACTATGAATATGTAGTAGTAGCAGTGTTAGTCAGAATAAG<br>TAGCATGCAATATGAACAACTTGACAACACACTATAAACATA<br>AATGATAAATAACTGACTGTTCCACTTATCCA[G/T]TGGTTCA<br>TTAATATCAAATATCAAACATCTTTGACAATTATTAGACATGC<br>ATACTCATGTGAAAAGGGAAAGGTAATTTTGATGTTGAAAAT<br>ATRCAGAATATGTATGTATACTACATACCATGGTTACTAATTA<br>CTATTTACTATCTACGGGATTGTAGGCTACAGCTACTATTGTT<br>ATACTCCACCTCTAGCTGAAAC | 264 |
| S01452-1 | TTCAAACCAACTTAGSAGCTTGAAGCTCAAGAATAGGAAGAT<br>AGGTCCCCAAAATGGAATTGAGTGTRAAGTAGAAACTGAAAA<br>TACATTTGATGGTGTTTTGGATCCTTCTGTTGTATGAGCATAA<br>GGATGCAGTCAAACAATGAATGATGAATCCAATAGCTATAAG<br>AGGAWACAAACATGTGGCATATGTGAAGCAA[C/T]TGGTCAC<br>AACAGACGAAAATGTATTGGTGGCTCTCAAAATGCACAACAT<br>GCAGTTGGTGGGTTTGGTATTCCTTCAAGTCAGCAAACATAC<br>AATGCTCCTAAACCTACAGTTGAGTATAATTATCATCTGGTAT<br>ATAATTGCTTACTTTAGCCTCATTAATTGTAAATGGTTGTTAT<br>TTAATCAATAGTTACTTAAGTAC | 269 |
| S11993-1 | CATCTCATTCTGAATCTTGCGCCGTTTCCCTCTCCCACTCGCC<br>AGGTACGTCATGTMGTTTTTGCTTCCCCGTTGTTGCGTCGATA<br>CGACTTGTCGTTTAGCACGTTCATGTTCATGTTCGGTTCGTGT<br>GTGTTGCAGTGAGGTGATTTGATTTGATTTGTGAGTGCTGCGG<br>ANTTTTTTTTTTCCATTTCCAGCACAAT[C/T]GATTCGTCGGTA<br>CAACTTGTCGTTTAGCACGTTCATGTTCATGTTTGATTCGTGT | 274 |

TABLE 27-continued provides the genomic region comprising the polymorphism associated with a reproductive growth phenotype in soybean.

| Locus | Genomic region | SEQ ID |
|---|---|---|
| | GTTGCATTGRTTTGATAGTGTTGCGGAATTTTTTAGAAGTGTG<br>AATGTTCGTTCATGCATGAGCGGCTCTTAAAGTTKCCTTGCGG<br>ATTCGATTGCGATATATTGAGACTGCGATGGCCTCAGCCGTC<br>GTGAATTTCTTGAACGC | |
| S13446-1 | GGGGTTTATAAGRCCTTAGACTTTCGAACTACAACAGCTAGC<br>ATCTATGGTGTGATTCTCCGAAGTTTAGTTTTTGGGGTGTGAT<br>TCTCCTAACCGAACTAGTCAAACAACTATTGCACAACCAGCC<br>TGCATGGGCACGGGGCTGCGCTACTTTCGTACTCAAGCCTTCT<br>GATACTGAATCCTAGATTATTCAATCTGAG[C/T]GTGGTGGGA<br>TGTTAAGATCCAATTTCAAGGTATGGTACTTATGTCCCACATT<br>AGAAGCYTGGGATTCTAGAGTAGGGTTTATAAGGCCTTAGGC<br>TTTCCAACTACAACAACTAGMATCTATGGCATGATTCTCCAA<br>AGGTTAGCTTTTGGGGTGTGATTCTCCCAACAAAACTAGTCA<br>AACGGCTAGTGCACAACCAACC | 279 |
| S00252-1 | TTTGTAAGAGAACCTAATTTTTGACTATAATGTGCTTGAATTT<br>GATACATATATCTTATTTAAGGAAGATCCAAACTCATATCAA<br>CCACATGTTGATTATATAACACATAATTAAATAATTAAGTGG<br>ATGGTATGAATTAGTTTTGGTGATGGCACATGTATGCATGCA<br>GCTGGGCAATAATGGATGGGGAAGCGGTCTC[A/T]TGGTACTA<br>TGATTCAAGCTCCCCGGACGGCACCGGTGCTTCTTCATCGGTG<br>GCATCTAAGAACATTGTCTCCGAGAGGAATAGAAGGAAGAA<br>GCTCAACGATAGGCTTTTGGCACTTAGAGCAGTGGTCCCCAA<br>CATTACCAAGGTACTCCATCACCTTAATTAATTAAACTAGCAA<br>TTATTATTGTTCATCATATATTT | 284 |
| S04060-1 | GCCGCCGGAACTGCTTCGGACTCCCTCACTCTTGGAGCGACTC<br>AGGTCCTTCCATAATCTTTCTCTCCACAAACATGTCCAACCCG<br>AGCCAGAGCCAGAGCCAGAACCTGAACCTGAAAAGCCGGAA<br>CTGGTTCGGAGTCCCTCGCTCTTGCAGCGGATTCAGTCCATAA<br>ACTTCTCCCATCTCTACAGATCCGACTTCA[C/G]TCACCGAGA<br>TGATGAGGATCCSGATTCGGGTTCGGATCCGGGTCGCGGTTC<br>GGGAAAGGCGGCGGAGATGAGGAAATCGGCGAGCGTGAGAG<br>GGGGTTTGACGGATAGCGAGTGGGAGGAGGTCGAGAAGCGG<br>AGGCCGCAGACGGCGAGGCCGGTTGAAACGACGACGTCGTG<br>GAGAGAAGACGAAGAAGTAGACGCCA | 289 |
| S02664-1 | AATCGTTTACAGTTGTGAAAAAACTGCATTGGTCCTTTAATTT<br>AATTTATAAAATGATAAATATATCTTTAGAATTTAGTTTAATR<br>AATTCTAAGGATGAGATTTAGAACTGCTGCACATTGCAGTTC<br>ATTTTTAAACTGCAGAGGTCCCATTCTCTGTAAAAAAAAGAA<br>TTTTCTTCCTCTGCTATTCCTTTCYATCTT[A/G]TTCGTTCATTT<br>CTCAACTAGTTCATCCTAAGGAAACCAAAACTACTAATATAT<br>GAAATGAAGGACACTATATAACTAAAGAGACATATGWCGGA<br>CCATTTTTAAATATATAAAACTCTATTAGAACTGCTAAAGTGA<br>AGATCCTTATTCTTTGCCTACAAATTTACTTACGTACAATACG<br>AAGGAGGAACTAAAGTTTAT | 294 |
| S00281-1 | AATTTTCTTGCTACCATACCCAAATGGATTGGGAGGTCCTACT<br>TTTTCCTTTTCATTGAGTGACATAGAGAAGAATTTGAAGGCTT<br>CATATTCCAATTCGGATATAGCTTCCATGGAGACACCATGATT<br>GATGACTTTGAAGAATCCAAACTCCTCACAAGCCTTCACTAT<br>AAGGGTCTTTGCATCAGGTTTGGAGAGGT[C/T]CACTATGGGA<br>ATTGTTGAGGAAAATTTGGTTGGCATGCAGTTCTTAATGTAGG<br>AGTATTGTTCTGTTGTTGCTTTGGACAACAACACCATTTTTCTT<br>GTTGTTTGCTCGGCCGTTRTTCTGTTTTGTGGTGTTAAGAAGT<br>GGAGTGAAAGATAGGGAGAAGGTACGTGAGAGAGGAACAGA<br>GATATTTGAAAAGCTTTTG | 299 |
| S01109-1 | GATTCTGGTGACCCTKCTCTCGGTTCTCTCTTCTGCATCGTGT<br>GCACGAATGGTTGGGGGGAAGACGGAGATCCCTGAAGTGAG<br>AAAAAACAGGCAAGTGCAAGAGCTTGGAAGGTTCGCGGTGG<br>AGGAGTATAACCTTGGTTTAAAGCTGTTGAAGAACAACAACG<br>TCGACAATGGGAGAGAACAGTTGAACTTTTCAG[A/C]GGTGGT<br>GGAGGCGCAGCAACAAGTGGTGTCAGGGATGAAGTACTACTT<br>GAAGATCTCTGCTACTCATAATGGTGTTCACGAAATGTTCAM<br>CTCTGTGGTGGTGGTCAAGCCATGGCTTCATTCCAAGCAGCTC<br>CTCCATTTTGCGCCTGCATCATCATCCACCACCACCACCACCA<br>CCACCATGCATCCAGTAGTACGTA | 304 |
| S13844-1 | GCCACCGTGTTTTTTAAGATCTGTGCTCATTAAGAAAAACAA<br>AGCAACTTGMTGAAACCTTTTATCCACATACACATATATGGTTA<br>GTTAACCTTAATCCCCATTGCTCAAGCAGATATTAAATATTCT<br>TTGTGAGCACTGAGCAGCCCTCATATGTTTATGTACTGAAAG | 309 |

TABLE 27-continued provides the genomic region comprising the polymorphism associated with a reproductive growth phenotype in soybean.

| Locus | Genomic region | SEQ ID |
|---|---|---|
| | ATCAATATTACTTGTTAGTGATAAAGACTAC[G/T]TAAGGGAT<br>AAGAATGAACATAGCTGCAGGAATATTCTTGGTTTTTTTTAGT<br>ACTGCACAATTAATTCTGTATTTATGTCTCTCTTTAGTCTTTTT<br>CGGCTTTCCATCATGCATATATCTAATATTTACTTTAAATTTAT<br>TGGTATCTTTTTTTTTTTACTCTTCCTGAATTTTATATTTCATAC<br>ATTCTTTTAATTAAAA | |
| S05058-1 | CCCTCAATACAGAGCCACTGGGCAGATACTCATCCATTTGAA<br>GTTCTCCCGACATTAATAGTGGATCTGTGAGTTTCCACCATTT<br>GAGTTGTGCTATATTATCACCATTTTTATCTTTTGACATGCTAT<br>TATTTGTAAATCAACCAAAAATGATACGCAATTTTGACTCAG<br>AATTGTTTAGACCAATTACTAATATTTGC[A/G]GTTCATTGTAC<br>TCCAATATTTGATAAGTTTGATTGGTAGGCATAACACATTAAT<br>CAATGAAATGGGGTGTAAAATACAACTAGATTATAGGGACAT<br>GTAACTTTCAAAGTGTTTTGAGTTAACCTGCTGTGACACTGAT<br>CAGCTGAACATGTCCTTTTTCTAGAAACTAGAAATACAATTGC<br>TTAATGTCAAAAACAAGA | 314 |
| S04660-1 | ATTGGAAGGAATAAAGTTGGGGTTTTGGAAGCAATGGAGTGG<br>AATTCATTCCATTCTAGTTTAACAAATTCAAACAATGGAACAT<br>ATCAAAATTCCATTCCATCCTACTCCATTCCTTCAATTTCCCC<br>ATATCCAATCACATTTCTCTGTTAATAGTTTGGGTGCAAAAAG<br>ATAGATCAAAGAAGTAGATACAGGAAGGA[C/T]GTAGATGCA<br>GAAATGAACTTCTATGACGAAGGCYGAGGCAGGCGGCAACT<br>AAGTGAGGGATATGCCTTAGTAACAAAACAAGGAATTAAAA<br>CTTGGTTTATTTTATTGGTAAAACATTGGCAACATTTTTCTCA<br>GCCATGTCCATGTAAATGTGCATTTGTAATAAAAGAGTTTGGT<br>GTAGTGGAGCATGGTTATTGTAA | 319 |
| S09955-1 | GGGTCAGATTAGAGAGTGAGATAMAGTGAGAGGGACTCATT<br>TGAGAGGAAAAAATAGTTAAAAATCATTGAGAGAGAAAGGA<br>GAGGRAAAATCATTRTGATTTTCGCATACCCACTAGAGAGCA<br>TTTTTCATATTGAAACARCAGATTGGTTCACCGTTGGATCGGG<br>ATGATTTTTGGAAATMTGGTTCAGCACACTTGA[C/T]ACTCCA<br>AGTTGTCTGGTTGGATCATGAAAAGATATCTGGAGAGAGAGA<br>TAAGTKCTTCATATTCTCTGTTCTATATTTTRGGATTTCCTCTT<br>CTTGTCTCTATTGTATCAACTCAGGGTCTGTTTTGATTTGGCTG<br>TTTGTAGCACATTTTAGTGTACTTGTTGGAGGCTCTCTTGTAT<br>CTTTATTGATTATAGTGGAGT | 324 |
| S08034-1 | TTGAACCAATCAGATGAAAGAGGTTGAAACTTTGCAAGACAA<br>TGGCGAAGAATTGCTATTCCAACCACGCCTTCAKCAACATCA<br>GTCAAGAGGCTGCACAATGCTTGCCMTCTGTATGTAAGAGAT<br>TCCTTTCTAAACCCTGCTGTGTATGCTAAAAATGGAACTATCC<br>AAGATCCTACAAACCAAAATGAGGCAATCCA[C/G]AGGAGCA<br>TTACCTGCAGAACCCAACTTAGTTTGCTCTTCTAGATGAGATG<br>AAACTAAGAAAGAGACCAATCAAATAAACTATATAGTTTCTG<br>AATATTTTTCAATTCCATCCATTCACAAGTTCTTAATTGAAGY<br>AGACTATAACAAATAGCCTTACTGTCAAATCAATAAAAAAAT<br>TATAATAAGTAACCAACTTTTAG | 329 |
| S10293-1 | TTTTTGTATTAGAATCATGAAAKTGTGACTGAGATTTTGTGTA<br>AATGATAAATTGAATATGTATTGAATTGTAAGATACATGTGT<br>ATTGAGATGTTGTGTGCATTGAGTTGTAAGCTATGAACCGTAC<br>AATCACACAACTTTAAGACCCTTTAAGGGRGAHGATTTAATG<br>CACGACGAGTATTGTGATGAGATCGACTGT[A/G]GAAACCCC<br>ACGAGTTTAATCACTTTKAGGCARGACRAGTTAAATTTATTTT<br>GAAAATAATTGAAGAGTCGTGTGTTTTGTATAATTCATAGAT<br>AAAGTCTGGATGCCCAACGAAGTTTTTTACTGACATGATACC<br>ATATTGCATATATGATTGAGTCTTAGTATATTTGTTGCATAAC<br>GCTTGTGTATTGATCGATATTG | 334 |
| S03813-1 | GTGCTCATCAYGTGTTGTGCATGGAATGGCAGAGTTGAAGAA<br>TCTCTTGAACTTTTCAGGGAGTTACAGTTTACTAGATTTGACC<br>GGAGGCAGTTCCCTTTTGCTACCTTGTTGAGCATTGCTGCAAA<br>TGCTTTGAAWCTGGAAATGGGTAGGCAAATCCATTCCCAGGC<br>TATTGTAACAGAAGCCATTTCAGAAATTCT[A/G]GTTAGGAAT<br>TCGTTAGTTGACATGTACGCTAAATGTGACAAATTTGGGGAA<br>GCAAATAGGATTTTTGCAGATCTGGCACATCAAAGTTCAGTT<br>CCATGGACAGCCTTGATCTCGGGTTATGTTCAGAAGGGACTC<br>CATGAAGATGGCCTAAAGCTATTCGTTGAGATGCAAAGAGCC<br>AAAATAGGTGCTGACTCGBCCAC | 339 |
| S02042-1 | CCTTGTGTTCTCTAAGAACTATGCATCTTCTTCGTTTTGCTTAG<br>ATGAACTTGTTAAAATCATGGAGTGTGTTAAGGCAAAGGGTC | 344 |

TABLE 27-continued provides the genomic region comprising the polymorphism associated with a reproductive growth phenotype in soybean.

| Locus | Genomic region | SEQ ID |
|---|---|---|
| | GGTTGATTTTTCCCATTTTTTATGATGTGGATCCTTGTCATGTG<br>CGGCATCAGTCTGGGAGTTATGGAGAAGCGTTGGCTATGCAC<br>GAGGAAAGGTTCACAAGTAGCAAGGAAA[A/G]CCTCAAGGAG<br>AACATGGAGAGKTTGCAGAAATGGAAGATGGCTCTTAACCAA<br>GCAGCTGATGTGTCTGGCAAGCATTACAAACTTGGGTATAGT<br>ACCCCTCTTCACGAGATTTTCCAATACAATCACGTGTTCATGG<br>TCCCGATCAATCTCCACGTGACATAGTCAAGGTCAAGATTGG<br>TCGGGACCATGATCACTTGGT | |
| S16601-001 | CAATCCCAAYAGCCTGCTYAAACATAGAAATAAAGGAATTTT<br>ATTTGAAAATTACTTATTTTTCAGCCTTTTGAAAGAAGTTTTG<br>AAAAAAAACAAACTATTATTTCTTAAAGGTAATCTCGTACC<br>AAACATAGTTGYATTGTATCTGAWTTCACACATGTACTAGGC<br>TTTGGCAATGCTCACAGTCCAAGCAGCTTCA[A/C]AACATTTA<br>CACCCTGAAGCATGTGGCAAGTCAAGCTGTGTGAAAGGTGGA<br>ATAGCAGTGATGTTCTACACATCACTGTGCTTGTTGGCATTGG<br>GAATGGGAGGGGTGAGAGGATCCATGACTGCATTTGGAGCTG<br>ACCAATTTGATGAGAAGGATCCAACTGAGGCAAAAGCCCTTG<br>CAAGTTTTTTCAATTGGCTTTTG | 349 |
| S01481-1 | AGCAATAATTCTATGGCTTTTACTTTATTTTTTAGTATAACTA<br>AAAAAAAAAGAAAAAAAGCCAGAGGCTACACCAGCATACTT<br>GACCAGAGATTTAACTTAAGCAATAATCATGAGATAAATGGT<br>TTCATCTGTCCTATATAGCAGCTYAAGCTTTCAGGCTGGCTGT<br>TTCTTTGACATGACCATAAAGCTTCAGTCAC[G/T]TTATGGTCC<br>AAAGTTTGACTTTGGCACCCAGAGTAGAAATGAGATCGTTTA<br>TCCTTATCTAACATGCAGTTTTAAATTCAGTAGTCCTTTRWAT<br>TCATATTATATATAGCACCAACAAWGGCCATGACATAGGAGA<br>TGGGAAAATACAAAAAATGGTGAAAGTCTATARCAGCMTAA<br>AATGGATTCATTACCTTCTTTCT | 354 |
| S11309-1 | GTTTAGTCAAGAAAAACAAAAAAAAAAGTAGTAAAAAATGT<br>TTTTAATAAAGTGAGAGTGGAAATTATTAATCGTGTAGATTTA<br>AAAATAGTTTTAGTTATCATGAAGAAGTAACATATATGGATA<br>GAAAGTTAAATAGAACTGGATCGGCGTATATATTGGGCTGGA<br>CCGGTCTGGGACAATGATTGGGCTCCAATTTC[A/T]TGGTTCT<br>CGTTCTTCTWGGGCAACTTGATTAAGTGATCTAACTTGTGGAT<br>AAAAAAGAGAAATAAATAAAAATAAAATTAACAATTAAA<br>TGTAAAATTAAAAAGTGTAAAAGATATAATATGCGTTTTTATT<br>TCTCTTCCATAGAATTTTGGTGTATATAATGGCGACAATAAGG<br>TTCAAACCTAAGTCCTTTCTCTT | 359 |
| S11320-1 | ACTATAGTTTTTATTTTATTGCGGTTGTAATATACATGTTTTGG<br>TTAATTTTTAGATATCTGCTCTGAGGAATTAAGTGTTTCTCAG<br>TCTTTTGAACTGGATGGTGTAATCTCACTTTTGAATCGGATGC<br>GAATATGAAGTGGTATTTGGATTATTTTTAATGGGTTGTGAAT<br>GAAAATAACGTTACCTGTTGAGATCGT[A/T]TGTTTTATAGCG<br>ATAGTGTTTCATAGTAGTGTAAGCTGGCTTACATTGCTTTTGA<br>ACTTTGGGCGGTCAACTGATGGTTCTATKTGTCTCGTATGTAT<br>ATGGTCGATCCTTTGCTGTTAATGCGGCGTGTGCCTTTGGTAT<br>GTTGGTTTTYGGGTGCTGCAATTTGTAGTTTCTTGGCAATCTC<br>GTCGATGGTACTTCAA | 364 |
| S04040-1 | AACTGCAAAGGTTCAAGTAGATACYTATTGGCCAACCTTATT<br>TGCTAAACTTGCTGAGAAGAAAAATCTTGGCGATTTGATAGC<br>CAATGCAGCAGGCGGTGGTGCACCAGTTGCTGTTGCAGCTGC<br>CCCTGTTGCTGCCTCWGGTGGTGGTGGTGCTGCTGCTGCCGC<br>CCCAGCTGCTGAGGAGAAAAAGAAGGTTTCCC[G/T]CTAGTG<br>AATTTGTTGTTCCTCCAATTGTTTTTCAATCCTGCTTTATGCTA<br>GTTAATGTGTATCTAATATGAATCTGTGTGTTTCTATTCTATA<br>GGAGGAACCTGAAGAAGAGAGTGATGATGATATGGGATTTG<br>GCTTGTTCGATTAGGGACATTCTCAATATGATTTGGTTAAATT<br>TTGTGGTTCTTTACCTTTAAGTT | 369 |
| S00863-1 | TGTGCTCCTAGAGGAATATTTTGTGTAGACTTTCTATTATCTTT<br>TATTTTTTCATTTTTTAAAATTCAAATGTTAACAATTCAAATA<br>AAGAGAGAAACTAAAATTTCATAAAAGAGAATACGTGTATTA<br>ATTYTATTTTTGGTTGACATGACTTTTTTCATACTAAGTTGGAC<br>ACCAATTGTGTGTGAGACTTATACCATC[A/T]TGTGAGTGTTG<br>AACATTCTTAGTGTATAACACTGATAATATAAAGGGRTAGAC<br>ACTTTTGGTCTTATAGCKTGTGTGATGCTGATTAATAATTAAC<br>AAAATATTTTCTTTTTTGWGTGTGGATGATATATGTGAATAAC<br>ACTTAAGTCCTTTAATAACTTTGCTCACGTCCACTTGTCATAA<br>ACTTATTAATATATNAAA | 374 |

TABLE 27-continued provides the genomic region comprising the polymorphism associated with a reproductive growth phenotype in soybean.

| Locus | Genomic region | SEQ ID |
|---|---|---|
| S17151-001 | ACGTTACCCTTGCACTGCAATGCGTCATTAGATTTTATTTTAT TTTNTTTTATCTRAAATAACTCAYAATAAATTTTACAAGTTTA GCTACGGAGAAGATAACTAGATAAAGGAGCGATTGATGTAC ATTTTGAGGGTGTATGTAGGTTGGAAAARGAGAGGCATGAGG GGGAAAAAGAAGAAAAAATTCCACTAATGTG[A/G]TATGAAA AAAAGAGTCACAGATTGACTGAGACTYGTCCCAAACAAGCAT GTTAATCCTTGCAAATGCGTAGACATAAACATTTTTTTAGTTA ATTACCTTTTTCATCTCTAGAGCTACAACAACTTTCTCATTTA ATTTTTATAGTTTAAACATCTCATTTTAGCTCTTATAAGTATAT AAAAAATTTAATCTTTTTTAT | 378 |
| S17153-001 | TAAAGTTYAAGAAGACACATGTTAWTTAAACATATTAGTTTA AAAWGTAAATTACACTAATTATCCCTAAAGTTTTGAGAAATT ACACAAATTTCCCCTACTTTTATCTACTCCTACACTAACCCCC TAATTTTTTGAAAATATATATTGATACACCTTATATACAACAA TAACTGCCCTTAATTGCTCAAATTTCCACT[A/C]TGAGCCTCTT TATCAAATCTCATATTGCATTGTCACACTCCACGTCAGTTGCA ATCACTCACACCCCTCCTATATAATACATCTTCACTCTTTGCA TCCTCACCCTAAACCAAACCAATCGAAGACAAAACAATTTT AACATCAATCTCAAGGGTATYTTTCTCTCTCTTTTCTCTTTCCT TATTTAGTTTAATATATA | 382 |
| S17154-001 | AAATTTTGCATATGGAGGAAATTGAATTGCTYTATCCAAACA AAGAATTTACAATGRAAGAAATTTGAATTGATTTATCCAAAC CAAGTATTTGAAAAATGAAAGAAATTAAAATCAAAACAATTC AAATTTTAGACATTTTAAATTCTTTGAAATTTCTGATYCCAAC ACAAGATAAATGTTTTTCTCGTGCTTGATTG[C/T]GATGGTCAT TTCCCACCGRTAAGGTTGGAATAACAATATTTGTTGAAATTTT AAGTCGCTTTAACTTAGAAATGTGGTTCTAGCAAGTGTTAATT TACCTTCCTTTGACAATTCATATAATATTTAAGATTGCTAATG AATGAGAAACAAAGTACTTTCGTTTTGCATTTTTTTTTCACAA GAAGTCAAAGAACCTTTTT | 386 |
| S17156-001 | GGTTATTTCTACTAAAGTTCTCGATCTAACGGCTTATTTAATT TTTTATTAGGAAAGGGAGGACAAATTCATTTCAAGAAAGCTA TAATTTTATTTGTTGACCATCATTAAAAGAAAAGAAAAATTA AGGCATACTAAATTTACAATTTAATTAAGGAAAAACTCAAGA ATGCCCTTCCAATGAAATAAAGCACTTGGAT[A/G]CCTGCAGG GTCAATTAGTTGTTGAAATCAGAARAACATTCTGAAAGCATC AACAACTTTCTCAGGCCTGTCAAAARTACAAAGGGTATATTC TTAAGAGGTTGAACAAATCATTTTACTATTCACTGAAATCCTA TGTTAACTAAAGTTACTTACCAGTCCTCTTGTGGCATATGACC AGCTCCTTCTATCAATTTAAGC | 390 |
| S17159-001 | AAATTAGTGAAAKAAATCTTATTTTAAAGAAGGTAGATGTAT ATATGCGTACGTGTACCGACATTCACAAGCAATTAATTCAAA TCAATAATTGAAATAACGTGGGGAAGTGCTCTTATGTTTTTTG AATAACATTGAAAAGAAACAGCGGCAATTTAAACTTYAAAGT CTCCAGCCYAACAAATCTCAAATGGGATCAT[A/G]GGTGGAC CACGTGTCTTCCASAATATAGARTGTTGCTAGGTGCACCCARC ATTCTTTAAAAATGAYAAAATTATCCCTGYYAATTTCTCCCCT TACCTTACGGATCAAATTGATCCGTAAAATACTTACGGATCA ACTTGATCCGTAAGGDATATTTTTGTCTTTTCGTGGTTAGTGC TRGATGCACCAGCAATAATACT | 394 |
| S08590-1 | CTTTCATGTAAGAAGTCATTTGATATTAACAATGAAGTTATTT ATCTTCTCTTGACGCTGATGGACTACTTGTCTATTTCCAGCTA TGAAGTTATTTATTAATTTGACTTCTCATTAACGCATTTTSTGT TCCTAATTRGTTTAGAACAACTAAAGACCCTTGAAAGACGAC CAAAATTGTTTGTCTTGTGTTGCAGATC[A/G]GTTGTCATTTGG CCCGCGTGTACGGCTGCGGATAAGTTATTTATCGAAATAAGT GTCAGATCAAAGGACGATCTACGTCCCTTAAAAAATTTCAATG ACAACAAACACATTATAAGAATTTATTTATATTTTAAATTAAG CATCGCCTTTCATCCTAACAAATGTATTTTTAACGCAGATTAT TCGTCYATAACATTATTT | 399 |
| S17242-001 | GTATGAAAATGATTAGTGCTGTGACCTGTGGAMTTTTCCTAA CTAAATACATTTCTTTCACAATTGATGACGTTACAAAGAAAGT GAACTACAACTAATGCATATAATGTGTCTTTGTATGACCGTAT CCAGGCATAACAAAACCATTTAAAGTTCAAGATACGCAATTA CTTGGGGAATAAACATCGTGCTTTATAATT[A/C]TTGTTGTTAT GTCACTACGTCAAGGCACTCTGCTATCACGCCATTGTATTTTA ATTTATCGCAATAATCAGTCTTAAATGTTTTCGAAAATAAGAT | 403 |

TABLE 27-continued provides the genomic region comprising the polymorphism associated with a reproductive growth phenotype in soybean.

| Locus | Genomic region | SEQ ID |
|---|---|---|
| | ATTGTTTTATGATATAAATTTTTTGCACTAAAGTCGAATAATG<br>TCTCTTTCTTTGTAAGCTTTCTTGTTATTGGGCACATGTATGCG<br>TTTACAAGGAGAAAATG | |
| S17166-<br>001 | ATGCATATGTGTGTGTGTATAAATGGGTTTTTAAAAAATGT<br>TGTCAACAAATAAAAAAAAGGTAATTTCATTGAATTTTATATT<br>AAGCTAACAATTTATTGCTGCAATTTTTATTTTGGCTCGATCA<br>TATTAAGCTTAATTAAGTCCGCAAACTGTAGTACAAATCAATT<br>TGGACCAACACATGTCCTCCACAAGACA[C/T]GCAGCAGAAG<br>CCCATTTAATCAAATGACAAAAGGTAAATGCTAAATAAACTT<br>YCCAAGTTACTTTCTACAACCCCCTTTTCGTTTTGATTTACCTT<br>TATTCCAAACTYACCTTTTATCTTCTTCAACTCCCTTTATAGTT<br>TTATTATATCABTCATGGGCACACTCCCTCTTCTCACAGTCGT<br>ACCAGTCATATATGCAC | 408 |
| S17167-<br>001 | GAAATTTTAACTAAATACATAAGACTTKTTTAGGGTGGTTATA<br>AGTTTTTTATTTTTGGTTTTCACATGTAATTTTCAAAACAAAA<br>CATTRTTTGATAAAGATAGAGTTCAAATAATTTTTAATTTAAT<br>TTTAAAATACTTTTACATTCATTTTTTAAACTAAAAAAAAAGA<br>TCTTAAAATTTGATTTTTAGTTTTAAAA[A/G]AGCACAGTTACC<br>CTACATTTGAAAATGACCCATTTTGTTATTGTTACCACTATTG<br>TTGAYACCACCAACATCACTATCATTTTCACCATCACTGACAC<br>TACAACCATCACAACCAATATCACCATTATCATTGTCAATCAC<br>AACTATCATCACCACCCGCCATTAACATTGGCATCACTGTTGT<br>TATTAYTGTCGTCATC | 413 |
| S08539-1 | TGTTAAATYTATTTTTTTAGTTAAATATATAAATACTCACTCT<br>TATTYTTTTCTTGTRTAACTNTTTTACNAATGTTATCTTTCAC<br>TTHTGTAAAGAGTCAACAAGARGTTATGCATATTTTTCATGAG<br>AGATTAACATGYTTTRAGTATCATGCATYCAAGATCAWTGRT<br>TGATCATCATTGTTAGAGCTTTGAAGA[A/G]TTCTTATTYTTT<br>GGACTCAARGTGTATTCAATTCAATAATCCGTTCATTYAAGAT<br>TATTTTTAAATATATTTTGATGATCATAATACAATTACAAAAC<br>CAARACRCTAAAAAATAATTTATTTAAATAATAAAAAWAATT<br>TATCCAAATGATTYCTAACATATATGTTGATGATCACAATACA<br>ATTGTAACACAAGRTC | 418 |
| S17178-<br>001 | ATCGCATTTAGTGTTCCTTTGCCATCGTTAATGAAGTTTTCCA<br>GTAGTGYTGCTTATTCGTTTTCCTTTTTTGGGAAATTTTTKATA<br>ATATGTCCATWGAATCCTYAACACTTGCAAATTAGATAAAGG<br>CCTCCATACTCAACATTGAATCTATGATTGTGAAACCAAACCT<br>GTCCCACCACCATTCGGCTAAAGTCAAT[C/T]TTTATACACAC<br>CTTGACWAACTTTTTTTATGATGCATCCATGGTTGAAATATCA<br>ATTCTCAYGGGTCGTTGTTCTGCTGAAGCTAAAGCTACAAGA<br>ACACTTTCATCATAATACTCTAACTCTAAAAACGAGATCTTTA<br>TCCAAACTAAGGTATTGTTAACCTTCATATTCAATGGTTTGAA<br>ATCCAACGACCGTAGTCT | 422 |
| S17179-<br>001 | AGGGAATATGCATGATAACGAAGCAGGACTCGAKCATTTTCT<br>TCTTCTTGGTCAACATATATATGGGGCCTAGCTAATTAACTTC<br>TTAAATTAATTAGATTATGTCTACAAATTTATTTCAATTGTAK<br>ATTTAWATTAAAAAATCATTTTTSAATCAAGTTCAAATTAAA<br>AAATATTTTCTAACTCTAAAAGCAAACTGG[A/G]ACATAATTT<br>GGGCACCTAACTAAGTAAACTGGGTTAGTGAGGTTTATCTCA<br>YCGATGTGGGYGTATTTTTTTGYAATAAGTTTCATTTTTGGCT<br>TATTKTTCAATAATATAGAAAAAAATGTGATACGATAAATTA<br>TTTTTGGTAATATTTAACCCAACTTTTTTNGTTTTTGTTTTTTT<br>CCTTAAACACTCTTTATGT | 426 |
| S17180-<br>001 | TATACAGATACTACTCATTTTTAACTTTAATTAGAAATAGTAT<br>CAAAACCACGTATTAAACTGTATCCAAGTTTATCTTTTAAGAA<br>ATTATTCGTTTTTATTTGGTTTGTTAACTAGTACTATTAATTTT<br>GTTCAGTGCATTTCCCATAGAAAGTTATTTGTTCTTTCTATTTT<br>GAATTTGATTGCAAGATATTCAACTT[A/C]ACTGAAAGCTTAC<br>TAGGTTTTATCATTTCTTCTAGTTTTATTATACAAATCTTTATA<br>ATACTTTTTRCAAKTTTTTTTTTTCTCATTTTATCCTATCTTGTC<br>TCAGATTTTTTTCTTATTTTTCTCACATTGTAAKAATTGTAAAA<br>AAAGAAAGGCGTACTTTACTCAGCGCAAAKAAATTAATCATT<br>AATTCATTATAG | 430 |
| S17181-<br>001 | TATTATTAGGCTTTTCACATTTAAGGACTGGTAAAAATRTGAC<br>TAGTTGACTGATATTAGTGTATTGTTATTCTTATCTAATTTTT<br>TATATGYAATTTTGAAATTTATATTGATACACTCACATATATC<br>CCAKCATATCGATTATTGATATACCGTATCACTATTTATAKGT<br>AATCACTAAAATTACACACTTAAATTA[C/G]CACTAACTTTAG | 434 |

TABLE 27-continued provides the genomic region comprising the polymorphism associated with a reproductive growth phenotype in soybean.

| Locus | Genomic region | SEQ ID |
|---|---|---|
| | RGCACATTATTTTCTGGAAAGATGTAATACAAAATTGGCCCA<br>TTAGCTCTTTTGAGTTTTGACCCTAAACCTTAAACACATTCCG<br>TTTCTGTATAGTCTGTGGTCTATGATTTTGATGTKTTCATTTGT<br>TTTATGTGCAACTAATATTAAACAAAAACACTTGAAAATCGA<br>TAAGCACAGAAGGTATC | |
| S17182-001 | AAAATTAATTGGTGAACCATATATCATCTCTAGAAATTATATT<br>TAGAAAGACCAAACTCATCCTCATGCTCCTGAAGAAGAACAG<br>AAAGAGCTTTGGTTATCTCTTCTGCTGCCGGAATAAACTAGGT<br>TTGGAGCTCTACCATAGCTTTGGACTCAGATATACATAGATG<br>AGAGGTGACAAGTGAAAACACCCTATTTTA[A/T]GAATATTCC<br>ATCAACATTTATGACCTATTACACTTACATATCTCTTTTTTCTC<br>TCTTTCTCTAAGCMTTGGATAGCATGCATGCATGGAGTGGTC<br>AATGCAACATTTTCCTATAATATTGTTACATCTTTATCTCAAA<br>CAACCTTTGTAGCAATGTTCCTATAAATAACCCCTGTCTCTTC<br>AACTCTCACAGTGACTTTG | 438 |
| S17183-001 | AAAAACTTATAAGGTATTTTTATTATTTAAATGAKTAATACCA<br>CCGACTTWGGCATAATTACATGACTAATTTTGCCGTTACTTGA<br>AATGAAGACGAGAGAACTTATAGCGTGGAATCCGTGGGAGC<br>ACAATGTTTGTGGGGCATGGGAGATCGGAGCCGTTCATTGA<br>CGATGTGGTTTGATCGTGCGGTGGATGTGAA[G/T]TGCCGACA<br>GGTAATACAGGTAAATGGTGGCCACGHATGCATGTAAAAAA<br>ATGAATGAAGTTTATCTGTTTATACATTGAATGATGAAAATG<br>GTGGTGGAGGAAGTCTTATTCTTCTTCGGTTGGTGGGTCCCMC<br>TTAGATTTTGGTTGAGGTGRCACCATCTTTGAAAAGAGATTTC<br>GGAAGATAGCTAGAATAAGTGAA | 442 |
| S02780-1 | GGCATGGAAGGGCTACATTTTCTGTTCTTCTTTTTCAGGTTCC<br>TTTGTAACTTACCATCTATCTAGAAACTGCAGGATTCTCTTGT<br>AAAATAAAATATTAAATGATATAATACTTGAGATATGTAGTT<br>GGCTAAAYTTCATCTTATATGAGGCATTTGCTTCAATTTTCCA<br>GACTATTGCCTTTACCTTCTAGACTCTGG[A/G]TAACCTGAACT<br>GCATATCMTATAGGGGCAAAAGTATGTTATTTTGTCAGCATA<br>TAAACATGTTTGCATCCTATACAGTCAAGTATTCTACACAGAT<br>ACTATAGAAAGTAGAAAGAATAGTGGTRCTTTTCACTTGTTTC<br>TGTTGAAAACTGAATACAAAGATATAGAGAGAGTAGAGAGA<br>AAAGGGAGATAAGGTTTCTC | 447 |
| S12107-1 | GAGAAGGTGATAATAATAAATATGAAAATGACTTGAGATTYT<br>GACTCTTGACTCCTAACCAAAATTTKAAAGCTTTTTTACACAG<br>GGAGTTCCACTTTGAATTCCCCATCCTTGAAAGAAGTGGGGTT<br>CACCMAATGCTACAGCACGAAACTTTTCCATCTTGGTGRCAA<br>AGTGCGAACAATATTGAAGGTGACAATAGA[G/T]GGAGYCGA<br>TTGGGAAGGTGATATAAATTCTGCGCCCATGCAACAGTTTGA<br>GGAGGAGGCAGCCTGAGTKAGTTTAATTTGGTGACAATTCCC<br>CTCGACTTGTATGTAAGTACATACATTGATAATTATTTCTCAT<br>GGACATGCAATTAATATATGCTGATCAACTGCTACTAACTGA<br>GNGAGAGAAGGCATTAAATATCT | 452 |
| S03624-1 | CTCTTGGTGCAAAAAAWNTACACTATAGAAATCATGGTAGG<br>TATGAMTTTTAAGGTAGTTATTGTACAGGCCAATAAACTTAC<br>CATCGATGTATAGACTATAGACKATTTTCTCTTTATATATGAG<br>CTGTTTATCCATACTTTTTTTTCTCAAAAACATTACATGCATA<br>ACCTCTCATCATGTAATCATTTAATATGTG[A/G]CACTAATGA<br>TGCTAACTTGAGAGAAATTTACCTCTAATCTTATTTGCAGATG<br>CATCTACTTCTTCATGCTCCACCGCAAGATCATCTGTTATTGT<br>AGTGATTATTCTAATCTCAGGGCAATCATCTTTACAAGAAAC<br>ATCAAGACTATCTGCTTCTTCTGGTCCTAACTGTTCATCCCGT<br>TCAGAAGAATAATGAATTAA | 457 |
| S01953-1 | TTATTGAAAAATATAGACTTATTCCGAAAGTATATCTCCAAT<br>WCTGTGAATCATAGTTCCAGAAATACATTTCTAGAATAGATA<br>TATGTAATTCTGGAAAGACATTTCCAAAAAGCAAAAGGAGTG<br>TACTTCTTTATGAAAAACGGTGAAGGGTATGAGGGTGTDCTT<br>AGGAAACTGGTGTAAATATCAAAATTCCTTCT[C/T]CACTTKA<br>TTGATTAAAAAAGAGGCACAAATCAAAGCAACAAAGGCTCC<br>AAAATTAGTGGCCCGACACGATAGATAAAAGGGAATTGCTAT<br>ATCCAGTTCCTCTTTTTGCTAATACACTCCCATTTTAATTTTTA<br>TTTTCAAAAGTACCCCTAATAAATACACTCCCTGTACCATGAC<br>ATCATCATCATCCAACCTACGAG | 462 |
| S00111-1 | TTTGGCCCAATCCAATCCTCATAATCAACCTCTCTCTCTGACT<br>GTTCACTCTGTGTTTGGAGGTGGAAACTTAGGGTATGATTTCT<br>GATTCCCCTTCCTTCTCGCTCGTTCTCTGCTTTAATCCATCAAC | 467 |

TABLE 27-continued provides the genomic region comprising the polymorphism associated with a reproductive growth phenotype in soybean.

| Locus | Genomic region | SEQ ID |
|---|---|---|
| | TATCCTTCTWACTCATATTTCTTCACTGATTCAAGATACGATC<br>AAGTTTCCTTATCATTTGCTCCTAATT[A/G]CGTTTACCCTATA<br>CACACTTTTCCAGTTATTCACCRAAACCAACAAATAACAAATT<br>TCAGGTTGTTGGAGAAATTGTTCTGTTGGGGGGATAYGATGT<br>CGATGGAGAAGGAAGCTTCAAGCTCCACACCTACGCGCAAAT<br>TGTCGTGCACTGCATGCTTCGACGCTGTCTATTTCTGCTACTG<br>TAATACCCATTGCCCTA | |
| S04180-1 | GATGATAAAACTTGGGGAGAATTTTGTCAAATCCTCCCCAGC<br>GCATTTCTTAGTCCATGCTAGCAGATTTACTTTTTTTTTTTCC<br>ATTTCTTCTGGTTGTGTAATTCAGGGATTAATYGATAATTAGA<br>CGACATGATTATGTAAATATATGTGCATTCACCATTTATGAAT<br>TTTGATCCTTATGTAGTCTTACATTGAC[A/G]CTGTTCCTTTCT<br>CTWTATAATTGTGGCACATTATTCTGGGTTTTCATTTTTCAGT<br>ATTTGATTTCTCTCWACATCATGCACTGAGCACCTGCGTTAGG<br>CTGAAAGAAAATAAATTAATAATGTTTTGATTCATAAMCTAC<br>AGAATTCAAGCTTTCCTTTAGTATYAACTTATTGAGTAGCTAA<br>TGGCMAAATTGGAATTG | 472 |
| S01008-1 | TATGTCAMCTTCACCTTGGGCAGRAAAGAAATTCCGTACTTG<br>GACTTAAAGAATTTTCATGTTAAGCTATAACAATCAGAGAAA<br>GATATTAATGAAGCAGCAAGCACATAATATGGAGATATGTGA<br>GTTGCACCTTCAATCTTGGAGGACAAATCATGCACTGGATTGT<br>GAAGAGAATATAAGCATATAGACTTACAGWG[C/G]AATTGTT<br>ACAYGTAGCAAAACTACATGAATAACAATCTAGTTAAAGCAA<br>GGGATGCATACTAACAAACATCAAACTCTTATCACCTCATCT<br>AGTCCCACGGTGGATCTAGTTTGAAACATGTAAGCAGTCTTA<br>AAGCAAAATAGCAGGCATATSGTATCTATCTCAAACAGAAGT<br>GGATAKAACAGTAAACCACATGCCA | 477 |
| S12862-1 | GGGACCTAATTTGAAACATTCAAGTAAAATATATTGTTTAATC<br>TACCTATTACATCAAGGTGATGACCTTTTTAACCTAACCTACT<br>ACTCACATCCTCACCAATATTCAAGGATTGAGTCATTATGAC<br>WTATCAATATGATACACGATTGCACCCATATCGACCTTATTG<br>TGTGTTCCATACTCTGAATATGATCGAATC[C/T]GATAAATGTT<br>CATCGAAACAACCGGATMAATTACAGCTTGAGGATACACAA<br>CCCTCGAACCTTAAGTATAATGTACGTAAAGGCTAAGGCTTG<br>AGGATCGGGTTASAATCCGAGATGTAATTCATTTTCGTTTTAG<br>TTCATGTTGACTGATACACATGTCATCCTGCACTTGTCACATG<br>GGGTGTCCTACGTGGTTTACT | 482 |
| S12867-1 | ATTGTAATATAATTGAAANAAAACATGCATTCATGATATGTA<br>TTACCGGCATTCCAACCATGGCGCGCGGATGATGAAAAATGG<br>TTGTAACTTCAATCAGACTTGTATTCACAATTAAGCAAACTG<br>AAACCCAAACACACGTTAAAACTCTTGTTCAGCTCGAGCTTA<br>TARCATTAMGAGATCATGACCACATGTAACT[A/G]TTATTATA<br>ACACACACATACACACATGAGAAGGGATCATATTTATTCTAG<br>GATCAAATATACATGTGTGGGACCACTTGAACACAAAGTTAT<br>GTAGARTAGTTGTTTCATGCCATTGCTAATCAGGACTTCTCAC<br>TGCCAATCTATGTGTCTCATTCTCTCTAATMTCTCTGTCATTTT<br>GTGTCTCATTCACTAGGATGA | 487 |
| S04966-1 | CTCATCACAGCATGCTTATGGCGTTGTCACACWAAAGCATTG<br>AAGATAGATGCAGATAAGGATGTTCGAATGATGGTCGCCGTC<br>AACGCACGTGCTAAGTTCAATCCTCCTTTACCTGTTGGTTATT<br>ACGGTAATGCCATTGCATACCCAGCAGCAGTCACCACAGCAG<br>GGAAGCTTTGTGGAAATCCATTTGGGTATGC[A/T]GTGGAATT<br>AATAAATAAAGTGAAAGGTAAGGCCACACAAGAGTAWATGC<br>ATTCTGTGGCAGATCTATTGGCTATTAAGGGACGATACATAC<br>CAAGAATGGTGAGGTCTCTTACTGTGTCAGATTTGAGAGGTTT<br>TGATCCCAGACAAATTGATTTTGGGTGGGGCCATGCTCTCTAT<br>GCTGGACCAGCTCAAGGAGGCCT | 492 |
| S10631-1 | AACCGTTATGGTTGGGGATCGTTGCTACCAAAACCAAAATCT<br>CGGGACGGATCAATGTCCCAATGCTTGGTATGTCTGATGCCA<br>CTTTTTGATTCTATGTCTCCTCAATTTTTTTTTCTGATTCCGTC<br>TATGATTGYTAGATTAGATCAAAAGAATTAGCCGGTTTACTT<br>GGAATGTTTGAATCATTTCTAATAAGATC[C/T]GAGTTGGAAG<br>AAAAGACACATGTCTAGAAATTCGACAGATCTTGCATCAAAT<br>AGAAGGGAAAATAATTAATCATTTTCATAATTTTTTTTAGTAT<br>TTACGTCCTAATTAGTAGTCAATATGATAATTCTACCAATGAG<br>GTTTATAGGTCATGTAAGTAACTGTTTATTATTCAGAAAAATA<br>GGAATACRTAACATAAAAT | 497 |

TABLE 27-continued provides the genomic region comprising the polymorphism associated with a reproductive growth phenotype in soybean.

| Locus | Genomic region | SEQ ID |
|---|---|---|
| S0174-1 | ATCATAATTATTGCAAAAACAATATCTGGTCTAGTGTGGGCT AGATAAATAAGTTTTCCCTATCRGTCTTTGATATCAAGCCTAT TTGAGCTCTCCCATTCCTATCCAATGATTTTGCTTGATGAGCT CTCCATATGTTTTACGACCCAATTTGCTTGTCTCTCTAAGAAG ATMAATGGCATATTTTCTTTGAGAGATAA[A/C]GATGCCTTTT TTGGAGCAGGCAACTTCTATTTTCAGGATTTTTTTCAGCTTTC CTAGTTGCTTCATTTCAAATTGAGTTGTCAACCTTTCCCTTAG GATTTGTTTTCAACTTCATCATTTCCTGCAACAAACATATCAT CTACTTAGACCAAAAGGATTGCCAATTTACCTGTCTGAAAAT GCTTTATAGAGTGTGGTCA | 502 |
| S16594-001 | CAGAGGTTGAATGGAGAATTTGCACCATTTGGGAAGCTGCTT ATGGCCTGATTCCTACAAGTTCCTCAGCTGTTGATCTTCCGGA AATTATAGTTGCAACCCCACTACAGCCTCCCGTGCTGTCATGG AATTTGTACATACCCCTATTGAAGGTCCTGGAATATCTTCCTC GTGGAAGCCCATCAGAGGCATGTCTTATG[A/T]AAATATTTGC TGCTACAGTGGAAGCTATTCTTCAGAGGACATTTCCACCTGA GTCCACTAGAGAACAAAACAGAAAATCAAAATACCTAGCTG GCATAGGCTTTGGCTCTGCCTCAAAAAACCTGGCCGTGGCAG AACTTCGTACAATGGTTCATTCACTCTTCTTAGAATCATGTGC ATCTGTAGAGCTTGCTTCACGC | 507 |
| S02777-1 | CTTTGAAAATATAAAGTAAAATATTTTTATGTGAATCTATATA TATAAAATCTAATATCACATTCACACCCKAAAATTTATCTCAT GCGAACATGCTTACAAAAGCATTGAATTGGAAAMAAACATA TCGAAGTGCAAATACGGTATATCATACTAAATATCAGTTATA TTTCCTTAATTTTAAAAGTTTGTTATCTTCC[A/G]CTTTAGACT ATATATTCATCATTTTCCAAAATTTCAGTTTCCATTTCAAGTC GAGTTTGATTCAATTCAGCTGTTTAGCGATDTTGAAGTGGAA ACAGTCAGTAGATTTAGTGTACTGATGAGGTTGAACACAAGT TAGGATATTACTGTCTTGCATGTGAATTTGTTGGTCAATTACA CTTGCTTCCATTCACWAAATT | 512 |

The SNP markers identified in these studies could be useful, for example, for detecting and/or selecting soybean plants with a preferred reproductive growth phenotype. The physical position of each SNP is provided in Table 24 based upon the JGI Glyma1 assembly (Schmutz et al. (2010) Nature 463:178-183). Any marker capable of detecting a polymorphism at one of these physical positions, or a marker associated, linked, or closely linked thereto, could also be useful, for example, for detecting and/or selecting soybean plants with an altered reproductive growth phenotype. In some examples, the SNP allele present in the first parental line could be used as a favorable allele to detect or select plants with altered time to R1, such as a shorter time to floral initiation. In other examples, the SNP allele present in the second parent line could be used as an allele to detect or select plants for unaltered time to R1.

These SNP markers could also be used to determine a preferred or non-preferred haplotype. In certain examples, a favorable haplotype would include any combinations of two or more of the alleles provided in Tables 24 and 25. In addition to the markers listed in the tables (e.g., Tables 26-27), other closely linked markers could also be useful for detecting and/or selecting soybean plants with a preferred reproductive growth phenotype, for example exemplary markers provided in Tables 28-46. Further, chromosome intervals containing the markers provided herein could also be used.

TABLE 28

| Locus | LG (ch) | Physical | Genetic (cM) |
|---|---|---|---|
| BARC-048987-10780 | A1_(5) | 266,909 | 0.00 |
| BARC-040651-07808 | A1_(5) | 620,344 | 2.45 |

TABLE 28-continued

| Locus | LG (ch) | Physical | Genetic (cM) |
|---|---|---|---|
| BARC-053261-11776 | A1_(5) | 937,369 | 3.45 |
| BARCSOYSSR_05_0046 | A1_(5) | 995,905 | 3.63 |
| Sat_137 | A1_(5) | 995,905 | 3.63 |
| BARC-023449-05395 | A1_(5) | 1,050,663 | 4.06 |
| BARC-023411-05376 | A1_(5) | 1,051,044 | 4.07 |
| BARC-023409-05375 | A1_(5) | 1,075,339 | 11.17 |
| BARC-014287-01306 | A1_(5) | 2,558,104 | 14.78 |
| BARCSOYSSR_05_0149 | A1_(5) | 2,887,437 | 16.35 |
| Sat_368 | A1_(5) | 2,887,437 | 16.35 |
| BARC-019415-03923 | A1_(5) | 3,021,580 | 17.65 |
| BARCSOYSSR_05_0179 | A1_(5) | 3,442,467 | 18.91 |
| Satt276 | A1_(5) | 3,442,467 | 18.91 |
| BARC-010741-00738 | A1_(5) | 3,507,636 | 19.30 |
| BARC-021573-04148 | A1_(5) | 3,645,205 | 20.28 |
| BARC-014883-01912 | A1_(5) | 4,043,928 | 24.07 |
| BARC-065065-19078 | A1_(5) | 4,359,496 | 24.96 |
| BARC-058785-15434 | A1_(5) | 6,852,194 | 27.64 |
| BARCSOYSSR_05_0427 | A1_(5) | 11,000,000 | 28.30 |
| Satt248 | A1_(5) | 11,000,000 | 28.30 |
| BARC-024893-10355 | A1_(5) | 20,004,473 | 28.39 |
| BARCSOYSSR_05_0581 | A1_(5) | 23,929,087 | 28.82 |
| Satt364 | A1_(5) | 23,929,087 | 28.82 |
| BARC-063687-18439 | A1_(5) | 26,716,236 | 30.63 |
| BARC-050075-09365 | A1_(5) | 27,637,336 | 31.37 |
| BARC-024801-10347 | A1_(5) | 28,414,533 | 32.10 |
| BARC-048025-10453 | A1_(5) | 28,878,538 | 32.40 |
| BARC-065675-19641 | A1_(5) | 29,021,677 | 32.61 |
| BARC-010403-00623 | A1_(5) | 29,178,219 | 32.62 |
| BARC-050757-09856 | A1_(5) | 29,489,647 | 32.90 |
| BARC-058161-15150 | A1_(5) | 30,394,323 | 33.43 |
| S01435-1 | A1_(5) | 30,568,085 | 33.61 |
| BARC-064245-18594 | A1_(5) | 30,754,815 | 33.81 |
| BARC-017329-02265 | A1_(5) | 31,297,779 | 34.18 |
| BARC-054977-12201 | A1_(5) | 31,506,542 | 35.05 |

TABLE 28-continued

| Locus | LG (ch) | Physical | Genetic (cM) |
|---|---|---|---|
| BARC-040459-07745 | A1_(5) | 31,674,074 | 36.10 |
| BARC-050067-09358 | A1_(5) | 31,676,019 | 36.10 |
| BARC-056463-14388 | A1_(5) | 31,773,037 | 37.40 |
| BARC-052343-11430 | A1_(5) | 31,884,662 | 37.90 |
| BARC-024619-05489 | A1_(5) | 31,891,048 | 37.90 |
| BARC-020479-04637 | A1_(5) | 32,055,300 | 38.96 |
| BARC-053443-11853 | A1_(5) | 32,393,030 | 41.63 |
| BARC-044557-08720 | A1_(5) | 32,913,357 | 44.01 |
| BARC-025997-05216 | A1_(5) | 33,489,849 | 46.79 |
| BARC-031361-07059 | A1_(5) | 33,680,124 | 47.27 |
| BARC-049091-10809 | A1_(5) | 33,699,369 | 47.27 |
| BARCSOYSSR_05_0991 | A1_(5) | 33,718,230 | 47.78 |
| Sat_407 | A1_(5) | 33,718,230 | 47.78 |
| BARC-042853-08438 | A1_(5) | 34,115,224 | 49.47 |
| BARCSOYSSR_05_1021 | A1_(5) | 34,158,338 | 50.27 |
| Satt648 | A1_(5) | 34,158,338 | 50.27 |
| BARC-031031-06987 | A1_(5) | 34,294,398 | 50.98 |
| BARC-018011-02495 | A1_(5) | 34,294,844 | 50.98 |
| BARC-030907-06967 | A1_(5) | 34,436,914 | 51.76 |
| BARC-020229-04499 | A1_(5) | 34,514,905 | 52.37 |
| BARC-020401-04601 | A1_(5) | 34,610,781 | 52.77 |
| BARC-026129-05274 | A1_(5) | 34,684,784 | 53.01 |
| BARC-037207-06739 | A1_(5) | 35,104,770 | 53.77 |
| BARC-047054-12831 | A1_(5) | 35,261,608 | 54.34 |
| BARC-049797-09148 | A1_(5) | 35,313,037 | 54.53 |
| BARC-038407-10072 | A1_(5) | 35,428,921 | 56.14 |
| BARC-039495-07502 | A1_(5) | 35,690,504 | 57.95 |
| BARCSOYSSR_05_1115 | A1_(5) | 35,700,565 | 59.24 |
| Satt619 | A1_(5) | 35,700,565 | 59.24 |
| BARC-052589-11517 | A1_(5) | 35,898,964 | 61.04 |
| BARC-031957-07230 | A1_(5) | 35,965,810 | 61.92 |
| BARCSOYSSR_05_1134 | A1_(5) | 36,180,326 | 62.70 |
| Satt545 | A1_(5) | 36,180,326 | 62.70 |
| BARC-051453-11119 | A1_(5) | 36,454,309 | 63.49 |

TABLE 29

| Locus | LG (ch) | Physical | Genetic (cM) |
|---|---|---|---|
| BARC-021937-04237 | A2_(8) | 1,466,024 | 9.57 |
| BARC-039839-07593 | A2_(8) | 2,035,742 | 11.55 |
| BARC-014435-01365 | A2_(8) | 2,246,693 | 12.86 |
| BARC-021463-04108 | A2_(8) | 2,986,176 | 14.66 |
| BARC-031701-07215 | A2_(8) | 3,056,358 | 15.45 |
| BARC-044051-08595 | A2_(8) | 3,174,985 | 16.44 |
| BARC-032579-08998 | A2_(8) | 3,307,480 | 16.96 |
| BARC-016965-02168 | A2_(8) | 3,341,884 | 20.27 |
| BARC-065591-19578 | A2_(8) | 3,533,588 | 21.02 |
| BARC-028679-05986 | A2_(8) | 3,800,144 | 22.79 |
| BARCSOYSSR_08_0206 | A2_(8) | 4,000,361 | 23.82 |
| Satt207 | A2_(8) | 4,000,361 | 23.82 |
| BARC-013537-01155 | A2_(8) | 4,316,426 | 25.69 |
| BARCSOYSSR_08_0262 | A2_(8) | 5,027,347 | 30.18 |
| Satt493 | A2_(8) | 5,027,347 | 30.18 |
| BARCSOYSSR_08_0273 | A2_(8) | 5,176,019 | 30.52 |
| Satt589 | A2_(8) | 5,176,019 | 30.52 |
| BARC-025925-05158 | A2_(8) | 5,278,616 | 31.20 |
| BARCSOYSSR_08_0305 | A2_(8) | 5,715,429 | 32.94 |
| Sat_409 | A2_(8) | 5,715,429 | 32.94 |
| BARC-039593-07509 | A2_(8) | 5,765,344 | 33.26 |
| BARCSOYSSR_08_0371 | A2_(8) | 6,751,708 | 38.87 |
| Satt315 | A2_(8) | 6,751,708 | 38.87 |
| BARC-025811-05087 | A2_(8) | 7,464,186 | 40.48 |
| S01239-1 | A2_(8) | 7,464,336 | 40.49 |
| BARC-028361-05840 | A2_(8) | 7,716,559 | 44.48 |
| BARC-021329-04038 | A2_(8) | 7,824,774 | 45.22 |
| BARC-062265-17733 | A2_(8) | 7,963,465 | 45.59 |
| BARC-028309-05824 | A2_(8) | 8,082,742 | 45.61 |
| BARC-045047-08867 | A2_(8) | 8,110,728 | 45.62 |
| BARCSOYSSR_08_0454 | A2_(8) | 8,219,326 | 46.28 |
| Satt632 | A2_(8) | 8,219,326 | 46.28 |
| BARC-012525-00285 | A2_(8) | 8,279,099 | 46.44 |
| BARCSOYSSR_08_0458 | A2_(8) | 8,279,445 | 46.56 |
| Sat_162 | A2_(8) | 8,279,445 | 46.56 |
| BARC-048453-10596 | A2_(8) | 8,368,060 | 47.08 |

TABLE 29-continued

| Locus | LG (ch) | Physical | Genetic (cM) |
|---|---|---|---|
| BARC-038291-07245 | A2_(8) | 8,380,220 | 47.08 |
| BARC-039247-07486 | A2_(8) | 8,469,553 | 47.11 |
| BARC-014511-01568 | A2_(8) | 8,887,107 | 47.38 |
| BARC-027690-06633 | A2_(8) | 8,943,498 | 47.56 |
| BARCSOYSSR_08_0506 | A2_(8) | 9,211,913 | 47.87 |
| Sat_215 | A2_(8) | 9,211,913 | 47.87 |
| BARC-059853-16139 | A2_(8) | 9,407,115 | 48.04 |
| BARC-027618-06622 | A2_(8) | 9,578,780 | 48.49 |
| BARC-026091-05255 | A2_(8) | 9,749,954 | 50.42 |
| BARC-043119-08535 | A2_(8) | 9,997,689 | 51.31 |
| BARC-039145-07456 | A2_(8) | 10,166,248 | 51.92 |
| BARC-038631-07266 | A2_(8) | 10,303,015 | 52.38 |
| BARCSOYSSR_08_0579 | A2_(8) | 10,721,802 | 53.55 |
| Satt424 | A2_(8) | 10,721,802 | 53.55 |
| BARC-030611-06911 | A2_(8) | 10,826,342 | 55.06 |
| BARC-020307-04548 | A2_(8) | 10,947,663 | 55.10 |
| BARC-045081-08872 | A2_(8) | 10,954,474 | 55.11 |
| BARC-029671-06303 | A2_(8) | 11,536,514 | 56.73 |
| BARC-027614-06619 | A2_(8) | 11,570,109 | 56.88 |
| BARC-040893-07862 | A2_(8) | 11,845,155 | 57.43 |
| BARC-044869-08827 | A2_(8) | 11,922,404 | 58.86 |
| BARC-018941-03041 | A2_(8) | 12,022,737 | 59.30 |
| BARC-014665-01618 | A2_(8) | 12,471,926 | 61.07 |
| BARC-040357-07716 | A2_(8) | 12,972,647 | 62.13 |
| BARC-029593-06225 | A2_(8) | 13,111,220 | 63.06 |
| BARC-044663-08756 | A2_(8) | 13,446,458 | 64.42 |
| BARC-041459-08002 | A2_(8) | 13,463,703 | 64.42 |
| BARC-029315-06150 | A2_(8) | 13,902,606 | 66.58 |
| BARC-055265-13154 | A2_(8) | 14,004,161 | 66.58 |
| BARC-032791-09038 | A2_(8) | 14,265,356 | 67.71 |
| BARC-038455-10089 | A2_(8) | 14,850,506 | 69.58 |
| BARCSOYSSR_08_0849 | A2_(8) | 15,140,599 | 70.95 |
| Sat_199 | A2_(8) | 15,140,599 | 70.95 |
| BARCSOYSSR_08_0879 | A2_(8) | 15,562,968 | 72.78 |
| Sat_233 | A2_(8) | 15,562,968 | 72.78 |
| BARC-031627-07124 | A2_(8) | 15,733,404 | 75.01 |
| BARC-039899-07603 | A2_(8) | 15,818,113 | 76.43 |
| S00780-1 | A2_(8) | 15,841,570 | 76.47 |
| BARC-029669-06297 | A2_(8) | 16,164,943 | 77.06 |
| BARC-049031-10792 | A2_(8) | 16,250,468 | 77.06 |
| BARC-049045-10806 | A2_(8) | 16,250,599 | 77.06 |
| BARCSOYSSR_08_0909 | A2_(8) | 16,427,750 | 77.51 |
| Satt377 | A2_(8) | 16,427,750 | 77.51 |
| BARC-042491-08277 | A2_(8) | 16,624,607 | 79.14 |
| BARC-022387-04319 | A2_(8) | 16,839,499 | 81.25 |
| BARCSOYSSR_08_0948 | A2_(8) | 17,076,816 | 83.61 |
| Satt525 | A2_(8) | 17,076,816 | 83.61 |
| BARC-031601-07118 | A2_(8) | 17,167,641 | 84.15 |
| BARC-022445-04327 | A2_(8) | 17,410,233 | 85.38 |
| BARC-063091-18238 | A2_(8) | 17,412,255 | 85.58 |
| BARC-028207-05794 | A2_(8) | 17,695,309 | 87.11 |
| BARC-013001-00417 | A2_(8) | 17,738,311 | 88.06 |
| BARC-054097-12336 | A2_(8) | 17,940,930 | 88.16 |
| BARC-038877-07374 | A2_(8) | 17,940,998 | 88.16 |
| BARC-054143-12351 | A2_(8) | 17,945,325 | 88.16 |
| BARC-059821-16111 | A2_(8) | 18,439,010 | 89.50 |
| BARC-041231-07943 | A2_(8) | 18,856,442 | 90.76 |
| BARC-027788-06671 | A2_(8) | 18,952,545 | 90.84 |
| BARC-050061-09354 | A2_(8) | 20,229,386 | 92.31 |
| BARC-020835-03959 | A2_(8) | 20,441,412 | 92.31 |
| BARC-021629-04158 | A2_(8) | 20,530,558 | 92.53 |
| BARC-010797-00750 | A2_(8) | 21,133,646 | 92.81 |
| BARC-019299-03876 | A2_(8) | 21,896,189 | 94.21 |
| BARC-011001-00815 | A2_(8) | 21,896,207 | 94.37 |
| BARC-065451-19476 | A2_(8) | 22,590,975 | 94.72 |
| BARCSOYSSR_08_1216 | A2_(8) | 22,995,965 | 97.59 |
| Sat_232 | A2_(8) | 22,995,965 | 97.59 |
| BARCSOYSSR_08_1226 | A2_(8) | 23,213,226 | 100.07 |
| Satt158 | A2_(8) | 23,213,226 | 100.07 |
| BARC-061573-17277 | A2_(8) | 23,456,372 | 101.45 |
| BARC-055297-13184 | A2_(8) | 23,691,540 | 101.47 |
| BARC-051883-11286 | A2_(8) | 24,848,454 | 101.52 |
| BARC-049593-09076 | A2_(8) | 29,150,451 | 101.52 |
| BARC-049595-09077 | A2_(8) | 29,158,623 | 101.52 |
| BARC-059127-15620 | A2_(8) | 34,040,540 | 101.52 |
| BARC-050571-09743 | A2_(8) | 34,793,726 | 101.52 |
| BARC-010965-00797 | A2_(8) | 35,156,936 | 101.52 |
| BARC-019295-03875 | A2_(8) | 35,156,963 | 101.52 |

TABLE 29-continued

| Locus | LG (ch) | Physical | Genetic (cM) |
|---|---|---|---|
| BARC-058307-15218 | A2_(8) | 35,334,725 | 101.52 |
| BARC-060765-16857 | A2_(8) | 35,475,655 | 101.58 |
| BARC-061979-17603 | A2_(8) | 35,484,031 | 101.58 |
| BARC-049905-09236 | A2_(8) | 36,079,891 | 101.92 |
| BARC-049903-09231 | A2_(8) | 36,240,677 | 101.92 |
| BARC-061059-17022 | A2_(8) | 36,596,871 | 102.46 |
| BARC-059569-15920 | A2_(8) | 37,183,791 | 102.46 |
| BARC-053631-11924 | A2_(8) | 37,319,425 | 102.46 |
| BARC-053637-11925 | A2_(8) | 37,564,284 | 102.46 |
| BARC-049851-09173 | A2_(8) | 38,097,310 | 102.94 |
| BARC-028775-06010 | A2_(8) | 38,238,572 | 103.30 |
| BARC-020321-04554 | A2_(8) | 38,332,877 | 103.34 |
| BARC-050125-09401 | A2_(8) | 38,344,641 | 103.34 |
| BARC-030625-06913 | A2_(8) | 38,346,614 | 103.34 |
| BARC-010341-00598 | A2_(8) | 38,999,975 | 103.57 |
| BARC-062129-17664 | A2_(8) | 39,451,763 | 103.87 |
| BARCSOYSSR_08_1502 | A2_(8) | 39,470,511 | 104.54 |
| Sat_097 | A2_(8) | 39,470,511 | 104.54 |
| BARC-017137-02222 | A2_(8) | 39,754,026 | 105.48 |
| BARC-043095-08525 | A2_(8) | 39,960,478 | 105.79 |

TABLE 30

| Locus | LG (ch) | Physical | Genetic (cM) |
|---|---|---|---|
| BARC-017811-02392 | B1_(11) | 29,924 | 5.55 |
| BARC-058339-15238 | B1_(11) | 559,320 | 4.58 |
| BARC-062833-18109 | B1_(11) | 560,024 | 4.58 |
| BARC-017915-02450 | B1_(11) | 1,481,336 | 2.82 |
| BARC-018583-02981 | B1_(11) | 1,656,830 | 2.54 |
| BARCSOYSSR_11_0142 | B1_(11) | 2,710,565 | 18.03 |
| Sat_272 | B1_(11) | 2,710,565 | 18.03 |
| BARC-041095-07905 | B1_(11) | 3,684,393 | 23.86 |
| BARCSOYSSR_11_0227 | B1_(11) | 4,224,531 | 25.64 |
| Sat_270 | B1_(11) | 4,224,531 | 25.64 |
| BARC-014611-01591 | B1_(11) | 4,250,965 | 26.17 |
| S06925-1 | B1_(11) | 4,674,824 | 28.92 |
| BARC-018713-03241 | B1_(11) | 5,089,529 | 31.61 |
| BARC-042439-08267 | B1_(11) | 5,123,196 | 31.81 |
| S09951-1 | B1_(11) | 5,231,500 | 32.04 |
| BARC-018099-02516 | B1_(11) | 5,270,796 | 32.12 |
| BARC-032437-08975 | B1_(11) | 5,287,056 | 32.13 |
| BARC-032333-08951 | B1_(11) | 5,287,077 | 32.13 |
| BARC-042989-08491 | B1_(11) | 5,938,208 | 37.81 |
| BARC-017097-02199 | B1_(11) | 6,020,848 | 37.95 |
| BARC-900941-00964 | B1_(11) | 6,166,382 | 38.32 |
| BARC-016137-02291 | B1_(11) | 6,174,078 | 38.37 |
| BARCSOYSSR_11_0380 | B1_(11) | 6,961,225 | 40.95 |
| Satt638 | B1_(11) | 6,961,225 | 40.95 |
| BARC-040851-07854 | B1_(11) | 7,619,584 | 44.65 |
| BARC-044037-08588 | B1_(11) | 7,688,341 | 45.33 |
| S00170-1 | B1_(11) | 7,847,341 | 45.37 |
| BARC-025873-05130 | B1_(11) | 7,847,370 | 45.37 |
| BARC-061085-17035 | B1_(11) | 7,952,601 | 45.43 |
| BARC-038623-10188 | B1_(11) | 7,996,138 | 45.45 |
| BARC-031547-07108 | B1_(11) | 8,492,651 | 46.25 |
| BARC-050091-09377 | B1_(11) | 8,582,563 | 46.56 |
| BARCSOYSSR_11_0482 | B1_(11) | 8,879,510 | 49.07 |
| Satt197 | B1_(11) | 8,879,510 | 49.07 |
| BARCSOYSSR_11_0496 | B1_(11) | 9,078,586 | 52.06 |
| Sat_247 | B1_(11) | 9,078,586 | 52.06 |
| BARC-032817-09052 | B1_(11) | 10,319,338 | 55.57 |
| BARC-016279-02316 | B1_(11) | 10,804,852 | 61.61 |
| BARC-022123-04287 | B1_(11) | 11,269,342 | 63.49 |
| BARC-050929-13806 | B1_(11) | 11,532,769 | 65.62 |
| BARC-054421-12081 | B1_(11) | 12,295,534 | 66.70 |
| BARC-061409-17191 | B1_(11) | 15,208,402 | 68.33 |
| BARC-053713-11954 | B1_(11) | 15,545,136 | 69.17 |
| BARC-040309-07711 | B1_(11) | 15,576,761 | 69.17 |
| BARCSOYSSR_11_0828 | B1_(11) | 16,893,706 | 72.09 |
| Sat_348 | B1_(11) | 16,893,706 | 72.09 |
| BARCSOYSSR_11_0839 | B1_(11) | 17,065,539 | 74.21 |
| Satt597 | B1_(11) | 17,065,539 | 74.21 |
| BARC-059803-16097 | B1_(11) | 17,822,677 | 76.86 |
| BARC-050205-09457 | B1_(11) | 17,822,703 | 76.86 |

TABLE 31

| Locus | LG (ch) | Physical | Genetic (cM) |
|---|---|---|---|
| BARCSOYSSR_14_0440 | B2_(14) | 7,818,064 | 43.15 |
| Sct_034 | B2_(14) | 7,818,064 | 43.15 |
| BARC-064873-18956 | B2_(14) | 8,340,001 | 45.46 |
| BARCSOYSSR_14_0485 | B2_(14) | 8,642,764 | 45.66 |
| Satt416 | B2_(14) | 8,642,764 | 45.66 |
| BARC-030967-06981 | B2_(14) | 8,902,647 | 50.05 |
| BARC-055677-13598 | B2_(14) | 9,318,033 | 53.92 |
| BARC-014309-01312 | B2_(14) | 9,642,001 | 54.51 |
| BARC-052759-11611 | B2_(14) | 10,018,294 | 55.50 |
| BARC-052757-11610 | B2_(14) | 10,149,510 | 55.50 |
| BARC-057817-14938 | B2_(14) | 10,667,555 | 55.79 |
| BARC-054615-12115 | B2_(14) | 10,699,554 | 56.10 |
| BARC-059553-15907 | B2_(14) | 10,708,292 | 56.10 |
| BARC-051601-1175 | B2_(14) | 11,283,799 | 56.33 |
| BARC-051599-1174 | B2_(14) | 11,320,165 | 56.36 |
| BARC-065009-19043 | B2_(14) | 12,765,699 | 56.60 |
| BARCSOYSSR_14_0663 | B2_(14) | 13,784,029 | 56.81 |
| Sat_355 | B2_(14) | 13,784,029 | 56.81 |
| BARC-023673-03446 | B2_(14) | 24,138,675 | 60.07 |
| BARC-059375-15776 | B2_(14) | 30,148,286 | 63.48 |
| BARC-055413-13266 | B2_(14) | 30,458,374 | 63.48 |
| BARC-062781-18055 | B2_(14) | 30,561,889 | 63.48 |
| BARC-057785-14922 | B2_(14) | 31,475,698 | 63.48 |
| BARC-049743-09137 | B2_(14) | 31,642,640 | 63.48 |
| BARC-032443-08976 | B2_(14) | 32,380,594 | 63.48 |
| BARC-056587-14511 | B2_(14) | 33,084,741 | 63.48 |
| BARC-013927-01275 | B2_(14) | 33,571,308 | 63.48 |
| BARC-062037-17640 | B2_(14) | 33,950,948 | 63.48 |
| BARC-018353-03589 | B2_(14) | 34,025,136 | 63.48 |
| BARC-031293-07038 | B2_(14) | 34,323,246 | 63.48 |
| BARC-030997-06983 | B2_(14) | 34,323,315 | 63.48 |
| BARC-060347-16622 | B2_(14) | 34,621,804 | 63.48 |
| BARC-058131-15103 | B2_(14) | 34,818,582 | 63.48 |
| BARC-057297-14680 | B2_(14) | 34,821,875 | 63.48 |
| BARC-061113-17055 | B2_(14) | 34,824,183 | 63.48 |
| BARC-058987-15541 | B2_(14) | 36,145,603 | 63.48 |
| BARC-057997-15049 | B2_(14) | 37,295,178 | 63.48 |
| BARC-061279-17151 | B2_(14) | 37,903,944 | 63.48 |
| BARC-047146-12873 | B2_(14) | 38,163,669 | 63.48 |
| BARC-060943-16979 | B2_(14) | 38,284,031 | 63.48 |
| BARC-062887-18145 | B2_(14) | 40,552,074 | 63.48 |
| BARC-023661-03445 | B2_(14) | 41,640,536 | 63.49 |
| BARC-061125-17061 | B2_(14) | 42,276,845 | 63.49 |
| BARC-055593-13466 | B2_(14) | 42,735,542 | 63.71 |
| BARC-049657-09098 | B2_(14) | 43,839,403 | 64.21 |
| BARC-901431-00997 | B2_(14) | 43,846,938 | 64.21 |
| BARC-052791-11622 | B2_(14) | 44,146,158 | 64.68 |
| BARC-052789-11619 | B2_(14) | 44,293,219 | 65.17 |
| BARC-063857-18474 | B2_(14) | 45,913,358 | 73.94 |
| S04059-1 | B2_(14) | 46,138,053 | 75.42 |
| BARC-038467-10112 | B2_(14) | 46,213,791 | 75.91 |
| BARCSOYSSR_14_1341 | B2_(14) | 46,246,865 | 78.09 |
| AW620774 | B2_(14) | 46,246,865 | 78.09 |
| BARC-065655-19613 | B2_(14) | 46,710,433 | 80.24 |
| BARC-013273-00464 | B2_(14) | 46,714,178 | 80.36 |
| BARC-016831-02340 | B2_(14) | 46,885,648 | 81.19 |
| S07851-1 | B2_(14) | 47,331,319 | 83.76 |
| BARCSOYSSR_14_1421 | B2_(14) | 47,849,686 | 86.76 |
| Satt560 | B2_(14) | 47,849,686 | 86.76 |
| BARC-053447-11854 | B2_(14) | 48,055,573 | 86.97 |
| BARC-024363-04860 | B2_(14) | 48,668,529 | 93.81 |
| BARC-024363-04857 | B2_(14) | 48,668,529 | 95.86 |
| BARC-059251-15691 | B2_(14) | 48,884,075 | 96.44 |
| BARC-017211-02251 | B2_(14) | 48,940,822 | 96.45 |
| BARC-030849-06952 | B2_(14) | 49,276,286 | 96.76 |

TABLE 31-continued

| Locus | LG (ch) | Physical | Genetic (cM) |
|---|---|---|---|
| BARC-013859-01259 | B2_(14) | 49,292,092 | 96.86 |
| BARC-041333-07967 | B2_(14) | 49,362,025 | 96.89 |
| BARC-030661-06918 | B2_(14) | 49,487,183 | 97.61 |
| BARC-017589-02630 | B2_(14) | 49,705,320 | 97.92 |

TABLE 32

| Locus | LG (ch) | Physical | Genetic (cM) |
|---|---|---|---|
| BARCSOYSSR_04_0025 | C1_(4) | 433,582 | 0.00 |
| Sct_186 | C1_(4) | 433,582 | 0.00 |
| BARCSOYSSR_04_0026 | C1_(4) | 447,227 | 2.11 |
| Satt690 | C1_(4) | 447,227 | 2.11 |
| BARCSOYSSR_04_0035 | C1_(4) | 525,154 | 2.97 |
| SOYGPATR | C1_(4) | 525,154 | 2.97 |
| BARC-030305-06851 | C1_(4) | 963,864 | 5.03 |
| BARC-044617-08741 | C1_(4) | 982,287 | 5.58 |
| BARC-018919-03036 | C1_(4) | 1,089,217 | 6.17 |
| BARC-031853-07222 | C1_(4) | 1,163,728 | 6.77 |
| BARC-057913-15004 | C1_(4) | 1,250,289 | 10.04 |
| BARC-014277-01301 | C1_(4) | 1,431,400 | 10.61 |
| BARC-016959-02166 | C1_(4) | 1,710,562 | 11.51 |
| BARC-030765-06943 | C1_(4) | 1,891,388 | 11.97 |
| BARC-054289-12451 | C1_(4) | 2,069,710 | 12.19 |
| BARC-029425-06191 | C1_(4) | 2,207,639 | 12.33 |
| BARCSOYSSR_04_0125 | C1_(4) | 2,402,268 | 13.37 |
| Satt194 | C1_(4) | 2,402,268 | 13.37 |
| BARC-039239-07481 | C1_(4) | 2,507,250 | 14.03 |
| BARC-016519-02081 | C1_(4) | 2,843,396 | 15.58 |
| BARC-015981-02030 | C1_(4) | 3,205,314 | 16.51 |
| BARC-022353-04316 | C1_(4) | 3,348,266 | 16.72 |
| BARC-031733-07217 | C1_(4) | 4,054,929 | 19.50 |
| BARC-044709-08764 | C1_(4) | 4,120,312 | 20.56 |
| BARCSOYSSR_04_0228 | C1_(4) | 4,172,835 | 20.97 |
| Sat_337 | C1_(4) | 4,172,835 | 20.97 |
| BARC-020447-04622 | C1_(4) | 5,392,117 | 27.44 |
| BARC-014361-01331 | C1_(4) | 5,468,471 | 27.65 |
| BARC-022437-04324 | C1_(4) | 5,468,475 | 27.71 |
| S11659-1 | C1_(4) | 5,754,268 | 29.24 |
| BARC-044691-08761 | C1_(4) | 6,322,293 | 32.27 |
| BARC-044521-08714 | C1_(4) | 6,378,204 | 33.11 |
| BARC-040777-07848 | C1_(4) | 6,428,283 | 34.00 |
| BARC-025825-05102 | C1_(4) | 6,684,059 | 36.48 |
| BARCSOYSSR_04_0416 | C1_(4) | 7,819,458 | 40.86 |
| Satt578 | C1_(4) | 7,819,458 | 40.86 |
| BARC-041405-07979 | C1_(4) | 7,882,994 | 41.75 |
| BARC-038309-10010 | C1_(4) | 8,030,160 | 42.42 |
| BARCSOYSSR_04_0430 | C1_(4) | 8,093,779 | 43.17 |
| Satt607 | C1_(4) | 8,093,779 | 43.17 |
| BARC-062641-17963 | C1_(4) | 8,154,438 | 44.48 |
| BARC-017023-02178 | C1_(4) | 8,224,268 | 45.67 |
| S04279-1 | C1_(4) | 8,295,779 | 45.75 |
| BARC-029943-06758 | C1_(4) | 8,465,328 | 45.96 |
| BARCSOYSSR_04_0460 | C1_(4) | 8,830,940 | 46.01 |
| Satt646 | C1_(4) | 8,830,940 | 46.01 |
| BARC-015923-02016 | C1_(4) | 8,915,160 | 46.45 |
| BARC-046068-10219 | C1_(4) | 9,120,496 | 47.07 |
| BARC-064923-19002 | C1_(4) | 9,168,034 | 47.07 |
| BARC-063455-18377 | C1_(4) | 9,170,865 | 47.07 |
| BARC-053223-11766 | C1_(4) | 9,236,857 | 48.48 |
| BARC-053219-11764 | C1_(4) | 9,300,071 | 48.87 |
| BARC-058645-15349 | C1_(4) | 9,789,291 | 50.76 |
| BARCSOYSSR_04_0579 | C1_(4) | 12,529,635 | 50.97 |
| Sat_404 | C1_(4) | 12,529,635 | 50.97 |
| BARC-055359-13232 | C1_(4) | 14,079,084 | 51.08 |
| BARC-007901-00205 | C1_(4) | 14,985,510 | 51.13 |
| BARC-060187-16464 | C1_(4) | 16,789,799 | 51.74 |
| BARC-020889-03981 | C1_(4) | 18,904,768 | 51.75 |
| BARC-057291-14674 | C1_(4) | 19,337,323 | 52.35 |
| BARC-063099-18239 | C1_(4) | 26,870,515 | 52.49 |
| BARCSOYSSR_04_0881 | C1_(4) | 33,321,553 | 52.71 |
| Satt399 | C1_(4) | 33,321,553 | 52.71 |
| BARC-063667-18427 | C1_(4) | 34,928,793 | 52.72 |
| BARC-058775-15427 | C1_(4) | 35,970,986 | 52.72 |
| BARC-060917-16967 | C1_(4) | 36,250,476 | 52.72 |

TABLE 32-continued

| Locus | LG (ch) | Physical | Genetic (cM) |
|---|---|---|---|
| BARC-061273-17145 | C1_(4) | 36,403,199 | 52.72 |
| BARCSOYSSR_04_0953 | C1_(4) | 37,475,216 | 53.17 |
| Sat_416 | C1_(4) | 37,475,216 | 53.17 |
| BARC-063499-18381 | C1_(4) | 38,018,967 | 53.30 |
| BARC-059291-15718 | C1_(4) | 38,496,133 | 53.84 |
| BARC-059947-16237 | C1_(4) | 38,929,141 | 53.84 |
| S02211-1 | C1_(4) | 39,691,731 | 54.48 |
| BARC-061329-17168 | C1_(4) | 40,179,629 | 54.89 |
| BARC-061983-17604 | C1_(4) | 40,650,236 | 55.78 |
| BARCSOYSSR_04_1062 | C1_(4) | 40,871,939 | 56.46 |
| Satt476 | C1_(4) | 40,871,939 | 56.46 |
| BARCSOYSSR_04_1072 | C1_(4) | 41,223,589 | 58.35 |
| Sat_042 | C1_(4) | 41,223,589 | 58.35 |
| BARC-020509-04645 | C1_(4) | 41,667,200 | 59.31 |
| BARC-038989-07419 | C1_(4) | 41,667,225 | 59.34 |
| BARC-056153-14127 | C1_(4) | 41,872,671 | 60.01 |
| BARCSOYSSR_04_1140 | C1_(4) | 42,571,776 | 63.13 |
| Satt670 | C1_(4) | 42,571,776 | 63.13 |
| BARCSOYSSR_04_1172 | C1_(4) | 43,039,754 | 66.04 |
| Sat_311 | C1_(4) | 43,039,754 | 66.04 |
| BARC-030647-06914 | C1_(4) | 43,097,230 | 66.35 |
| BARC-042189-08197 | C1_(4) | 43,684,210 | 68.85 |
| BARC-040387-07722 | C1_(4) | 44,012,162 | 75.21 |
| S08942-1 | C1_(4) | 44,725,098 | 80.59 |
| BARC-044373-08692 | C1_(4) | 44,746,648 | 80.76 |
| BARC-052267-11398 | C1_(4) | 45,015,005 | 82.17 |
| BARC-022447-04328 | C1_(4) | 46,306,130 | 96.50 |
| BARC-019093-03301 | C1_(4) | 46,484,136 | 96.83 |
| BARC-013699-01240 | C1_(4) | 46,578,102 | 97.43 |
| BARC-024187-04790 | C1_(4) | 46,813,397 | 100.53 |
| BARC-015121-02570 | C1_(4) | 46,896,236 | 100.57 |
| BARCSOYSSR_04_1362 | C1_(4) | 46,964,916 | 101.22 |
| Satt338 | C1_(4) | 46,964,916 | 101.22 |
| BARC-044427-08705 | C1_(4) | 47,116,996 | 102.47 |
| BARCSOYSSR_04_1382 | C1_(4) | 47,335,984 | 104.01 |
| Satt682 | C1_(4) | 47,335,984 | 104.01 |
| BARC-061009-17004 | C1_(4) | 47,396,872 | 104.61 |
| BARC-018629-03208 | C1_(4) | 47,621,366 | 105.84 |
| BARC-028671-05985 | C1_(4) | 48,121,255 | 108.24 |
| BARC-062835-18113 | C1_(4) | 48,196,149 | 108.93 |
| BARC-032045-07244 | C1_(4) | 48,918,109 | 110.22 |
| BARC-041047-07901 | C1_(4) | 48,959,049 | 110.26 |
| BARC-029125-06087 | C1_(4) | 49,173,958 | 112.20 |

TABLE 33

| Locus | LG (ch) | Physical | Genetic (cM) |
|---|---|---|---|
| S05742-1 | C2_(6) | 410,442 | 4.88 |
| BARCSOYSSR_06_0028 | C2_(6) | 488,872 | 4.98 |
| Satt681 | C2_(6) | 488,872 | 4.98 |
| BARC-053027-11697 | C2_(6) | 651,027 | 5.19 |
| BARC-015973-02029 | C2_(6) | 825,798 | 6.11 |
| BARC-035239-07157 | C2_(6) | 1,655,968 | 11.62 |
| BARCSOYSSR_06_0107 | C2_(6) | 1,839,799 | 12.98 |
| Sat_130 | C2_(6) | 1,839,799 | 12.98 |
| BARC-056069-14029 | C2_(6) | 2,100,582 | 16.39 |
| BARC-064413-18929 | C2_(6) | 3,130,074 | 23.21 |
| BARC-024137-04780 | C2_(6) | 3,370,117 | 23.66 |
| BARC-042045-08161 | C2_(6) | 3,427,039 | 23.81 |
| BARC-016957-02165 | C2_(6) | 3,790,397 | 26.08 |
| BARCSOYSSR_06_0268 | C2_(6) | 4,677,084 | 29.63 |
| Satt640 | C2_(6) | 4,677,084 | 29.63 |
| BARCSOYSSR_06_0283 | C2_(6) | 4,947,481 | 31.78 |
| Sat_062 | C2_(6) | 4,947,481 | 31.78 |
| BARC-024049-04718 | C2_(6) | 5,375,750 | 33.01 |
| BARC-027846-06691 | C2_(6) | 5,400,643 | 33.29 |
| BARC-013887-01262 | C2_(6) | 5,400,860 | 33.29 |
| BARC-014949-01931 | C2_(6) | 5,404,840 | 33.29 |
| BARC-059985-16274 | C2_(6) | 5,443,313 | 34.40 |
| BARC-022163-04290 | C2_(6) | 5,492,796 | 34.43 |
| BARC-059997-16280 | C2_(6) | 5,498,347 | 35.37 |
| BARC-045145-08894 | C2_(6) | 5,895,495 | 36.09 |
| BARC-044639-08743 | C2_(6) | 6,080,236 | 36.77 |
| BARCSOYSSR_06_0348 | C2_(6) | 6,288,376 | 37.43 |

TABLE 33-continued

| Locus | LG (ch) | Physical | Genetic (cM) |
|---|---|---|---|
| Satt432 | C2_(6) | 6,288,376 | 37.43 |
| BARCSOYSSR_06_0362 | C2_(6) | 6,524,110 | 38.90 |
| Satt281 | C2_(6) | 6,524,110 | 38.90 |
| BARC-027948-06704 | C2_(6) | 6,706,819 | 40.25 |
| BARC-056271-14211 | C2_(6) | 6,914,147 | 41.46 |
| BARC-024221-04807 | C2_(6) | 7,072,465 | 41.51 |
| BARC-014321-01317 | C2_(6) | 7,190,150 | 42.30 |
| BARC-031455-07095 | C2_(6) | 7,313,010 | 42.54 |
| BARCSOYSSR_06_0408 | C2_(6) | 7,320,698 | 42.94 |
| Satt291 | C2_(6) | 7,320,698 | 42.94 |
| BARCSOYSSR_06_0473 | C2_(6) | 8,782,880 | 52.51 |
| Satt457 | C2_(6) | 8,782,880 | 52.51 |
| BARCSOYSSR_06_0547 | C2_(6) | 10,231,895 | 57.29 |
| Sat_153 | C2_(6) | 10,231,895 | 57.29 |
| BARC-029937-06757 | C2_(6) | 10,901,074 | 65.04 |
| BARC-040587-07787 | C2_(6) | 11,108,066 | 65.67 |
| BARC-041867-08122 | C2_(6) | 11,196,820 | 65.73 |
| BARC-063259-18282 | C2_(6) | 11,337,217 | 66.09 |
| S09155-1 | C2_(6) | 11,659,627 | 69.29 |
| BARC-024429-04882 | C2_(6) | 11,824,221 | 70.92 |
| BARC-018663-03235 | C2_(6) | 11,898,756 | 71.60 |
| BARC-039613-07521 | C2_(6) | 11,938,892 | 71.86 |
| BARC-031571-07112 | C2_(6) | 12,129,054 | 72.39 |
| BARC-022299-04310 | C2_(6) | 12,273,626 | 72.39 |
| BARCSOYSSR_06_0667 | C2_(6) | 12,310,043 | 73.19 |
| Satt322 | C2_(6) | 12,310,043 | 73.19 |
| BARC-028177-05786 | C2_(6) | 13,551,011 | 80.28 |
| BARC-017285-02260 | C2_(6) | 13,674,273 | 81.14 |
| BARC-013837-01254 | C2_(6) | 14,247,199 | 86.27 |
| BARC-052917-11675 | C2_(6) | 14,272,287 | 86.96 |
| BARC-016423-02585 | C2_(6) | 14,285,575 | 86.96 |
| BARC-014305-01308 | C2_(6) | 14,424,366 | 87.41 |
| BARC-015081-02562 | C2_(6) | 14,424,385 | 87.41 |
| BARC-047715-10388 | C2_(6) | 14,849,172 | 88.14 |
| S02037-1 | C2_(6) | 15,457,913 | 89.19 |
| BARCSOYSSR_06_0840 | C2_(6) | 15,756,463 | 89.71 |
| Satt363 | C2_(6) | 15,756,463 | 89.71 |
| BARCSOYSSR_06_0850 | C2_(6) | 15,958,859 | 90.53 |
| Sat_076 | C2_(6) | 15,958,859 | 90.53 |
| BARC-021735-04194 | C2_(6) | 15,980,393 | 90.88 |
| BARC-020031-04407 | C2_(6) | 16,050,227 | 91.43 |
| BARC-054075-12325 | C2_(6) | 16,050,267 | 92.10 |
| BARCSOYSSR_06_0858 | C2_(6) | 16,057,524 | 92.67 |
| Satt643 | C2_(6) | 16,057,524 | 92.67 |
| BARC-041165-07922 | C2_(6) | 16,155,041 | 93.21 |
| BARCSOYSSR_06_0876 | C2_(6) | 16,367,712 | 94.58 |
| Sat_402 | C2_(6) | 16,367,712 | 94.58 |
| S13136-1 | C2_(6) | 16,391,391 | 94.84 |
| S17291-001 | C2_(6) | 16,499,786 | 96.04 |
| S13139-1 | C2_(6) | 16,593,381 | 97.08 |
| BARC-025707-05008 | C2_(6) | 16,659,438 | 97.81 |
| S17292-001 | C2_(6) | 16,670,047 | 97.84 |
| S13146-1 | C2_(6) | 16,804,435 | 98.23 |
| BARC-056573-14503 | C2_(6) | 16,914,099 | 98.55 |
| BARC-063591-18406 | C2_(6) | 16,927,469 | 98.55 |
| BARC-013687-01230 | C2_(6) | 16,941,331 | 98.55 |
| BARC-014491-01561 | C2_(6) | 17,424,176 | 100.17 |
| S17293-001 | C2_(6) | 17,498,270 | 100.29 |
| BARC-064115-18558 | C2_(6) | 17,899,364 | 100.94 |
| BARC-020405-04602 | C2_(6) | 18,123,648 | 101.71 |
| S17294-001 | C2_(6) | 18,203,962 | 101.72 |
| BARC-065853-19796 | C2_(6) | 18,860,236 | 101.76 |
| BARC-040213-07685 | C2_(6) | 18,953,546 | 101.85 |
| S17581-001 | C2_(6) | 19,743,496 | 102.13 |
| S17691-001 | C2_(6) | 19,986,645 | 102.20 |
| S17701-001 | C2_(6) | 20,007,173 | 102.20 |
| BARCSOYSSR_06_1041 | C2_(6) | 20,018,876 | 102.23 |
| Satt557 | C2_(6) | 20,018,876 | 102.23 |
| S03703-1 | C2_(6) | 20,084,642 | 102.26 |
| S17297-001 | C2_(6) | 20,501,491 | 102.43 |
| S17298-001 | C2_(6) | 21,197,184 | 102.71 |
| BARC-029239-06133 | C2_(6) | 21,487,556 | 102.83 |
| S17299-001 | C2_(6) | 21,500,085 | 102.83 |
| BARC-054471-12090 | C2_(6) | 21,745,662 | 102.83 |
| BARC-050867-09934 | C2_(6) | 22,004,492 | 102.83 |
| S17300-001 | C2_(6) | 22,501,610 | 102.93 |
| S17301-001 | C2_(6) | 22,700,011 | 102.97 |
| BARCSOYSSR_06_1129 | C2_(6) | 23,874,403 | 103.22 |
| Satt489 | C2_(6) | 23,874,403 | 103.22 |
| BARC-060711-16810 | C2_(6) | 25,068,452 | 103.28 |
| S17306-001 | C2_(6) | 25,700,006 | 103.29 |
| BARC-057907-14996 | C2_(6) | 27,768,566 | 103.30 |
| S17310-001 | C2_(6) | 28,501,458 | 103.30 |
| S17311-001 | C2_(6) | 28,671,736 | 103.30 |
| S17312-001 | C2_(6) | 29,499,523 | 103.30 |
| S17313-001 | C2_(6) | 30,203,054 | 103.31 |
| S17316-001 | C2_(6) | 31,694,650 | 103.31 |
| S17317-001 | C2_(6) | 32,503,141 | 103.31 |
| S17318-001 | C2_(6) | 33,196,184 | 103.32 |
| BARCSOYSSR_06_1255 | C2_(6) | 35,215,338 | 103.32 |
| Sat_312 | C2_(6) | 35,215,338 | 103.32 |
| S17322-001 | C2_(6) | 35,509,548 | 103.37 |
| BARC-024923-10366 | C2_(6) | 36,069,731 | 103.45 |
| S17326-001 | C2_(6) | 37,712,913 | 103.79 |
| BARC-015077-02559 | C2_(6) | 38,136,028 | 103.88 |
| S17327-001 | C2_(6) | 38,467,854 | 104.00 |
| S17328-001 | C2_(6) | 39,168,136 | 104.25 |
| S17329-001 | C2_(6) | 39,533,730 | 104.38 |
| BARC-061147-17083 | C2_(6) | 39,878,533 | 104.50 |
| S10746-1 | C2_(6) | 40,766,974 | 104.94 |
| BARC-056379-14289 | C2_(6) | 41,204,571 | 105.16 |
| BARC-029025-06051 | C2_(6) | 41,308,555 | 105.73 |
| S17331-001 | C2_(6) | 41,476,201 | 105.80 |
| S17332-001 | C2_(6) | 42,450,296 | 106.19 |
| BARC-058239-15169 | C2_(6) | 42,603,052 | 106.26 |
| BARC-011045-00827 | C2_(6) | 42,963,664 | 106.36 |
| BARC-059303-15722 | C2_(6) | 42,991,306 | 106.36 |
| BARC-023203-03824 | C2_(6) | 43,185,037 | 106.47 |
| BARC-023277-05311 | C2_(6) | 43,397,269 | 106.59 |
| BARCSOYSSR_06_1476 | C2_(6) | 43,950,998 | 106.85 |
| Satt079 | C2_(6) | 43,950,998 | 106.85 |
| BARC-051929-11299 | C2_(6) | 45,363,053 | 107.60 |
| BARC-062515-17881 | C2_(6) | 46,063,176 | 108.55 |
| BARCSOYSSR_06_1579 | C2_(6) | 46,273,201 | 109.58 |
| Sct_028 | C2_(6) | 46,273,201 | 109.58 |
| BARCSOYSSR_06_1581 | C2_(6) | 46,286,900 | 109.96 |
| Satt307 | C2_(6) | 46,286,900 | 109.96 |
| BARC-010777-00746 | C2_(6) | 47,413,265 | 113.05 |
| S17337-001 | C2_(6) | 47,500,976 | 113.10 |
| S13093-1 | C2_(6) | 47,521,797 | 113.11 |
| BARC-021425-04104 | C2_(6) | 47,782,099 | 113.24 |
| BARCSOYSSR_06_1680 | C2_(6) | 47,820,539 | 114.18 |
| Satt202 | C2_(6) | 47,820,539 | 114.18 |
| S12211-1 | C2_(6) | 48,475,049 | 116.04 |
| BARCSOYSSR_06_1726 | C2_(6) | 48,582,450 | 116.34 |
| Sat_252 | C2_(6) | 48,582,450 | 116.34 |
| BARC-038923-07396 | C2_(6) | 48,635,024 | 126.95 |
| BARC-047703-10385 | C2_(6) | 48,635,266 | 126.95 |
| BARC-042663-08339 | C2_(6) | 48,658,985 | 126.95 |
| BARC-016969-02170 | C2_(6) | 48,677,811 | 126.95 |
| BARCSOYSSR_06_1762 | C2_(6) | 49,159,652 | 127.93 |
| Satt371 | C2_(6) | 49,159,652 | 127.93 |
| BARC-064859-18826 | C2_(6) | 49,329,186 | 128.37 |
| BARC-064297-18613 | C2_(6) | 49,411,956 | 129.53 |
| BARC-038861-07350 | C2_(6) | 49,975,437 | 132.41 |
| S04555-1 | C2_(6) | 49,978,151 | 132.43 |
| BARC-025179-06455 | C2_(6) | 50,324,535 | 135.04 |
| BARC-030551-06898 | C2_(6) | 50,372,013 | 135.04 |
| BARC-030551-06899 | C2_(6) | 50,372,013 | 136.12 |
| BARC-018915-03279 | C2_(6) | 50,602,830 | 136.51 |

TABLE 34

| Locus | LG (ch) | Physical | Genetic (cM) |
|---|---|---|---|
| BARC-024147-04784 | D1a_(1) | 398,072 | 0.00 |
| BARC-028843-06027 | D1a_(1) | 507,545 | 5.38 |
| S08519-1 | D1a_(1) | 759,365 | 8.96 |
| BARC-035199-07136 | D1a_(1) | 1,030,879 | 12.82 |
| BARC-038883-07384 | D1a_(1) | 1,490,280 | 15.98 |
| BARC-045297-08928 | D1a_(1) | 1,744,924 | 16.72 |
| BARC-047699-10383 | D1a_(1) | 1,888,906 | 17.33 |
| BARC-016475-02622 | D1a_(1) | 2,205,640 | 18.59 |

TABLE 34-continued

| Locus | LG (ch) | Physical | Genetic (cM) |
|---|---|---|---|
| BARC-015477-01982 | D1a_(1) | 2,280,958 | 19.67 |
| BARC-056093-14075 | D1a_(1) | 2,345,161 | 20.84 |
| BARC-024477-04900 | D1a_(1) | 2,699,581 | 24.80 |
| BARC-042721-08396 | D1a_(1) | 3,318,354 | 26.90 |
| BARCSOYSSR_01_0206 | D1a_(1) | 3,758,425 | 31.67 |
| Satt531 | D1a_(1) | 3,758,425 | 31.67 |
| BARC-030973-06982 | D1a_(1) | 4,324,690 | 33.54 |
| BARC-060833-16926 | D1a_(1) | 4,831,837 | 37.14 |

TABLE 35

| Locus | LG (ch) | Physical | Genetic (cM) |
|---|---|---|---|
| BARC-029753-06334 | D1b_(2) | 97,825 | 0.01 |
| BARC-048593-10672 | D1b_(2) | 600,925 | 0.95 |
| BARC-041773-08087 | D1b_(2) | 653,480 | 3.54 |
| BARC-032497-08984 | D1b_(2) | 841,950 | 4.85 |
| BARC-041475-08016 | D1b_(2) | 842,010 | 4.88 |
| BARC-025791-05070 | D1b_(2) | 1,071,624 | 5.75 |
| BARC-013995-01298 | D1b_(2) | 1,893,325 | 12.38 |
| BARCSOYSSR_02_0106 | D1b_(2) | 1,974,569 | 14.06 |
| Sat_279 | D1b_(2) | 1,974,569 | 14.06 |
| BARC-022263-04301 | D1b_(2) | 2,351,102 | 17.97 |
| BARC-029969-06762 | D1b_(2) | 2,454,222 | 18.80 |
| BARC-029431-06192 | D1b_(2) | 2,903,075 | 19.78 |
| BARC-020103-04462 | D1b_(2) | 3,111,610 | 20.45 |
| BARC-054295-12453 | D1b_(2) | 3,295,143 | 21.46 |
| BARC-032525-08992 | D1b_(2) | 3,469,712 | 21.96 |
| BARC-020481-04638 | D1b_(2) | 4,033,363 | 25.12 |
| BARC-050661-09809 | D1b_(2) | 4,190,107 | 26.14 |
| BARC-018187-02537 | D1b_(2) | 4,344,986 | 27.01 |
| BARC-065787-19749 | D1b_(2) | 4,549,822 | 28.43 |
| BARCSOYSSR_02_0263 | D1b_(2) | 4,844,986 | 29.38 |
| Sat_351 | D1b_(2) | 4,844,986 | 29.38 |
| S12876-1 | D1b_(2) | 4,893,148 | 29.48 |
| BARC-046124-10284 | D1b_(2) | 5,319,977 | 30.39 |
| BARC-056237-14178 | D1b_(2) | 5,455,197 | 30.67 |
| BARC-906883-01023 | D1b_(2) | 5,555,734 | 30.67 |
| BARC-051039-10958 | D1b_(2) | 5,900,203 | 32.40 |
| BARCSOYSSR_02_0339 | D1b_(2) | 6,307,499 | 34.56 |
| Satt095 | D1b_(2) | 6,307,499 | 34.56 |
| BARC-048341-10551 | D1b_(2) | 6,660,140 | 36.12 |
| BARC-041307-07962 | D1b_(2) | 6,879,228 | 36.88 |
| BARCSOYSSR_02_0385 | D1b_(2) | 6,977,734 | 37.46 |
| BE021153 | D1b_(2) | 6,977,734 | 37.46 |
| BARC-028393-05861 | D1b_(2) | 7,260,557 | 40.33 |
| BARC-050325-09554 | D1b_(2) | 7,265,879 | 41.69 |
| BARC-019149-03317 | D1b_(2) | 7,472,850 | 42.10 |
| BARC-019149-03315 | D1b_(2) | 7,472,850 | 44.25 |
| BARC-063497-18380 | D1b_(2) | 7,601,722 | 44.46 |
| BARC-053459-11856 | D1b_(2) | 8,172,878 | 45.03 |
| BARCSOYSSR_02_0478 | D1b_(2) | 8,738,209 | 46.70 |
| Satt698 | D1b_(2) | 8,738,209 | 46.70 |
| BARCSOYSSR_02_0480 | D1b_(2) | 8,742,635 | 46.70 |
| Sat_211 | D1b_(2) | 8,742,635 | 46.70 |
| BARC-057545-14810 | D1b_(2) | 9,055,833 | 46.85 |
| BARC-062191-17700 | D1b_(2) | 9,094,347 | 47.08 |
| BARCSOYSSR_02_0502 | D1b_(2) | 9,385,720 | 47.44 |
| Sat_173 | D1b_(2) | 9,385,720 | 47.44 |
| BARC-025955-05182 | D1b_(2) | 9,590,972 | 47.93 |
| BARC-062989-18203 | D1b_(2) | 9,714,336 | 48.44 |
| S05937-1 | D1b_(2) | 9,714,426 | 48.44 |
| BARC-016079-02059 | D1b_(2) | 9,793,931 | 48.50 |
| BARC-062943-18169 | D1b_(2) | 9,938,165 | 49.10 |
| BARC-030665-06919 | D1b_(2) | 10,233,955 | 50.25 |
| BARCSOYSSR_02_0555 | D1b_(2) | 10,538,050 | 52.98 |
| Satt558 | D1b_(2) | 10,538,050 | 52.98 |
| BARC-025183-06457 | D1b_(2) | 10,630,472 | 53.70 |
| BARCSOYSSR_02_0578 | D1b_(2) | 11,076,972 | 55.79 |
| Sat_254 | D1b_(2) | 11,076,972 | 55.79 |
| BARCSOYSSR_02_0583 | D1b_(2) | 11,234,567 | 58.22 |
| AI856415 | D1b_(2) | 11,234,567 | 58.22 |
| S08575-1 | D1b_(2) | 11,502,780 | 58.78 |
| BARCSOYSSR_02_0676 | D1b_(2) | 12,956,582 | 61.84 |
| Satt542 | D1b_(2) | 12,956,582 | 61.84 |

TABLE 35-continued

| Locus | LG (ch) | Physical | Genetic (cM) |
|---|---|---|---|
| BARC-031301-07041 | D1b_(2) | 14,031,310 | 65.18 |
| BARC-048815-10726 | D1b_(2) | 14,106,291 | 66.18 |
| BARC-013487-00500 | D1b_(2) | 14,418,339 | 68.12 |
| BARC-047945-10443 | D1b_(2) | 14,851,469 | 71.70 |
| S08669-1 | D1b_(2) | 15,446,229 | 76.53 |
| BARC-043983-08572 | D1b_(2) | 15,490,882 | 76.90 |
| BARC-018819-03259 | D1b_(2) | 15,718,441 | 79.16 |
| BARC-018781-03247 | D1b_(2) | 15,718,559 | 79.16 |
| BARC-027390-06561 | D1b_(2) | 16,502,802 | 79.17 |
| BARCSOYSSR_02_0846 | D1b_(2) | 17,474,784 | 81.46 |
| Satt428 | D1b_(2) | 17,474,784 | 81.46 |
| BARCSOYSSR_02_0855 | D1b_(2) | 19,409,056 | 82.59 |
| Satt579 | D1b_(2) | 19,409,056 | 82.59 |
| BARC-061653-17307 | D1b_(2) | 30,848,974 | 83.01 |
| BARCSOYSSR_02_1048 | D1b_(2) | 32,526,214 | 83.26 |
| Satt600 | D1b_(2) | 32,526,214 | 83.26 |
| S11212-1 | D1b_(2) | 33,158,449 | 83.28 |
| BARC-057711-14907 | D1b_(2) | 36,102,833 | 83.35 |
| BARC-052515-11484 | D1b_(2) | 38,644,397 | 83.36 |
| BARC-060135-16407 | D1b_(2) | 39,922,914 | 83.38 |
| BARC-018381-03605 | D1b_(2) | 40,362,445 | 83.93 |
| BARC-049713-09132 | D1b_(2) | 40,552,642 | 84.11 |
| BARC-053163-11724 | D1b_(2) | 40,596,174 | 84.31 |
| BARC-063685-18434 | D1b_(2) | 40,623,295 | 84.31 |
| BARC-053161-11723 | D1b_(2) | 40,704,043 | 84.69 |
| BARCSOYSSR_02_1257 | D1b_(2) | 40,884,780 | 85.66 |
| Sat_169 | D1b_(2) | 40,884,780 | 85.66 |
| BARCSOYSSR_02_1268 | D1b_(2) | 41,290,043 | 87.01 |
| Satt644 | D1b_(2) | 41,290,043 | 87.01 |
| BARC-032679-09011 | D1b_(2) | 41,923,345 | 88.86 |
| BARC-055839-13759 | D1b_(2) | 42,622,375 | 90.55 |
| BARCSOYSSR_02_1386 | D1b_(2) | 43,775,594 | 93.94 |
| Satt546 | D1b_(2) | 43,775,594 | 93.94 |
| BARC-018115-02528 | D1b_(2) | 44,075,539 | 94.55 |
| BARC-032025-07239 | D1b_(2) | 44,109,165 | 94.88 |
| BARC-024409-04868 | D1b_(2) | 44,522,551 | 95.29 |
| BARC-021561-04146 | D1b_(2) | 44,574,118 | 95.45 |
| BARCSOYSSR_02_1436 | D1b_(2) | 44,879,014 | 98.37 |
| Sat_139 | D1b_(2) | 44,879,014 | 98.37 |
| BARCSOYSSR_02_1500 | D1b_(2) | 45,655,561 | 103.25 |
| Satt703 | D1b_(2) | 45,655,561 | 103.25 |
| BARC-030479-06875 | D1b_(2) | 45,682,686 | 103.61 |
| S00543-1 | D1b_(2) | 45,776,142 | 103.71 |
| BARC-040187-07679 | D1b_(2) | 45,948,050 | 103.90 |
| BARC-021647-04164 | D1b_(2) | 46,042,031 | 103.90 |
| BARCSOYSSR_02_1540 | D1b_(2) | 46,353,760 | 105.87 |
| Sat_069 | D1b_(2) | 46,353,760 | 105.87 |
| BARCSOYSSR_02_1602 | D1b_(2) | 47,404,748 | 113.32 |
| Sat_183 | D1b_(2) | 47,404,748 | 113.32 |
| BARC-017895-02427 | D1b_(2) | 47,548,016 | 114.69 |
| BARC-045013-08865 | D1b_(2) | 48,138,016 | 116.48 |
| BARC-028373-05856 | D1b_(2) | 48,185,260 | 116.49 |
| BARC-054149-12354 | D1b_(2) | 48,374,309 | 118.34 |
| BARCSOYSSR_02_1682 | D1b_(2) | 48,621,937 | 119.18 |
| Sat_198 | D1b_(2) | 48,621,937 | 119.18 |
| BARC-057665-14892 | D1b_(2) | 48,703,378 | 120.41 |
| BARC-040169-07675 | D1b_(2) | 49,388,450 | 125.79 |
| BARC-044747-08795 | D1b_(2) | 49,530,080 | 126.26 |
| BARC-054217-12380 | D1b_(2) | 49,541,234 | 126.26 |
| BARCSOYSSR_02_1759 | D1b_(2) | 50,122,136 | 129.78 |
| Sat_289 | D1b_(2) | 50,122,136 | 129.78 |
| BARC-059321-15931 | D1b_(2) | 50,231,557 | 130.71 |
| BARC-051677-11199 | D1b_(2) | 50,270,411 | 130.81 |
| BARC-039799-07588 | D1b_(2) | 50,691,457 | 131.85 |
| BARC-019805-04379 | D1b_(2) | 51,243,272 | 133.30 |
| BARC-041469-08004 | D1b_(2) | 51,407,018 | 133.85 |
| BARC-020293-04543 | D1b_(2) | 51,541,368 | 134.02 |
| BARC-906743-01012 | D1b_(2) | 51,549,897 | 134.02 |

TABLE 36

| Locus | LG (ch) | Physical | Genetic (cM) |
|---|---|---|---|
| BARC-012687-00367 | D2_(17) | 8,987,706 | 42.45 |
| BARCSOYSSR_17_0510 | D2_(17) | 9,088,821 | 42.69 |

TABLE 36-continued

| Locus | LG (ch) | Physical | Genetic (cM) |
|---|---|---|---|
| Satt002 | D2_(17) | 9,088,821 | 42.69 |
| BARC-024449-04894 | D2_(17) | 9,260,050 | 44.74 |
| BARCSOYSSR_17_0554 | D2_(17) | 9,863,263 | 46.77 |
| Satt154 | D2_(17) | 9,863,263 | 46.77 |
| BARCSOYSSR_17_0561 | D2_(17) | 9,949,913 | 47.18 |
| Satt582 | D2_(17) | 9,949,913 | 47.18 |
| BARC-031145-07005 | D2_(17) | 10,534,591 | 50.41 |
| BARC-025885-05138 | D2_(17) | 11,157,614 | 55.59 |
| BARC-025885-05137 | D2_(17) | 11,157,614 | 55.78 |
| BARC-017191-02247 | D2_(17) | 11,260,712 | 57.18 |
| BARC-063551-18386 | D2_(17) | 11,372,457 | 57.33 |
| BARCSOYSSR_17_0669 | D2_(17) | 11,724,512 | 58.74 |
| Satt397 | D2_(17) | 11,724,512 | 58.74 |
| BARC-013637-01186 | D2_(17) | 11,915,457 | 59.92 |
| BARC-013969-01290 | D2_(17) | 12,666,290 | 62.79 |
| BARCSOYSSR_17_0731 | D2_(17) | 12,771,421 | 62.88 |
| Sat_292 | D2_(17) | 12,771,421 | 62.88 |
| BARCSOYSSR_17_0754 | D2_(17) | 13,150,232 | 63.94 |
| Sat_222 | D2_(17) | 13,150,232 | 63.94 |
| BARC-047685-10379 | D2_(17) | 13,354,764 | 64.72 |
| BARCSOYSSR_17_0807 | D2_(17) | 14,024,929 | 68.20 |
| Satt389 | D2_(17) | 14,024,929 | 68.20 |
| BARC-051665-11191 | D2_(17) | 14,849,946 | 72.14 |
| BARC-047829-10399 | D2_(17) | 14,938,405 | 72.23 |
| BARC-048389-10562 | D2_(17) | 15,128,584 | 72.65 |
| BARC-059581-15926 | D2_(17) | 16,113,309 | 73.34 |
| S01452-1 | D2_(17) | 16,136,646 | 73.34 |
| BARC-060511-16708 | D2_(17) | 17,995,210 | 73.34 |
| BARC-062079-17648 | D2_(17) | 18,355,304 | 73.34 |
| BARC-062127-17661 | D2_(17) | 18,480,666 | 73.34 |
| BARCSOYSSR_17_0930 | D2_(17) | 18,770,886 | 73.91 |
| Satt514 | D2_(17) | 18,770,886 | 73.91 |
| BARCSOYSSR_17_0973 | D2_(17) | 19,746,681 | 74.20 |
| Satt082 | D2_(17) | 19,746,681 | 74.20 |
| BARCSOYSSR_17_0988 | D2_(17) | 20,710,130 | 74.25 |
| Sat_300 | D2_(17) | 20,710,130 | 74.25 |
| BARC-010289-00577 | D2_(17) | 24,102,133 | 75.05 |
| BARC-028773-06009 | D2_(17) | 24,177,949 | 75.06 |
| BARC-065605-19580 | D2_(17) | 25,895,720 | 75.44 |
| BARC-060353-16626 | D2_(17) | 27,486,421 | 75.44 |
| BARC-065169-19205 | D2_(17) | 28,115,010 | 75.44 |
| BARC-065239-19278 | D2_(17) | 31,882,561 | 75.85 |
| BARC-057449-14753 | D2_(17) | 34,117,998 | 76.12 |
| BARC-050501-09705 | D2_(17) | 36,462,106 | 77.39 |
| BARC-040531-07786 | D2_(17) | 37,275,595 | 78.31 |
| BARC-019787-04375 | D2_(17) | 37,418,900 | 78.52 |
| BARC-064095-18554 | D2_(17) | 37,769,021 | 79.94 |
| BARC-037179-06731 | D2_(17) | 38,089,554 | 82.62 |
| BARCSOYSSR_17_1425 | D2_(17) | 38,091,254 | 84.17 |
| GMHSP179 | D2_(17) | 38,091,254 | 84.17 |
| BARC-013653-01222 | D2_(17) | 38,730,417 | 86.45 |
| BARC-025927-05161 | D2_(17) | 38,916,720 | 87.84 |
| BARCSOYSSR_17_1477 | D2_(17) | 39,057,375 | 90.28 |
| Satt310 | D2_(17) | 39,057,375 | 90.28 |
| BARC-049255-10878 | D2_(17) | 39,399,533 | 95.97 |
| BARCSOYSSR_17_1511 | D2_(17) | 39,561,506 | 98.51 |
| Sat_326 | D2_(17) | 39,561,506 | 98.51 |
| S11993-1 | D2_(17) | 39,804,515 | 99.75 |
| BARCSOYSSR_17_1540 | D2_(17) | 40,043,057 | 100.96 |
| Satt413 | D2_(17) | 40,043,057 | 100.96 |
| BARC-010861-00784 | D2_(17) | 40,052,990 | 101.43 |
| BARC-055793-13720 | D2_(17) | 40,053,275 | 101.43 |
| BARC-029859-06448 | D2_(17) | 40,146,564 | 104.31 |
| BARC-029279-06138 | D2_(17) | 41,007,685 | 109.10 |
| BARC-014747-01639 | D2_(17) | 41,146,946 | 110.80 |
| BARC-019021-03292 | D2_(17) | 41,237,076 | 111.26 |
| BARCSOYSSR_17_1639 | D2_(17) | 41,333,788 | 114.29 |
| Sat_220 | D2_(17) | 41,333,788 | 114.29 |
| BARC-039151-07458 | D2_(17) | 41,489,936 | 116.10 |
| BARC-051411-11102 | D2_(17) | 41,520,637 | 117.24 |
| BARC-030531-06894 | D2_(17) | 41,806,677 | 117.79 |
| BARC-001489-00142 | D2_(17) | 41,821,321 | 118.12 |

TABLE 37

| Locus | LG (ch) | Physical | Genetic (cM) |
|---|---|---|---|
| BARC-017755-03124 | E_(15) | 11,798,929 | 59.38 |
| BARC-018461-02916 | E_(15) | 12,256,121 | 61.36 |
| BARC-062799-18070 | E_(15) | 13,676,958 | 66.03 |
| BARC-066103-17539 | E_(15) | 13,735,240 | 66.03 |
| BARC-057283-14667 | E_(15) | 13,762,803 | 68.06 |
| BARC-030079-06803 | E_(15) | 14,032,584 | 68.46 |
| BARC-038377-10061 | E_(15) | 14,329,242 | 69.39 |
| BARC-054023-12243 | E_(15) | 14,753,749 | 69.79 |
| BARCSOYSSR_15_0692 | E_(15) | 14,918,775 | 70.47 |
| Satt606 | E_(15) | 14,918,775 | 70.47 |
| BARC-054095-12332 | E_(15) | 15,100,427 | 70.60 |
| BARC-016029-02040 | E_(15) | 15,100,540 | 70.60 |
| BARC-023525-05447 | E_(15) | 15,443,300 | 71.20 |
| BARC-060905-16966 | E_(15) | 15,743,043 | 71.42 |
| BARCSOYSSR_15_0753 | E_(15) | 16,668,418 | 72.02 |
| Sat_136 | E_(15) | 16,668,418 | 72.02 |
| BARCSOYSSR_15_0765 | E_(15) | 17,025,474 | 74.32 |
| Sat_380 | E_(15) | 17,025,474 | 74.32 |
| BARCSOYSSR_15_0766 | E_(15) | 17,054,779 | 74.37 |
| Satt706 | E_(15) | 17,054,779 | 74.37 |
| BARC-029637-06273 | E_(15) | 17,582,453 | 74.81 |
| BARCSOYSSR_15_0800 | E_(15) | 17,692,405 | 75.28 |
| Sat_107 | E_(15) | 17,692,405 | 75.28 |
| BARC-052575-11504 | E_(15) | 18,539,487 | 75.81 |
| BARC-054787-12166 | E_(15) | 19,024,123 | 75.94 |
| BARC-059455-15814 | E_(15) | 20,019,884 | 76.10 |
| BARC-030059-06795 | E_(15) | 20,686,689 | 76.37 |
| BARC-059689-16003 | E_(15) | 21,179,215 | 76.60 |
| BARC-061007-17001 | E_(15) | 22,274,650 | 76.87 |
| BARC-059873-16177 | E_(15) | 23,625,526 | 77.04 |
| BARC-062747-18029 | E_(15) | 30,330,055 | 77.04 |
| BARC-059537-15899 | E_(15) | 32,251,236 | 77.04 |
| BARCSOYSSR_15_1125 | E_(15) | 34,902,080 | 77.04 |
| Satt483 | E_(15) | 34,902,080 | 77.04 |
| BARC-039931-07614 | E_(15) | 36,577,083 | 77.27 |
| BARC-063963-18516 | E_(15) | 37,088,862 | 77.41 |
| BARC-051429-11107 | E_(15) | 37,297,779 | 77.49 |
| BARC-058493-15308 | E_(15) | 39,652,366 | 78.62 |
| BARC-007650-00171 | E_(15) | 41,305,413 | 78.64 |
| BARC-001485-00045 | E_(15) | 41,305,449 | 78.64 |
| BARC-014501-01563 | E_(15) | 41,841,189 | 78.66 |
| BARC-044083-08609 | E_(15) | 43,374,464 | 79.23 |
| BARC-028805-06018 | E_(15) | 43,849,421 | 79.25 |
| BARC-028221-05799 | E_(15) | 43,851,079 | 79.27 |
| BARC-050947-10881 | E_(15) | 45,424,612 | 80.37 |
| BARC-055571-13451 | E_(15) | 47,021,065 | 81.62 |
| BARC-055527-13350 | E_(15) | 47,080,727 | 82.28 |
| BARC-051565-11166 | E_(15) | 47,427,853 | 82.70 |
| BARC-040965-07871 | E_(15) | 48,222,867 | 84.93 |
| BARC-016083-02061 | E_(15) | 48,657,557 | 85.49 |
| BARC-043041-08509 | E_(15) | 48,694,488 | 85.88 |
| BARC-052379-11435 | E_(15) | 48,781,847 | 86.52 |
| BARC-020425-04614 | E_(15) | 48,863,918 | 86.64 |
| BARC-016131-02290 | E_(15) | 49,621,518 | 88.47 |
| BARC-013073-00440 | E_(15) | 49,883,172 | 90.16 |
| BARC-022009-04249 | E_(15) | 50,061,005 | 91.30 |
| BARC-042937-08466 | E_(15) | 50,114,250 | 92.37 |
| S13446-1 | E_(15) | 50,237,460 | 92.65 |
| BARCSOYSSR_15_1568 | E_(15) | 50,282,274 | 92.75 |
| Sat_381 | E_(15) | 50,282,274 | 92.75 |
| BARC-013235-00458 | E_(15) | 50,334,269 | 93.35 |
| BARC-025839-05112 | E_(15) | 50,395,865 | 93.42 |
| BARC-017767-03127 | E_(15) | 50,396,230 | 93.53 |
| BARCSOYSSR_15_1582 | E_(15) | 50,497,750 | 96.42 |
| Satt231 | E_(15) | 50,497,750 | 96.42 |

TABLE 38

| Locus | LG (ch) | Physical | Genetic (cM) |
|---|---|---|---|
| S00252-1 | F_(13) | 235,439 | 0.00 |
| BARC-010699-00711 | F_(13) | 614,924 | 0.00 |
| BARC-017209-02250 | F_(13) | 730,833 | 5.44 |
| BARCSOYSSR_13_0062 | F_(13) | 1,294,413 | 9.67 |
| Satt659 | F_(13) | 1,294,413 | 9.67 |

TABLE 38-continued

| Locus | LG (ch) | Physical | Genetic (cM) |
|---|---|---|---|
| BARC-025291-06469 | F_(13) | 1,456,775 | 10.02 |
| BARCSOYSSR_13_0099 | F_(13) | 1,909,350 | 11.55 |
| Sat_039 | F_(13) | 1,909,350 | 11.55 |
| BARC-027474-06587 | F_(13) | 2,028,114 | 11.77 |
| BARC-032373-08957 | F_(13) | 2,708,409 | 13.08 |
| BARC-065403-19439 | F_(13) | 2,776,800 | 13.08 |
| BARC-051955-11307 | F_(13) | 3,140,575 | 15.04 |
| BARC-064051-18538 | F_(13) | 4,198,168 | 18.38 |
| BARC-016463-02617 | F_(13) | 4,208,231 | 18.42 |
| BARC-051237-11031 | F_(13) | 4,227,643 | 18.55 |
| BARC-051235-11030 | F_(13) | 4,246,363 | 18.61 |
| BARC-066191-19815 | F_(13) | 4,553,351 | 19.16 |
| BARC-035375-07174 | F_(13) | 4,556,823 | 19.18 |
| BARC-059869-16174 | F_(13) | 4,583,951 | 20.08 |
| BARC-043267-08567 | F_(13) | 5,043,469 | 20.99 |
| BARCSOYSSR_13_0272 | F_(13) | 5,376,598 | 22.62 |
| Satt252 | F_(13) | 5,376,598 | 22.62 |
| BARCSOYSSR_13_0282 | F_(13) | 5,491,280 | 23.35 |
| Satt348 | F_(13) | 5,491,280 | 23.35 |
| BARC-013115-01441 | F_(13) | 6,069,736 | 24.26 |
| BARCSOYSSR_13_0340 | F_(13) | 6,580,549 | 27.45 |
| Satt269 | F_(13) | 6,580,549 | 27.45 |
| BARCSOYSSR_13_0341 | F_(13) | 6,593,658 | 27.61 |
| Satt145 | F_(13) | 6,593,658 | 27.61 |
| BARC-042289-08234 | F_(13) | 6,780,758 | 27.94 |
| BARC-049723-09133 | F_(13) | 7,103,710 | 29.63 |
| BARC-051405-11095 | F_(13) | 7,521,465 | 31.01 |
| BARC-058031-15072 | F_(13) | 7,700,339 | 31.36 |
| BARC-059611-15942 | F_(13) | 7,755,550 | 31.55 |
| BARC-046112-10273 | F_(13) | 7,858,072 | 32.14 |
| BARC-043173-08548 | F_(13) | 8,264,459 | 33.67 |
| BARC-016943-02391 | F_(13) | 8,529,450 | 33.93 |
| BARC-018551-02971 | F_(13) | 8,529,473 | 34.07 |
| BARCSOYSSR_13_0445 | F_(13) | 8,722,718 | 34.39 |
| Satt030 | F_(13) | 8,722,718 | 34.39 |
| BARCSOYSSR_13_0458 | F_(13) | 9,567,240 | 34.72 |
| Satt569 | F_(13) | 9,567,240 | 34.72 |
| BARC-064377-18635 | F_(13) | 10,551,898 | 34.86 |
| BARC-024749-05639 | F_(13) | 10,719,759 | 35.01 |
| BARC-023287-05318 | F_(13) | 10,722,785 | 35.01 |
| BARCSOYSSR_13_0518 | F_(13) | 11,494,492 | 35.29 |
| Satt343 | F_(13) | 11,494,492 | 35.29 |
| BARC-019391-03903 | F_(13) | 11,513,020 | 35.44 |
| BARC-014099-01531 | F_(13) | 11,513,023 | 35.44 |
| BARC-049859-09180 | F_(13) | 12,279,425 | 35.98 |
| BARC-024639-05505 | F_(13) | 12,952,996 | 36.54 |
| BARC-064897-18988 | F_(13) | 13,803,730 | 36.66 |
| BARC-061105-17048 | F_(13) | 13,826,582 | 36.67 |
| BARC-064849-18822 | F_(13) | 17,609,468 | 36.68 |
| BARC-062009-17616 | F_(13) | 19,330,460 | 36.74 |
| S04060-1 | F_(13) | 20,365,663 | 36.90 |
| S02664-1 | F_(13) | 20,744,030 | 36.96 |
| BARC-044797-08809 | F_(13) | 23,987,460 | 37.47 |
| BARCSOYSSR_13_0877 | F_(13) | 24,451,400 | 39.62 |
| Satt663 | F_(13) | 24,451,400 | 39.62 |
| BARCSOYSSR_13_0952 | F_(13) | 25,789,165 | 43.04 |
| Sat_297 | F_(13) | 25,789,165 | 43.04 |
| BARC-050657-09804 | F_(13) | 26,009,844 | 45.03 |
| BARC-025897-05144 | F_(13) | 27,144,939 | 49.42 |
| BARC-008001-00154 | F_(13) | 27,569,047 | 50.40 |
| BARC-038413-10074 | F_(13) | 27,781,754 | 50.71 |
| BARCSOYSSR_13_1098 | F_(13) | 28,415,998 | 51.20 |
| Satt334 | F_(13) | 28,415,998 | 51.20 |
| BARC-007567-00030 | F_(13) | 29,549,705 | 52.26 |
| BARC-041671-08065 | F_(13) | 30,268,846 | 53.20 |
| BARC-063863-18477 | F_(13) | 30,396,785 | 53.20 |
| BARC-030853-06954 | F_(13) | 30,581,858 | 54.08 |
| BARC-047961-10449 | F_(13) | 30,582,406 | 54.08 |
| BARC-013633-01184 | F_(13) | 30,771,429 | 55.32 |
| BARC-043227-08562 | F_(13) | 30,863,656 | 55.99 |
| BARC-015903-02010 | F_(13) | 30,965,576 | 56.03 |
| BARCSOYSSR_13_1241 | F_(13) | 30,984,460 | 56.89 |
| Sat_317 | F_(13) | 30,984,460 | 56.89 |
| BARC-018079-02510 | F_(13) | 31,994,036 | 60.49 |
| BARC-061189-17109 | F_(13) | 32,064,753 | 64.12 |
| BARC-039631-07532 | F_(13) | 32,179,461 | 65.09 |
| BARC-013257-00462 | F_(13) | 32,207,393 | 65.13 |
| BARC-038503-10136 | F_(13) | 32,623,088 | 66.91 |
| BARC-041649-08056 | F_(13) | 33,280,536 | 68.55 |
| BARC-024045-04714 | F_(13) | 33,302,688 | 68.70 |
| BARC-039765-07568 | F_(13) | 33,302,789 | 68.73 |
| BARCSOYSSR_13_1369 | F_(13) | 33,555,511 | 69.12 |
| Sct_188 | F_(13) | 33,555,511 | 69.12 |
| BARC-047893-10417 | F_(13) | 33,591,576 | 69.33 |
| BARCSOYSSR_13_1385 | F_(13) | 33,860,249 | 69.98 |
| Sat_375 | F_(13) | 33,860,249 | 69.98 |
| BARC-018605-02982 | F_(13) | 33,962,287 | 70.04 |
| BARC-027502-06598 | F_(13) | 34,222,888 | 71.11 |
| BARC-032717-09021 | F_(13) | 34,437,496 | 71.22 |
| BARC-044875-08829 | F_(13) | 34,624,490 | 71.26 |
| BARC-055229-13122 | F_(13) | 34,739,895 | 71.89 |
| BARC-031567-07110 | F_(13) | 34,841,259 | 71.89 |
| BARC-045235-08913 | F_(13) | 34,855,765 | 71.89 |
| S00281-1 | F_(13) | 35,174,140 | 73.16 |
| BARC-018007-02494 | F_(13) | 35,393,757 | 74.03 |
| BARC-063121-18247 | F_(13) | 35,533,783 | 74.33 |
| BARC-027622-06625 | F_(13) | 35,617,394 | 74.54 |
| BARC-025859-05126 | F_(13) | 35,862,469 | 75.44 |
| BARC-018177-02535 | F_(13) | 36,054,552 | 75.95 |
| BARC-055613-13490 | F_(13) | 36,204,226 | 77.16 |
| BARCSOYSSR_13_1522 | F_(13) | 36,401,759 | 77.32 |
| Sat_197 | F_(13) | 36,401,759 | 77.32 |
| BARC-025561-06521 | F_(13) | 36,822,800 | 78.34 |
| BARC-014657-01608 | F_(13) | 37,024,135 | 79.43 |
| BARC-039175-07463 | F_(13) | 37,452,579 | 80.29 |
| BARC-027792-06674 | F_(13) | 38,023,035 | 85.18 |
| BARC-046144-10286 | F_(13) | 38,030,995 | 85.18 |
| BARCSOYSSR_13_1617 | F_(13) | 38,075,339 | 87.79 |
| Satt554 | F_(13) | 38,075,339 | 87.79 |
| BARCSOYSSR_13_1646 | F_(13) | 38,558,080 | 91.39 |
| Satt657 | F_(13) | 38,558,080 | 91.39 |
| BARC-061571-17276 | F_(13) | 38,566,348 | 91.63 |
| BARC-063309-18328 | F_(13) | 38,566,921 | 91.63 |
| BARCSOYSSR_13_1672 | F_(13) | 38,955,502 | 93.73 |
| Satt522 | F_(13) | 38,955,502 | 93.73 |
| BARC-026113-05263 | F_(13) | 39,216,776 | 95.85 |
| BARC-038355-10050 | F_(13) | 39,539,890 | 96.91 |
| BARCSOYSSR_13_1747 | F_(13) | 40,160,823 | 98.17 |
| AW756935 | F_(13) | 40,160,823 | 98.17 |
| BARC-013325-00483 | F_(13) | 40,685,775 | 99.37 |
| BARC-013325-00484 | F_(13) | 40,685,775 | 100.61 |
| BARC-042953-08476 | F_(13) | 41,219,915 | 102.16 |
| BARCSOYSSR_13_1803 | F_(13) | 41,259,685 | 102.95 |
| Sat_090 | F_(13) | 41,259,685 | 102.95 |
| BARCSOYSSR_13_1837 | F_(13) | 41,868,210 | 104.84 |
| Sat_417 | F_(13) | 41,868,210 | 104.84 |
| BARCSOYSSR_13_1838 | F_(13) | 41,885,014 | 106.55 |
| Satt656 | F_(13) | 41,885,014 | 106.55 |
| BARC-018741-02997 | F_(13) | 41,885,841 | 107.33 |
| BARC-014363-01336 | F_(13) | 42,334,157 | 108.26 |
| BARC-017179-02236 | F_(13) | 42,483,466 | 108.82 |
| BARC-064221-18586 | F_(13) | 42,797,894 | 111.07 |
| BARC-050361-09572 | F_(13) | 42,797,918 | 111.08 |
| BARC-014299-01307 | F_(13) | 42,920,500 | 112.25 |
| BARC-021845-04222 | F_(13) | 43,826,000 | 116.89 |
| BARC-028899-06036 | F_(13) | 44,238,149 | 118.26 |

TABLE 39

| Locus | LG (ch) | Physical | Genetic (cM) |
|---|---|---|---|
| BARC-020027-04405 | G_(18) | 181,064 | 0.00 |
| BARC-052957-11678 | G_(18) | 187,414 | 0.00 |
| BARC-064665-18774 | G_(18) | 224,648 | 0.11 |
| S01109-1 | G_(18) | 305,113 | 0.92 |
| BARC-043197-08552 | G_(18) | 305,200 | 0.92 |
| BARC-060195-16470 | G_(18) | 470,340 | 1.64 |
| BARC-018387-03171 | G_(18) | 488,479 | 7.01 |
| BARC-022431-04323 | G_(18) | 734,360 | 7.43 |
| BARC-020839-03962 | G_(18) | 981,378 | 8.12 |
| BARC-900558-00952 | G_(18) | 999,063 | 8.12 |
| BARC-049013-10791 | G_(18) | 1,277,303 | 8.39 |
| BARC-015371-01813 | G_(18) | 1,431,827 | 8.63 |

TABLE 39-continued

| Locus | LG (ch) | Physical | Genetic (cM) |
|---|---|---|---|
| BARCSOYSSR_18_0093 | G_(18) | 1,621,261 | 9.44 |
| Sat_210 | G_(18) | 1,621,261 | 9.44 |
| BARC-048245-10515 | G_(18) | 1,718,204 | 9.94 |
| BARC-G00219-00248 | G_(18) | 1,726,610 | 9.96 |
| BARCSOYSSR_18_0102 | G_(18) | 1,736,324 | 10.10 |
| Satt309 | G_(18) | 1,736,324 | 10.10 |
| BARC-012285-01798 | G_(18) | 1,945,192 | 11.01 |
| BARC-010917-01706 | G_(18) | 1,955,436 | 11.09 |
| BARC-012289-01799 | G_(18) | 1,957,590 | 11.12 |
| BARC-028299-05817 | G_(18) | 1,958,726 | 11.86 |
| BARC-061523-17249 | G_(18) | 1,979,049 | 12.10 |
| BARC-030055-06792 | G_(18) | 2,033,662 | 12.15 |
| BARC-025777-05064 | G_(18) | 2,296,490 | 12.92 |
| BARCSOYSSR_18_0142 | G_(18) | 2,409,497 | 13.98 |
| Sat_141 | G_(18) | 2,409,497 | 13.98 |
| BARC-004952-00267 | G_(18) | 2,664,887 | 14.20 |
| BARCSOYSSR_18_0158 | G_(18) | 2,665,098 | 14.70 |
| Satt610 | G_(18) | 2,665,098 | 14.70 |
| BARC-047665-10370 | G_(18) | 2,833,064 | 15.97 |
| BARC-047787-10396 | G_(18) | 2,853,047 | 16.14 |
| BARCSOYSSR_18_0177 | G_(18) | 3,162,740 | 17.19 |
| Satt570 | G_(18) | 3,162,740 | 17.19 |
| BARC-014395-01348 | G_(18) | 3,448,063 | 19.48 |
| BARCSOYSSR_18_0195 | G_(18) | 3,603,119 | 20.57 |
| AW734137 | G_(18) | 3,603,119 | 20.57 |
| BARC-003432-00279 | G_(18) | 3,643,846 | 21.48 |
| BARCSOYSSR_18_0250 | G_(18) | 4,692,375 | 22.22 |
| Satt217 | G_(18) | 4,692,375 | 22.22 |
| BARCSOYSSR_18_0257 | G_(18) | 4,800,515 | 24.96 |
| Satt235 | G_(18) | 4,800,515 | 24.96 |
| BARCSOYSSR_18_0295 | G_(18) | 5,330,646 | 29.20 |
| Sat_315 | G_(18) | 5,330,646 | 29.20 |
| BARCSOYSSR_18_0305 | G_(18) | 5,470,147 | 31.02 |
| Sat_290 | G_(18) | 5,470,147 | 31.02 |
| BARCSOYSSR_18_0316 | G_(18) | 5,675,379 | 32.88 |
| Sat_131 | G_(18) | 5,675,379 | 32.88 |
| BARCSOYSSR_18_0324 | G_(18) | 5,890,285 | 35.43 |
| Satt324 | G_(18) | 5,890,285 | 35.43 |
| BARCSOYSSR_18_0348 | G_(18) | 6,169,586 | 36.97 |
| Sat_403 | G_(18) | 6,169,586 | 36.97 |
| BARC-040265-07700 | G_(18) | 7,275,891 | 39.86 |
| BARC-901121-00988 | G_(18) | 8,415,710 | 40.41 |
| BARC-063985-18522 | G_(18) | 8,791,883 | 40.41 |
| BARC-039993-07626 | G_(18) | 9,012,214 | 40.81 |
| BARCSOYSSR_18_0550 | G_(18) | 11,400,889 | 43.03 |
| Sat_308 | G_(18) | 11,400,889 | 43.03 |
| BARC-053419-11845 | G_(18) | 12,638,074 | 44.99 |
| BARC-056521-14449 | G_(18) | 14,167,067 | 47.51 |
| BARC-059783-16090 | G_(18) | 14,285,415 | 47.51 |
| BARC-054849-12183 | G_(18) | 14,335,308 | 47.51 |
| BARC-049885-09225 | G_(18) | 14,570,865 | 48.21 |
| BARC-064283-18606 | G_(18) | 14,893,358 | 48.21 |
| BARC-017647-02654 | G_(18) | 15,242,485 | 48.33 |
| BARC-059485-15839 | G_(18) | 15,676,568 | 48.95 |
| BARC-040485-07753 | G_(18) | 15,723,524 | 48.95 |
| BARC-018333-03580 | G_(18) | 16,483,354 | 50.04 |
| BARC-018333-03581 | G_(18) | 16,483,354 | 50.24 |
| BARC-019465-03616 | G_(18) | 16,505,062 | 50.88 |
| BARC-013677-01228 | G_(18) | 16,668,537 | 52.04 |
| BARC-061001-16998 | G_(18) | 16,797,216 | 52.04 |
| BARC-047404-12924 | G_(18) | 17,550,827 | 52.04 |
| BARC-046912-12782 | G_(18) | 17,553,931 | 52.04 |
| BARC-046994-12826 | G_(18) | 17,575,698 | 52.04 |
| BARC-046874-12778 | G_(18) | 17,592,240 | 52.04 |
| BARC-046872-12776 | G_(18) | 17,600,728 | 52.04 |
| BARC-046920-12786 | G_(18) | 17,603,029 | 52.04 |
| BARC-046930-12795 | G_(18) | 17,611,727 | 52.04 |
| BARC-046926-12788 | G_(18) | 17,626,176 | 52.04 |
| BARC-046922-12787 | G_(18) | 17,630,432 | 52.04 |
| BARC-057295-14678 | G_(18) | 17,781,283 | 52.04 |
| BARC-020159-04488 | G_(18) | 17,925,069 | 52.04 |
| BARC-060837-16930 | G_(18) | 18,410,099 | 52.04 |
| BARC-058413-15279 | G_(18) | 20,526,141 | 53.38 |
| BARC-060825-16919 | G_(18) | 21,121,950 | 54.45 |
| BARC-047150-12874 | G_(18) | 21,364,220 | 54.45 |
| BARC-047112-12860 | G_(18) | 21,365,038 | 54.45 |
| BARC-047096-12838 | G_(18) | 21,384,584 | 54.45 |
| BARC-063705-18440 | G_(18) | 21,701,030 | 54.45 |
| BARC-055557-13432 | G_(18) | 21,724,083 | 54.45 |
| BARC-062097-17654 | G_(18) | 22,120,170 | 54.45 |
| BARCSOYSSR_18_0845 | G_(18) | 22,150,302 | 54.97 |
| Satt303 | G_(18) | 22,150,302 | 54.97 |
| BARC-060189-16468 | G_(18) | 22,483,339 | 55.60 |
| BARC-047504-12947 | G_(18) | 22,535,676 | 55.60 |
| BARC-061785-17386 | G_(18) | 22,585,948 | 55.60 |
| BARC-047502-12946 | G_(18) | 22,588,708 | 55.60 |
| BARC-047102-12842 | G_(18) | 22,603,647 | 55.60 |
| BARC-055855-13794 | G_(18) | 23,123,288 | 55.60 |
| BARC-061111-17050 | G_(18) | 24,129,395 | 55.60 |
| BARC-058369-15257 | G_(18) | 27,610,750 | 55.60 |
| BARC-060613-16749 | G_(18) | 27,931,082 | 55.60 |
| BARC-013825-01251 | G_(18) | 30,313,907 | 55.60 |
| BARC-061647-17305 | G_(18) | 31,080,816 | 55.60 |
| BARC-056139-14122 | G_(18) | 31,828,672 | 55.60 |
| BARC-059397-15790 | G_(18) | 33,110,626 | 55.60 |
| BARC-062783-18056 | G_(18) | 33,753,070 | 55.60 |
| BARC-030691-06926 | G_(18) | 34,178,194 | 55.60 |
| BARC-057565-14836 | G_(18) | 34,232,818 | 55.60 |
| BARC-056267-14204 | G_(18) | 36,963,309 | 55.60 |
| BARC-061197-17134 | G_(18) | 39,413,323 | 55.60 |
| BARC-051485-11122 | G_(18) | 39,512,471 | 55.60 |
| BARC-014783-01660 | G_(18) | 41,560,487 | 55.60 |
| BARC-061717-17358 | G_(18) | 41,730,041 | 55.60 |
| BARC-044235-08650 | G_(18) | 42,206,429 | 55.60 |
| BARC-059239-15686 | G_(18) | 43,529,731 | 56.18 |
| BARC-056035-13999 | G_(18) | 45,468,441 | 56.71 |
| BARC-050493-09699 | G_(18) | 45,951,229 | 56.82 |
| BARCSOYSSR_18_1146 | G_(18) | 46,265,580 | 57.07 |
| Satt533 | G_(18) | 46,265,580 | 57.07 |
| BARCSOYSSR_18_1210 | G_(18) | 48,532,689 | 57.82 |
| Satt504 | G_(18) | 48,532,689 | 57.82 |
| BARCSOYSSR_18_1348 | G_(18) | 52,189,343 | 59.89 |
| Sat_185 | G_(18) | 52,189,343 | 59.89 |
| BARCSOYSSR_18_1349 | G_(18) | 52,210,836 | 59.90 |
| Sat_203 | G_(18) | 52,210,836 | 59.90 |
| BARCSOYSSR_18_1364 | G_(18) | 52,465,758 | 60.60 |
| Satt199 | G_(18) | 52,465,758 | 60.60 |
| BARCSOYSSR_18_1385 | G_(18) | 52,746,490 | 60.97 |
| Sat_260 | G_(18) | 52,746,490 | 60.97 |
| BARCSOYSSR_18_1418 | G_(18) | 53,445,942 | 63.44 |
| Satt012 | G_(18) | 53,445,942 | 63.44 |
| BARC-056635-14538 | G_(18) | 53,471,513 | 63.92 |
| BARCSOYSSR_18_1426 | G_(18) | 53,656,489 | 65.78 |
| Sat_164 | G_(18) | 53,656,489 | 65.78 |
| BARCSOYSSR_18_1431 | G_(18) | 53,769,539 | 66.39 |
| Satt517 | G_(18) | 53,769,539 | 66.39 |
| BARC-027694-06635 | G_(18) | 54,764,508 | 67.91 |
| BARC-050613-09770 | G_(18) | 54,942,320 | 69.50 |
| BARC-024489-04936 | G_(18) | 55,001,002 | 70.62 |
| BARC-055139-13077 | G_(18) | 55,458,709 | 71.46 |
| BARC-061783-18883 | G_(18) | 55,506,257 | 72.02 |
| BARC-048761-10703 | G_(18) | 56,086,706 | 72.84 |
| BARC-016867-02359 | G_(18) | 56,429,486 | 73.34 |
| BARC-018441-03188 | G_(18) | 56,429,542 | 73.80 |
| BARC-052045-11324 | G_(18) | 57,071,922 | 75.00 |
| BARC-026013-05225 | G_(18) | 57,185,832 | 75.64 |
| BARC-015063-02553 | G_(18) | 57,353,963 | 76.88 |
| BARC-008223-00022 | G_(18) | 57,436,269 | 78.05 |
| BARC-032277-08935 | G_(18) | 57,462,526 | 79.40 |
| BARC-041705-08069 | G_(18) | 57,781,784 | 80.96 |
| BARC-032785-09037 | G_(18) | 57,781,833 | 80.96 |
| S13844-1 | G_(18) | 58,086,324 | 85.55 |
| BARCSOYSSR_18_1703 | G_(18) | 58,093,491 | 85.66 |
| Sct_199 | G_(18) | 58,093,491 | 85.66 |
| BARCSOYSSR_18_1708 | G_(18) | 58,136,286 | 85.98 |
| Satt472 | G_(18) | 58,136,286 | 85.98 |
| BARC-048095-10484 | G_(18) | 58,177,377 | 86.59 |
| BARC-038873-07372 | G_(18) | 58,438,994 | 87.30 |
| BARCSOYSSR_18_1750 | G_(18) | 58,722,839 | 89.37 |
| Satt191 | G_(18) | 58,722,839 | 89.37 |
| BARCSOYSSR_18_1767 | G_(18) | 58,879,563 | 91.08 |
| Sat_117 | G_(18) | 58,879,563 | 91.08 |
| BARC-010491-00654 | G_(18) | 59,279,444 | 93.00 |
| BARC-010495-00656 | G_(18) | 59,283,702 | 93.23 |
| BARC-024251-04812 | G_(18) | 59,472,425 | 94.30 |
| BARC-020069-04425 | G_(18) | 59,797,088 | 96.31 |

TABLE 39-continued

| Locus | LG (ch) | Physical | Genetic (cM) |
|---|---|---|---|
| BARC-062677-18004 | G_(18) | 59,995,654 | 97.32 |
| BARC-062769-18043 | G_(18) | 60,441,813 | 100.16 |
| BARCSOYSSR_18_1853 | G_(18) | 60,463,067 | 100.37 |
| Sct_187 | G_(18) | 60,463,067 | 100.37 |
| BARC-044363-08678 | G_(18) | 60,487,624 | 100.44 |
| BARCSOYSSR_18_1858 | G_(18) | 60,612,599 | 101.82 |
| Sat_064 | G_(18) | 60,612,599 | 101.82 |
| BARC-054735-12156 | G_(18) | 60,802,269 | 102.33 |
| BARC-013647-01216 | G_(18) | 60,909,921 | 103.22 |
| BARC-055537-13406 | G_(18) | 61,041,397 | 103.40 |
| BARC-039397-07314 | G_(18) | 61,188,102 | 103.55 |
| BARC-043995-08576 | G_(18) | 61,306,670 | 104.09 |
| BARC-064703-18782 | G_(18) | 61,480,202 | 105.53 |
| BARC-049989-09280 | G_(18) | 61,591,089 | 105.85 |
| S05058-1 | G_(18) | 61,591,142 | 105.85 |
| S04660-1 | G_(18) | 61,831,970 | 106.50 |
| BARC-017669-03102 | G_(18) | 62,046,576 | 107.09 |

TABLE 40

| Locus | LG (ch) | Physical | Genetic (cM) |
|---|---|---|---|
| BARC-030145-06814 | H_(12) | 5,407,750 | 33.89 |
| BARCSOYSSR_12_0301 | H_(12) | 5,945,172 | 40.93 |
| Satt192 | H_(12) | 5,945,172 | 40.93 |
| BARC-020263-04537 | H_(12) | 6,151,630 | 42.24 |
| BARCSOYSSR_12_0320 | H_(12) | 6,361,611 | 43.39 |
| Satt442 | H_(12) | 6,361,611 | 43.39 |
| BARC-041917-08135 | H_(12) | 6,370,716 | 43.68 |
| BARC-055349-13226 | H_(12) | 6,621,623 | 45.18 |
| BARC-044091-08619 | H_(12) | 6,846,615 | 46.92 |
| BARC-018437-03181 | H_(12) | 7,430,953 | 49.44 |
| BARC-014937-01927 | H_(12) | 7,559,662 | 50.56 |
| BARC-018477-03197 | H_(12) | 7,580,895 | 50.56 |
| BARC-011573-00291 | H_(12) | 7,708,831 | 51.54 |
| BARC-032147-07327 | H_(12) | 7,942,630 | 52.74 |
| BARCSOYSSR_12_0484 | H_(12) | 9,096,372 | 55.66 |
| Sat_334 | H_(12) | 9,096,372 | 55.66 |
| BARC-050381-09573 | H_(12) | 9,333,744 | 56.14 |
| BARC-063305-18323 | H_(12) | 9,470,906 | 56.16 |
| BARC-018577-02980 | H_(12) | 10,342,254 | 57.76 |
| BARC-062921-18158 | H_(12) | 10,442,496 | 57.76 |
| BARC-050237-09522 | H_(12) | 11,092,912 | 58.34 |
| BARC-050239-09523 | H_(12) | 11,096,770 | 58.60 |
| S09955-1 | H_(12) | 11,512,115 | 58.82 |
| BARC-055493-13324 | H_(12) | 16,472,555 | 61.44 |
| BARC-056309-14242 | H_(12) | 16,472,572 | 61.45 |
| BARC-062469-17821 | H_(12) | 17,814,132 | 61.53 |
| BARC-060801-16905 | H_(12) | 17,818,053 | 61.54 |
| BARCSOYSSR_12_0796 | H_(12) | 18,644,153 | 63.30 |
| Satt253 | H_(12) | 18,644,153 | 63.30 |
| BARCSOYSSR_12_0933 | H_(12) | 27,755,144 | 63.49 |
| Satt279 | H_(12) | 27,755,144 | 63.49 |
| BARCSOYSSR_12_1006 | H_(12) | 32,468,260 | 64.59 |
| Sat_205 | H_(12) | 32,468,260 | 64.59 |
| BARCSOYSSR_12_1008 | H_(12) | 32,497,101 | 65.39 |
| Satt676 | H_(12) | 32,497,101 | 65.39 |
| BARCSOYSSR_12_1065 | H_(12) | 33,808,521 | 68.67 |
| Satt629 | H_(12) | 33,808,521 | 68.67 |
| BARCSOYSSR_12_1068 | H_(12) | 33,904,742 | 69.47 |
| Sat_158 | H_(12) | 33,904,742 | 69.47 |
| BARC-014455-01377 | H_(12) | 34,233,214 | 73.09 |
| BARC-021753-04197 | H_(12) | 34,421,276 | 74.86 |
| BARC-044073-08598 | H_(12) | 34,428,011 | 74.86 |
| BARC-017975-02490 | H_(12) | 34,693,967 | 75.36 |
| BARC-031017-06986 | H_(12) | 34,778,965 | 75.59 |
| BARC-051831-11255 | H_(12) | 34,896,373 | 77.45 |
| BARC-055767-13699 | H_(12) | 34,981,769 | 78.30 |
| BARC-039403-07492 | H_(12) | 35,019,859 | 78.39 |
| BARC-050003-09283 | H_(12) | 35,088,372 | 78.39 |
| BARCSOYSSR_12_1142 | H_(12) | 35,108,116 | 78.95 |
| Satt302 | H_(12) | 35,108,116 | 78.95 |
| BARC-021693-04179 | H_(12) | 35,195,967 | 79.70 |
| BARC-064633-18761 | H_(12) | 35,317,729 | 81.36 |
| BARC-032397-08964 | H_(12) | 35,442,153 | 81.66 |

TABLE 40-continued

| Locus | LG (ch) | Physical | Genetic (cM) |
|---|---|---|---|
| BARC-044357-08676 | H_(12) | 35,442,160 | 81.67 |
| BARCSOYSSR_12_1175 | H_(12) | 35,565,380 | 82.68 |
| Satt637 | H_(12) | 35,565,380 | 82.68 |
| BARC-049209-10821 | H_(12) | 35,718,223 | 83.15 |
| BARC-019331-03879 | H_(12) | 36,046,607 | 84.20 |
| BARC-017985-02493 | H_(12) | 36,162,584 | 84.21 |
| BARC-050707-09846 | H_(12) | 36,518,632 | 85.62 |
| BARCSOYSSR_12_1229 | H_(12) | 36,600,716 | 86.22 |
| Sat_175 | H_(12) | 36,600,716 | 86.22 |
| BARC-015079-02561 | H_(12) | 36,780,206 | 89.38 |

TABLE 41

| Locus | LG (ch) | Physical | Genetic (cM) |
|---|---|---|---|
| BARC-017193-02248 | I_(20) | 33,440,941 | 40.09 |
| BARC-015861-02878 | I_(20) | 34,090,779 | 41.90 |
| BARC-026051-05237 | I_(20) | 34,101,285 | 42.31 |
| BARCSOYSSR_20_0803 | I_(20) | 34,223,200 | 42.60 |
| Satt270 | I_(20) | 34,223,200 | 42.60 |
| BARC-060119-16401 | I_(20) | 34,288,590 | 43.26 |
| BARC-029461-06196 | I_(20) | 34,439,725 | 43.99 |
| BARC-039067-07437 | I_(20) | 34,505,216 | 44.00 |
| BARC-024125-04772 | I_(20) | 34,670,085 | 44.27 |
| BARC-017311-02261 | I_(20) | 34,670,172 | 44.34 |
| BARC-055423-13277 | I_(20) | 34,916,007 | 44.95 |
| BARC-025913-05152 | I_(20) | 35,186,441 | 46.14 |
| BARC-025913-05155 | I_(20) | 35,186,441 | 49.13 |
| BARC-050455-09643 | I_(20) | 35,480,417 | 49.93 |
| BARC-029803-06418 | I_(20) | 35,760,720 | 50.85 |
| BARC-025987-05207 | I_(20) | 36,254,964 | 53.77 |
| BARC-024031-04707 | I_(20) | 36,260,991 | 53.77 |
| BARC-016541-02090 | I_(20) | 36,299,485 | 55.24 |
| BARCSOYSSR_20_0935 | I_(20) | 36,694,570 | 56.11 |
| Sat_104 | I_(20) | 36,694,570 | 56.11 |
| BARC-041445-07985 | I_(20) | 37,025,923 | 57.46 |
| BARC-048283-10541 | I_(20) | 37,239,375 | 59.44 |
| BARC-020019-04404 | I_(20) | 37,240,160 | 59.44 |
| BARC-025847-05113 | I_(20) | 37,342,870 | 60.00 |
| BARC-017939-02461 | I_(20) | 37,645,405 | 60.30 |
| BARC-039753-07565 | I_(20) | 37,996,627 | 64.00 |
| BARCSOYSSR_20_1041 | I_(20) | 38,389,919 | 66.82 |
| Sat_418 | I_(20) | 38,389,919 | 66.82 |
| BARCSOYSSR_20_1053 | I_(20) | 38,657,712 | 67.56 |
| Sat_170 | I_(20) | 38,657,712 | 67.56 |
| BARC-053725-11957 | I_(20) | 38,960,000 | 70.92 |
| S08034-1 | I_(20) | 39,051,858 | 71.47 |
| BARC-022381-04318 | I_(20) | 39,289,431 | 72.90 |
| BARC-041051-07902 | I_(20) | 39,521,589 | 74.61 |
| BARC-029151-06100 | I_(20) | 39,900,787 | 76.68 |
| BARCSOYSSR_20_1170 | I_(20) | 40,299,039 | 78.82 |
| Satt162 | I_(20) | 40,299,039 | 78.82 |
| BARCSOYSSR_20_1227 | I_(20) | 41,048,634 | 84.61 |
| Satt623 | I_(20) | 41,048,634 | 84.61 |
| S10293-1 | I_(20) | 41,216,234 | 85.10 |
| BARC-044361-08677 | I_(20) | 41,309,309 | 85.38 |
| BARC-025815-05092 | I_(20) | 41,492,675 | 87.03 |
| BARC-045029-08866 | I_(20) | 41,705,956 | 88.64 |
| BARC-027542-06603 | I_(20) | 41,803,540 | 89.73 |
| BARCSOYSSR_20_1271 | I_(20) | 41,816,857 | 89.76 |
| Sat_420 | I_(20) | 41,816,857 | 89.76 |
| BARCSOYSSR_20_1273 | I_(20) | 41,836,507 | 89.76 |
| Sat_419 | I_(20) | 41,836,507 | 89.76 |
| BARC-042685-08348 | I_(20) | 41,982,978 | 90.45 |
| BARC-007970-00180 | I_(20) | 42,348,122 | 91.74 |
| BARC-060361-16629 | I_(20) | 42,397,180 | 92.03 |
| BARCSOYSSR_20_1312 | I_(20) | 42,518,153 | 92.22 |
| Sat_299 | I_(20) | 42,518,153 | 92.22 |
| BARCSOYSSR_20_1319 | I_(20) | 43,370,538 | 96.80 |
| AQ851518 | I_(20) | 43,370,538 | 96.80 |
| BARC-055173-13105 | I_(20) | 43,686,515 | 97.41 |
| BARC-015569-02005 | I_(20) | 44,042,061 | 99.91 |
| BARC-055331-13213 | I_(20) | 44,397,389 | 103.80 |
| BARC-042389-08249 | I_(20) | 44,488,499 | 104.76 |
| BARC-029707-06329 | I_(20) | 44,590,034 | 105.09 |

TABLE 41-continued

| Locus | LG (ch) | Physical | Genetic (cM) |
|---|---|---|---|
| BARC-021793-04213 | I_(20) | 44,790,257 | 105.66 |
| BARC-016665-02164 | I_(20) | 44,817,525 | 105.67 |
| BARC-014559-01579 | I_(20) | 44,848,445 | 106.09 |
| BARC-051303-11083 | I_(20) | 44,947,571 | 106.93 |
| BARC-051301-11081 | I_(20) | 44,947,600 | 106.93 |
| BARC-062771-18047 | I_(20) | 45,428,117 | 109.07 |
| BARCSOYSSR_20_1322 | I_(20) | 45,550,639 | 109.27 |
| Sct_189 | I_(20) | 45,550,639 | 109.27 |
| BARC-050097-09382 | I_(20) | 45,627,350 | 109.40 |
| BARCSOYSSR_20_1323 | I_(20) | 45,659,683 | 109.55 |
| Satt440 | I_(20) | 45,659,683 | 109.55 |
| BARC-052289-11404 | I_(20) | 45,686,195 | 109.58 |
| BARC-063851-18472 | I_(20) | 45,794,065 | 110.09 |
| BARC-017873-02409 | I_(20) | 45,939,159 | 110.44 |
| BARC-015559-02004 | I_(20) | 46,031,805 | 110.64 |
| BARC-028901-06041 | I_(20) | 46,108,591 | 110.85 |
| BARC-048041-10476 | I_(20) | 46,127,952 | 111.28 |
| BARC-048631-10683 | I_(20) | 46,135,344 | 111.28 |
| BARC-055209-13116 | I_(20) | 46,596,717 | 112.77 |

TABLE 42

| Locus | LG (ch) | Physical | Genetic (cM) |
|---|---|---|---|
| BARC-016027-02038 | J_(16) | 133,348 | 2.34 |
| BARC-028423-05867 | J_(16) | 724,502 | 4.91 |
| BARC-013639-01204 | J_(16) | 774,054 | 5.42 |
| BARC-063377-18348 | J_(16) | 1,061,926 | 8.18 |
| BARC-024473-04898 | J_(16) | 1,103,589 | 8.58 |
| BARCSOYSSR_16_0062 | J_(16) | 1,141,072 | 10.55 |
| Satt249 | J_(16) | 1,141,072 | 10.55 |
| BARC-013651-01218 | J_(16) | 1,348,520 | 11.40 |
| BARCSOYSSR_16_0083 | J_(16) | 1,543,289 | 12.13 |
| Satt674 | J_(16) | 1,543,289 | 12.13 |
| BARCSOYSSR_16_0090 | J_(16) | 1,631,806 | 12.21 |
| Satt287 | J_(16) | 1,631,806 | 12.21 |
| BARC-018981-03289 | J_(16) | 2,314,419 | 19.26 |
| BARCSOYSSR_16_0171 | J_(16) | 2,893,992 | 22.52 |
| Sct_046 | J_(16) | 2,893,992 | 22.52 |
| BARCSOYSSR_16_0179 | J_(16) | 3,050,011 | 22.97 |
| Sat_228 | J_(16) | 3,050,011 | 22.97 |
| BARC-028599-05966 | J_(16) | 3,137,659 | 23.17 |
| BARC-059355-15761 | J_(16) | 3,363,314 | 24.28 |
| BARC-042521-08287 | J_(16) | 3,534,838 | 24.37 |
| BARC-013299-00471 | J_(16) | 3,597,317 | 24.82 |
| BARC-014573-01581 | J_(16) | 3,597,402 | 24.82 |
| BARC-018093-02513 | J_(16) | 3,847,598 | 25.29 |
| BARC-045157-08897 | J_(16) | 3,900,245 | 25.35 |
| BARC-014467-01559 | J_(16) | 3,962,333 | 25.69 |
| S03813-1 | J_(16) | 4,678,569 | 30.57 |
| BARC-029477-06200 | J_(16) | 4,763,389 | 31.14 |
| BARC-031525-07106 | J_(16) | 4,924,406 | 34.78 |
| BARC-031195-07010 | J_(16) | 4,924,462 | 34.78 |
| BARC-028307-05823 | J_(16) | 4,936,902 | 34.78 |
| BARC-031951-07227 | J_(16) | 4,936,964 | 34.94 |
| BARC-065799-19753 | J_(16) | 5,040,869 | 35.44 |
| BARCSOYSSR_16_0377 | J_(16) | 6,273,768 | 38.03 |
| Satt693 | J_(16) | 6,273,768 | 38.03 |
| BARC-018889-03032 | J_(16) | 6,474,327 | 38.62 |
| BARCSOYSSR_16_0424 | J_(16) | 7,054,261 | 40.67 |
| Sat_370 | J_(16) | 7,054,261 | 40.67 |
| BARC-028159-05778 | J_(16) | 7,070,781 | 41.63 |
| BARC-059919-16214 | J_(16) | 7,165,978 | 42.08 |
| BARC-053335-11801 | J_(16) | 7,237,770 | 42.31 |
| BARC-048299-10543 | J_(16) | 7,446,239 | 43.04 |
| BARC-060769-16868 | J_(16) | 9,593,463 | 44.34 |
| BARC-058125-15101 | J_(16) | 10,818,091 | 44.60 |
| BARC-058115-15097 | J_(16) | 13,368,263 | 44.60 |
| BARC-058941-15515 | J_(16) | 14,534,998 | 44.60 |
| BARC-060857-16934 | J_(16) | 14,887,272 | 44.61 |
| BARC-056593-14514 | J_(16) | 15,091,717 | 44.61 |
| BARC-052587-11515 | J_(16) | 15,536,387 | 44.61 |
| BARC-062281-17737 | J_(16) | 16,322,634 | 44.61 |
| BARC-025801-05075 | J_(16) | 16,552,294 | 44.61 |
| BARC-059701-16014 | J_(16) | 19,326,141 | 44.61 |

TABLE 42-continued

| Locus | LG (ch) | Physical | Genetic (cM) |
|---|---|---|---|
| BARC-038343-10046 | J_(16) | 19,423,620 | 44.61 |
| BARC-013151-01456 | J_(16) | 20,512,221 | 44.61 |
| BARC-010869-00787 | J_(16) | 21,152,273 | 44.61 |
| BARC-051521-11150 | J_(16) | 21,264,807 | 44.61 |
| BARCSOYSSR_16_0703 | J_(16) | 23,096,039 | 45.66 |
| Satt529 | J_(16) | 23,096,039 | 45.66 |
| BARC-059377-15777 | J_(16) | 25,697,824 | 46.05 |
| BARCSOYSSR_16_0803 | J_(16) | 26,813,827 | 46.10 |
| Sat_165 | J_(16) | 26,813,827 | 46.10 |
| BARCSOYSSR_16_0840 | J_(16) | 27,633,714 | 46.11 |
| Satt622 | J_(16) | 27,633,714 | 46.11 |
| BARCSOYSSR_16_0885 | J_(16) | 28,589,375 | 47.36 |
| Satt215 | J_(16) | 28,589,375 | 47.36 |
| BARC-029037-06053 | J_(16) | 29,156,483 | 51.57 |
| BARC-038949-07404 | J_(16) | 30,065,357 | 57.70 |
| BARC-059837-16121 | J_(16) | 30,151,468 | 58.39 |
| BARC-042193-08207 | J_(16) | 30,395,923 | 62.96 |
| BARC-032663-09006 | J_(16) | 30,962,138 | 65.78 |
| BARC-017697-03107 | J_(16) | 31,075,508 | 66.45 |
| BARC-024047-04716 | J_(16) | 31,105,844 | 66.47 |
| BARC-022077-04282 | J_(16) | 31,154,859 | 66.56 |
| BARC-014795-01662 | J_(16) | 31,155,317 | 66.56 |
| BARC-042895-08450 | J_(16) | 31,292,648 | 67.05 |
| BARC-043111-08534 | J_(16) | 31,461,544 | 67.48 |
| BARC-060179-16450 | J_(16) | 31,613,798 | 67.74 |
| BARC-011645-00322 | J_(16) | 31,635,367 | 67.90 |
| BARCSOYSSR_16_1073 | J_(16) | 31,795,061 | 68.81 |
| Sctt011 | J_(16) | 31,795,061 | 68.81 |
| BARC-010297-00580 | J_(16) | 31,996,027 | 69.90 |
| BARC-017835-02393 | J_(16) | 32,526,995 | 71.32 |
| BARC-012971-00414 | J_(16) | 32,573,581 | 71.56 |
| BARC-024115-04764 | J_(16) | 32,962,414 | 71.92 |
| BARC-040393-07727 | J_(16) | 33,410,287 | 73.26 |
| BARC-025217-06463 | J_(16) | 33,513,918 | 73.90 |
| BARCSOYSSR_16_1165 | J_(16) | 33,538,157 | 74.90 |
| Satt547 | J_(16) | 33,538,157 | 74.90 |
| BARC-028589-05965 | J_(16) | 33,853,031 | 76.14 |
| BARC-053847-12078 | J_(16) | 34,475,602 | 77.27 |
| BARC-051715-11216 | J_(16) | 35,032,380 | 77.40 |
| BARC-045099-08885 | J_(16) | 35,208,435 | 78.97 |
| BARC-025851-05117 | J_(16) | 35,571,437 | 80.79 |
| BARC-044031-08587 | J_(16) | 35,587,464 | 81.41 |
| BARCSOYSSR_16_1234 | J_(16) | 35,718,507 | 82.03 |
| Satt431 | J_(16) | 35,718,507 | 82.03 |
| BARC-045133-08889 | J_(16) | 36,163,500 | 84.07 |
| BARC-015307-02272 | J_(16) | 36,221,550 | 84.76 |
| S02042-1 | J_(16) | 36,524,407 | 85.53 |
| BARC-011625-00310 | J_(16) | 36,544,211 | 85.58 |
| BARC-024229-04809 | J_(16) | 36,641,788 | 86.17 |
| BARC-048135-10500 | J_(16) | 36,732,539 | 86.82 |
| BARC-019219-03397 | J_(16) | 36,921,370 | 87.38 |
| BARC-030203-06832 | J_(16) | 37,108,010 | 87.58 |
| BARC-029163-06102 | J_(16) | 37,181,366 | 88.51 |
| BARC-030817-06946 | J_(16) | 37,289,136 | 88.93 |

TABLE 43

| Locus | LG (ch) | Physical | Genetic (cM) |
|---|---|---|---|
| BARCSOYSSR_19_1128 | L_(19) | 41,423,108 | 55.66 |
| Satt076 | L_(19) | 41,423,108 | 55.66 |
| BARC-055739-13676 | L_(19) | 42,048,498 | 59.18 |
| BARCSOYSSR_19_1176 | L_(19) | 42,110,356 | 59.44 |
| Sat_113 | L_(19) | 42,110,356 | 59.44 |
| BARCSOYSSR_19_1213 | L_(19) | 42,830,781 | 61.40 |
| Satt678 | L_(19) | 42,830,781 | 61.40 |
| BARC-047494-12937 | L_(19) | 42,846,587 | 61.48 |
| BARC-011641-00318 | L_(19) | 42,955,778 | 61.87 |
| BARC-044913-08839 | L_(19) | 43,125,513 | 62.31 |
| BARCSOYSSR_19_1251 | L_(19) | 43,523,563 | 69.12 |
| Sat_099 | L_(19) | 43,523,563 | 69.12 |
| BARC-044465-08706 | L_(19) | 44,175,110 | 72.22 |
| BARC-035235-07156 | L_(19) | 44,566,701 | 74.76 |
| BARC-013505-00505 | L_(19) | 44,810,522 | 76.10 |
| BARCSOYSSR_19_1329 | L_(19) | 44,978,924 | 77.47 |

TABLE 43-continued

| Locus | LG (ch) | Physical | Genetic (cM) |
|---|---|---|---|
| Sat_286 | L_(19) | 44,978,924 | 77.47 |
| BARC-029975-06765 | L_(19) | 45,144,453 | 78.09 |
| BARC-013007-00419 | L_(19) | 45,472,890 | 79.01 |
| BARC-021733-04193 | L_(19) | 45,993,209 | 80.75 |
| BARCSOYSSR_19_1381 | L_(19) | 46,001,862 | 81.03 |
| Satt006 | L_(19) | 46,001,862 | 81.03 |
| BARCSOYSSR_19_1383 | L_(19) | 46,109,715 | 81.33 |
| Satt664 | L_(19) | 46,109,715 | 81.33 |
| BARC-014655-01607 | L_(19) | 46,478,087 | 84.05 |
| BARC-030101-06809 | L_(19) | 46,516,411 | 84.05 |
| BARC-029419-06181 | L_(19) | 46,611,807 | 84.53 |
| BARC-028787-06014 | L_(19) | 46,761,021 | 85.15 |
| BARC-022199-04295 | L_(19) | 46,811,335 | 85.15 |
| BARC-015493-01985 | L_(19) | 46,811,560 | 85.20 |
| BARC-064839-18815 | L_(19) | 47,117,038 | 86.12 |
| BARC-021321-04035 | L_(19) | 47,258,614 | 86.15 |
| S16601-001 | L_(19) | 47,535,046 | 87.73 |
| BARC-018175-02534 | L_(19) | 47,721,962 | 88.79 |
| S01481-1 | L_(19) | 47,826,727 | 89.53 |
| BARC-055107-13809 | L_(19) | 47,867,062 | 89.81 |
| BARC-055773-13715 | L_(19) | 48,037,516 | 90.42 |
| BARC-013129-01447 | L_(19) | 48,074,048 | 90.44 |
| BARC-013053-00429 | L_(19) | 48,174,962 | 90.85 |
| S11309-1 | L_(19) | 48,252,040 | 91.10 |
| BARC-052179-11387 | L_(19) | 48,307,020 | 91.27 |
| BARC-027414-06567 | L_(19) | 48,407,210 | 91.61 |
| S11320-1 | L_(19) | 48,638,646 | 92.18 |
| BARC-030273-06844 | L_(19) | 49,088,662 | 93.28 |
| BARCSOYSSR_19_1543 | L_(19) | 49,191,367 | 93.95 |
| Satt373 | L_(19) | 49,191,367 | 93.95 |
| BARC-051673-11193 | L_(19) | 49,340,378 | 94.04 |
| BARC-041915-08133 | L_(19) | 49,845,318 | 99.11 |
| BARCSOYSSR_19_1580 | L_(19) | 50,023,695 | 101.14 |
| Sat_245 | L_(19) | 50,023,695 | 101.14 |
| S04040-1 | L_(19) | 50,222,676 | 100.89 |
| BARC-028353-05838 | L_(19) | 50,302,422 | 100.79 |
| BARC-042699-08377 | L_(19) | 50,414,357 | 100.58 |
| BARC-019039-03054 | L_(19) | 50,424,707 | 99.67 |

TABLE 44

| Locus | LG (ch) | Physical | Genetic (cM) |
|---|---|---|---|
| BARCSOYSSR_07_0017 | M_(7) | 220,579 | 1.17 |
| Satt404 | M_(7) | 220,579 | 1.17 |
| BARC-059421-15798 | M_(7) | 226,537 | 4.97 |
| BARC-015439-01969 | M_(7) | 376,594 | 5.47 |
| BARC-008017-00148 | M_(7) | 580,840 | 6.81 |
| S00863-1 | M_(7) | 1,141,099 | 8.09 |
| BARCSOYSSR_07_0075 | M_(7) | 1,201,859 | 8.23 |
| Satt636 | M_(7) | 1,201,859 | 8.23 |
| BARC-044075-08603 | M_(7) | 1,421,872 | 8.57 |
| BARC-029703-06326 | M_(7) | 1,628,392 | 10.60 |
| S17151-001 | M_(7) | 1,830,296 | 11.64 |
| S17153-001 | M_(7) | 1,923,026 | 12.12 |
| BARCSOYSSR_07_0109 | M_(7) | 2,006,120 | 12.55 |
| Satt201 | M_(7) | 2,006,120 | 12.55 |
| BARC-039741-07564 | M_(7) | 2,041,844 | 12.66 |
| S17154-001 | M_(7) | 2,179,883 | 13.97 |
| BARC-042621-08316 | M_(7) | 2,196,306 | 14.13 |
| BARC-035447-07202 | M_(7) | 2,279,904 | 15.14 |
| S17156-001 | M_(7) | 2,310,058 | 15.53 |
| BARCSOYSSR_07_0134 | M_(7) | 2,414,495 | 16.86 |
| Satt150 | M_(7) | 2,414,495 | 16.86 |
| BARC-025961-05189 | M_(7) | 2,477,005 | 17.71 |
| S17159-001 | M_(7) | 2,679,749 | 18.14 |
| BARC-061549-17261 | M_(7) | 2,737,694 | 18.27 |
| BARC-059899-16208 | M_(7) | 2,924,066 | 18.54 |
| S08590-1 | M_(7) | 3,009,018 | 19.96 |
| BARC-042631-08332 | M_(7) | 3,184,418 | 22.91 |
| BARC-054347-12492 | M_(7) | 3,301,644 | 24.46 |
| BARC-013845-01256 | M_(7) | 3,598,752 | 27.93 |
| BARC-050315-09547 | M_(7) | 4,241,757 | 31.48 |
| S17242-001 | M_(7) | 4,282,676 | 31.68 |
| S17166-001 | M_(7) | 4,319,368 | 31.87 |

TABLE 44-continued

| Locus | LG (ch) | Physical | Genetic (cM) |
|---|---|---|---|
| S17167-001 | M_(7) | 4,342,479 | 31.99 |
| BARC-015945-02020 | M_(7) | 4,380,782 | 32.18 |
| BARC-012947-00412 | M_(7) | 4,380,831 | 32.18 |
| BARCSOYSSR_07_0247 | M_(7) | 4,510,496 | 32.75 |
| Satt567 | M_(7) | 4,510,496 | 32.75 |
| BARCSOYSSR_07_0263 | M_(7) | 4,963,009 | 34.27 |
| Satt540 | M_(7) | 4,963,009 | 34.27 |
| S08539-1 | M_(7) | 5,576,650 | 36.74 |
| BARC-028455-05917 | M_(7) | 5,899,369 | 38.05 |
| BARC-044469-08707 | M_(7) | 6,036,308 | 38.74 |
| BARC-050461-09646 | M_(7) | 6,209,838 | 39.88 |
| S17178-001 | M_(7) | 6,288,899 | 40.59 |
| BARC-055563-13436 | M_(7) | 6,302,756 | 40.72 |
| S17179-001 | M_(7) | 6,340,656 | 40.83 |
| S17180-001 | M_(7) | 6,347,675 | 40.85 |
| BARC-039195-07465 | M_(7) | 6,528,733 | 41.37 |
| S17181-001 | M_(7) | 6,614,649 | 41.66 |
| S17182-001 | M_(7) | 6,616,695 | 41.66 |
| S17183-001 | M_(7) | 6,623,333 | 41.69 |
| S02780-1 | M_(7) | 6,671,535 | 41.85 |
| BARC-015057-02547 | M_(7) | 6,914,368 | 42.66 |
| S12107-1 | M_(7) | 7,096,376 | 43.16 |
| S03624-1 | M_(7) | 7,774,056 | 45.02 |
| BARC-044841-08824 | M_(7) | 7,812,440 | 45.13 |
| BARCSOYSSR_07_0435 | M_(7) | 8,194,675 | 46.19 |
| Sat_244 | M_(7) | 8,194,675 | 46.19 |
| BARCSOYSSR_07_0437 | M_(7) | 8,243,975 | 46.27 |
| Satt463 | M_(7) | 8,243,975 | 46.27 |
| BARCSOYSSR_07_0445 | M_(7) | 8,510,809 | 47.88 |
| Sat_253 | M_(7) | 8,510,809 | 47.88 |
| S01953-1 | M_(7) | 8,674,220 | 48.13 |
| BARC-032703-09018 | M_(7) | 8,935,981 | 48.52 |
| BARC-032703-09019 | M_(7) | 8,935,981 | 48.71 |
| BARC-047466-12935 | M_(7) | 9,329,297 | 49.17 |
| BARC-016783-02329 | M_(7) | 9,628,588 | 50.25 |
| BARCSOYSSR_07_0518 | M_(7) | 9,862,864 | 51.86 |
| Satt220 | M_(7) | 9,862,864 | 51.86 |
| BARCSOYSSR_07_0548 | M_(7) | 10,415,548 | 55.87 |
| Satt323 | M_(7) | 10,415,548 | 55.87 |
| BARC-060941-16977 | M_(7) | 11,007,250 | 57.32 |
| BARC-061507-17243 | M_(7) | 11,259,822 | 56.82 |
| BARCSOYSSR_07_0634 | M_(7) | 12,909,853 | 56.61 |
| Satt702 | M_(7) | 12,909,853 | 56.61 |
| BARCSOYSSR_07_0683 | M_(7) | 14,632,112 | 56.16 |
| Sat_258 | M_(7) | 14,632,112 | 56.16 |
| BARCSOYSSR_07_0690 | M_(7) | 14,773,940 | 57.44 |
| Sat_148 | M_(7) | 14,773,940 | 57.44 |
| BARC-023101-03770 | M_(7) | 15,305,701 | 59.55 |
| BARC-023593-05477 | M_(7) | 15,305,813 | 61.29 |
| BARCSOYSSR_07_0721 | M_(7) | 15,307,117 | 61.93 |
| Satt175 | M_(7) | 15,307,117 | 61.93 |
| BARC-062193-17703 | M_(7) | 15,402,867 | 65.75 |
| BARC-059473-15817 | M_(7) | 15,607,282 | 66.44 |
| BARC-020517-04647 | M_(7) | 15,694,453 | 66.44 |
| BARCSOYSSR_07_0783 | M_(7) | 16,428,157 | 67.54 |
| Satt494 | M_(7) | 16,428,157 | 67.54 |
| BARC-015385-01815 | M_(7) | 17,116,792 | 67.73 |
| BARC-016743-03360 | M_(7) | 17,126,320 | 67.73 |
| BARC-020797-03938 | M_(7) | 17,175,180 | 67.73 |
| BARCSOYSSR_07_0825 | M_(7) | 17,482,347 | 69.18 |
| AF186183 | M_(7) | 17,482,347 | 69.18 |
| BARC-024721-05599 | M_(7) | 17,600,424 | 69.78 |
| BARCSOYSSR_07_0844 | M_(7) | 17,679,888 | 71.26 |
| Satt677 | M_(7) | 17,679,888 | 71.26 |
| BARC-014217-02710 | M_(7) | 17,702,808 | 71.56 |
| BARC-012865-00400 | M_(7) | 18,216,965 | 72.63 |
| BARC-015627-02769 | M_(7) | 18,318,866 | 72.63 |
| BARC-023229-03835 | M_(7) | 19,040,647 | 72.96 |
| BARC-024731-05607 | M_(7) | 19,080,789 | 72.98 |
| BARC-052787-11614 | M_(7) | 19,705,692 | 74.41 |
| BARC-061433-17197 | M_(7) | 20,072,882 | 74.41 |
| BARC-057751-14916 | M_(7) | 20,087,945 | 74.41 |
| BARC-062101-17658 | M_(7) | 20,151,855 | 74.41 |
| BARC-014249-03141 | M_(7) | 21,419,677 | 74.41 |
| BARC-061055-17021 | M_(7) | 24,939,884 | 74.41 |
| BARC-038383-10069 | M_(7) | 30,064,223 | 74.41 |
| BARC-065185-19208 | M_(7) | 34,321,453 | 74.41 |
| BARC-058289-15194 | M_(7) | 35,107,980 | 74.78 |

TABLE 44-continued

| Locus | LG (ch) | Physical | Genetic (cM) |
|---|---|---|---|
| S00111-1 | M_(7) | 35,590,550 | 79.14 |
| BARC-042549-08299 | M_(7) | 36,166,319 | 84.34 |
| S04180-1 | M_(7) | 36,459,825 | 86.05 |
| S01008-1 | M_(7) | 36,638,366 | 87.09 |
| BARC-055145-13086 | M_(7) | 36,740,933 | 87.68 |
| BARC-028385-05858 | M_(7) | 36,812,411 | 87.68 |
| BARC-040209-07684 | M_(7) | 36,978,441 | 87.85 |
| BARCSOYSSR_07_1237 | M_(7) | 37,174,173 | 89.45 |
| Satt551 | M_(7) | 37,174,173 | 89.45 |
| BARC-007320-00155 | M_(7) | 37,262,929 | 89.84 |
| BARCSOYSSR_07_1332 | M_(7) | 38,616,059 | 96.26 |
| Sat_121 | M_(7) | 38,616,059 | 96.26 |
| BARC-026077-05254 | M_(7) | 38,986,948 | 96.96 |
| BARC-065255-19294 | M_(7) | 39,211,695 | 98.54 |
| BARCSOYSSR_07_1431 | M_(7) | 40,343,666 | 106.12 |
| Satt346 | M_(7) | 40,343,666 | 106.12 |
| BARCSOYSSR_07_1527 | M_(7) | 42,251,426 | 113.89 |
| Sat_147 | M_(7) | 42,251,426 | 113.89 |
| BARC-007900-00197 | M_(7) | 42,385,545 | 117.51 |
| BARCSOYSSR_07_1556 | M_(7) | 42,876,624 | 122.55 |
| Satt308 | M_(7) | 42,876,624 | 122.55 |
| BARC-028517-05936 | M_(7) | 43,709,205 | 127.90 |
| BARCSOYSSR_07_1644 | M_(7) | 44,418,256 | 132.42 |
| Sat_330 | M_(7) | 44,418,256 | 132.42 |

TABLE 45

| Locus | LG (ch) | Physical | Genetic (cM) |
|---|---|---|---|
| BARCSOYSSR_03_0257 | N_(3) | 4,554,677 | 23.27 |
| Satt641 | N_(3) | 4,554,677 | 23.27 |
| BARC-064081-18547 | N_(3) | 4,993,899 | 23.85 |
| BARC-016199-02307 | N_(3) | 5,808,783 | 25.97 |
| BARC-024681-05527 | N_(3) | 6,922,908 | 26.81 |
| BARC-051729-11232 | N_(3) | 8,704,943 | 27.18 |
| BARCSOYSSR_03_0483 | N_(3) | 13,899,275 | 28.39 |
| Satt485 | N_(3) | 13,899,275 | 28.39 |
| BARC-057823-14942 | N_(3) | 14,987,500 | 28.46 |
| BARC-061115-17056 | N_(3) | 18,958,974 | 29.59 |
| BARC-050955-10882 | N_(3) | 19,182,593 | 29.60 |
| BARC-060803-16908 | N_(3) | 24,935,361 | 30.52 |
| BARC-047929-10431 | N_(3) | 27,977,273 | 30.59 |
| BARC-047931-10433 | N_(3) | 27,979,865 | 30.59 |
| BARC-062511-17877 | N_(3) | 28,330,059 | 30.72 |
| BARC-060707-16809 | N_(3) | 29,090,285 | 30.86 |
| BARC-052725-11576 | N_(3) | 30,470,826 | 31.10 |
| BARC-016467-02618 | N_(3) | 33,396,107 | 32.62 |
| BARCSOYSSR_03_0983 | N_(3) | 34,710,442 | 35.19 |
| Sat_280 | N_(3) | 34,710,442 | 35.19 |
| BARC-065459-19489 | N_(3) | 35,169,567 | 37.47 |
| BARC-013561-01160 | N_(3) | 35,318,305 | 37.89 |
| BARC-013599-01171 | N_(3) | 35,583,354 | 38.00 |
| BARCSOYSSR_03_1075 | N_(3) | 36,046,736 | 39.72 |
| Sat_266 | N_(3) | 36,046,736 | 39.72 |
| BARC-035433-07199 | N_(3) | 36,785,458 | 42.40 |
| BARC-039287-07269 | N_(3) | 36,785,533 | 42.40 |
| BARC-050433-09624 | N_(3) | 37,047,429 | 44.99 |
| BARC-019375-03900 | N_(3) | 37,309,808 | 45.59 |
| BARCSOYSSR_03_1165 | N_(3) | 37,622,075 | 47.24 |
| Sat_236 | N_(3) | 37,622,075 | 47.24 |
| BARC-021465-04122 | N_(3) | 37,828,068 | 47.79 |
| BARC-002118-00086 | N_(3) | 38,031,755 | 48.25 |
| BARC-010179-00543 | N_(3) | 38,032,014 | 49.69 |
| BARC-018929-03038 | N_(3) | 38,076,895 | 50.43 |
| BARC-040277-07705 | N_(3) | 38,389,688 | 53.13 |
| S12862-1 | N_(3) | 38,491,492 | 53.56 |
| BARCSOYSSR_03_1258 | N_(3) | 39,360,431 | 57.27 |
| Satt549 | N_(3) | 39,360,431 | 57.27 |
| S12867-1 | N_(3) | 39,583,405 | 58.35 |
| BARCSOYSSR_03_1275 | N_(3) | 39,627,567 | 58.57 |
| Satt660 | N_(3) | 39,627,567 | 58.57 |
| BARC-038823-07342 | N_(3) | 39,692,625 | 58.66 |
| BARC-014927-01923 | N_(3) | 39,795,065 | 59.27 |
| BARCSOYSSR_03_1302 | N_(3) | 39,840,201 | 59.54 |
| GMAB AB | N_(3) | 39,840,201 | 59.54 |
| BARC-010211-00550 | N_(3) | 39,840,815 | 59.65 |
| BARC-048763-10711 | N_(3) | 39,842,964 | 59.91 |
| BARCSOYSSR_03_1307 | N_(3) | 39,934,569 | 60.17 |
| Satt339 | N_(3) | 39,934,569 | 60.17 |
| BARC-024777-05683 | N_(3) | 40,018,491 | 60.48 |
| BARC-023367-05353 | N_(3) | 40,088,284 | 60.66 |
| BARC-023365-05350 | N_(3) | 40,115,382 | 60.67 |
| BARC-046426-12582 | N_(3) | 40,307,332 | 60.96 |
| BARC-028205-05791 | N_(3) | 40,462,431 | 61.33 |
| BARC-016485-02069 | N_(3) | 40,585,252 | 61.48 |
| BARC-029415-06172 | N_(3) | 40,805,854 | 61.80 |
| BARC-020101-04452 | N_(3) | 41,146,718 | 62.62 |
| BARC-046692-12696 | N_(3) | 41,231,762 | 63.13 |
| BARC-046758-12733 | N_(3) | 41,234,262 | 63.13 |
| BARCSOYSSR_03_1387 | N_(3) | 41,732,537 | 65.90 |
| Satt312 | N_(3) | 41,732,537 | 65.90 |
| BARC-013865-01261 | N_(3) | 41,779,870 | 66.30 |
| BARC-047693-10381 | N_(3) | 42,027,991 | 67.51 |
| BARCSOYSSR_03_1412 | N_(3) | 42,180,031 | 69.28 |
| Satt234 | N_(3) | 42,180,031 | 69.28 |
| BARCSOYSSR_03_1454 | N_(3) | 42,834,621 | 71.71 |
| Sat_239 | N_(3) | 42,834,621 | 71.71 |
| BARCSOYSSR_03_1469 | N_(3) | 43,078,322 | 73.01 |
| Sat_241 | N_(3) | 43,078,322 | 73.01 |
| BARC-028745-06004 | N_(3) | 43,242,194 | 73.63 |
| BARC-028539-05944 | N_(3) | 43,488,305 | 74.16 |
| BARC-021293-04029 | N_(3) | 43,504,295 | 74.29 |
| BARCSOYSSR_03_1492 | N_(3) | 43,533,807 | 74.71 |
| Satt257 | N_(3) | 43,533,807 | 74.71 |
| BARCSOYSSR_03_1493 | N_(3) | 43,594,194 | 76.65 |
| Sat_306 | N_(3) | 43,594,194 | 76.65 |
| BARC-048557-10665 | N_(3) | 43,809,381 | 79.05 |
| BARC-061771-17371 | N_(3) | 44,172,012 | 80.70 |
| BARCSOYSSR_03_1540 | N_(3) | 44,682,640 | 84.45 |
| Satt022 | N_(3) | 44,682,640 | 84.45 |
| BARC-065687-19660 | N_(3) | 44,732,101 | 85.08 |
| BARCSOYSSR_03_1546 | N_(3) | 44,771,047 | 85.40 |
| Sat_125 | N_(3) | 44,771,047 | 85.40 |
| BARC-027930-06703 | N_(3) | 44,947,921 | 85.82 |
| BARC-044603-08734 | N_(3) | 45,007,813 | 85.82 |
| BARC-031999-07236 | N_(3) | 45,098,078 | 86.21 |
| BARC-060109-16388 | N_(3) | 45,391,016 | 86.91 |
| BARC-016535-02085 | N_(3) | 45,416,293 | 88.23 |
| BARC-018125-02530 | N_(3) | 45,517,348 | 88.78 |
| BARC-014575-01582 | N_(3) | 45,597,671 | 91.19 |
| BARC-060031-16308 | N_(3) | 46,177,225 | 92.06 |
| S04966-1 | N_(3) | 46,209,939 | 92.16 |
| BARC-029409-06170 | N_(3) | 46,403,735 | 92.72 |
| BARC-054507-12102 | N_(3) | 46,416,790 | 92.72 |
| BARC-045143-08893 | N_(3) | 47,154,494 | 94.69 |
| BARC-030669-06920 | N_(3) | 47,161,222 | 94.69 |
| BARC-900569-00953 | N_(3) | 47,181,930 | 94.69 |
| BARC-039729-07559 | N_(3) | 47,463,739 | 96.07 |

TABLE 46

| Locus | LG (ch) | Physical | Genetic (cM) |
|---|---|---|---|
| BARCSOYSSR_10_1072 | O_(10) | 38,408,903 | 63.99 |
| BE801128 | O_(10) | 38,408,903 | 63.99 |
| BARC-058227-15165 | O_(10) | 38,679,136 | 65.56 |
| BARC-054045-12290 | O_(10) | 38,888,903 | 66.82 |
| BARC-060257-16508 | O_(10) | 39,359,776 | 69.80 |
| BARCSOYSSR_10_1148 | O_(10) | 39,749,488 | 77.31 |
| Satt477 | O_(10) | 39,749,488 | 77.31 |
| BARC-020735-04704 | O_(10) | 40,604,308 | 80.18 |
| BARC-022409-04322 | O_(10) | 40,671,311 | 80.78 |
| BARC-042373-08248 | O_(10) | 40,805,085 | 81.69 |
| BARC-038447-10088 | O_(10) | 41,264,139 | 83.71 |
| BARC-065285-19314 | O_(10) | 41,475,551 | 84.27 |
| BARC-056633-14536 | O_(10) | 41,589,284 | 84.48 |
| BARC-032641-09002 | O_(10) | 41,739,507 | 85.42 |
| BARC-048879-10743 | O_(10) | 42,430,468 | 89.53 |
| BARC-008209-01052 | O_(10) | 42,430,516 | 89.80 |
| BARC-037165-06725 | O_(10) | 42,439,079 | 89.80 |

TABLE 46-continued

| Locus | LG (ch) | Physical | Genetic (cM) |
|---|---|---|---|
| BARCSOYSSR_10_1339 | O_(10) | 42,983,878 | 91.36 |
| Satt592 | O_(10) | 42,983,878 | 91.36 |
| BARC-008021-00209 | O_(10) | 43,283,444 | 92.39 |
| BARC-042813-08418 | O_(10) | 43,303,071 | 92.39 |
| BARC-014965-01938 | O_(10) | 43,563,691 | 92.39 |
| BARC-043247-08565 | O_(10) | 43,812,144 | 92.79 |
| S10631-1 | O_(10) | 43,974,548 | 94.20 |
| BARCSOYSSR_10_1400 | O_(10) | 44,136,478 | 95.60 |
| Satt581 | O_(10) | 44,136,478 | 95.60 |
| S01574-1 | O_(10) | 44,725,777 | 99.55 |
| S16594-001 | O_(10) | 44,732,850 | 99.55 |
| BARC-015925-02017 | O_(10) | 44,753,396 | 99.69 |
| BARCSOYSSR_10_1480 | O_(10) | 45,480,419 | 103.64 |
| Sat_038 | O_(10) | 45,480,419 | 103.64 |
| BARCSOYSSR_10_1513 | O_(10) | 45,959,182 | 106.32 |
| Satt153 | O_(10) | 45,959,182 | 106.32 |
| BARCSOYSSR_10_1517 | O_(10) | 46,088,357 | 107.31 |
| Satt243 | O_(10) | 46,088,357 | 107.31 |
| BARCSOYSSR_10_1568 | O_(10) | 46,827,438 | 110.86 |
| Sat_307 | O_(10) | 46,827,438 | 110.86 |
| BARC-035161-07127 | O_(10) | 46,889,635 | 112.70 |
| BARC-035395-07191 | O_(10) | 46,889,662 | 112.80 |
| BARC-018693-02992 | O_(10) | 47,120,942 | 114.57 |
| BARC-042437-08266 | O_(10) | 47,314,439 | 115.58 |
| BARC-043129-08536 | O_(10) | 47,345,878 | 115.75 |
| BARC-008241-00035 | O_(10) | 47,395,171 | 116.29 |
| BARC-019823-04401 | O_(10) | 47,828,150 | 117.16 |
| BARC-047374-12913 | O_(10) | 47,975,138 | 117.38 |
| BARC-046788-12746 | O_(10) | 48,019,353 | 117.38 |
| BARC-040575-07784 | O_(10) | 48,020,280 | 117.38 |
| BARC-047426-12927 | O_(10) | 48,033,218 | 117.38 |
| BARC-065783-19748 | O_(10) | 48,265,046 | 117.86 |
| BARC-041027-07899 | O_(10) | 48,822,964 | 119.92 |
| BARC-024123-04768 | O_(10) | 49,066,283 | 120.11 |
| BARC-048777-10716 | O_(10) | 49,312,430 | 120.78 |
| BARC-015689-02817 | O_(10) | 49,402,851 | 121.16 |
| BARC-015167-02733 | O_(10) | 49,408,941 | 121.18 |
| BARC-015199-02739 | O_(10) | 49,411,491 | 121.18 |
| BARC-015685-02814 | O_(10) | 49,411,604 | 121.18 |
| BARC-011313-00862 | O_(10) | 49,433,740 | 121.18 |
| BARC-015681-02809 | O_(10) | 49,468,084 | 121.41 |
| BARC-015751-02829 | O_(10) | 49,482,356 | 121.41 |
| BARC-015683-02812 | O_(10) | 49,494,791 | 121.54 |
| BARC-030491-06877 | O_(10) | 49,524,668 | 121.73 |
| BARC-017339-02269 | O_(10) | 49,718,185 | 122.68 |
| BARC-031993-07234 | O_(10) | 49,839,294 | 122.85 |
| S02777-1 | O_(10) | 50,495,033 | 129.25 |
| BARC-042325-08242 | O_(10) | 50,814,271 | 132.37 |
| BARC-053181-11734 | O_(10) | 50,825,960 | 132.41 |
| BARC-056147-14126 | O_(10) | 50,865,837 | 132.41 |
| BARC-029629-06265 | O_(10) | 50,903,999 | 132.50 |

What is claimed is:

1. A method of producing a soybean plant or soybean germplasm with a late maturity phenotype, the method comprising:
   (a) isolating nucleic acids from a genome of a first soybean plant or soybean germplasm;
   (b) detecting in the first soybean plant or soybean germplasm at least one favorable allele of one or more marker locus selected from the group consisting of:
      I. at least marker locus S08590-1-Q1;
      II. at least one marker within a region of SEQ ID NO: 399;
      III. at least one marker within 5 cM of Gm07:3009018; and
      IV. at least a polynucleotide comprising a polymorphism at a genomic position of Gm07:3009018,
   wherein the at least one favorable allele is an A at Gm07:3009018 for marker S08590-1-Q1;
   (c) selecting said first soybean plant or soybean germplasm, or selecting a progeny of said first soybean plant or soybean germplasm, wherein the plant germplasm or progeny thereof comprise the at least one favorable allele associated with the late maturity phenotype; and
   (d) crossing said selected first soybean plant or soybean germplasm with a second soybean plant or soybean germplasm, thus producing a soybean plant or soybean germplasm with a marker profile associated with the late maturity phenotype wherein said produced soybean plant or germplasm has a marker profile comprising at least an A at Gm07:3009018.

2. The method of claim 1, wherein said detecting comprises detection of a haplotype comprising markers S08590-1-Q1 and S08539-1-Q1.

3. The method of claim 1, wherein the detecting comprises sequencing at least one of said marker loci.

4. The method of claim 1, wherein the detecting comprises amplifying the marker locus or a portion of the marker locus and detecting the resulting amplified marker amplicon.

5. The method of claim 4, wherein the amplifying comprises:
   a) admixing an amplification primer or amplification primer pair with a nucleic acid isolated from the first soybean plant or germplasm, wherein the primer or primer pair is complementary or partially complementary to at least a portion of the marker locus and is capable of initiating DNA polymerization by a DNA polymerase using the soybean nucleic acid as a template; and
   b) extending the primer or primer pair in a DNA polymerization reaction comprising a DNA polymerase and a template nucleic acid to generate at least one amplicon.

6. The method of claim 5, wherein the admixing of step a) further comprises admixing at least one nucleic acid probe.

7. The method of claim 5, wherein the amplifying comprises PCR analysis.

8. The method of claim 1, wherein the detecting comprises sequencing.

9. The method of claim 1, wherein the second soybean plant or soybean germplasm comprises an exotic soybean strain or an elite soybean strain.

* * * * *

SEQUENCE LISTING

```
<160> NUMBER OF SEQ ID NOS: 512

<210> SEQ ID NO 1
<211> LENGTH: 24
<212> TYPE: DNA
<213> ORGANISM: Glycine max

<400> SEQUENCE: 1
gcctctacta gaatccgtgc atac                                             24

<210> SEQ ID NO 2
<211> LENGTH: 22
<212> TYPE: DNA
<213> ORGANISM: Glycine max

<400> SEQUENCE: 2
ggaagtgctc ttggaacaca at                                               22

<210> SEQ ID NO 3
<211> LENGTH: 18
<212> TYPE: DNA
<213> ORGANISM: Artificial sequence
<220> FEATURE:
<223> OTHER INFORMATION: S01435-1 Probe1

<400> SEQUENCE: 3
cagtactttc gtcaataa                                                    18

<210> SEQ ID NO 4
<211> LENGTH: 18
<212> TYPE: DNA
<213> ORGANISM: Artificial sequence
<220> FEATURE:
<223> OTHER INFORMATION: S01435-1 Probe2

<400> SEQUENCE: 4
cagtacattc gtcaataa                                                    18
```

<210> SEQ ID NO 5
<211> LENGTH: 401
<212> TYPE: DNA
<213> ORGANISM: Glycine max

<400> SEQUENCE: 5

```
tgttgatgag ggggccatat accatcagga acatgccaat gcttattaga gaatggaaac      60
ytgattttaa cctgaagcaa gacatgctac ggactcttcc tatttgggta caactccctc     120
aactgccatt gcatttatgg ggtggaaaaa gcctaggcaa aattggaagt gctcttggaa     180
cacaattggt tattgacgaa wgtactgcaa ataaacttcg ggtctcgtat gcacdgattc     240
tagtagaggc agatgtcacg ccagaactga gaaacgaaat tactataaag gacaatgagg     300
ggcggaggat cactcaaaaa ktcgaatatg agtggaaacc aatgttttgt gataagtgcc     360
aaaagtttgg ccayaaatgt ggtgaagtaa agccaaggaa g                         401
```

<210> SEQ ID NO 6
<211> LENGTH: 24
<212> TYPE: DNA
<213> ORGANISM: Glycine max

<400> SEQUENCE: 6

```
tgagaattga tgctcattta ggaa                                             24
```

<210> SEQ ID NO 7
<211> LENGTH: 22
<212> TYPE: DNA
<213> ORGANISM: Glycine max

<400> SEQUENCE: 7

```
ccctttgttt cattttccct ct                                               22
```

<210> SEQ ID NO 8
<211> LENGTH: 17
<212> TYPE: DNA
<213> ORGANISM: Artificial sequence
<220> FEATURE:
<223> OTHER INFORMATION: S01239-1 Probe1

<400> SEQUENCE: 8

```
acttgttaac agcattc                                                     17
```

<210> SEQ ID NO 9
<211> LENGTH: 15
<212> TYPE: DNA
<213> ORGANISM: Artificial sequence
<220> FEATURE:
<223> OTHER INFORMATION: S01239-1 Probe2

<400> SEQUENCE: 9

```
ttgttagcag cattc                                                       15
```

<210> SEQ ID NO 10
<211> LENGTH: 401
<212> TYPE: DNA
<213> ORGANISM: Glycine max

<400> SEQUENCE: 10

```
attttatag ttatatttct caaaattata ttcaagaatc agaaaacaga aaataatgt        60
tataaattts atgcatatct tccattaaaa caggttagat ccatagttgt tgctagtcaa     120
taaccttatg gttagcagtg ccatcccttd caacaatgag aattgatgct catttaggaa    180
```

```
gtcaacactt gtacttgtta rcagcattcy ggaaagaaac aagagggaaa atgaaacaaa      240
gggtgttttt caaaaaatat tggctgatca tgattttttg atcatgattt ttacrtgttc      300
tgttaagact aaagtacatt aatttcactg tgttggcacc tgaatagtta ttgagcatta      360
tgtgaggtgg caattaagta tacagttttg tcaygactt t                          401

<210> SEQ ID NO 11
<211> LENGTH: 24
<212> TYPE: DNA
<213> ORGANISM: Glycine max

<400> SEQUENCE: 11
tgtagtccca ttgccatatg aggc                                             24

<210> SEQ ID NO 12
<211> LENGTH: 24
<212> TYPE: DNA
<213> ORGANISM: Glycine max

<400> SEQUENCE: 12
cattaggggt ttcaccactg tcca                                             24

<210> SEQ ID NO 13
<211> LENGTH: 17
<212> TYPE: DNA
<213> ORGANISM: Artificial sequence
<220> FEATURE:
<223> OTHER INFORMATION: S00780-1 Probe1

<400> SEQUENCE: 13
ctcgttttaa accttct                                                     17

<210> SEQ ID NO 14
<211> LENGTH: 16
<212> TYPE: DNA
<213> ORGANISM: Artificial sequence
<220> FEATURE:
<223> OTHER INFORMATION: S00780-1 Probe2

<400> SEQUENCE: 14
ctcgttttaa gccttc                                                      16

<210> SEQ ID NO 15
<211> LENGTH: 401
<212> TYPE: DNA
<213> ORGANISM: Glycine max

<400> SEQUENCE: 15
acaatgaaga aggaagtact ttgcaggtat tgcaataaga agttcagttg ttaccaagcc      60
ttgggtggac atcataattc tcacaaggcg gaaagagcag cagaaataca tagcaaggct     120
tctgcttgtt acaaaacata tggttatggg ttttgtggca aaacattagg ggtttcacca     180
ctgtccatga ctcgttttaa rccttctatt attgttggcc tcatatggca atgggactac    240
atgactgact atcatcatgt tgcatggcca aggcaccaga ttttgaatcc tcctcaaccc    300
accatgtatc aattcatggc tgaagggagt ggatctcacc aacaccacaa attatattar   360
cctttgagtt cttctatagt cagaggagga ccaacaaatt c                         401

<210> SEQ ID NO 16
<211> LENGTH: 22
<212> TYPE: DNA
```

```
<213> ORGANISM: Glycine max

<400> SEQUENCE: 16 tgagggggaaa ttaagaaatt gg                                          22

<210> SEQ ID NO 17
<211> LENGTH: 22
<212> TYPE: DNA
<213> ORGANISM: Glycine max

<400> SEQUENCE: 17 tgagggggaaa ttaagaaatt gg                                          22

<210> SEQ ID NO 18
<211> LENGTH: 15
<212> TYPE: DNA
<213> ORGANISM: Artificial sequence
<220> FEATURE:
<223> OTHER INFORMATION: S06925-1 Probe1

<400> SEQUENCE: 18
caccgtgatg ctatt                                                   15

<210> SEQ ID NO 19
<211> LENGTH: 18
<212> TYPE: DNA
<213> ORGANISM: Artificial sequence
<220> FEATURE:
<223> OTHER INFORMATION: S06925-1 Probe2

<400> SEQUENCE: 19
catcattttc accgcgat                                                18

<210> SEQ ID NO 20
<211> LENGTH: 401
<212> TYPE: DNA
<213> ORGANISM: Glycine max

<400> SEQUENCE: 20
agtccattga acattcctca tattgttcca tgcactttgt gtgaaactgc agtggcaccg    60
gttcttttgg gggaagtaga tcagcttcaa agattgcagc ttttcatttt gcttattttc   120
catattttat gagggggaaat taagaaattg gttgttaaat agagaaacaa agatttgtct   180
ccactgcatc attttcaccg ygatgctatt gctatatctt gttccatatt agctgtgaat   240
ccttgtcact tatggggggat attaggctta cccgggtaga gcaaggtcaa acaaagatta   300
gaaatgttcc aattgctgtc accctgaag gattttggtg ttgccmtact cctgttgggt    360
ttcagaaaag cctcaaacct caaaaccctt tgaataaact c                       401

<210> SEQ ID NO 21
<211> LENGTH: 22
<212> TYPE: DNA
<213> ORGANISM: Glycine max

<400> SEQUENCE: 21
tgccgtaagt aacacacaca aa                                           22

<210> SEQ ID NO 22
<211> LENGTH: 20
<212> TYPE: DNA
<213> ORGANISM: Glycine max

<400> SEQUENCE: 22
```
caagagcaca ccatcacctg                                            20

<210> SEQ ID NO 23
<211> LENGTH: 19
<212> TYPE: DNA
<213> ORGANISM: Artificial sequence
<220> FEATURE:
<223> OTHER INFORMATION: S09951-1 Probe1

<400> SEQUENCE: 23
cacttgatta aattcctgt                                             19

<210> SEQ ID NO 24
<211> LENGTH: 15
<212> TYPE: DNA
<213> ORGANISM: Artificial sequence
<220> FEATURE:
<223> OTHER INFORMATION: S09951-1 Probe2

<400> SEQUENCE: 24
cttgattcaa ttcct                                                 15

<210> SEQ ID NO 25
<211> LENGTH: 401
<212> TYPE: DNA
<213> ORGANISM: Glycine max

<400> SEQUENCE: 25
cgagcccttg ctataaaaac gggactgaag ctcatttcaa cggggaaaat tcccaaatct    60
gttttagctc gccccaactg gccatacacg ttgctcccac agctcaagag cacaccatca   120
cctgatatag catatagtaa aaaacttaag ttttgaaaac gcatgcatac atcttaatga   180
tctaacttgc tacaggaatt kaatcaagtg tttggtgttt gtgtgtgtta cttacggcaa   240
agaatcagag agtgatcaag gccacacgca atgtccagaa catgaacacc gtgtaattct   300
tcgaccaagc ggggytccca tactattggc atgttattct cctgytccat tccttgcaag   360
actctctttt cagcagcttc awggtcckcg agagctgtga g                      401

<210> SEQ ID NO 26
<211> LENGTH: 24
<212> TYPE: DNA
<213> ORGANISM: Glycine max

<400> SEQUENCE: 26
gctgataccg ttttggtgtt tcca                                        24

<210> SEQ ID NO 27
<211> LENGTH: 22
<212> TYPE: DNA
<213> ORGANISM: Glycine max

<400> SEQUENCE: 27
tgcaacatcc cgtgaaagga tt                                          22

<210> SEQ ID NO 28
<211> LENGTH: 15
<212> TYPE: DNA
<213> ORGANISM: Artificial sequence
<220> FEATURE:
<223> OTHER INFORMATION: S00170-1 Probe1

<400> SEQUENCE: 28

```
tgcatctgca gacgt                                                  15

<210> SEQ ID NO 29
<211> LENGTH: 16
<212> TYPE: DNA
<213> ORGANISM: Artificial sequence
<220> FEATURE:
<223> OTHER INFORMATION: S00170-1 Probe2

<400> SEQUENCE: 29
tgcatctgct gacgtg                                                 16

<210> SEQ ID NO 30
<211> LENGTH: 401
<212> TYPE: DNA
<213> ORGANISM: Glycine max
<220> FEATURE:
<221> NAME/KEY: misc_feature
<222> LOCATION: (17)..(17)
<223> OTHER INFORMATION: n is a, c, g, or t
<220> FEATURE:
<221> NAME/KEY: misc_feature
<222> LOCATION: (19)..(19)
<223> OTHER INFORMATION: n is a, c, g, or t

<400> SEQUENCE: 30
tsacgagtag aatttcnant agaatttcaa gtaattttcg gactgaatca aataatccaa    60
accaaagagt agattacaag ccaggtaaat tttcaaggat ccaaatgtgg taggaccagg   120
tcactgggat acacaatgca tcatatatat atgtacgtgc aacatcccgt gaaaggattt   180
tgcctaggtc gttgcmcgtc wgcagatgca ttttatttgt acctaagaat aatacactcg   240
agtacacagc tatttatttc agtcttgagc acttgaaaac atcatgttaa gtccacataa   300
attcattaaa gacattggaa acaccaaaac ggtatcagca actgaggcta tccaaagcca   360
gagatccaaa attacaaagg caaaatgata aaatacggaa t                      401

<210> SEQ ID NO 31
<211> LENGTH: 20
<212> TYPE: DNA
<213> ORGANISM: Glycine max

<400> SEQUENCE: 31
caccatcagc aagctttgag                                             20

<210> SEQ ID NO 32
<211> LENGTH: 20
<212> TYPE: DNA
<213> ORGANISM: Glycine max

<400> SEQUENCE: 32
gaagggcact tcaacagagc                                             20

<210> SEQ ID NO 33
<211> LENGTH: 16
<212> TYPE: DNA
<213> ORGANISM: Artificial sequence
<220> FEATURE:
<223> OTHER INFORMATION: S04059-1 Probe1

<400> SEQUENCE: 33
cctctgagtt agcctt                                                 16

<210> SEQ ID NO 34
<211> LENGTH: 15
```

<212> TYPE: DNA
<213> ORGANISM: Artificial sequence
<220> FEATURE:
<223> OTHER INFORMATION: S04059-1 Probe2

<400> SEQUENCE: 34
ctctgagttg gcctt                                                    15

<210> SEQ ID NO 35
<211> LENGTH: 401
<212> TYPE: DNA
<213> ORGANISM: Glycine max

<400> SEQUENCE: 35
aaattccaaa cgattattat tctgggaaga gtcgaagcac aatactcatt aacaagaaaa    60
ttcggttgta cccataaaat accgattcct acccgcactt agattgatca gtacttgtag   120
tcctcaacat ggaggctctc tgaggcacca tcagcaagct ttgagttacc cttgtaggtt   180
cccagagttg cctctgagtt rgccttggct cttaccaaaa gggcttcctg agccttcttc   240
acattctcct cttttccact ccatgcctta agggtgctct gttgaagtgc ccttccaaag   300
gagaaagaga gtgaccatgg cttctttcca ttgacctggt taatggcatt gaggttaacg   360
gatgcctcct cctcactctg cccaccagac aagaaaacga t                       401

<210> SEQ ID NO 36
<211> LENGTH: 20
<212> TYPE: DNA
<213> ORGANISM: Glycine max

<400> SEQUENCE: 36
cttttccttg gacggtacga                                               20

<210> SEQ ID NO 37
<211> LENGTH: 20
<212> TYPE: DNA
<213> ORGANISM: Glycine max

<400> SEQUENCE: 37
cgtgtgaatg gaagaaagca                                               20

<210> SEQ ID NO 38
<211> LENGTH: 15
<212> TYPE: DNA
<213> ORGANISM: Artificial Sequence
<220> FEATURE:
<223> OTHER INFORMATION: S07851-1 Probe1

<400> SEQUENCE: 38
cactgtacaa atcaa                                                    15

<210> SEQ ID NO 39
<211> LENGTH: 13
<212> TYPE: DNA
<213> ORGANISM: Artificial Sequence
<220> FEATURE:
<223> OTHER INFORMATION: S07851-1 Probe2

<400> SEQUENCE: 39
cactgcacaa atc                                                      13

<210> SEQ ID NO 40
<211> LENGTH: 401
<212> TYPE: DNA

```
<213> ORGANISM: Glycine max

<400> SEQUENCE: 40
tgtaaaaggt ttacgtaacc atactgcaat ttrcaaccac atgctgcagt cgtatcagct    60
atattttctt gtaactgwga ttaattataa tcgcaatcta aattcattat tagagataaa   120
tgaccaccat gcatcctgat ttatgcgtgt gaatggaaga aagcatatac agatgttgac   180
atatccaagc attgatttgt rcagtgatct ccaaatattt cgtaccgtcc aaggaaaaga   240
tcaggctcta gccacatatc ttccgagcca catacatgaa ctgagcttga atcatatacc   300
ataattagca taaagggat  gaattaatgc agaggagttt aattataaag ctttattttt   360
cgcttcarag tttcagcaag attttatata tatatatata t                      401

<210> SEQ ID NO 41
<211> LENGTH: 20
<212> TYPE: DNA
<213> ORGANISM: Glycine max

<400> SEQUENCE: 41
tctgtcccaa tgctcaatca                                               20

<210> SEQ ID NO 42
<211> LENGTH: 20
<212> TYPE: DNA
<213> ORGANISM: Glycine max

<400> SEQUENCE: 42
cttggagggg aaggtctagc                                               20

<210> SEQ ID NO 43
<211> LENGTH: 15
<212> TYPE: DNA
<213> ORGANISM: Artificial Sequence
<220> FEATURE:
<223> OTHER INFORMATION: S11659-1 Probe1

<400> SEQUENCE: 43
catgatgaca acctc                                                    15

<210> SEQ ID NO 44
<211> LENGTH: 16
<212> TYPE: DNA
<213> ORGANISM: Artificial Sequence
<220> FEATURE:
<223> OTHER INFORMATION: S11659-1 Probe2

<400> SEQUENCE: 44
atgatggcaa cctcta                                                   16

<210> SEQ ID NO 45
<211> LENGTH: 401
<212> TYPE: DNA
<213> ORGANISM: Glycine max

<400> SEQUENCE: 45
taaaaatgat ttaattatta ttaatttaac trtagttgaa tgattgaatc ttgaactaat    60
accttcttct tcattgattg aatggaaaat ctaatttat  aaacattgat twgcctcatt   120
tgtcgaggsc cactaatgaa atgtgagatt tccttggagg ggaaggtctw gctctaaaaa   180
gcccagctag ctagaggttg ycatcatgta cgcaatctta aatgattgag cattgggaca   240
gagcttgcca tgtactttac taccaatgct catatttccc mtgttgattg tgtctccctt   300
```

```
tctatcttta tatcaacttt ccaagttgtt gaccatgtcc atgtacaaag gatcatagct    360
gctcttttct tttttctttc tgttgtgctt ctcaccttac c                        401

<210> SEQ ID NO 46
<211> LENGTH: 20
<212> TYPE: DNA
<213> ORGANISM: Glycine max

<400> SEQUENCE: 46
aacaactccc tctggtgtcc                                                 20

<210> SEQ ID NO 47
<211> LENGTH: 26
<212> TYPE: DNA
<213> ORGANISM: Glycine max

<400> SEQUENCE: 47 catagggag tagattatat ggcttt                                           26

<210> SEQ ID NO 48
<211> LENGTH: 17
<212> TYPE: DNA
<213> ORGANISM: Artificial Sequence
<220> FEATURE:
<223> OTHER INFORMATION: S04279-1 Probe1

<400> SEQUENCE: 48
atctccttct cttcctt                                                    17

<210> SEQ ID NO 49
<211> LENGTH: 15
<212> TYPE: DNA
<213> ORGANISM: Artificial Sequence
<220> FEATURE:
<223> OTHER INFORMATION: S04279-1 Probe2

<400> SEQUENCE: 49
tctccttcac ttcct                                                      15

<210> SEQ ID NO 50
<211> LENGTH: 401
<212> TYPE: DNA
<213> ORGANISM: Glycine max

<400> SEQUENCE: 50
tagattaact gcaaggagac acatttcatc ttgaattttc tatgtaactt tgtattacaa     60
caaagccttg tcccgctagg tgaggtcagt tatatggatc acacgatgcc atttgacttg    120
gttgaaggcc aaatcttawg agatattatt taccatgaga tccctcttaa caactccctc    180
tggtgtcctt gatctccttc wcttcctttt cacaaaacta aaagccatat aatctactcc    240
cctatgtagc agtgtaatac atcctggatt ttctgtgaaa agttatacat tttttcagaa    300
aattgaaggt cctatttatt ttcataatgg ccacatgtct atatgataca cycttagccc    360
atgtatatat aaaaaatatg ggctgggaaa gaaatggcac a                        401

<210> SEQ ID NO 51
<211> LENGTH: 27
<212> TYPE: DNA
<213> ORGANISM: Glycine max

<400> SEQUENCE: 51
```
cctctctcat tctcgttcac gatgtaa                                           27

<210> SEQ ID NO 52
<211> LENGTH: 28
<212> TYPE: DNA
<213> ORGANISM: Glycine max

<400> SEQUENCE: 52
cttttggttc atttaaattc catttgct                                          28

<210> SEQ ID NO 53
<211> LENGTH: 19
<212> TYPE: DNA
<213> ORGANISM: Artificial Sequence
<220> FEATURE:
<223> OTHER INFORMATION: S02211-1 Probe1

<400> SEQUENCE: 53
caatttatcg taacatcag                                                    19

<210> SEQ ID NO 54
<211> LENGTH: 17
<212> TYPE: DNA
<213> ORGANISM: Artificial Sequence
<220> FEATURE:
<223> OTHER INFORMATION: S02211-1 Probe2

<400> SEQUENCE: 54
caatttaccg taacatc                                                      17

<210> SEQ ID NO 55
<211> LENGTH: 401
<212> TYPE: DNA
<213> ORGANISM: Glycine max
<220> FEATURE:
<221> NAME/KEY: misc_feature
<222> LOCATION: (94)..(94)
<223> OTHER INFORMATION: n is a, c, g, or t

<400> SEQUENCE: 55
gagctctgca aacagatcta ggaggagaga gagcgcacyg agtttcgtct tcttcaggag        60
aaagctagcc tcgtttcgta atttcccctt tccnattcaa ttttatttt ttagggtttt       120 caatttgtac tgtagtgtaa gtgaatttgg aaagatgctt ttggttcatt taaattccat      180
ttgctcgaac tgatgttacg rtaaattgct tttcttttt acatcgtgaa cgagaatgag       240
agaggaatgg ygtggcgacg ttggcgtcac agagaaggaa gaagaagaag tgacgttgat      300
gaagaagaag agtaagagaa atgagagggt tggtgccgca aagaaggaat atgaagaaga      360
ataagagaac gaagagggag cggtggtgct ccactgtgca t                          401

<210> SEQ ID NO 56
<211> LENGTH: 20
<212> TYPE: DNA
<213> ORGANISM: Glycine max

<400> SEQUENCE: 56
cgtgatccta cgcctctctt                                                   20

<210> SEQ ID NO 57
<211> LENGTH: 19
<212> TYPE: DNA
<213> ORGANISM: Glycine max

<400> SEQUENCE: 57
aggtcatgtc cacgacgaa                                                    19

<210> SEQ ID NO 58
<211> LENGTH: 15
<212> TYPE: DNA
<213> ORGANISM: Artificial Sequence
<220> FEATURE:
<223> OTHER INFORMATION: S08942-1 Probe1

<400> SEQUENCE: 58
tcacgatcgc agtct                                                        15

<210> SEQ ID NO 59
<211> LENGTH: 15
<212> TYPE: DNA
<213> ORGANISM: Artificial Sequence
<220> FEATURE:
<223> OTHER INFORMATION: S08942-1 Probe2

<400> SEQUENCE: 59
tcacgatcgg agtct                                                        15

<210> SEQ ID NO 60
<211> LENGTH: 401
<212> TYPE: DNA
<213> ORGANISM: Glycine max

<400> SEQUENCE: 60
ttaaataatt tgttagatc tctcttattt taaatatttt tatttaaata tttattaaat         60
taatataatt atgtaaatat tcggtttctc tccttgtttt tttttcttct atttttatt       120
tttttttact tccctctccc gtgatcctac gcctctcttc tttcttttc ctcctttttt       180
ctttccctcc atcacgatcg sagtctcctt tcaccttccc cttcgtcgtg gacatgacct      240
ccctcccct tcctttccgt cacggcctcc tccccattct cctccgtcgc gagcccctt       300
tactccttcc gaaactctat cacgacctcc ttccccatgt gtcaatatgt atattttgtt     360
tttatggttt gttttattt gtttcttttt aatcattcca t                          401

<210> SEQ ID NO 61
<211> LENGTH: 22
<212> TYPE: DNA
<213> ORGANISM: Glycine max

<400> SEQUENCE: 61
acgacgtcaa gaagttcctt tc                                                22

<210> SEQ ID NO 62
<211> LENGTH: 20
<212> TYPE: DNA
<213> ORGANISM: Glycine max

<400> SEQUENCE: 62
ggccgaactc ggttctaatc                                                   20

<210> SEQ ID NO 63
<211> LENGTH: 15
<212> TYPE: DNA
<213> ORGANISM: Artificial Sequence
<220> FEATURE:
<223> OTHER INFORMATION: S05742-1 Probe1

<400> SEQUENCE: 63

```
tccgaaatca taatc                                                      15
```

<210> SEQ ID NO 64
<211> LENGTH: 15
<212> TYPE: DNA
<213> ORGANISM: Artificial Sequence
<220> FEATURE:
<223> OTHER INFORMATION: S05742-1 Probe2

<400> SEQUENCE: 64

```
ccgaaatcct aatcc                                                      15
```

<210> SEQ ID NO 65
<211> LENGTH: 401
<212> TYPE: DNA
<213> ORGANISM: Glycine max

<400> SEQUENCE: 65

```
gagaggactc ccaggtttgg gctgggacga ttttctgggc ttccaaacgc agataactct     60
ctttggcaac aactccgcca cggtcttccc gaaaacggcg tcgtcctgat ggatcagatg    120
ctcccccagc tgttcctcca ggtacttgtc gaattcggga gggtcctcgt ggccgaactc    180
ggttctaatc tccaggatta kgatttcgga ctgcgtgtcg gaaaggaact tcttgacgtc    240
gttgaggacg aggtcaacgc cgtaggtgag gaggataccg tggcagacgc ggcggtgttc    300
ttggacgcgg atgtcgagga cgcgggtgcc gagggagagc tggcggtaga tggagaggga    360
ttggcactgg gcgaaggggc gagtgaggag agggatgcca a                        401
```

<210> SEQ ID NO 66
<211> LENGTH: 20
<212> TYPE: DNA
<213> ORGANISM: Glycine max

<400> SEQUENCE: 66

```
ctattgccga gaagctcgat                                                 20
```

<210> SEQ ID NO 67
<211> LENGTH: 20
<212> TYPE: DNA
<213> ORGANISM: Glycine max

<400> SEQUENCE: 67

```
tcatcctccg tgagatagcc                                                 20
```

<210> SEQ ID NO 68
<211> LENGTH: 16
<212> TYPE: DNA
<213> ORGANISM: Artificial Sequence
<220> FEATURE:
<223> OTHER INFORMATION: S09155-1 Probe1

<400> SEQUENCE: 68

```
caacgttttg tcatca                                                     16
```

<210> SEQ ID NO 69
<211> LENGTH: 16
<212> TYPE: DNA
<213> ORGANISM: Artificial Sequence
<220> FEATURE:
<223> OTHER INFORMATION: S09155-1 Probe2

<400> SEQUENCE: 69

```
caacgtttcg tcatca                                                     16
```

<210> SEQ ID NO 70
<211> LENGTH: 401
<212> TYPE: DNA
<213> ORGANISM: Glycine max

<400> SEQUENCE: 70

```
tactcatgga tcttgtccta aacctgatat gaatgattca agcccaacac gggygacaag    60
actgatttcg agagtgtgga ctgtagccaa acaggaagtg tttggtcwtg aacttcctat   120
ggttcatact cattttttcat gcaatctgca atacgatcat cctccgtgag atagccaggc   180
agaacaacag gattgatgac raaacgttgc aatttatgcg ccttgatcac tggttcgaca   240
tgcwgtcgtc agtgaaggta gtttgaatca tcgagcttct cggcaatagt gtttgggaac   300
aactgagata caggattcga aggtacggaa gccatggata cacagatctt gaatgataac   360
tacaaaggat aggctctcga taccatattt gataaaactg a                       401
```

<210> SEQ ID NO 71
<211> LENGTH: 21
<212> TYPE: DNA
<213> ORGANISM: Glycine max

<400> SEQUENCE: 71

```
tccatcaaca aagccctttt a                                              21
```

<210> SEQ ID NO 72
<211> LENGTH: 27
<212> TYPE: DNA
<213> ORGANISM: Glycine max

<400> SEQUENCE: 72

```
aaaatatcta gttgagttgg accaaga                                        27
```

<210> SEQ ID NO 73
<211> LENGTH: 15
<212> TYPE: DNA
<213> ORGANISM: Artificial Sequence
<220> FEATURE:
<223> OTHER INFORMATION: S02037-1 Probe1

<400> SEQUENCE: 73

```
aatgcttcaa gatca                                                     15
```

<210> SEQ ID NO 74
<211> LENGTH: 15
<212> TYPE: DNA
<213> ORGANISM: Artificial Sequence
<220> FEATURE:
<223> OTHER INFORMATION: S02037-1 Probe2

<400> SEQUENCE: 74

```
atgcttcgag atcaa                                                     15
```

<210> SEQ ID NO 75
<211> LENGTH: 401
<212> TYPE: DNA
<213> ORGANISM: Glycine max

<400> SEQUENCE: 75

```
gaaggatagc cctgayagga agggtgtctt tacacgcttt ccaaatcatg tttttggcct    60
aggggattgc ttttgttttc cacatcrcct ttcaaaagct cctggaattt ccattrgaca   120
```

```
aggcatagga agaattatcc atcaacaaag ccctttata cccagatttg acaacatacc    180
ttccatgttg tgaatgcttc ragatcaaat cattactagt cttggtccaa ctcaactaga    240
tattttgaat aatttgagag atatgttata ggaataaaga gtttatggaa gtgttgttcc    300
aagatttgga ccctggctca ataaggtcct taaccttcaa aataggatcc attgtagaac    360
catttggagg atcgagakag tgcctygcca gatttagaat y                       401

<210> SEQ ID NO 76
<211> LENGTH: 20
<212> TYPE: DNA
<213> ORGANISM: Glycine max

<400> SEQUENCE: 76
cgtgcgccct atcagtctat                                                20

<210> SEQ ID NO 77
<211> LENGTH: 20
<212> TYPE: DNA
<213> ORGANISM: Glycine max

<400> SEQUENCE: 77
gagttgttgc ttgcattgga                                                20

<210> SEQ ID NO 78
<211> LENGTH: 13
<212> TYPE: DNA
<213> ORGANISM: Artificial Sequence
<220> FEATURE:
<223> OTHER INFORMATION: S13136-1 Probe1

<400> SEQUENCE: 78
accaccatgt cgc                                                       13

<210> SEQ ID NO 79
<211> LENGTH: 13
<212> TYPE: DNA
<213> ORGANISM: Artificial Sequence
<220> FEATURE:
<223> OTHER INFORMATION: S13136-1 Probe2

<400> SEQUENCE: 79
accaccacgt cgc                                                       13

<210> SEQ ID NO 80
<211> LENGTH: 401
<212> TYPE: DNA
<213> ORGANISM: Glycine max

<400> SEQUENCE: 80
ttaactttgg tggatttta atttttaa tttgcttttc aaattccaat ttgtgatatt       60
ccaatttgta tgtgtgaggt tgcttgtgtt tgattgtgtt gaattgagtt gtygcttgca    120
ttggatgcag ttgataggat ggtgaagtgt gagaagtgga ttcgggatga tgaakatcac    180
ttggaggggt ctaaggcgac rtggtggttg aatagactga tagggcgcac gaagaaagta    240
actgttgact ggccattccc gttttctgag gggaagcttt tgttcttac tgttagtgct     300 gggctggagg ggtatcrtgt ttctgttgat gggaggcatg tgacctcttt tccttatggc    360
actgtaagtk atatatatct ttctcctcga agttgctaac c                        401

<210> SEQ ID NO 81
<211> LENGTH: 29
```

<212> TYPE: DNA
<213> ORGANISM: Glycine max

<400> SEQUENCE: 81
agggcaatag tttgaagatt tgggatgaa                                    29

<210> SEQ ID NO 82
<211> LENGTH: 46
<212> TYPE: DNA
<213> ORGANISM: Artificial Sequence
<220> FEATURE:
<223> OTHER INFORMATION: S17291-001 Probe1

<400> SEQUENCE: 82
gaaggtgacc aagttcatgc ttttcctttt gctattttg actcgg                  46

<210> SEQ ID NO 83
<211> LENGTH: 50
<212> TYPE: DNA
<213> ORGANISM: Artificial Sequence
<220> FEATURE:
<223> OTHER INFORMATION: S17291-001 Probe2

<400> SEQUENCE: 83
gaaggtcgga gtcaacggat taacttttcc ttttgctatt tttgactcga             50

<210> SEQ ID NO 84
<211> LENGTH: 401
<212> TYPE: DNA
<213> ORGANISM: Glycine max

<400> SEQUENCE: 84 aagacccta tgcacaccta gcaacctaca ttgagattgt aatacaacca agatttccgg    60
tgtgccagag gatgcaatta ggttgagttt gttttcattt tcactgtctg gagaagctaa  120
gagatggcta ctctcattta agggcaatag tttgaagatt tgggatgaag ttattgaaaa  180
attcttgaag aaatattttc ycgagtcaaa aatagcaaaa ggaaaagttg tcatctcttt  240
ttttcaccaa ttcctagatg aatccttgag tgaagttcta gaaagattcc gtagcttgct  300
acgaaaaact ctgactcatg gattcccaga gccgattcaa cttaatatct ttattgatgg  360
gttaaggtca yagtcaaagc agtttcttga tgcttctgct t                      401

<210> SEQ ID NO 85
<211> LENGTH: 20
<212> TYPE: DNA
<213> ORGANISM: Glycine max

<400> SEQUENCE: 85
aatctttccc cgtttcttgg                                              20

<210> SEQ ID NO 86
<211> LENGTH: 21
<212> TYPE: DNA
<213> ORGANISM: Glycine max

<400> SEQUENCE: 86
ttgcagaggc aaatagagct t                                            21

<210> SEQ ID NO 87
<211> LENGTH: 14
<212> TYPE: DNA
<213> ORGANISM: Artificial Sequence
<220> FEATURE:

```
<223> OTHER INFORMATION: S13139-1 Probe1

<400> SEQUENCE: 87
agatcccatt catg                                                           14

<210> SEQ ID NO 88
<211> LENGTH: 19
<212> TYPE: DNA
<213> ORGANISM: Artificial Sequence
<220> FEATURE:
<223> OTHER INFORMATION: S13139-1 Probe2

<400> SEQUENCE: 88
tatatagatc ccgttcatg                                                      19

<210> SEQ ID NO 89
<211> LENGTH: 401
<212> TYPE: DNA
<213> ORGANISM: Glycine max

<400> SEQUENCE: 89
gctgaatgat atgattctaa taactgtggt ttagactttta cactttgttc tatttccatt         60
tactattgtt tttttgttca atcagttcc gaattagtgg atgctgtcaa aggtagtggt          120
gatgccatac acaaaaagga agagactcat agaatkgcag aggcaaatag agcttttgca         180
cattttcatt aattcatgaa ygggatctat atagacagac ccatatagag agtattttga         240
aaattgtaat ctgacaatta atctattacc ctattacttc caagaaacgg ggaaagattt         300
gccttgtttg gtacttacac cataaatatc ttttttaggaa aaattctgct ttggttcttt       360
tacatctgag aagtggatat ttgtgttttt tgacaatatt t                             401

<210> SEQ ID NO 90
<211> LENGTH: 30
<212> TYPE: DNA
<213> ORGANISM: Glycine max

<400> SEQUENCE: 90
crggacacat ttttagctta cgtagttaaa                                          30

<210> SEQ ID NO 91
<211> LENGTH: 52
<212> TYPE: DNA
<213> ORGANISM: Artificial Sequence
<220> FEATURE:
<223> OTHER INFORMATION: S17292-001 Probe1

<400> SEQUENCE: 91
gaaggtgacc aagttcatgc tcaatgtaat catttaagta cattatccca ca                 52

<210> SEQ ID NO 92
<211> LENGTH: 51
<212> TYPE: DNA
<213> ORGANISM: Artificial Sequence
<220> FEATURE:
<223> OTHER INFORMATION: S17292-001 Probe2

<400> SEQUENCE: 92
gaaggtcgga gtcaacggat taatgtaatc atttaagtac attatcccac g                  51

<210> SEQ ID NO 93
<211> LENGTH: 401
<212> TYPE: DNA
<213> ORGANISM: Glycine max
```

<400> SEQUENCE: 93

```
tataaattt cttgtatcat gttcaattct tattgataaa aaaaaatacc tctcatctct    60
atttaccata bccaagttga agtawggggc tgtgctaaat cttatttmta gagaatcaag   120
tatgtattaa ttgaatcaac tatccatcaa taatttctta ccgtctttaa caatgtaatc   180
atttaagtac attatcccac rttctttatt caaatcattt cattcttttt cacataacta   240
cttaattatc ctatttaact acgtaagcta aaaatgtgtc cygtcaaata atcattttca   300
ttattatggt tattggttaa gacaccgaca caacacaggg tttaaatcta gttatgcaaa   360
aaataaaaat attattattg cttcactctt aaactgactt c                      401
```

<210> SEQ ID NO 94
<211> LENGTH: 20
<212> TYPE: DNA
<213> ORGANISM: Glycine max

<400> SEQUENCE: 94

```
gtcatcatag ccgcaatcaa                                               20
```

<210> SEQ ID NO 95
<211> LENGTH: 22
<212> TYPE: DNA
<213> ORGANISM: Glycine max

<400> SEQUENCE: 95

```
tccaaatctt tgttgagtcg tg                                            22
```

<210> SEQ ID NO 96
<211> LENGTH: 17
<212> TYPE: DNA
<213> ORGANISM: Artificial Sequence
<220> FEATURE:
<223> OTHER INFORMATION: S13146-1 Probe1

<400> SEQUENCE: 96

```
aagttcatca aagccat                                                  17
```

<210> SEQ ID NO 97
<211> LENGTH: 16
<212> TYPE: DNA
<213> ORGANISM: Artificial Sequence
<220> FEATURE:
<223> OTHER INFORMATION: S13146-1 Probe2

<400> SEQUENCE: 97

```
aagttcatcg aagcca                                                   16
```

<210> SEQ ID NO 98
<211> LENGTH: 401
<212> TYPE: DNA
<213> ORGANISM: Glycine max

<400> SEQUENCE: 98

```
tgctgctagt tatgttaaat aggtgattag gaagtatttg gagaaaaagg actcaaaaat    60
aggccaaaaa ytgatgaagt tggactctaa ctattcatca tggctatgat gagtcatcat   120
agccgcaatc aaacataggc atcatcaaag tcgtgatcct ttaatcatag cccaatgaca   180
gaaaagttat gaagttcatc raagccatga tcttttgatc acgactcaac aaagatttgg   240
atttgaagga tcatcatgam tttgatgaat ccatcctagc cgtgatgagg acacgttggc   300
```

```
agtcacgtaa catatttata taaatagcct tttttagacc ctaggtttct agtcttttat    360
tcttttkcag ttttgagaag ttctgggagg caagagtgct a                       401
```

<210> SEQ ID NO 99
<211> LENGTH: 30
<212> TYPE: DNA
<213> ORGANISM: Glycine max

<400> SEQUENCE: 99

```
gcctaaagac caacaatttg taagagtaaa                                     30
```

<210> SEQ ID NO 100
<211> LENGTH: 49
<212> TYPE: DNA
<213> ORGANISM: Artificial Sequence
<220> FEATURE:
<223> OTHER INFORMATION: S17293-001 Probe1

<400> SEQUENCE: 100

```
gaaggtgacc aagttcatgc tgtgttttaa ctcactcagt ttcgaatgt                49
```

<210> SEQ ID NO 101
<211> LENGTH: 47
<212> TYPE: DNA
<213> ORGANISM: Artificial Sequence
<220> FEATURE:
<223> OTHER INFORMATION: S17293-001 Probe2

<400> SEQUENCE: 101

```
gaaggtcgga gtcaacggat tgttttaact cactcagttt cgaatgc                  47
```

<210> SEQ ID NO 102
<211> LENGTH: 401
<212> TYPE: DNA
<213> ORGANISM: Glycine max

<400> SEQUENCE: 102

```
tagaaaacac atgaccaaat aaaaccatta accctaattc ctaaacaata tctctaatat    60
ataaagacca acgatttata aaagtaaaaa taacattcaa aattaggtga ataaaaacaa   120
tttaatataa aatttaaatt attaaacctt aaacaatatc tctaaagcct aaagaccaac   180
aatttgtaag agtaaaaaca rcattcgaaa ctgagtgagt taaaacacat gaacaaataa   240
aaccaattta atataaaatt taaatgatta aaacctaaac cctaaatctt aaaacttaat   300
cttagcataa aatcacttaa atcaattatt aaaatctaac cctaactccc taaaaaacgt   360
gtttgatgat tgggtgaagc cacccaattt ggcgccacca a                       401
```

<210> SEQ ID NO 103
<211> LENGTH: 27
<212> TYPE: DNA
<213> ORGANISM: Glycine max

<400> SEQUENCE: 103

```
cacacaggag acaaatcayg tcgataa                                        27
```

<210> SEQ ID NO 104
<211> LENGTH: 53
<212> TYPE: DNA
<213> ORGANISM: Artificial Sequence
<220> FEATURE:
<223> OTHER INFORMATION: S17294-001 Probe1

<400> SEQUENCE: 104

-continued

```
gaaggtgacc aagttcatgc tagaaagtaa ggaaaatttc taattttcat tgc        53
```

<210> SEQ ID NO 105
<211> LENGTH: 54
<212> TYPE: DNA
<213> ORGANISM: Artificial Sequence
<220> FEATURE:
<223> OTHER INFORMATION: S17294-001 Probe2

<400> SEQUENCE: 105

```
gaaggtcgga gtcaacggat tgagaaagta aggaaaattt ctaattttca ttgt        54
```

<210> SEQ ID NO 106
<211> LENGTH: 401
<212> TYPE: DNA
<213> ORGANISM: Glycine max
<220> FEATURE:
<221> NAME/KEY: misc_feature
<222> LOCATION: (279)..(279)
<223> OTHER INFORMATION: n is a, c, g, or t

<400> SEQUENCE: 106

```
aaaaataaaa cataaaaaag gatatataat aagttgaaaa gttaataaga taaaaaaata        60
aacacacttg ctaaagttaa atcaacaaca cataataata ataataataa taataataay      120
aataataata ataataaaat aaattaatta attaattaaa tacaaaaaga gaaagtaagg      180
aaaatttcta atttttcattg yattatcgac rtgatttgtc tcytgtgtga atctcagcat     240
taaagttgat agagtatttt caattacaat aaataaaana attcagagta taattttgwtt    300
tcacccataa atataaaarag aaataactaa aatacacaga aratcagaaa tatattatgt    360
aaataaaaat gcadgaagca atcavcaaga taaaaatara a                          401
```

<210> SEQ ID NO 107
<211> LENGTH: 21
<212> TYPE: DNA
<213> ORGANISM: Glycine max

<400> SEQUENCE: 107

```
acgaatgcaa aattggaaat g                                             21
```

<210> SEQ ID NO 108
<211> LENGTH: 19
<212> TYPE: DNA
<213> ORGANISM: Glycine max

<400> SEQUENCE: 108

```
tcttccttcg tccgtgtca                                                19
```

<210> SEQ ID NO 109
<211> LENGTH: 17
<212> TYPE: DNA
<213> ORGANISM: Artificial Sequence
<220> FEATURE:
<223> OTHER INFORMATION: S17581-001 Probe1

<400> SEQUENCE: 109

```
ttgaggacgt gtagttg                                                  17
```

<210> SEQ ID NO 110
<211> LENGTH: 18
<212> TYPE: DNA
<213> ORGANISM: Artificial Sequence
<220> FEATURE:

<223> OTHER INFORMATION: S17581-001 Probe2

<400> SEQUENCE: 110
ttgaggacgt gtagctgt                                                     18

<210> SEQ ID NO 111
<211> LENGTH: 401
<212> TYPE: DNA
<213> ORGANISM: Glycine max

<400> SEQUENCE: 111
aacaaacaaa tacaaatcct atttaaaaac attttttaaa acataaataa caaattttgc       60
aaaaaaaaaa ttaaaaacgt tcatacakag gaagttacac ttacggatga acttcaccag      120
tacraatgca aaattggaaa tgcgcaaatg ccattaacgg agacgtgaag cttacctcga      180
cgrtggaaga ccaaakcaca rctacacgtc ctcaatgcct atggtgaatc accctatgtg      240
acacggacga aggaagaaga agctcgatcg gygaygagag gagaagaagr aggaggtcga      300
aggcgctgcg gaaggaagaa ggaagygtat gaaaataagc tggtgcgcga sttttaaatt      360
ttaagtgaag ggaattttcg cccattcact taaaatgttg g                          401

<210> SEQ ID NO 112
<211> LENGTH: 23
<212> TYPE: DNA
<213> ORGANISM: Glycine max

<400> SEQUENCE: 112
cctcttttcc ttggctatgt gat                                              23

<210> SEQ ID NO 113
<211> LENGTH: 24
<212> TYPE: DNA
<213> ORGANISM: Glycine max

<400> SEQUENCE: 113
caatcttaac atggttccaa aaca                                             24

<210> SEQ ID NO 114
<211> LENGTH: 18
<212> TYPE: DNA
<213> ORGANISM: Artificial Sequence
<220> FEATURE:
<223> OTHER INFORMATION: S17691-001 Probe

<400> SEQUENCE: 114
cttctcatca ttgtggac                                                    18

<210> SEQ ID NO 115
<211> LENGTH: 401
<212> TYPE: DNA
<213> ORGANISM: Glycine max

<400> SEQUENCE: 115
tacattggtt tagacatttg tgactctagc tatgatcatt gtgtgattga tttgtacaca       60
agttgaatag ttagcatgat cttccttgct agtgatttca ctgacattag tcatgcatat      120
ttgtgaagat ttgagcttga acaataaggt tttattacac tatatatcta tgcctctttt      180
ccttggctat gtgattaagc ttctcatcat tgtggactct agaatttgtt ttggaaccat      240
gttaagattt tgtactagtt tgcattaatg aagatgatca aggcacatag gaaaattctt      300
tctggccctt gaattagttg agagytgttg ccccttatta gccaaatttg agcctaacac      360

```
tcttgttatt tggtaccttt gcatttgttg aaatattata t                    401
```

<210> SEQ ID NO 116
<211> LENGTH: 23
<212> TYPE: DNA
<213> ORGANISM: Glycine max

<400> SEQUENCE: 116

```
gaccctattc atctcttcca aca                                         23
```

<210> SEQ ID NO 117
<211> LENGTH: 24
<212> TYPE: DNA
<213> ORGANISM: Glycine max

<400> SEQUENCE: 117

```
gatgtcctaa agttagaggc ttcg                                        24
```

<210> SEQ ID NO 118
<211> LENGTH: 16
<212> TYPE: DNA
<213> ORGANISM: Artificial Sequence
<220> FEATURE:
<223> OTHER INFORMATION: S17701-001 Probe1

<400> SEQUENCE: 118

```
tggatttcct cttctt                                                 16
```

<210> SEQ ID NO 119
<211> LENGTH: 15
<212> TYPE: DNA
<213> ORGANISM: Artificial Sequence
<220> FEATURE:
<223> OTHER INFORMATION: S17701-001 Probe2

<400> SEQUENCE: 119

```
atggtggatt tcgtc                                                  15
```

<210> SEQ ID NO 120
<211> LENGTH: 401
<212> TYPE: DNA
<213> ORGANISM: Glycine max

<400> SEQUENCE: 120

```
gccttcactt ccatttcaca aatacacaaa aaaaaaaaaa aatgctagta gtgwaaacac  60
tcaaaacact caaattaagc cctttcaacc tttcttcttt atgagtttac aatctcaaag  120
cccatcaaag ttcacgaccc tattcatctc ttccaacatg agcaacccttt cagatgaaag  180
ggagcagtgt caaaagaaga sgaaatccac catatgcgaa gcctctaact ttaggacatc  240
aaggagaaga ttctgcagca acaacaaaaa tgaagaggag atgaacaata agggagtttc  300
aacaacactg aagctttacg atgatccttg gaagatcaag aagacgctaa ccgatagcga  360
tttgggaatc ctaagtagac tcttgctggc tgcagatttg g                      401
```

<210> SEQ ID NO 121
<211> LENGTH: 21
<212> TYPE: DNA
<213> ORGANISM: Glycine max

<400> SEQUENCE: 121

```
cccaaggact aaccaggatt c                                           21
```

<210> SEQ ID NO 122
<211> LENGTH: 26
<212> TYPE: DNA
<213> ORGANISM: Glycine max

<400> SEQUENCE: 122
tttattaaat ggagtgagaa ggtgtc    26

<210> SEQ ID NO 123
<211> LENGTH: 15
<212> TYPE: DNA
<213> ORGANISM: Artificial Sequence
<220> FEATURE:
<223> OTHER INFORMATION: S03703-1 Probe1

<400> SEQUENCE: 123
acacaagtcg ctacc    15

<210> SEQ ID NO 124
<211> LENGTH: 14
<212> TYPE: DNA
<213> ORGANISM: Artificial Sequence
<220> FEATURE:
<223> OTHER INFORMATION: S03703-1 Probe2

<400> SEQUENCE: 124
cacaagccgc tacc    14

<210> SEQ ID NO 125
<211> LENGTH: 401
<212> TYPE: DNA
<213> ORGANISM: Glycine max

<400> SEQUENCE: 125
gttggaggat cataaaccac ttttttttgc taacaatggt attggtacaa agaagccctg    60
ccmgaagcgg tgactaatct tcgtcraaga ctatgagcat acaakagatg agtgtacgta   120
ttcccctccc aacrtgattt attcataccc aaggactaac caggattcaa acyatgaatc   180
atttgattaa gcgacamaag ycgctaccac ttgtgtcaac cgttgttrgt atcataaacc   240
acatttataa gcttaattag acaccttctc actccattta ataaattatt ttgaatatta   300 cttttttatta atatgttggt gtgaaaataa gtcaattggt cagtcgtgtc atcttattac   360
caacaagtga tttcctttag gcgactaact caagaaagaa a   401

<210> SEQ ID NO 126
<211> LENGTH: 30
<212> TYPE: DNA
<213> ORGANISM: Glycine max

<400> SEQUENCE: 126
gtaagaaagt ttttttgtgt gtaaactgat    30

<210> SEQ ID NO 127
<211> LENGTH: 54
<212> TYPE: DNA
<213> ORGANISM: Artificial Sequence
<220> FEATURE:
<223> OTHER INFORMATION: S17297-001 Probe1

<400> SEQUENCE: 127
gaaggtgacc aagttcatgc tcacaacact atttaattta tttctgaaaa gcaa    54

```
<210> SEQ ID NO 128
<211> LENGTH: 54
<212> TYPE: DNA
<213> ORGANISM: Artificial Sequence
<220> FEATURE:
<223> OTHER INFORMATION: S17297-001 Probe2

<400> SEQUENCE: 128
gaaggtcgga gtcaacggat tcacaacact atttaattta tttctgaaaa gcat         54

<210> SEQ ID NO 129
<211> LENGTH: 401
<212> TYPE: DNA
<213> ORGANISM: Glycine max

<400> SEQUENCE: 129
akagtaccaa accatttttt tatactttca aatgtttctt aatgctyaaa tatattaatt   60
caacaaaata aaaataatt attawtaagt aataatttta caacatatt taatttatta    120 ttatacagat ataacatata caabtraaaa gaaataaatt aataatttca caacactatt  180
taatttattt ctgaaaagca wtaaacaaca ttttcacaac aatatttaat ttataatatt  240
aaacatatca gtttacacac aaaaaaactt tcttacatat gtatttgata gttacaatat 300 aatattttt ttctaaaaaa aacttacttt attattagtt gtatttgcta aacaaatatt  360
tgaatcacgt aactaaaaag aaaagaattt gtatctgtcg c                      401

<210> SEQ ID NO 130
<211> LENGTH: 24
<212> TYPE: DNA
<213> ORGANISM: Glycine max

<400> SEQUENCE: 130
ctcgcgcttg aaggcatcaa tctt                                          24

<210> SEQ ID NO 131
<211> LENGTH: 44
<212> TYPE: DNA
<213> ORGANISM: Artificial Sequence
<220> FEATURE:
<223> OTHER INFORMATION: S17298-001 Probe1

<400> SEQUENCE: 131
gaaggtgacc aagttcatgc tctcgcttag aggaagaacg tgta                    44

<210> SEQ ID NO 132
<211> LENGTH: 44
<212> TYPE: DNA
<213> ORGANISM: Artificial Sequence
<220> FEATURE:
<223> OTHER INFORMATION: S17298-001 Probe2

<400> SEQUENCE: 132
gaaggtcgga gtcaacggat tctcgcttag aggaagaacg tgtc                    44

<210> SEQ ID NO 133
<211> LENGTH: 401
<212> TYPE: DNA
<213> ORGANISM: Glycine max

<400> SEQUENCE: 133
agttcttgtt gctatatatt cgttatcctt aattaaccac atacgtgaaa tttaaagatg   60
ccatcacaag cagagctaag catgatggat tacaagccct acagctactc hacactgctg  120
```

```
aaatcatttt tagatcaaac tgaaactgat cagacctaca agcttgaaga gttcctctct    180
cgcttagagg aagaacgtgt maagattgat gccttcaagc gcgagcttcc tctctgcatg    240
caactcctca ccaacggtac aagtttcaat caatcatcat catggtttca ccaaagaaac    300
atatcaaacg tagttgatga tattccaaat tccaatgaac caattaaaac atggaatgtc    360
ctaaacccta aagtttcatc atacccccat gatgaaaata t                       401
```

```
<210> SEQ ID NO 134
<211> LENGTH: 29
<212> TYPE: DNA
<213> ORGANISM: Glycine max

<400> SEQUENCE: 134 ggcctttac atcggttcta atgactttt                                      29
```

```
<210> SEQ ID NO 135
<211> LENGTH: 42
<212> TYPE: DNA
<213> ORGANISM: Artificial Sequence
<220> FEATURE:
<223> OTHER INFORMATION: S17299-001 Probe1

<400> SEQUENCE: 135
gaaggtgacc aagttcatgc tgactaccac cacgcgtcat ag                      42
```

```
<210> SEQ ID NO 136
<211> LENGTH: 43
<212> TYPE: DNA
<213> ORGANISM: Artificial Sequence
<220> FEATURE:
<223> OTHER INFORMATION: S17299-001 Probe2

<400> SEQUENCE: 136
gaaggtcgga gtcaacggat tggactacca ccacgcgtca taa                     43
```

```
<210> SEQ ID NO 137
<211> LENGTH: 401
<212> TYPE: DNA
<213> ORGANISM: Glycine max

<400> SEQUENCE: 137
cactataaca aaattgactt gtttttttt taaataacaa aactgactta tactaagtag     60
gttatatttt gcttataaar agaagtagct tatattttaa tctttcaaca cataaaacat   120
tgtcaataaa tagtagaggt grcttacact actaaaaaaa aaggcctttt acatcggttc   180
taatgacttt tctacatcaa ytatgacgcg tggtggtagt ccaatgttgt cvaataacga   240
catcggttga aggaccgtct ttgaagaaca ttgrtacgaa gacgagcatg gtaccaaact   300
cttcttagaa tgggaattgt tctatatcgg ttgtgtaggt acaacaaatg tagaatgtta   360
gttttctaca tcggttctka gggtgaaacc gatgtagaat g                      401
```

```
<210> SEQ ID NO 138
<211> LENGTH: 28
<212> TYPE: DNA
<213> ORGANISM: Glycine max

<400> SEQUENCE: 138
ttgtgaagga cactcaacta ttccacta                                      28
```

```
<210> SEQ ID NO 139
<211> LENGTH: 50
```

```
<212> TYPE: DNA
<213> ORGANISM: Artificial Sequence
<220> FEATURE:
<223> OTHER INFORMATION: S17300-001 Probe1

<400> SEQUENCE: 139
gaaggtgacc aagttcatgc tcatataagt agagatgtca aattttcgac          50

<210> SEQ ID NO 140
<211> LENGTH: 53
<212> TYPE: DNA
<213> ORGANISM: Artificial Sequence
<220> FEATURE:
<223> OTHER INFORMATION: S17300-001 Probe2

<400> SEQUENCE: 140
gaaggtcgga gtcaacggat taatcatata agtagagatg tcaaattttc gat       53

<210> SEQ ID NO 141
<211> LENGTH: 401
<212> TYPE: DNA
<213> ORGANISM: Glycine max

<400> SEQUENCE: 141
gtcggatgct cttattttac tcttattatt ttccagtatt tcgtttctgg ctatccatat   60
caaggagatg ctaaatttta gaagaataga tattgatatt attagtaatt atactggatg  120
gttatttggc tgatgaaata gtcggatacc ccctccttga ttaaaaaata atcatataag  180
tagagatgtc aaattttcga ytagtggaat agttgagtgt ccttcacaac ccactaaaag  240
acaatctcag acatctagcc accagagtgt ctgaatactt cctagaacat aaatgtcaga  300
yggcaagaca aatatagacc ttgacctttt ggttggtcgg atgcccggat atgcatttgg  360
ccacccgaat aatcaaatac tcaataaaga gtaaactcga c                     401

<210> SEQ ID NO 142
<211> LENGTH: 25
<212> TYPE: DNA
<213> ORGANISM: Glycine max

<400> SEQUENCE: 142
ccctatcacc tgtcatatac ccctt                                       25

<210> SEQ ID NO 143
<211> LENGTH: 51
<212> TYPE: DNA
<213> ORGANISM: Artificial Sequence
<220> FEATURE:
<223> OTHER INFORMATION: S17301-001 Probe1

<400> SEQUENCE: 143
gaaggtgacc aagttcatgc tatactttat cctgagtatt tctcatgatc t          51

<210> SEQ ID NO 144
<211> LENGTH: 51
<212> TYPE: DNA
<213> ORGANISM: Artificial Sequence
<220> FEATURE:
<223> OTHER INFORMATION: S17301-001 Probe2

<400> SEQUENCE: 144
gaaggtgacc aagttcatgc tatactttat cctgagtatt tctcatgatc t          51

<210> SEQ ID NO 145
```

```
<211> LENGTH: 401
<212> TYPE: DNA
<213> ORGANISM: Glycine max

<400> SEQUENCE: 145
aatagtatgc tattcaaaag taggttatcg aaatgtgttt gaatgactca tgttcgcaag      60
gaaaatatca gtacaaaaga cctcaatttta ccatacaatt tgataagggg aacaacttay    120
agaaaacatt atcggacaag aaaatttgga ttagtaaaga ataaccctat cacctgtcat    180
ataccccttt atagatagca rgatcatgag aaatactcrg gataaagtat agtctaagga    240
aacaacttta tctcttagct tggcaatatc taactattta actatgctat ttgtaactaa    300
attgtgccct aacgratctc aaggtcttga catttctctc aacaatgtyg tctcgaacta    360
atccatacat agccttaaac tactcaccat ttraggtgtc t                        401

<210> SEQ ID NO 146
<211> LENGTH: 25
<212> TYPE: DNA
<213> ORGANISM: Glycine max

<400> SEQUENCE: 146
ccctcatcct tctccatggg atttt                                           25

<210> SEQ ID NO 147
<211> LENGTH: 53
<212> TYPE: DNA
<213> ORGANISM: Artificial Sequence
<220> FEATURE:
<223> OTHER INFORMATION: S17306-001 Probe1

<400> SEQUENCE: 147
gaaggtgacc aagttcatgc tatttttaag aaacatgttt ttaggaaact ata            53

<210> SEQ ID NO 148
<211> LENGTH: 53
<212> TYPE: DNA
<213> ORGANISM: Artificial Sequence
<220> FEATURE:
<223> OTHER INFORMATION: S17306-001 Probe2

<400> SEQUENCE: 148
gaaggtgacc aagttcatgc tatttttaag aaacatgttt ttaggaaact ata            53

<210> SEQ ID NO 149
<211> LENGTH: 401
<212> TYPE: DNA
<213> ORGANISM: Glycine max

<400> SEQUENCE: 149
ggataaagaa aataaaaaca ttttttttc tttctttctc tttcttttca ttaaaggcta      60
tgtttgacaa ctagccggaa agctagctag aaattaatgt tttaagaaaa tgtaacttca    120
aacaaagtta ctaaaaaagt taaaacttaa ttttcatgt ttgatatgta ttttaagaa     180 acatgttttt aggaaactat raaactatga ttcttaggaa taattttaa ctcacattct    240 tgcaaaaaca aaaatccca tggagaagga tgagggtag aatcttactt tttaaagttt     300 aatttttgc ttcactataa taaaaacagg tgctactctt attaagttat tcaatgtggt    360 aaatttaaa gttattgata aaaatatcac gtaaattttt t                         401

<210> SEQ ID NO 150
<211> LENGTH: 29
```

<212> TYPE: DNA
<213> ORGANISM: Glycine max

<400> SEQUENCE: 150
tcattgatgg tgcctctttta ttgcactttt                               29

<210> SEQ ID NO 151
<211> LENGTH: 45
<212> TYPE: DNA
<213> ORGANISM: Artificial Sequence
<220> FEATURE:
<223> OTHER INFORMATION: S17310-001 Probe1

<400> SEQUENCE: 151
gaaggtgacc aagttcatgc tgaaaatacg caaggagctc tgttc              45

<210> SEQ ID NO 152
<211> LENGTH: 46
<212> TYPE: DNA
<213> ORGANISM: Artificial Sequence
<220> FEATURE:
<223> OTHER INFORMATION: S17310-001 Probe2

<400> SEQUENCE: 152
gaaggtcgga gtcaacggat tcgaaaatac gcaaggagct ctgtta             46

<210> SEQ ID NO 153
<211> LENGTH: 401
<212> TYPE: DNA
<213> ORGANISM: Glycine max

<400> SEQUENCE: 153
cgatgatcgc aaagtttggc tacgacaata gcttgagtga gggaaggtgg ttggaaggcc    60
agtacctcat ggcgcaattc tggtgtaagg ccggaaatgg agcaactcat caggaatgtt   120
ggagcaaggc ccacaatgcg attagccaag tgttcgaatt ccgtgaggta ttcattgatg   180
gtgcctcttt attgcacttt kaacagagct ccttgcgtat tttcgtagaa ggacgaggaa   240
aactgagact ctaaggccta aagcatagtt gaccatgaca tgaagaagcc gttgcgggac   300
atccatgggt accacgagaa cgttgggccc tccatgtaaa aggaggccac ggtcaagygt   360
tcatggttca agagacccta ataatcaaag aattgtgata t                      401

<210> SEQ ID NO 154
<211> LENGTH: 25
<212> TYPE: DNA
<213> ORGANISM: Glycine max

<400> SEQUENCE: 154
cgcaggagtc atggatcttg tcaat                                    25

<210> SEQ ID NO 155
<211> LENGTH: 47
<212> TYPE: DNA
<213> ORGANISM: Artificial Sequence
<220> FEATURE:
<223> OTHER INFORMATION: S17311-001 Probe1

<400> SEQUENCE: 155
gaaggtgacc aagttcatgc taagtatcct attacaacca tcaacgg            47

<210> SEQ ID NO 156
<211> LENGTH: 50
<212> TYPE: DNA

```
<213> ORGANISM: Artificial Sequence
<220> FEATURE:
<223> OTHER INFORMATION: S17311-001 Probe2

<400> SEQUENCE: 156
gaaggtcgga gtcaacggat tgataagtat cctattacaa ccatcaacga        50

<210> SEQ ID NO 157
<211> LENGTH: 401
<212> TYPE: DNA
<213> ORGANISM: Glycine max

<400> SEQUENCE: 157
aaaatttgaa ttcatcgtgg attggaaagt atctagggta ttcacaagac caaatggagt   60
cgtgaagtgc tcataatgac cttcgtkagt gtgaaaggaa attttgggaa tgttagattc   120
ccttatgcgg atctgatgaa atctagattt taaatcaagc ttcgagtaga cgcaggagtm   180
atggatcttg tcaatgagcc ycgttgatgg ttgtaatagg atacttatct aggacaagga   240
ccttattgag ggccctaaag tccacacata tcctttatga ttcatctttc ttcactaaga   300
tgatagggct cgaaaatgga ctaattgagt gacggatgat gtcctttgtg agaagctctt   360
gcacttgtcg cttaatctcg tccttgtgat ggtaagcatt t                      401

<210> SEQ ID NO 158
<211> LENGTH: 26
<212> TYPE: DNA
<213> ORGANISM: Glycine max

<400> SEQUENCE: 158
gaagaccaac gcgttctcta cttgtt                                       26

<210> SEQ ID NO 159
<211> LENGTH: 51
<212> TYPE: DNA
<213> ORGANISM: Artificial Sequence
<220> FEATURE:
<223> OTHER INFORMATION: S17312-001 Probe1

<400> SEQUENCE: 159
gaaggtgacc aagttcatgc taagaaagaa aatcacgcaa cataaatgtt g            51

<210> SEQ ID NO 160
<211> LENGTH: 54
<212> TYPE: DNA
<213> ORGANISM: Artificial Sequence
<220> FEATURE:
<223> OTHER INFORMATION: S17312-001 Probe2

<400> SEQUENCE: 160
gaaggtcgga gtcaacggat taaaagaaa gaaaatcacg caacataaat gttt          54

<210> SEQ ID NO 161
<211> LENGTH: 401
<212> TYPE: DNA
<213> ORGANISM: Glycine max

<400> SEQUENCE: 161
ttgtttgcag ycgacaagtg tactggatcg cacaagtagt ataaaacgat aagaaccaag   60
tatcaaactc ttggggaact tgtgttatct atcaagctat ttcgrtaaat aggtgtctgg   120
tatgaaaaga tgattgtggt tatgaacaag tatgtaaact atctatgcaa aaagaaagaa   180
aatcacgcaa cataaatgtt ktgtaaaaac aagtagagaa cgcgttggtc ttcctaatwg   240
```

```
gttcctgatg ctaaaacgga tgttctctat ctaacaatgc tcatgtattc ctatgttgtc      300
tcctggactg ttagacccccg attcctcatg atagcctagc gtaatcctga tcaagtctca     360
tccgcagatt cctcttgtaa gactaaactc attcaggacc g                          401
```

<210> SEQ ID NO 162
<211> LENGTH: 25
<212> TYPE: DNA
<213> ORGANISM: Glycine max

<400> SEQUENCE: 162

```
agtcctttga agaggaggac gtgta                                             25
```

<210> SEQ ID NO 163
<211> LENGTH: 41
<212> TYPE: DNA
<213> ORGANISM: Artificial Sequence
<220> FEATURE:
<223> OTHER INFORMATION: S17313-001 Probe1

<400> SEQUENCE: 163

```
gaaggtgacc aagttcatgc tggtacggcc tcgatcacac c                           41
```

<210> SEQ ID NO 164
<211> LENGTH: 41
<212> TYPE: DNA
<213> ORGANISM: Artificial Sequence
<220> FEATURE:
<223> OTHER INFORMATION: S17313-001 Probe2

<400> SEQUENCE: 164

```
gaaggtcgga gtcaacggat tggtacggcc tcgatcacac g                           41
```

<210> SEQ ID NO 165
<211> LENGTH: 401
<212> TYPE: DNA
<213> ORGANISM: Glycine max

<400> SEQUENCE: 165

```
aatattagta gtttygtatt ccatttatt tgttcttctc tttaattacc aaacaaccaa        60
cccccccccc cmycgttact gttactgcaa gtatattatg aacatttggc ttgtcactgc      120
tcgttgggaa acgacctagg atcacttcct agttactgca ttttcatgtt tatttgattc      180
gggtacggcc tcgatcacac sccctcgcct tcagaggact acacgtcctc ctcttcaaag      240
gactatacgt cctcttcttc agaggaccac acrtcctccc cttcagagga cttcacgtcc      300
ttgccatcag aggactacay gtcctcacct tcagagggat acacatcctc accttcatag      360
gattacacgt cctccccttc asagggctgc acgccctcgc c                          401
```

<210> SEQ ID NO 166
<211> LENGTH: 29
<212> TYPE: DNA
<213> ORGANISM: Glycine max

<400> SEQUENCE: 166

```
tcggatgttc gattgtgtcc cataatata                                         29
```

<210> SEQ ID NO 167
<211> LENGTH: 46
<212> TYPE: DNA
<213> ORGANISM: Artificial Sequence
<220> FEATURE:

<223> OTHER INFORMATION: S17316-001 Probe1

<400> SEQUENCE: 167
gaaggtgacc aagttcatgc taagagcttc cattttcgat tacgaa                46

<210> SEQ ID NO 168
<211> LENGTH: 46
<212> TYPE: DNA
<213> ORGANISM: Artificial Sequence
<220> FEATURE:
<223> OTHER INFORMATION: S17316-001 Probe2

<400> SEQUENCE: 168
gaaggtcgga gtcaacggat taagagcttc cattttcgat tacgag                46

<210> SEQ ID NO 169
<211> LENGTH: 401
<212> TYPE: DNA
<213> ORGANISM: Glycine max
<220> FEATURE:
<221> NAME/KEY: misc_feature
<222> LOCATION: (400)..(401)
<223> OTHER INFORMATION: n is a, c, g, or t

<400> SEQUENCE: 169
ttctrttttc aataacgagc gtctcgatat attacgvgac tcaatcggag atcygtgtaa     60
aaagttattg tcgtttgatt tttctcagag cttcagtttt caattccgag cgtctcgata    120
tactacggga cacaatcrga catccgastt aaaatttatt gtcgtttgat atttctaaga    180
gcttccattt tcgattacga rgattttgat atattayggg acacaatcga acatccgagt    240
aaaaagttat ttcgtttgat ttttctcaga gcttcagttt tcwatttcga gcgtctcgat    300
ataccacggg acacmatcar acatmckagt caaaagttat tgtcgttyra atttgctaag    360
agcttctgtt ttcaattacg agcrccagcc ccacgtcatn n                       401

<210> SEQ ID NO 170
<211> LENGTH: 29
<212> TYPE: DNA
<213> ORGANISM: Glycine max

<400> SEQUENCE: 170
gagttggtga actaattttc cctgttgat                                     29

<210> SEQ ID NO 171
<211> LENGTH: 45
<212> TYPE: DNA
<213> ORGANISM: Artificial Sequence
<220> FEATURE:
<223> OTHER INFORMATION: S17317-001 Probe1

<400> SEQUENCE: 171
gaaggtgacc aagttcatgc ttgagaaaat ccctcctcca tttta                   45

<210> SEQ ID NO 172
<211> LENGTH: 47
<212> TYPE: DNA
<213> ORGANISM: Artificial Sequence
<220> FEATURE:
<223> OTHER INFORMATION: S17317-001 Probe2

<400> SEQUENCE: 172
gaaggtcgga gtcaacggat tcttgagaaa atccctcctc cattttc                 47

<210> SEQ ID NO 173
<211> LENGTH: 401
<212> TYPE: DNA
<213> ORGANISM: Glycine max

<400> SEQUENCE: 173

```
tcaattattt cagcatgaaa tacaaaarga tcttcagatg ggtgtttcat agcatcaaga      60
atattaaaat gaacagttat atcaccaaac tccatagata gtgtgcctgc atatacatct    120
atcttagttc tagcagtttt cataaaaggt ctgcctagaa tgatgggaac tgatccttga    180
gaaaatccct cctccatttt maaaatataa aaatcaacag ggaaaattag ttcaccaact    240
ctaactaaga catcctctat gaaaccagca ggataggcaa cacttctatt agctaaatga    300
attaccacat cagttgrctg caaaggacca agagatagag aattaaaaat agacagaggc    360
ataacactaa cagaagctcc taaatcyagc atggcattgt c                       401
```

<210> SEQ ID NO 174
<211> LENGTH: 28
<212> TYPE: DNA
<213> ORGANISM: Glycine max

<400> SEQUENCE: 174

```
ccttgatgct ctatttcttt tctcccaa                                        28
```

<210> SEQ ID NO 175
<211> LENGTH: 46
<212> TYPE: DNA
<213> ORGANISM: Artificial Sequence
<220> FEATURE:
<223> OTHER INFORMATION: S17318-001 Probe1

<400> SEQUENCE: 175

```
gaaggtgacc aagttcatgc taacaggaag ggaaaacaaa gtgtcg                    46
```

<210> SEQ ID NO 176
<211> LENGTH: 47
<212> TYPE: DNA
<213> ORGANISM: Artificial Sequence
<220> FEATURE:
<223> OTHER INFORMATION: S17318-001 Probe2

<400> SEQUENCE: 176

```
gaaggtcgga gtcaacggat tgaacaggaa gggaaaacaa agtgtca                   47
```

<210> SEQ ID NO 177
<211> LENGTH: 401
<212> TYPE: DNA
<213> ORGANISM: Glycine max

<400> SEQUENCE: 177

```
aatcttaaat agatagttag agtttttaca tcaagagtgc tcagtggaaa aattctctaa     60
caatgaagtg tttagccctc cattagcarg gagggctcaa tacaaggttg aaacaagata    120
gaaattgagt ggtgaagtga atgtgtgaag aaagtagctt ccttcagcct tgatgctcta    180
tttcttttct cccaacctgc ygacactttg ttttcccttc ctgttctatt tttaatgact    240
tttgggattc tcggattatg aatgcgcact cagccagcat gtctcgctga gtgagagtta    300
gtgattaggc tcttagcgag ctttgacacg ctaagcgcga gaagcgacaa aggcttcgct    360
gggcgggctg gttgcgtgct tagcacgttg ctctctgaat t                       401
```

<210> SEQ ID NO 178

-continued

```
<211> LENGTH: 30
<212> TYPE: DNA
<213> ORGANISM: Glycine max

<400> SEQUENCE: 178
atgttgtttg tgtagattaa catcggcttt                              30

<210> SEQ ID NO 179
<211> LENGTH: 54
<212> TYPE: DNA
<213> ORGANISM: Artificial Sequence
<220> FEATURE:
<223> OTHER INFORMATION: S17322-001 Probe1

<400> SEQUENCE: 179
gaaggtgacc aagttcatgc tattttgggt ttttttttgt aaaaacagaa agtc   54

<210> SEQ ID NO 180
<211> LENGTH: 51
<212> TYPE: DNA
<213> ORGANISM: Artificial Sequence
<220> FEATURE:
<223> OTHER INFORMATION: S17322-001 Probe2

<400> SEQUENCE: 180
gaaggtcgga gtcaacggat tttgggtttt tttttgtaaa aacagaaagt g      51

<210> SEQ ID NO 181
<211> LENGTH: 401
<212> TYPE: DNA
<213> ORGANISM: Glycine max

<400> SEQUENCE: 181
ttgaatatta attattgata gttattaata aattatttat tcatagttat caattgattt   60
tttacaattg atagtttact agctagcttt ctgctaaaaa ctgtttgaaa gcaaaatgca  120
aatgctatat gctgtgttgt gtggtctgat ttgaaattta caggttaaat tttgggtttt  180
tttttgtaaa aacagaaagt statttaaaa aaaatcctaa taacaacatc gattttttta  240
taaaaaaaag ccgatgttaa tctacacaaa caacattggt tttttggaaa aatcgatgtt  300
aatatccaaa arcgttaaca tcgrtttctg tgaaaaaccg atgttaacat agaaaatgtt  360
aacatcggtt ttctatagtt cacatcggtt tttgactgaa a                     401

<210> SEQ ID NO 182
<211> LENGTH: 29
<212> TYPE: DNA
<213> ORGANISM: Glycine max

<400> SEQUENCE: 182
cacaacactg cttacagcaa attgcataa                                29

<210> SEQ ID NO 183
<211> LENGTH: 51
<212> TYPE: DNA
<213> ORGANISM: Artificial Sequence
<220> FEATURE:
<223> OTHER INFORMATION: S17326-001 Probe1

<400> SEQUENCE: 183
gaaggtgacc aagttcatgc taaaatagct gaaattgcat ttatggtgca a       51

<210> SEQ ID NO 184
<211> LENGTH: 48
```

```
<212> TYPE: DNA
<213> ORGANISM: Artificial Sequence
<220> FEATURE:
<223> OTHER INFORMATION: S17326-001 Probe2

<400> SEQUENCE: 184
gaaggtcgga gtcaacggat tatagctgaa attgcattta tggtgcac         48

<210> SEQ ID NO 185
<211> LENGTH: 401
<212> TYPE: DNA
<213> ORGANISM: Glycine max

<400> SEQUENCE: 185
gggcayggta acagctggt tagtgaacta gattcttgtt ctttcttttc aaagtgtttc    60
aagatatcct gaactaaygt aatttgatgc tccctgtaac tcccgtagtc ccgctgtatg  120
btgtgttgaa ttgcttgctc aggcagcttg aaggagcaca ttgctaaggt taaaatagct  180
gaaattgcat ttatggtgca mttatgcaat ttgctgtaag cagtgttgtg gtagtaatgt  240
tctaaatctt gaaagtgttg tttcctaggt ttatagcatc tatttaagga ctcatgagaa  300
atcccagttt attggaacat gtttgtctcg ctgacatcta tctgctgtag cattcaacta  360
gtctgtgttt tggtaactgt gtggacatgc cattcaatcc c                      401

<210> SEQ ID NO 186
<211> LENGTH: 30
<212> TYPE: DNA
<213> ORGANISM: Glycine max

<400> SEQUENCE: 186
gacctcatat gaaagaatat gtccaatctt                                    30

<210> SEQ ID NO 187
<211> LENGTH: 46
<212> TYPE: DNA
<213> ORGANISM: Artificial Sequence
<220> FEATURE:
<223> OTHER INFORMATION: S17327-001 Probe1

<400> SEQUENCE: 187
gaaggtgacc aagttcatgc taagtagcag ttaaagagga ctggtc                  46

<210> SEQ ID NO 188
<211> LENGTH: 48
<212> TYPE: DNA
<213> ORGANISM: Artificial Sequence
<220> FEATURE:
<223> OTHER INFORMATION: S17327-001 Probe2

<400> SEQUENCE: 188
gaaggtcgga gtcaacggat taaaagtagc agttaaagag gactggtt               48

<210> SEQ ID NO 189
<211> LENGTH: 401
<212> TYPE: DNA
<213> ORGANISM: Glycine max
<220> FEATURE:
<221> NAME/KEY: misc_feature
<222> LOCATION: (60)..(60)
<223> OTHER INFORMATION: n is a, c, g, or t

<400> SEQUENCE: 189
atagtggatg taactagagt ctaacagaga gactatggtg gttataggca gtcttcttcn  60
```

-continued

```
gccatgtaaa gataatacca gtctaattgc tccatagtga agatgagtgt atccttggtg      120
ttgctaactt ctgatcagtt gtttaggaat ctcaatatta acatattgct cctcaaaagt      180
agcagttaaa gaggactggt ycattcttaa agattggaca tattctttca tatgaggtct      240
tctagtggtg atcaagttgg taatagatct taaagagtaa cgatgtcttt taaatatatg      300
gtaagggctc aacaagggat ttagtgactg agagatttga gcatcttctg gaatatatga      360
atattctaca agattctcta tttttctgaa agagttttgg a                         401
```

<210> SEQ ID NO 190
<211> LENGTH: 29
<212> TYPE: DNA
<213> ORGANISM: Glycine max

<400> SEQUENCE: 190

```
ttctacaagg cgaaggacca ttttatcat                                        29
```

<210> SEQ ID NO 191
<211> LENGTH: 46
<212> TYPE: DNA
<213> ORGANISM: Artificial Sequence
<220> FEATURE:
<223> OTHER INFORMATION: S17328-001 Probe1

<400> SEQUENCE: 191

```
gaaggtgacc aagttcatgc tatccacctt gctttacaat gcatcc                     46
```

<210> SEQ ID NO 192
<211> LENGTH: 47
<212> TYPE: DNA
<213> ORGANISM: Artificial Sequence
<220> FEATURE:
<223> OTHER INFORMATION: S17328-001 Probe2

<400> SEQUENCE: 192

```
gaaggtcgga gtcaacggat tcatccacct tgctttacaa tgcatct                    47
```

<210> SEQ ID NO 193
<211> LENGTH: 401
<212> TYPE: DNA
<213> ORGANISM: Glycine max

<400> SEQUENCE: 193

```
rtctctacca agagattcag caagatccac gtgttttgga gtccatagat tcaatchcat      60
ttgttgaaac tcctttgcat gttgctgcat ctcttggtca ttttgagttt gctayraga       120 tcatgacact gaaaccttma cttgctgtga aactaaatcc agaaggcttc actcccatcm     180
accttgcttt acaatgcatc yatgataaaa tggtccttcr ccttgtagaa atgarcaaag      240
atctcgtccg agtcaaaggg agtgaaggct tcactccact gcattttgca agtcaacaaw     300
gtaaaactga gcttttkgat aagttcctca aggcttgtcc agattccatt gaggatgtga      360
ctaccagaag tgaraccgca ctacatattg cagtgaaaca t                         401
```

<210> SEQ ID NO 194
<211> LENGTH: 29
<212> TYPE: DNA
<213> ORGANISM: Glycine max

<400> SEQUENCE: 194

```
ctccaatcat ctttcttcct tctccatttt                                       29
```

```
<210> SEQ ID NO 195
<211> LENGTH: 45
<212> TYPE: DNA
<213> ORGANISM: Artificial Sequence
<220> FEATURE:
<223> OTHER INFORMATION: S17329-001 Probe1

<400> SEQUENCE: 195
gaaggtgacc aagttcatgc tcctttgctt cttgaagatc atggc              45

<210> SEQ ID NO 196
<211> LENGTH: 47
<212> TYPE: DNA
<213> ORGANISM: Artificial Sequence
<220> FEATURE:
<223> OTHER INFORMATION: S17329-001 Probe2

<400> SEQUENCE: 196
gaaggtcgga gtcaacggat tgtcctttgc ttcttgaaga tcatgga            47

<210> SEQ ID NO 197
<211> LENGTH: 401
<212> TYPE: DNA
<213> ORGANISM: Glycine max

<400> SEQUENCE: 197
atcatttgag aattatactt cmaagttcag acctcatttg aggcacaaaa tttcktgctc    60
cttctctccy tctccctcca ctcatcttcy ccttccttcr agctcttatc cayggcttcc   120
tgtggtggtg agcttyttct tgactcatct tctccttgaa gtggcrtctc caatcatctt   180
tcttccttct ccatttygct kccatgatct tcaagaagca aaggactcca ttgatgaaga   240
agatccaagg cctacaagct ccacatagag ctacatcact tagcaactct ccaatggtca   300
atacctggat tactctaata tcttcctaac attccaactr caaaagcaat gccagacctt   360
gtgcatactt gagcatacat aaggcttcca acaactaaag c                      401

<210> SEQ ID NO 198
<211> LENGTH: 20
<212> TYPE: DNA
<213> ORGANISM: Glycine max

<400> SEQUENCE: 198
attgggatcc tgatcaacca                                              20

<210> SEQ ID NO 199
<211> LENGTH: 20
<212> TYPE: DNA
<213> ORGANISM: Glycine max

<400> SEQUENCE: 199
cccaggcatt ggtgtttaag                                              20

<210> SEQ ID NO 200
<211> LENGTH: 16
<212> TYPE: DNA
<213> ORGANISM: Artificial Sequence
<220> FEATURE:
<223> OTHER INFORMATION: S10746-1 Probe1

<400> SEQUENCE: 200
caacaatgag cctaat                                                  16

<210> SEQ ID NO 201
```

```
<211> LENGTH: 15
<212> TYPE: DNA
<213> ORGANISM: Artificial Sequence
<220> FEATURE:
<223> OTHER INFORMATION: S10746-1 Probe2

<400> SEQUENCE: 201
caacaacgag cctaa                                                          15

<210> SEQ ID NO 202
<211> LENGTH: 401
<212> TYPE: DNA
<213> ORGANISM: Glycine max

<400> SEQUENCE: 202
tggttgattc gaagaacaat tdggttttga ttaaygtgat gaaggtgttt gctaagttgg          60
ctcccttgga acctaggttg gggaagattg ttgagcctgt ttgtgaccad atgaggcgct         120
ctggggccca ggcattggtg tttaagtgtg ttaggactgt gctcactagc ttgagtgatt         180
atcattytgc tattaggctc rttgttgaga aggctaggga tttgttggtt gatcaggatc         240
ccaatcttag atatcttggt ctgtaggcgc ttttggttgc cactcataag cacttgtggg         300
tggtgataga gaatakggaa gtggtggtta agtcgttgag tgatgatgat ttgactatca         360
agatcytgty agtrcgattk ttgatgggca tatatggtgt c                             401

<210> SEQ ID NO 203
<211> LENGTH: 25
<212> TYPE: DNA
<213> ORGANISM: Glycine max

<400> SEQUENCE: 203
cggttgtctc tgstcttctc agatt                                               25

<210> SEQ ID NO 204
<211> LENGTH: 50
<212> TYPE: DNA
<213> ORGANISM: Artificial Sequence
<220> FEATURE:
<223> OTHER INFORMATION: S17331-001 Probe1

<400> SEQUENCE: 204
gaaggtgacc aagttcatgc tgggaaatga agacaattaa taacatcgtg                    50

<210> SEQ ID NO 205
<211> LENGTH: 50
<212> TYPE: DNA
<213> ORGANISM: Artificial Sequence
<220> FEATURE:
<223> OTHER INFORMATION: S17331-001 Probe2

<400> SEQUENCE: 205
gaaggtcgga gtcaacggat tgggaaatga agacaattaa taacatcgta                    50

<210> SEQ ID NO 206
<211> LENGTH: 401
<212> TYPE: DNA
<213> ORGANISM: Glycine max

<400> SEQUENCE: 206
ttcattggaa tggaatataa caaagtaatt agattagata agaaraatag ttggaaatga          60
gacgttagtg tggtgtgcga ggcgaggcca tgtgctccaa tgcggcggtt atttaaatat         120
gtcgtattgt ttagktacac acattaacgt caaagtttca aactatatgc ggttgtctcy         180
```

```
gstcttctca gattctctcc yacgatgtta ttaattgtct tcatttccca tctctattct    240
ctatttgatc acaccgttaa catgttccca ttccatctca ttgacaatac aaaataaatt    300
atttatgcac tgaaattaat atcttaacac acatttttat ttttttggta acgtcacaca    360
tttttatttc attgtaaatt atcaggtgta ataaatttaw t                        401
```

```
<210> SEQ ID NO 207
<211> LENGTH: 30
<212> TYPE: DNA
<213> ORGANISM: Glycine max

<400> SEQUENCE: 207
aaccttaccc taacaacata caactaagaa                                      30

<210> SEQ ID NO 208
<211> LENGTH: 49
<212> TYPE: DNA
<213> ORGANISM: Artificial Sequence
<220> FEATURE:
<223> OTHER INFORMATION: S17332-001 Probe1

<400> SEQUENCE: 208
gaaggtgacc aagttcatgc tcaaacctta ggatagatga cttcttgtt                 49

<210> SEQ ID NO 209
<211> LENGTH: 49
<212> TYPE: DNA
<213> ORGANISM: Artificial Sequence
<220> FEATURE:
<223> OTHER INFORMATION: S17332-001 Probe2

<400> SEQUENCE: 209
gaaggtcgga gtcaacggat tcaaaccttc ggatagatga cttcttgta                 49

<210> SEQ ID NO 210
<211> LENGTH: 401
<212> TYPE: DNA
<213> ORGANISM: Glycine max

<400> SEQUENCE: 210
tccaaaattt taayagttac gatgaacara ctaagcgcaa caggcgcgyt tagcacgttc     60
atcgctattt ccaaacaaaa ccacagggt yttcacccgt tttagccaca tggccctaa     120 tgggcttcta agttacctaa aatcctatat tgactaaccc taaaactaat aaccttaccc    180
taacaacata caactaagaa wacaagaagt catctatcct aaggtttgaa gaatgaaaaa    240
tggaaataga aaagtactca cttacttgga ttgttcttga aatgaagcaa agaagatgya    300
gacaagcagt acacacacag caaaaataca cacttgctya gggttcacaa atgtagaagc    360
tgaaggtatt tggggtaaca cccaagatcc ttagccttg t                         401

<210> SEQ ID NO 211
<211> LENGTH: 30
<212> TYPE: DNA
<213> ORGANISM: Glycine max

<400> SEQUENCE: 211
cctattgacc gtgatattaa ttaagacttt                                      30

<210> SEQ ID NO 212
<211> LENGTH: 53
<212> TYPE: DNA
```

<213> ORGANISM: Artificial Sequence
<220> FEATURE:
<223> OTHER INFORMATION: S17337-001 Probe1

<400> SEQUENCE: 212
gaaggtgacc aagttcatgc ttgattgata attttttta ttatgtacat gac        53

<210> SEQ ID NO 213
<211> LENGTH: 52
<212> TYPE: DNA
<213> ORGANISM: Artificial Sequence
<220> FEATURE:
<223> OTHER INFORMATION: S17337-001 Probe2

<400> SEQUENCE: 213
gaaggtcgga gtcaacggat tgattgataa tttttttat tatgtacatg at         52

<210> SEQ ID NO 214
<211> LENGTH: 401
<212> TYPE: DNA
<213> ORGANISM: Glycine max

<400> SEQUENCE: 214
tagtcttgtt attttttaat tgagacaatt tattyccaat tttaaaaagt ttataatttt    60
artctcctat tttttaaatt agacgtttcg tctttcactt ttaaaaaaat caataatttt   120 aatcttatg tccaatttca aacgttgatc tatacactttt tgtaaatgtt gattgataat   180 ttttttatt atgtacatga yaaatatttt ttttataatt atttaattgt tatcaagctt   240
aatttattaa agaattaaa aaaagtctta attaatatca cggtcaatag gttttaaatt   300
gatcaaggag attaaaatta taaatttttt tttaaaaata gaggacgaaa tgttacaatt   360
aaaaaaaata aggagactaa aattgtatat tttttwaaat g                       401

<210> SEQ ID NO 215
<211> LENGTH: 20
<212> TYPE: DNA
<213> ORGANISM: Glycine max

<400> SEQUENCE: 215
catcgagtct ccagcaagtg                                               20

<210> SEQ ID NO 216
<211> LENGTH: 21
<212> TYPE: DNA
<213> ORGANISM: Glycine max

<400> SEQUENCE: 216
tgagattcac gaagtgggtt c                                             21

<210> SEQ ID NO 217
<211> LENGTH: 15
<212> TYPE: DNA
<213> ORGANISM: Artificial Sequence
<220> FEATURE:
<223> OTHER INFORMATION: S13093-1 Probe1

<400> SEQUENCE: 217
attggcactt ttaac                                                    15

<210> SEQ ID NO 218
<211> LENGTH: 17
<212> TYPE: DNA
<213> ORGANISM: Artificial Sequence

```
<220> FEATURE:
<223> OTHER INFORMATION: S13093-1 Probe2

<400> SEQUENCE: 218
cacttctaac atcaatg                                                   17

<210> SEQ ID NO 219
<211> LENGTH: 401
<212> TYPE: DNA
<213> ORGANISM: Glycine max
<220> FEATURE:
<221> NAME/KEY: misc_feature
<222> LOCATION: (96)..(96)
<223> OTHER INFORMATION: n is a, c, g, or t

<400> SEQUENCE: 219
taaacacatg aatttttttt atcgacaaat attaatcatt aatttgttag taagaggatm     60
gaactgcgcs atatttttct tgttccgtta aattanacac atgaattaat atgaagggaa    120
aattaaacaa caacatgata catacctcag catgcacaac atgaagcatc gagtctccag    180
margtgagga attggcactt ytaacatcaa tgttctcttc atgcagcatt cgaatgatct    240
cagagaaaat gaactggtgg tctaatccac aagtaagaac aacttgtaaa gaagaaccca    300
cttcgtgaat ctcaagttgt ggcgattttg ggaaacctgc agaagttgca gcaaaattgg    360
tactattatt ggagaagcaa tcacgggatc tctttctaat t                        401

<210> SEQ ID NO 220
<211> LENGTH: 26
<212> TYPE: DNA
<213> ORGANISM: Glycine max

<400> SEQUENCE: 220
gaccagaggt agtagattcc aaaagt                                         26

<210> SEQ ID NO 221
<211> LENGTH: 28
<212> TYPE: DNA
<213> ORGANISM: Glycine max

<400> SEQUENCE: 221
tgcattaagc tcactcagtt atgtatta                                       28

<210> SEQ ID NO 222
<211> LENGTH: 15
<212> TYPE: DNA
<213> ORGANISM: Artificial Sequence
<220> FEATURE:
<223> OTHER INFORMATION: S12211-1 Probe1

<400> SEQUENCE: 222
ctgcaatgcc atact                                                     15

<210> SEQ ID NO 223
<211> LENGTH: 14
<212> TYPE: DNA
<213> ORGANISM: Artificial Sequence
<220> FEATURE:
<223> OTHER INFORMATION: S12211-1 Probe2

<400> SEQUENCE: 223
ctgcaacgcc atac                                                      14

<210> SEQ ID NO 224
```

<211> LENGTH: 401
<212> TYPE: DNA
<213> ORGANISM: Glycine max

<400> SEQUENCE: 224
tactagacac tcactcattg gattatgagt attggtatta aatgtgacca tcacttacaa      60
catttaaact tatgatagta ttaaatgtga ccaccacttt ccttggtctt gatgatttgt     120
cctatatttc ttatatatag gaccagaggt agtagattcc aaaagtttat gctaccacaa     180
tattacttgt aaagctgcaa ygccatacta aaccataata cataactgag tgagcttaat     240
gcaaattgct tgttcaccag aaataaatag aagattcagg cacgcggtac aacaggataa     300
tggagtcaaa acacaaaact aaagttattt atagactacc atgtattta ttaaatgacc     360 actaatttgt gatataggcc attaaaaaac aatttcatca a                         401

<210> SEQ ID NO 225
<211> LENGTH: 19
<212> TYPE: DNA
<213> ORGANISM: Glycine max

<400> SEQUENCE: 225
aaatcgccac taggcttgc                                                   19

<210> SEQ ID NO 226
<211> LENGTH: 21
<212> TYPE: DNA
<213> ORGANISM: Glycine max

<400> SEQUENCE: 226
ctagggttct gcagttcatc g                                                21

<210> SEQ ID NO 227
<211> LENGTH: 14
<212> TYPE: DNA
<213> ORGANISM: Artificial Sequence
<220> FEATURE:
<223> OTHER INFORMATION: S04555-1 Probe1

<400> SEQUENCE: 227
cagcactgga tctt                                                        14

<210> SEQ ID NO 228
<211> LENGTH: 13
<212> TYPE: DNA
<213> ORGANISM: Artificial Sequence
<220> FEATURE:
<223> OTHER INFORMATION: S04555-1 Probe2

<400> SEQUENCE: 228
cagcaccgga tct                                                         13

<210> SEQ ID NO 229
<211> LENGTH: 401
<212> TYPE: DNA
<213> ORGANISM: Glycine max

<400> SEQUENCE: 229
cttcaatggc atggccgtgg aaagaaacag agcttagatt ctctgttttt aattctccaa      60
cgaggaagct ccgattcgaa aattgcctcc gctagggttc tgcagttcat cgccgtggac     120
gcggatgcga agatytcaat cgycgagaag caaggcgtgg tggccgagtt gctgaaatcg     180
gccgcaccag agaaagatcc rgtgctgatc gaggccgcgc tggcaagcct agtggmgatt     240

```
tcggtgccga agcggaacaa actgaagmtg gtgaacctcg gagcggtgaa ggcgatgaag    300
aggctgttga aggaggcgaa tttgggcgcg gtggagaagg tgctgaaaga gaatgagaat    360
ggaagagtgg acgacaatga gaatggaaaa ctgagggtag a                       401
```

<210> SEQ ID NO 230
<211> LENGTH: 20
<212> TYPE: DNA
<213> ORGANISM: Glycine max

<400> SEQUENCE: 230

```
acagttcatt ggccttgaca                                                20
```

<210> SEQ ID NO 231
<211> LENGTH: 20
<212> TYPE: DNA
<213> ORGANISM: Glycine max

<400> SEQUENCE: 231

```
ggcttcacac ttgaggaggt                                                20
```

<210> SEQ ID NO 232
<211> LENGTH: 16
<212> TYPE: DNA
<213> ORGANISM: Artificial Sequence
<220> FEATURE:
<223> OTHER INFORMATION: S08519-1 Probe1

<400> SEQUENCE: 232

```
tcagctctgc caatag                                                    16
```

<210> SEQ ID NO 233
<211> LENGTH: 16
<212> TYPE: DNA
<213> ORGANISM: Artificial Sequence
<220> FEATURE:
<223> OTHER INFORMATION: S08519-1 Probe2

<400> SEQUENCE: 233

```
tcagctctgg caatag                                                    16
```

<210> SEQ ID NO 234
<211> LENGTH: 401
<212> TYPE: DNA
<213> ORGANISM: Glycine max

<400> SEQUENCE: 234

```
tttgaaagaa raaagaaagt gctcactgct accaatatac taataccgaa ccatccaacc    60
aaattatctt tcgtctatac tttttaggct tcacacttga ggaggtgtga actgtatggc   120
caaattctat caacagacca atcaaatatt aacccataaa tggctcacca tgtccaatca   180
ggctcatggc tgatctattg scagagctga ctcaatgtca aggccaatga actgttgtgc   240
actgatagca ggaagacact agagctgtga agaattggca ggccaactag tcttggcggc   300
ccaacdtaac agtctcttga tccttctcat ggatctagct aaagtgtcat tggccagaac   360
agttaaagaa tggcacactt gttaaatagg tgtgactagt c                      401
```

<210> SEQ ID NO 235
<211> LENGTH: 20
<212> TYPE: DNA
<213> ORGANISM: Glycine max

<400> SEQUENCE: 235
cccgccacaa ctcttgttat                                                   20

<210> SEQ ID NO 236
<211> LENGTH: 20
<212> TYPE: DNA
<213> ORGANISM: Glycine max

<400> SEQUENCE: 236
gggaggtgtt tggcaatatc                                                   20

<210> SEQ ID NO 237
<211> LENGTH: 14
<212> TYPE: DNA
<213> ORGANISM: Artificial Sequence
<220> FEATURE:
<223> OTHER INFORMATION: S12876-1 Probe1

<400> SEQUENCE: 237
cacgcttcca atct                                                         14

<210> SEQ ID NO 238
<211> LENGTH: 15
<212> TYPE: DNA
<213> ORGANISM: Artificial Sequence
<220> FEATURE:
<223> OTHER INFORMATION: S12876-1 Probe2

<400> SEQUENCE: 238
aagcacgctt cgaat                                                        15

<210> SEQ ID NO 239
<211> LENGTH: 401
<212> TYPE: DNA
<213> ORGANISM: Glycine max

<400> SEQUENCE: 239
gaaaggtctt cccctggttc atttccttgc ttcttggctg actcacgagg acttcaatcg       60
ttttctgcga agctcttagg gtcgtggctc gaattgggat cagggattc tctctttctc       120
cgatgatctc caaaattgga accgggaggt gtttggcaat atcttccgaa atagggtctc      180
cttaagcaaa ttcagagatt sgaagcgtgc ttgggctcct ccttttctga tgatctcgtt      240
tacagataac aagagttgtg gcgggaatag gagcaagtgc tgatacagga ggaactatta      300
tggttacaaa atctttttg ttacagcagg ggatttcgtc catttctatt tatctaactc      360
tttccctgag ttggacatgt tggctgccag gccagcttgg t                         401

<210> SEQ ID NO 240
<211> LENGTH: 23
<212> TYPE: DNA
<213> ORGANISM: Glycine max

<400> SEQUENCE: 240
gcaaaattaa ggagaggacc ttg                                               23

<210> SEQ ID NO 241
<211> LENGTH: 20
<212> TYPE: DNA
<213> ORGANISM: Glycine max

<400> SEQUENCE: 241
ctctcttgca aaatgcacca                                                   20

<210> SEQ ID NO 242
<211> LENGTH: 17
<212> TYPE: DNA
<213> ORGANISM: Artificial Sequence
<220> FEATURE:
<223> OTHER INFORMATION: S05937-1 Probe1

<400> SEQUENCE: 242
catcagctat gaccatg                                                    17

<210> SEQ ID NO 243
<211> LENGTH: 14
<212> TYPE: DNA
<213> ORGANISM: Artificial Sequence
<220> FEATURE:
<223> OTHER INFORMATION: S05937-1 Probe2

<400> SEQUENCE: 243
catccgctat gacc                                                       14

<210> SEQ ID NO 244
<211> LENGTH: 401
<212> TYPE: DNA
<213> ORGANISM: Glycine max

<400> SEQUENCE: 244 gaaggggget gggttggagt aacacaaggg gaactcatag tcaggcttga tagaccatgc      60
ccaaaggagt aaggagaaga attagaatyc awgtagagga aattattgag aagcaaacag    120
gaaatggcaa caattgaatt gttcccatgt cccaatgggc aaagtccagc aaaattaagg    180 agaggaccett gataatcatc mgctatgacc atgtgcactg gtgcattttg caagagagcc    240
aactcagcca agggatcttc acaatataac cataaaggct ctaatgctct gtttcatgac    300
gaactggagt cggaggtggg ctgcagggta agtttgagtt aagtcaccaa caataccatg    360
aaaaacaaag gcgctagggg agcaagggcg ttcacatgct t                        401

<210> SEQ ID NO 245
<211> LENGTH: 25
<212> TYPE: DNA
<213> ORGANISM: Glycine max

<400> SEQUENCE: 245
aactatgcac ttatgctcat ggtaa                                           25

<210> SEQ ID NO 246
<211> LENGTH: 20
<212> TYPE: DNA
<213> ORGANISM: Glycine max

<400> SEQUENCE: 246
tggatccaaa catgcgtcta                                                 20

<210> SEQ ID NO 247
<211> LENGTH: 16
<212> TYPE: DNA
<213> ORGANISM: Artificial Sequence
<220> FEATURE:
<223> OTHER INFORMATION: S08575-1 Probe1

<400> SEQUENCE: 247
acttcttgct gaatct                                                     16

```
<210> SEQ ID NO 248
<211> LENGTH: 16
<212> TYPE: DNA
<213> ORGANISM: Artificial Sequence
<220> FEATURE:
<223> OTHER INFORMATION: S08575-1 Probe2

<400> SEQUENCE: 248
aacttcttgc cgaatc                                                    16

<210> SEQ ID NO 249
<211> LENGTH: 401
<212> TYPE: DNA
<213> ORGANISM: Glycine max

<400> SEQUENCE: 249
gcaatttgag tataattagc tgcttctttg gacatatgtt tgtactgtgt gtttagtagt    60
gctttcacca ggtccaatgt gcatcaaaac agaagcaact aaaactagct tccacatttt   120
tttagatgat atgaggtgat ttaagcttca aacatgcata tttggagtgg atccaaacat   180
gcgtctagtc taagagattc rgcaagaagt tcaaagagat gaagctctaa atttattatt   240
tttgtaatat tcagaaatta agcttattac catgagcata agtgcatagt tacaacaatt   300
tactgagacc tctttcatta tggttgctca taaatggaat aacattttca ttttttaatta  360 tatcatgtta ttctcwacat cttccgattg cttagtttga a                        401

<210> SEQ ID NO 250
<211> LENGTH: 20
<212> TYPE: DNA
<213> ORGANISM: Glycine max

<400> SEQUENCE: 250
gtggtgggtt ggttttgac                                                 20

<210> SEQ ID NO 251
<211> LENGTH: 23
<212> TYPE: DNA
<213> ORGANISM: Glycine max

<400> SEQUENCE: 251
tccaatattc tcagcctctt cag                                            23

<210> SEQ ID NO 252
<211> LENGTH: 16
<212> TYPE: DNA
<213> ORGANISM: Artificial Sequence
<220> FEATURE:
<223> OTHER INFORMATION: S08669-1 Probe1

<400> SEQUENCE: 252
tcttatggga catttc                                                    16

<210> SEQ ID NO 253
<211> LENGTH: 16
<212> TYPE: DNA
<213> ORGANISM: Artificial Sequence
<220> FEATURE:
<223> OTHER INFORMATION: S08669-1 Probe2

<400> SEQUENCE: 253
tcttatggga catctc                                                    16
```

```
<210> SEQ ID NO 254
<211> LENGTH: 401
<212> TYPE: DNA
<213> ORGANISM: Glycine max

<400> SEQUENCE: 254
cctccattca tctagataaa magttgaagt ttagcacaag gtatgttatg cttgtacatt      60
gtccacactt caagcccaaa acgtcttgca tgaggtggtg ggttggtttt tgacatatca     120
taatatgtgt atcttgtgct aactgatcag aaacttcatt acattatctg ttttttctgg    180
gtcattttct tatgggacat ytcctctakg tcctcagatc tgaagaggct gagaatattg    240
gatatgtgat tcctacaact gttgtatctc attttttgac cgattatgaa aggaatggca    300
ggtatactgg taagaaactc ttctagaata tggttatatt tgatagattt ggcatgtcac    360
tatgtcttat ttgagtaagc acactggatt gtgtattttt t                        401

<210> SEQ ID NO 255
<211> LENGTH: 20
<212> TYPE: DNA
<213> ORGANISM: Glycine max

<400> SEQUENCE: 255
ctccaagacc ttgccttcct                                                  20

<210> SEQ ID NO 256
<211> LENGTH: 24
<212> TYPE: DNA
<213> ORGANISM: Glycine max

<400> SEQUENCE: 256
gatcccaaat gagattagga gact                                             24

<210> SEQ ID NO 257
<211> LENGTH: 14
<212> TYPE: DNA
<213> ORGANISM: Artificial Sequence
<220> FEATURE:
<223> OTHER INFORMATION: S11212-1 Probe1

<400> SEQUENCE: 257
ccccgtttac ttcc                                                        14

<210> SEQ ID NO 258
<211> LENGTH: 13
<212> TYPE: DNA
<213> ORGANISM: Artificial Sequence
<220> FEATURE:
<223> OTHER INFORMATION: S11212-1 Probe2

<400> SEQUENCE: 258
cccggttact tcc                                                         13

<210> SEQ ID NO 259
<211> LENGTH: 401
<212> TYPE: DNA
<213> ORGANISM: Glycine max

<400> SEQUENCE: 259
tagtcttata agaacttcaa gacttgtttc tttaaggtga caataaaktc gattactggg     60
aataacttat tctttgattc aaagaaatcc ttgtttcctt tatataggct kccatatctg    120
tgtyagtatg atgaatacct taaggatttt ttttascaaa aggagctcca agaccttgcc    180
```

```
ttcctcgaga ccctccccccg kttacttcct gttaaacaaa tattttcccct ccttaagtct      240 cctaatctca tttgggatct tgagggttag ttgttttttct tttgtgcaca tbtcattttt      300
tgcccaaact ttctgattta ttattttga cttgtttcag gtataacgac tcaagcacgc       360
gccaacatga ctgctttcta acttgcccac aaaaactgta t                          401
```

```
<210> SEQ ID NO 260
<211> LENGTH: 26
<212> TYPE: DNA
<213> ORGANISM: Glycine max

<400> SEQUENCE: 260
gcatgcaata tgaacaactt gacaac                                            26

<210> SEQ ID NO 261
<211> LENGTH: 25
<212> TYPE: DNA
<213> ORGANISM: Glycine max

<400> SEQUENCE: 261
cccttttcac atgagtatgc atgtc                                             25

<210> SEQ ID NO 262
<211> LENGTH: 17
<212> TYPE: DNA
<213> ORGANISM: Artificial Sequence
<220> FEATURE:
<223> OTHER INFORMATION: S00543-1 Probe1

<400> SEQUENCE: 262
cacttatcca ttggttc                                                      17

<210> SEQ ID NO 263
<211> LENGTH: 17
<212> TYPE: DNA
<213> ORGANISM: Artificial Sequence
<220> FEATURE:
<223> OTHER INFORMATION: S00543-1 Probe2

<400> SEQUENCE: 263
cacttatcca gtggttc                                                      17

<210> SEQ ID NO 264
<211> LENGTH: 401
<212> TYPE: DNA
<213> ORGANISM: Glycine max

<400> SEQUENCE: 264
cttcaattga taaagcattt gcaagctgtg aattgaagtt gcaaaccac aacttcatgg       60 aaatccttca agaaaataaa ctagaaacta tgaatatgta gtagtagcag tgttagtcag      120
aataagtagc atgcaatatg aacaacttga caacacacta taaacataaa tgataaataa     180
ctgactgttc cacttatcca ktggttcatt aatatcaaat atcaaacatc tttgacaatt     240
attagacatg catactcatg tgaaaaggga aggtaatttt tgatgttgaa aatatrcaga     300
atatgtatgt atactacata ccatggttac taattactat ttactatcta cgggattgta     360
ggctacagct actattgtta tactccacct ctagctgaaa c                          401

<210> SEQ ID NO 265
<211> LENGTH: 23
<212> TYPE: DNA
<213> ORGANISM: Glycine max
```

```
<400> SEQUENCE: 265
caaacaatga atgatgaatc caa                                              23

<210> SEQ ID NO 266
<211> LENGTH: 21
<212> TYPE: DNA
<213> ORGANISM: Glycine max

<400> SEQUENCE: 266
gcattttgag agccaccaat a                                                21

<210> SEQ ID NO 267
<211> LENGTH: 17
<212> TYPE: DNA
<213> ORGANISM: Artificial Sequence
<220> FEATURE:
<223> OTHER INFORMATION: S01452-1 Probe1

<400> SEQUENCE: 267
aagcaattgg tcacaac                                                     17

<210> SEQ ID NO 268
<211> LENGTH: 16
<212> TYPE: DNA
<213> ORGANISM: Artificial Sequence
<220> FEATURE:
<223> OTHER INFORMATION: S01452-1 Probe2

<400> SEQUENCE: 268
aagcaactgg tcacaa                                                      16

<210> SEQ ID NO 269
<211> LENGTH: 401
<212> TYPE: DNA
<213> ORGANISM: Glycine max

<400> SEQUENCE: 269
ttcaaaccaa cttagsagct tgaagctcaa gaataggaag ataggtcccc aaaatggaat      60
tgagtgtraa gtagaaactg aaaatacatt tgatggtgtt ttggatccttt ctgttgtatg    120 agcataagga tgcagtcaaa caatgaatga tgaatccaat agctataaga ggawacaaac    180
atgtggcata tgtgaagcaa ytggtcacaa cagacgaaaa tgtattggtg gctctcaaaa    240
tgcacaacat gcagttggtg ggtttggtat tccttcaagt cagcaaacat acaatgctcc    300
taaacctaca gttgagtata attatcatct ggtatataat tgcttacttt agcctcatta    360
attgtaaatg gttgttattt aatcaatagt tacttaagta c                         401

<210> SEQ ID NO 270
<211> LENGTH: 20
<212> TYPE: DNA
<213> ORGANISM: Glycine max

<400> SEQUENCE: 270
atttgtgagt gctgcggatt                                                  20

<210> SEQ ID NO 271
<211> LENGTH: 21
<212> TYPE: DNA
<213> ORGANISM: Glycine max

<400> SEQUENCE: 271
```

```
tgaacatgaa cgtgctaaac g                                              21
```

<210> SEQ ID NO 272
<211> LENGTH: 14
<212> TYPE: DNA
<213> ORGANISM: Artificial Sequence
<220> FEATURE:
<223> OTHER INFORMATION: S11993-1 Probe1

<400> SEQUENCE: 272

```
ccagcacaat tgat                                                      14
```

<210> SEQ ID NO 273
<211> LENGTH: 13
<212> TYPE: DNA
<213> ORGANISM: Artificial Sequence
<220> FEATURE:
<223> OTHER INFORMATION: S11993-1 Probe2

<400> SEQUENCE: 273

```
ccagcacaat cga                                                       13
```

<210> SEQ ID NO 274
<211> LENGTH: 401
<212> TYPE: DNA
<213> ORGANISM: Glycine max
<220> FEATURE:
<221> NAME/KEY: misc_feature
<222> LOCATION: (174)..(174)
<223> OTHER INFORMATION: n is a, c, g, or t

<400> SEQUENCE: 274

```
catctcattc tgaatcttgc gccgtttccc tctcccactc gccaggtacg tcatgtmgtt     60
tttgcttccc cgttgttgcg tcgatacgac ttgtcgttta gcacgttcat gttcatgttc    120
ggttcgtgtg tgttgcagtg aggtgatttg atttgatttg tgagtgctgc gganttttt    180
ttttccattt ccagcacaat ygattcgtcg gtacaacttg tcgtttagca cgttcatgtt    240
catgtttgat tcgtgtgttg cattgrtttg atagtgttgc ggaatttttt agaagtgtga    300
atgttcgttc atgcatgagc ggctcttaaa gttkccttgc ggattcgatt gcgatatatt    360
gagactgcga tggcctcagc cgtcgtgaat ttcttgaacg c                        401
```

<210> SEQ ID NO 275
<211> LENGTH: 20
<212> TYPE: DNA
<213> ORGANISM: Glycine max

<400> SEQUENCE: 275

```
atcccaggct tctaatgtgg                                                20
```

<210> SEQ ID NO 276
<211> LENGTH: 20
<212> TYPE: DNA
<213> ORGANISM: Glycine max

<400> SEQUENCE: 276

```
ggctgcgcta ctttcgtact                                                20
```

<210> SEQ ID NO 277
<211> LENGTH: 13
<212> TYPE: DNA
<213> ORGANISM: Artificial Sequence
<220> FEATURE:
<223> OTHER INFORMATION: S13446-1 Probe1

```
<400> SEQUENCE: 277
cccaccacac tca                                                        13

<210> SEQ ID NO 278
<211> LENGTH: 12
<212> TYPE: DNA
<213> ORGANISM: Artificial Sequence
<220> FEATURE:
<223> OTHER INFORMATION: S13446-1 Probe2

<400> SEQUENCE: 278
cccaccacgc tc                                                         12

<210> SEQ ID NO 279
<211> LENGTH: 401
<212> TYPE: DNA
<213> ORGANISM: Glycine max

<400> SEQUENCE: 279
ggggtttata agrccttaga ctttcgaact acaacagcta gcatctatgg tgtgattctc     60
cgaagtttag tttttggggt gtgattctcc taaccgaact agtcaaacaa ctattgcaca    120
accagcctgc atgggcacgg ggctgcgcta ctttcgtact caagccttct gatactgaat    180
cctagattat tcaatctgag ygtggtggga tgttaagatc caatttcaag gtatggtact    240
tatgtcccac attagaagcy tgggattcta gagtagggtt tataaggcct taggctttcc    300
aactacaaca actagmatct atggcatgat tctccaaagg ttagcttttg gggtgtgatt    360
ctcccaacaa aactagtcaa acggctagtg cacaaccaac c                        401

<210> SEQ ID NO 280
<211> LENGTH: 22
<212> TYPE: DNA
<213> ORGANISM: Glycine max

<400> SEQUENCE: 280
atgcatgcag ctgggcaata at                                              22

<210> SEQ ID NO 281
<211> LENGTH: 22
<212> TYPE: DNA
<213> ORGANISM: Glycine max

<400> SEQUENCE: 281
gatgccaccg atgaagaagc ac                                              22

<210> SEQ ID NO 282
<211> LENGTH: 17
<212> TYPE: DNA
<213> ORGANISM: Artificial Sequence
<220> FEATURE:
<223> OTHER INFORMATION: S00252-1 Probe1

<400> SEQUENCE: 282
cggtctcttg gtactat                                                    17

<210> SEQ ID NO 283
<211> LENGTH: 17
<212> TYPE: DNA
<213> ORGANISM: Artificial Sequence
<220> FEATURE:
<223> OTHER INFORMATION: S00252-1 Probe2
```

```
<400> SEQUENCE: 283
cggtctcatg gtactat                                                    17

<210> SEQ ID NO 284
<211> LENGTH: 401
<212> TYPE: DNA
<213> ORGANISM: Glycine max

<400> SEQUENCE: 284
tttgtaagag aacctaattt ttgactataa tgtgcttgaa tttgatacat atatcttatt     60
taaggaagat ccaaactcat atcaaccaca tgttgattat ataacacata attaaataat    120
taagtggatg gtatgaatta gttttggtga tggcacatgt atgcatgcag ctgggcaata    180
atggatgggg aagcggtctc wtggtactat gattcaagct ccccggacgg caccggtgct    240
tcttcatcgg tggcatctaa gaacattgtc tccgagagga atagaaggaa gaagctcaac    300
gataggcttt tggcacttag agcagtggtc cccaacatta ccaaggtact ccatcacctt    360
aattaattaa actagcaatt attattgttc atcatatatt t                        401

<210> SEQ ID NO 285
<211> LENGTH: 20
<212> TYPE: DNA
<213> ORGANISM: Glycine max

<400> SEQUENCE: 285
ctcttgcagc ggattcagtc                                                 20

<210> SEQ ID NO 286
<211> LENGTH: 19
<212> TYPE: DNA
<213> ORGANISM: Glycine max

<400> SEQUENCE: 286
ctcgccgatt tcctcatct                                                  19

<210> SEQ ID NO 287
<211> LENGTH: 14
<212> TYPE: DNA
<213> ORGANISM: Artificial Sequence
<220> FEATURE:
<223> OTHER INFORMATION: S04060-1 Probe1

<400> SEQUENCE: 287
cgacttcact cacc                                                       14

<210> SEQ ID NO 288
<211> LENGTH: 17
<212> TYPE: DNA
<213> ORGANISM: Artificial Sequence
<220> FEATURE:
<223> OTHER INFORMATION: S04060-1 Probe2

<400> SEQUENCE: 288
acttcagtca ccgagat                                                    17

<210> SEQ ID NO 289
<211> LENGTH: 401
<212> TYPE: DNA
<213> ORGANISM: Glycine max

<400> SEQUENCE: 289
gccgccggaa ctgcttcgga ctccctcact cttggagcga ctcaggtcct tccataatct     60
```

```
ttctctccac aaacatgtcc aacccgagcc agagccagag ccagaacctg aacctgaaaa      120
gccggaactg gttcggagtc cctcgctctt gcagcggatt cagtccataa acttctccca      180
tctctacaga tccgacttca stcaccgaga tgatgaggat ccsgattcgg gttcggatcc      240
gggtcgcggt tcgggaaagg cggcggagat gaggaaatcg gcgagcgtga gaggggttt      300 gacggatagc gagtgggagg aggtcgagaa gcggaggccg cagacggcga ggccggttga      360
aacgacgacg tcgtggagag aagacgaaga agtagacgcc a                          401
```

<210> SEQ ID NO 290
<211> LENGTH: 24
<212> TYPE: DNA
<213> ORGANISM: Glycine max

<400> SEQUENCE: 290

```
gttttggttt ccttaggatg aact                                              24
```

<210> SEQ ID NO 291
<211> LENGTH: 20
<212> TYPE: DNA
<213> ORGANISM: Glycine max

<400> SEQUENCE: 291

```
atgtgcagag gtcccattct                                                   20
```

<210> SEQ ID NO 292
<211> LENGTH: 16
<212> TYPE: DNA
<213> ORGANISM: Artificial Sequence
<220> FEATURE:
<223> OTHER INFORMATION: S02664-1 Probe1

<400> SEQUENCE: 292

```
ctttccatct tattcg                                                       16
```

<210> SEQ ID NO 293
<211> LENGTH: 16
<212> TYPE: DNA
<213> ORGANISM: Artificial Sequence
<220> FEATURE:
<223> OTHER INFORMATION: S02664-1 Probe2

<400> SEQUENCE: 293

```
ctttccatct tgttcg                                                       16
```

<210> SEQ ID NO 294
<211> LENGTH: 401
<212> TYPE: DNA
<213> ORGANISM: Glycine max

<400> SEQUENCE: 294

```
aatcgtttac agttgtgaaa aaactgcatt ggtcctttaa tttaatttat aaaatgataa      60
atatatcttt agaatttagt ttaatraatt ctaaggatga gatttagaac tgctgcacat      120
tgcagttcat ttttaaactg cagaggtccc attctctgta aaaaaagaa ttttcttcct       180 ctgctattcc tttcyatctt rttcgttcat ttctcaacta gttcatccta aggaaaccaa      240
aactactaat atatgaaatg aaggacacta taactaaa gagacatatg wcggaccatt        300
tttaaatata taaaactcta ttagaactgc taaagtgaag atccttattc tttgcctaca      360
aatttactta cgtacaatac gaaggaggaa ctaaagttta t                          401
```

```
<210> SEQ ID NO 295
<211> LENGTH: 22
<212> TYPE: DNA
<213> ORGANISM: Glycine max

<400> SEQUENCE: 295
ggccgagcaa acaacaagaa aa                                              22

<210> SEQ ID NO 296
<211> LENGTH: 23
<212> TYPE: DNA
<213> ORGANISM: Glycine max

<400> SEQUENCE: 296
tccaaactcc tcacaagcct tca                                             23

<210> SEQ ID NO 297
<211> LENGTH: 15
<212> TYPE: DNA
<213> ORGANISM: Artificial Sequence
<220> FEATURE:
<223> OTHER INFORMATION: S00281-1 Probe1

<400> SEQUENCE: 297
catagtgaac ctctc                                                      15

<210> SEQ ID NO 298
<211> LENGTH: 15
<212> TYPE: DNA
<213> ORGANISM: Artificial Sequence
<220> FEATURE:
<223> OTHER INFORMATION: S00281-1 Probe2

<400> SEQUENCE: 298
ccatagtgga cctct                                                      15

<210> SEQ ID NO 299
<211> LENGTH: 401
<212> TYPE: DNA
<213> ORGANISM: Glycine max

<400> SEQUENCE: 299
aattttcttg ctaccatacc caaatggatt gggaggtcct acttttcct tttcattgag       60 tgacatagag aagaatttga aggcttcata ttccaattcg gatatagctt ccatggagac    120
accatgattg atgactttga agaatccaaa ctcctcacaa gccttcacta taagggtctt    180
tgcatcaggt ttggagaggt ycactatggg aattgttgag gaaaatttgg ttggcatgca    240
gttcttaatg taggagtatt gttctgttgt tgctttggac aacaacacca tttttcttgt    300
tgtttgctcg gccgttrttc tgttttgtgg tgttaagaag tggagtgaaa gatagggaga    360
aggtacgtga gagaggaaca gagatatttg aaaagctttt g                        401

<210> SEQ ID NO 300
<211> LENGTH: 24
<212> TYPE: DNA
<213> ORGANISM: Glycine max

<400> SEQUENCE: 300
agtagtactt catccctgac acca                                            24

<210> SEQ ID NO 301
<211> LENGTH: 26
```

```
<212> TYPE: DNA
<213> ORGANISM: Glycine max

<400> SEQUENCE: 301
aggagtataa ccttggttta aagctg                                          26

<210> SEQ ID NO 302
<211> LENGTH: 15
<212> TYPE: DNA
<213> ORGANISM: Artificial Sequence
<220> FEATURE:
<223> OTHER INFORMATION: S01109-1 Probe1

<400> SEQUENCE: 302
ccaccacctc tgaaa                                                      15

<210> SEQ ID NO 303
<211> LENGTH: 14
<212> TYPE: DNA
<213> ORGANISM: Artificial Sequence
<220> FEATURE:
<223> OTHER INFORMATION: S01109-1 Probe2

<400> SEQUENCE: 303
accaccgctg aaaa                                                       14

<210> SEQ ID NO 304
<211> LENGTH: 401
<212> TYPE: DNA
<213> ORGANISM: Glycine max

<400> SEQUENCE: 304
gattctggtg accctkctct cggttctctc ttctgcatcg tgtgcacgaa tggttggggg     60
gaagacggag atccctgaag tgagaaaaaa caggcaagtg caagagcttg gaaggttcgc    120
ggtggaggag tataaccttg gtttaaagct gttgaagaac aacaacgtcg acaatgggag    180
agaacagttg aacttttcag mggtggtgga ggcgcagcaa caagtggtgt cagggatgaa    240
gtactacttg aagatctctg ctactcataa tggtgttcac gaaatgttca mctctgtggt    300
ggtggtcaag ccatggcttc attccaagca gctcctccat tttgcgcctg catcatcatc    360
caccaccacc accaccacca ccatgcatcc agtagtacgt a                        401

<210> SEQ ID NO 305
<211> LENGTH: 20
<212> TYPE: DNA
<213> ORGANISM: Glycine max

<400> SEQUENCE: 305
tgatggaaag ccgaaaaaga                                                 20

<210> SEQ ID NO 306
<211> LENGTH: 21
<212> TYPE: DNA
<213> ORGANISM: Glycine max

<400> SEQUENCE: 306
ctgagcagcc ctcatatgtt t                                               21

<210> SEQ ID NO 307
<211> LENGTH: 17
<212> TYPE: DNA
<213> ORGANISM: Artificial Sequence
<220> FEATURE:
```

```
<223> OTHER INFORMATION: S13844-1 Probe1

<400> SEQUENCE: 307
tcccttaagt agtcttt                                                    17

<210> SEQ ID NO 308
<211> LENGTH: 17
<212> TYPE: DNA
<213> ORGANISM: Artificial Sequence
<220> FEATURE:
<223> OTHER INFORMATION: S13844-1 Probe

<400> SEQUENCE: 308
atcccttacg tagtctt                                                    17

<210> SEQ ID NO 309
<211> LENGTH: 401
<212> TYPE: DNA
<213> ORGANISM: Glycine max

<400> SEQUENCE: 309
gccaccgtgt tttttaagat ctgtgctcat taagaaaaac aaagcaactt gmtgaaacct      60
tttatccaca tacatatatg gttagttaac cttaatcccc attgctcaag cagatattaa    120
atattctttg tgagcactga gcagccctca tatgtttatg tactgaaaga tcaatattac    180
ttgttagtga taaagactac ktaagggata agaatgaaca tagctgcagg aatattcttg    240 gttttttta gtactgcaca attaattctg tatttatgtc tctctttagt ctttttcggc     300
tttccatcat gcatatatct aatatttact ttaaatttat tggtatcttt ttttttttac    360
tcttcctgaa ttttatattt catacattct tttaattaaa a                        401

<210> SEQ ID NO 310
<211> LENGTH: 24
<212> TYPE: DNA
<213> ORGANISM: Glycine max

<400> SEQUENCE: 310
aaatgatacg caattttgac tcag                                           24

<210> SEQ ID NO 311
<211> LENGTH: 24
<212> TYPE: DNA
<213> ORGANISM: Glycine max

<400> SEQUENCE: 311
tgtgttatgc ctaccaatca aact                                           24

<210> SEQ ID NO 312
<211> LENGTH: 18
<212> TYPE: DNA
<213> ORGANISM: Artificial Sequence
<220> FEATURE:
<223> OTHER INFORMATION: S05058-1 Probe1

<400> SEQUENCE: 312
atttgcagtt cattgtac                                                  18

<210> SEQ ID NO 313
<211> LENGTH: 17
<212> TYPE: DNA
<213> ORGANISM: Artificial Sequence
<220> FEATURE:
<223> OTHER INFORMATION: S05058-1 Probe2
```

```
<400> SEQUENCE: 313
atttgcggtt cattgta                                                    17

<210> SEQ ID NO 314
<211> LENGTH: 401
<212> TYPE: DNA
<213> ORGANISM: Glycine max

<400> SEQUENCE: 314
ccctcaatac agagccactg ggcagatact catccatttg aagttctccc gacattaata     60
gtggatctgt gagtttccac catttgagtt gtgctatatt atcaccattt ttatcttttg    120
acatgctatt atttgtaaat caaccaaaaa tgatacgcaa ttttgactca gaattgttta    180
gaccaattac taatatttgc rgttcattgt actccaatat ttgataagtt tgattggtag    240
gcataacaca ttaatcaatg aaatggggtg taaaatacaa ctagattata gggacatgta    300
actttcaaag tgttttgagt taacctgctg tgacactgat cagctgaaca tgtccttttt    360
ctagaaacta gaaatacaat tgcttaatgt caaaaacaag a                        401

<210> SEQ ID NO 315
<211> LENGTH: 20
<212> TYPE: DNA
<213> ORGANISM: Glycine max

<400> SEQUENCE: 315
tcggccttcg tcatagaagt                                                 20

<210> SEQ ID NO 316
<211> LENGTH: 21
<212> TYPE: DNA
<213> ORGANISM: Glycine max

<400> SEQUENCE: 316
tccttcaatt tccccatatc c                                               21

<210> SEQ ID NO 317
<211> LENGTH: 15
<212> TYPE: DNA
<213> ORGANISM: Artificial Sequence
<220> FEATURE:
<223> OTHER INFORMATION: S04660-1 Probe1

<400> SEQUENCE: 317
catctacatc cttcc                                                      15

<210> SEQ ID NO 318
<211> LENGTH: 15
<212> TYPE: DNA
<213> ORGANISM: Artificial Sequence
<220> FEATURE:
<223> OTHER INFORMATION: S04660-1 Probe2

<400> SEQUENCE: 318
catctacgtc cttcc                                                      15

<210> SEQ ID NO 319
<211> LENGTH: 401
<212> TYPE: DNA
<213> ORGANISM: Glycine max

<400> SEQUENCE: 319
```

```
attggaagga ataaagttgg ggttttggaa gcaatggagt ggaattcatt ccattctagt    60
ttaacaaatt caaacaatgg aacatatcaa aattccattc catcctactc cattccttca   120
atttccccat atccaatcac atttctctgt taatagtttg ggtgcaaaaa gatagatcaa   180
agaagtagat acaggaagga ygtagatgca gaaatgaact tctatgacga aggcygaggc   240
aggcggcaac taagtgaggg atatgcctta gtaacaaaac aaggaattaa aacttggttt   300 atttattgg taaaacattg gcaacatttt tctcagccat gtccatgtaa atgtgcattt    360
gtaataaaag agtttggtgt agtggagcat ggttattgta a                      401
```

<210> SEQ ID NO 320
<211> LENGTH: 20
<212> TYPE: DNA
<213> ORGANISM: Glycine max

<400> SEQUENCE: 320

```
gatcgggatg atttttggaa                                               20
```

<210> SEQ ID NO 321
<211> LENGTH: 22
<212> TYPE: DNA
<213> ORGANISM: Glycine max

<400> SEQUENCE: 321

```
cttttcatga tccaaccaga ca                                            22
```

<210> SEQ ID NO 322
<211> LENGTH: 16
<212> TYPE: DNA
<213> ORGANISM: Artificial Sequence
<220> FEATURE:
<223> OTHER INFORMATION: S09955-1 Probe1

<400> SEQUENCE: 322

```
cacacttgat actcca                                                   16
```

<210> SEQ ID NO 323
<211> LENGTH: 16
<212> TYPE: DNA
<213> ORGANISM: Artificial Sequence
<220> FEATURE:
<223> OTHER INFORMATION: S09955-1 Probe2

<400> SEQUENCE: 323

```
cacacttgac actcca                                                   16
```

<210> SEQ ID NO 324
<211> LENGTH: 401
<212> TYPE: DNA
<213> ORGANISM: Glycine max

<400> SEQUENCE: 324

```
gggtcagatt agagagtgag atamagtgag agggactcat ttgagaggaa aaaatagtta    60
aaaatcattg agagagaaag gagaggraaa atcattrtga ttttcgcata cccactagag   120 agcattttc atattgaaac arcagattgg ttcaccgttg gatcgggatg atttttggaa   180
atmtggttca gcacacttga yactccaagt tgtctggttg gatcatgaaa agatatctgg   240
agagagagat aagtkcttca tattctctgt tctatatttt rggatttcct cttcttgtct   300
ctattgtatc aactcagggt ctgttttgat ttggctgttt gtagcacatt ttagtgtact   360
tgttggaggc tctcttgtat ctttattgat tatagtggag t                      401
```

<210> SEQ ID NO 325
<211> LENGTH: 21
<212> TYPE: DNA
<213> ORGANISM: Glycine max

<400> SEQUENCE: 325
tcctttctaa accctgctgt g                                      21

<210> SEQ ID NO 326
<211> LENGTH: 26
<212> TYPE: DNA
<213> ORGANISM: Glycine max

<400> SEQUENCE: 326
ttggtctctt tcttagtttc atctca                                 26

<210> SEQ ID NO 327
<211> LENGTH: 16
<212> TYPE: DNA
<213> ORGANISM: Artificial Sequence
<220> FEATURE:
<223> OTHER INFORMATION: S08034-1 Probe1

<400> SEQUENCE: 327
caatccacag gagcat                                            16

<210> SEQ ID NO 328
<211> LENGTH: 16
<212> TYPE: DNA
<213> ORGANISM: Artificial Sequence
<220> FEATURE:
<223> OTHER INFORMATION: S08034-1 Probe2

<400> SEQUENCE: 328
caatccagag gagcat                                            16

<210> SEQ ID NO 329
<211> LENGTH: 401
<212> TYPE: DNA
<213> ORGANISM: Glycine max

<400> SEQUENCE: 329
ttgaaccaat cagatgaaag aggttgaaac tttgcaagac aatggcgaag aattgctatt       60
ccaaccacgc cttcakcaac atcagtcaag aggctgcaca atgcttgccm tctgtatgta      120
agagattcct ttctaaaccc tgctgtgtat gctaaaaatg gaactatcca agatcctaca      180
aaccaaaatg aggcaatcca saggagcatt acctgcagaa cccaacttag tttgctcttc      240
tagatgagat gaaactaaga aagagaccaa tcaaataaac tatatagttt ctgaatattt      300
ttcaattcca tccattcaca agttcttaat tgaagyagac tataacaaat agccttactg      360
tcaaatcaat aaaaaaatta taataagtaa ccaactttta g                         401

<210> SEQ ID NO 330
<211> LENGTH: 23
<212> TYPE: DNA
<213> ORGANISM: Glycine max

<400> SEQUENCE: 330
gggcatccag actttatcta tga                                   23

<210> SEQ ID NO 331

```
<211> LENGTH: 21
<212> TYPE: DNA
<213> ORGANISM: Glycine max

<400> SEQUENCE: 331
acgatttaat gcacgacgag t                                              21

<210> SEQ ID NO 332
<211> LENGTH: 17
<212> TYPE: DNA
<213> ORGANISM: Artificial Sequence
<220> FEATURE:
<223> OTHER INFORMATION: S10293-1 Probe1

<400> SEQUENCE: 332
tttctacagt cgatctc                                                   17

<210> SEQ ID NO 333
<211> LENGTH: 15
<212> TYPE: DNA
<213> ORGANISM: Artificial Sequence
<220> FEATURE:
<223> OTHER INFORMATION: S10293-1 Probe2

<400> SEQUENCE: 333
tttccacagt cgatc                                                     15

<210> SEQ ID NO 334
<211> LENGTH: 401
<212> TYPE: DNA
<213> ORGANISM: Glycine max

<400> SEQUENCE: 334
tttttgtatt agaatcatga aaktgtgact gagattttgt gtaaatgata aattgaatat      60
gtattgaatt gtaagataca tgtgtattga gatgttgtgt gcattgagtt gtaagctatg     120
aaccgtacaa tcacacaact ttaagaccct ttaagggrga hgatttaatg cacgacgagt     180
attgtgatga gatcgactgt rgaaaccccca cgagtttaat cactttkagg cargacragt    240
taaatttatt ttgaaaataa ttgaagagtc gtgtgttttg tataattcat agataaagtc     300
tggatgccca acgaagtttt ttactgacat gataccatat tgcatatatg attgagtctt     360
agtatatttg ttgcataacg cttgtgtatt gatcgatatt g                         401

<210> SEQ ID NO 335
<211> LENGTH: 25
<212> TYPE: DNA
<213> ORGANISM: Glycine max

<400> SEQUENCE: 335
atttagcgta catgtcaact aacga                                          25

<210> SEQ ID NO 336
<211> LENGTH: 20
<212> TYPE: DNA
<213> ORGANISM: Glycine max

<400> SEQUENCE: 336
tgcaaatgct ttgaatctgg                                                20

<210> SEQ ID NO 337
<211> LENGTH: 15
<212> TYPE: DNA
<213> ORGANISM: Artificial Sequence
```

```
<220> FEATURE:
<223> OTHER INFORMATION: S03813-1 Probe1

<400> SEQUENCE: 337
cctaactaga atttc                                                      15

<210> SEQ ID NO 338
<211> LENGTH: 14
<212> TYPE: DNA
<213> ORGANISM: Artificial Sequence
<220> FEATURE:
<223> OTHER INFORMATION: S03813-1 Probe2

<400> SEQUENCE: 338
cctaaccaga attt                                                       14

<210> SEQ ID NO 339
<211> LENGTH: 401
<212> TYPE: DNA
<213> ORGANISM: Glycine max

<400> SEQUENCE: 339
gtgctcatca ygtgttgtgc atggaatggc agagttgaag aatctcttga acttttcagg     60
gagttacagt ttactagatt tgaccggagg cagttccctt ttgctacctt gttgagcatt    120
gctgcaaatg ctttgaawct ggaaatgggt aggcaaatcc attcccaggc tattgtaaca    180
gaagccattt cagaaattct rgttaggaat tcgttagttg acatgtacgc taaatgtgac    240
aaatttgggg aagcaaatag gattttttgca gatctggcac atcaaagttc agttccatgg   300
acagccttga tctcgggtta tgttcagaag ggactccatg aagatggcct aaagctattc    360
gttgagatgc aaagagccaa aataggtgct gactcgbcca c                        401

<210> SEQ ID NO 340
<211> LENGTH: 22
<212> TYPE: DNA
<213> ORGANISM: Glycine max

<400> SEQUENCE: 340
gccatcttcc atttctgcaa cc                                              22

<210> SEQ ID NO 341
<211> LENGTH: 22
<212> TYPE: DNA
<213> ORGANISM: Glycine max

<400> SEQUENCE: 341
agaagcgttg gctatgcacg ag                                              22

<210> SEQ ID NO 342
<211> LENGTH: 15
<212> TYPE: DNA
<213> ORGANISM: Artificial Sequence
<220> FEATURE:
<223> OTHER INFORMATION: S02042-1 Probe1

<400> SEQUENCE: 342
ctccttgagg ttttc                                                      15

<210> SEQ ID NO 343
<211> LENGTH: 14
<212> TYPE: DNA
<213> ORGANISM: Artificial Sequence
<220> FEATURE:
```

<223> OTHER INFORMATION: S02042-1 Probe2

<400> SEQUENCE: 343
ctccttgagg cttt              14

<210> SEQ ID NO 344
<211> LENGTH: 401
<212> TYPE: DNA
<213> ORGANISM: Glycine max

<400> SEQUENCE: 344
ccttgtgttc tctaagaact atgcatcttc ttcgttttgc ttagatgaac ttgttaaaat      60
catggagtgt gttaaggcaa agggtcggtt gattttcccc atttttatg atgtggatcc     120
ttgtcatgtg cggcatcagt ctgggagtta tggagaagcg ttggctatgc acgaggaaag    180
gttcacaagt agcaaggaaa rcctcaagga gaacatggag agkttgcaga aatggaagat    240
ggctcttaac caagcagctg atgtgtctgg caagcattac aaactggggt atagtacccc    300
tcttcacgag attttccaat acaatcacgt gttcatggtc ccgatcaatc tccacgtgac    360
atagtcaagg tcaagattgg tcgggaccat gatcacttgg t                        401

<210> SEQ ID NO 345
<211> LENGTH: 23
<212> TYPE: DNA
<213> ORGANISM: Glycine max

<400> SEQUENCE: 345
ttcacacatg tactaggctt tgg              23

<210> SEQ ID NO 346
<211> LENGTH: 20
<212> TYPE: DNA
<213> ORGANISM: Glycine max

<400> SEQUENCE: 346
ccacctttca cacagcttga              20

<210> SEQ ID NO 347
<211> LENGTH: 15
<212> TYPE: DNA
<213> ORGANISM: Artificial Sequence
<220> FEATURE:
<223> OTHER INFORMATION: S16601-001 Probe1

<400> SEQUENCE: 347
cagcttcaaa acatt              15

<210> SEQ ID NO 348
<211> LENGTH: 15
<212> TYPE: DNA
<213> ORGANISM: Artificial Sequence
<220> FEATURE:
<223> OTHER INFORMATION: S16601-001 Probe2

<400> SEQUENCE: 348
cagcttcaca acatt              15

<210> SEQ ID NO 349
<211> LENGTH: 401
<212> TYPE: DNA
<213> ORGANISM: Glycine max

<400> SEQUENCE: 349

```
caatcccaay agcctgctya aacatagaaa taaaggaatt ttatttgaaa attacttatt      60
tttcagcctt ttgaaagaag ttttgaaaaa aaaacaaact attatttctt aaaggtaatc     120
tcgtaccaaa catagttgya ttgtatctga wttcacacat gtactaggct ttggcaatgc     180
tcacagtcca agcagcttca maacatttac accctgaagc atgtggcaag tcaagctgtg     240
tgaaaggtgg aatagcagtg atgttctaca catcactgtg cttgttggca ttgggaatgg     300 gagggggtgag aggatccatg actgcatttg gagctgacca atttgatgag aaggatccaa    360
ctgaggcaaa agcccttgca agttttttca attggctttt g                        401
```

```
<210> SEQ ID NO 350
<211> LENGTH: 20
<212> TYPE: DNA
<213> ORGANISM: Glycine max

<400> SEQUENCE: 350
tttcaggctg gctgtttctt                                                  20
```

```
<210> SEQ ID NO 351
<211> LENGTH: 20
<212> TYPE: DNA
<213> ORGANISM: Glycine max

<400> SEQUENCE: 351
actctgggtg ccaaagtcaa                                                  20
```

```
<210> SEQ ID NO 352
<211> LENGTH: 17
<212> TYPE: DNA
<213> ORGANISM: Artificial Sequence
<220> FEATURE:
<223> OTHER INFORMATION: S01481-1 Probe1

<400> SEQUENCE: 352
cagtcacttt atggtcc                                                     17
```

```
<210> SEQ ID NO 353
<211> LENGTH: 16
<212> TYPE: DNA
<213> ORGANISM: Artificial Sequence
<220> FEATURE:
<223> OTHER INFORMATION: S01481-1 Probe2

<400> SEQUENCE: 353
cagtcacgtt atggtc                                                      16
```

```
<210> SEQ ID NO 354
<211> LENGTH: 401
<212> TYPE: DNA
<213> ORGANISM: Glycine max

<400> SEQUENCE: 354
agcaataatt ctatggcttt tactttattt tttagtataa ctaaaaaaaa agaaaaaaa       60 gccagaggct acaccagcat acttgaccag agatttaact taagcaataa tcatgagata    120
aatggtttca tctgtcctat atagcagcty aagctttcag gctggctgtt tctttgacat    180
gaccataaag cttcagtcac kttatggtcc aaagtttgac tttggcaccc agagtagaaa    240
tgagatcgtt tatccttatc taacatgcag ttttaaattc agtagtcctt trwattcata    300
ttatatatag caccaacaaw ggccatgaca taggagatgg gaaaatacaa aaaatggtga    360
```

```
aagtctatar cagcmtaaaa tggattcatt accttctttc t                          401
```

<210> SEQ ID NO 355
<211> LENGTH: 18
<212> TYPE: DNA
<213> ORGANISM: Glycine max

<400> SEQUENCE: 355

```
gaccggtctg ggacaatg                                                    18
```

<210> SEQ ID NO 356
<211> LENGTH: 23
<212> TYPE: DNA
<213> ORGANISM: Glycine max

<400> SEQUENCE: 356

```
cacttaatca agttgcccaa gaa                                              23
```

<210> SEQ ID NO 357
<211> LENGTH: 15
<212> TYPE: DNA
<213> ORGANISM: Artificial Sequence
<220> FEATURE:
<223> OTHER INFORMATION: S11309-1 Probe1

<400> SEQUENCE: 357

```
atttcatggt tctcg                                                       15
```

<210> SEQ ID NO 358
<211> LENGTH: 16
<212> TYPE: DNA
<213> ORGANISM: Artificial Sequence
<220> FEATURE:
<223> OTHER INFORMATION: S11309-1 Probe2

<400> SEQUENCE: 358

```
caatttcttg gttctc                                                      16
```

<210> SEQ ID NO 359
<211> LENGTH: 401
<212> TYPE: DNA
<213> ORGANISM: Glycine max

<400> SEQUENCE: 359

```
gtttagtcaa gaaaacaaa aaaaaaagta gtaaaaatg ttttaataa agtgagagtg         60 gaaattatta atcgtgtaga tttaaaaata gttttagtta tcatgaagaa gtaacatata    120
tggatagaaa gttaaataga actggatcgg cgtatatatt gggctggacc ggtctgggac    180
aatgattggg ctccaatttc wtggttctcg ttcttctwgg gcaacttgat taagtgatct    240
aacttgtgga taaaaaaga gaaataaat aaaaataaaa ttaacaatta aatgtaaaat      300 taaaagtgt aaaagatata atatgcgttt ttatttctct tccatagaat tttggtgtat     360
ataatggcga cataaggtt caaacctaag tcctttctct t                         401
```

<210> SEQ ID NO 360
<211> LENGTH: 20
<212> TYPE: DNA
<213> ORGANISM: Glycine max

<400> SEQUENCE: 360

```
gcccaaagtt caaaagcaat                                                  20
```

```
<210> SEQ ID NO 361
<211> LENGTH: 20
<212> TYPE: DNA
<213> ORGANISM: Glycine max

<400> SEQUENCE: 361
tcggatgcga atatgaagtg                                                    20

<210> SEQ ID NO 362
<211> LENGTH: 17
<212> TYPE: DNA
<213> ORGANISM: Artificial Sequence
<220> FEATURE:
<223> OTHER INFORMATION: S11320-1 Probe1

<400> SEQUENCE: 362
aaacaaacga tctcaac                                                       17

<210> SEQ ID NO 363
<211> LENGTH: 17
<212> TYPE: DNA
<213> ORGANISM: Artificial Sequence
<220> FEATURE:
<223> OTHER INFORMATION: S11320-1 Probe2

<400> SEQUENCE: 363
aaacatacga tctcaac                                                       17

<210> SEQ ID NO 364
<211> LENGTH: 401
<212> TYPE: DNA
<213> ORGANISM: Glycine max

<400> SEQUENCE: 364
actatagttt ttattttatt gcggttgtaa tatacatgtt ttggttaatt tttagatatc         60
tgctctgagg aattaagtgt ttctcagtct tttgaactgg atggtgtaat ctcacttttg        120
aatcggatgc gaatatgaag tggtatttgg attattttta atgggttgtg aatgaaaata        180
acgttacctg ttgagatcgt wtgttttata gcgatagtgt ttcatagtag tgtaagctgg        240
cttacattgc ttttgaactt tgggcggtca actgatggtt ctatktgtct cgtatgtata        300
tggtcgatcc tttgctgtta atgcggcgtg tgcctttggt atgttggttt tygggtgctg        360
caatttgtag tttcttggca atctcgtcga tggtacttca a                            401

<210> SEQ ID NO 365
<211> LENGTH: 18
<212> TYPE: DNA
<213> ORGANISM: Glycine max

<400> SEQUENCE: 365
cccagctgct gaggagaa                                                      18

<210> SEQ ID NO 366
<211> LENGTH: 22
<212> TYPE: DNA
<213> ORGANISM: Glycine max

<400> SEQUENCE: 366
ggattgaaaa acaattggag ga                                                 22

<210> SEQ ID NO 367
<211> LENGTH: 17
<212> TYPE: DNA
```

```
<213> ORGANISM: Artificial Sequence
<220> FEATURE:
<223> OTHER INFORMATION: S04040-1 Probe1

<400> SEQUENCE: 367
aaggtttccc tctagtg                                                    17

<210> SEQ ID NO 368
<211> LENGTH: 16
<212> TYPE: DNA
<213> ORGANISM: Artificial Sequence
<220> FEATURE:
<223> OTHER INFORMATION: S04040-1 Probe2

<400> SEQUENCE: 368
aaggtttccc gctagt                                                     16

<210> SEQ ID NO 369
<211> LENGTH: 401
<212> TYPE: DNA
<213> ORGANISM: Glycine max

<400> SEQUENCE: 369
aactgcaaag gttcaagtag atacytattg gccaacctta tttgctaaac ttgctgagaa      60
gaaaaatctt ggcgatttga tagccaatgc agcaggcggt ggtgcaccag ttgctgttgc     120 agctgccct gttgctgcct cwggtggtgg tggtgctgct gctgccgccc cagctgctga      180
ggagaaaaag aaggtttccc kctagtgaat ttgttgttcc tccaattgtt tttcaatcct    240
gctttatgct agttaatgtg tatctaatat gaatctgtgt gtttctattc tataggagga    300
acctgaagaa gagagtgatg atgatatggg atttggcttg ttcgattagg acattctca     360 atatgatttg gttaaatttt gtggttcttt acctttaagt t                        401

<210> SEQ ID NO 370
<211> LENGTH: 25
<212> TYPE: DNA
<213> ORGANISM: Glycine max

<400> SEQUENCE: 370
cagcatcaca cacgctataa gacca                                           25

<210> SEQ ID NO 371
<211> LENGTH: 30
<212> TYPE: DNA
<213> ORGANISM: Glycine max

<400> SEQUENCE: 371
catgactttt tcatactaag ttggacacca                                      30

<210> SEQ ID NO 372
<211> LENGTH: 16
<212> TYPE: DNA
<213> ORGANISM: Artificial Sequence
<220> FEATURE:
<223> OTHER INFORMATION: S00863-1 Probe1

<400> SEQUENCE: 372
tcaacactca caagat                                                     16

<210> SEQ ID NO 373
<211> LENGTH: 16
<212> TYPE: DNA
<213> ORGANISM: Artificial Sequence
```

<220> FEATURE:
<223> OTHER INFORMATION: S00863-1 Probe2

<400> SEQUENCE: 373
tcaacactca catgat                                                      16

<210> SEQ ID NO 374
<211> LENGTH: 401
<212> TYPE: DNA
<213> ORGANISM: Glycine max
<220> FEATURE:
<221> NAME/KEY: misc_feature
<222> LOCATION: (398)..(398)
<223> OTHER INFORMATION: n is a, c, g, or t

<400> SEQUENCE: 374
tgtgctccta gaggaatatt ttgtgtagac tttctattat cttttatttt ttcatttttt      60
aaaattcaaa tgttaacaat tcaaataaag agagaaacta aaatttcata aaagagaata     120
cgtgtattaa ttytatttt ggttgacatg acttttcat actaagttgg acaccaattg      180
tgtgtgagac ttataccatc wtgtgagtgt tgaacattct tagtgtataa cactgataat     240
ataaagggrt agacactttt ggtcttatag cktgtgtgat gctgattaat aattaacaaa     300
atattttctt ttttgwgtgt ggatgatata tgtgaataac acttaagtcc tttaataact     360
ttgctcacgt ccacttgtca taaacttatt aatatatnaa a                         401

<210> SEQ ID NO 375
<211> LENGTH: 27
<212> TYPE: DNA
<213> ORGANISM: Glycine max

<400> SEQUENCE: 375
cragtctcag tcaatctgtg actcttt                                          27

<210> SEQ ID NO 376
<211> LENGTH: 52
<212> TYPE: DNA
<213> ORGANISM: Artificial Sequence
<220> FEATURE:
<223> OTHER INFORMATION: S17151-001 Probe1

<400> SEQUENCE: 376
gaaggtgacc aagttcatgc tggaaaaaga agaaaaaatt ccactaatgt ga              52

<210> SEQ ID NO 377
<211> LENGTH: 51
<212> TYPE: DNA
<213> ORGANISM: Artificial Sequence
<220> FEATURE:
<223> OTHER INFORMATION: S17151-001 Probe2

<400> SEQUENCE: 377
gaaggtcgga gtcaacggat tgaaaagaa gaaaaaattc cactaatgtg g                51

<210> SEQ ID NO 378
<211> LENGTH: 401
<212> TYPE: DNA
<213> ORGANISM: Glycine max
<220> FEATURE:
<221> NAME/KEY: misc_feature
<222> LOCATION: (47)..(47)
<223> OTHER INFORMATION: n is a, c, g, or t

<400> SEQUENCE: 378

```
acgttaccct tgcactgcaa tgcgtcatta gattttattt tattttnttt tatctraaat    60
aactcayaat aaattttaca agtttagcta cggagaagat aactagataa aggagcgatt   120
gatgtacatt ttgagggtgt atgtaggttg gaaaargaga ggcatgaggg ggaaaaagaa   180
gaaaaaattc cactaatgtg rtatgaaaaa aagagtcaca gattgactga gactygtccc   240
aaacaagcat gttaatcctt gcaaatgcgt agacataaac attttttag ttaattacct    300 ttttcatctc tagagctaca acaactttct catttaattt ttatagttta aacatctcat   360
tttagctctt ataagtatat aaaaaattta atcttttta t                       401
```

```
<210> SEQ ID NO 379
<211> LENGTH: 25
<212> TYPE: DNA
<213> ORGANISM: Glycine max

<400> SEQUENCE: 379
ctgacgtgga gtgtgacaat gcaat                                         25

<210> SEQ ID NO 380
<211> LENGTH: 47
<212> TYPE: DNA
<213> ORGANISM: Artificial Sequence
<220> FEATURE:
<223> OTHER INFORMATION: S17153-001 Probe1

<400> SEQUENCE: 380
gaaggtgacc aagttcatgc tgcccttaat tgctcaaatt tccacta                 47

<210> SEQ ID NO 381
<211> LENGTH: 47
<212> TYPE: DNA
<213> ORGANISM: Artificial Sequence
<220> FEATURE:
<223> OTHER INFORMATION: S17153-001 Probe2

<400> SEQUENCE: 381
gaaggtcgga gtcaacggat tgcccttaat tgctcaaatt tccactc                 47

<210> SEQ ID NO 382
<211> LENGTH: 401
<212> TYPE: DNA
<213> ORGANISM: Glycine max

<400> SEQUENCE: 382
```

```
taaagttyaa gaagacacat gttawttaaa catattagtt taaaawgtaa attacactaa    60
ttatccctaa agttttgaga aattacacaa atttcccta cttttatcta ctcctacact    120
aaccccctaa ttttttgaaa atatatattg atacaccta tatacaacaa taactgccct    180
taattgctca aatttccact mtgagcctct ttatcaaatc tcatattgca ttgtcacact   240
ccacgtcagt tgcaatcact cacacccctc ctatataata catcttcact ctttgcatcc   300
tcaccctaaa ccaaaccaaa tcgaagacaa acaattttta acatcaatct caagggtaty   360
tttctctctc ttttctcttt ccttatttag tttaatatat a                      401
```

```
<210> SEQ ID NO 383
<211> LENGTH: 30
<212> TYPE: DNA
<213> ORGANISM: Glycine max

<400> SEQUENCE: 383
gaaccacatt tctaagttaa agcgacttaa                                    30
```

<210> SEQ ID NO 384
<211> LENGTH: 46
<212> TYPE: DNA
<213> ORGANISM: Artificial Sequence
<220> FEATURE:
<223> OTHER INFORMATION: S17154-001 Probe1

<400> SEQUENCE: 384
gaaggtgacc aagttcatgc taaatgtttt tctcgtgctt gattgc                46

<210> SEQ ID NO 385
<211> LENGTH: 48
<212> TYPE: DNA
<213> ORGANISM: Artificial Sequence
<220> FEATURE:
<223> OTHER INFORMATION: S17154-001 Probe2

<400> SEQUENCE: 385
gaaggtcgga gtcaacggat tmtaaatgtt tttctcgtgc ttgattgt              48

<210> SEQ ID NO 386
<211> LENGTH: 401
<212> TYPE: DNA
<213> ORGANISM: Glycine max

<400> SEQUENCE: 386 aaatttgca tatggaggaa attgaattgc tytatccaaa caaagaattt acaatgraag   60
aaatttgaat tgatttatcc aaaccaagta tttgaaaaat gaaagaaatt aaaatcaaaa  120
caattcaaat tttagacatt ttaaattctt tgaaatttct gatyccaaca caagataaat  180 gttttttctcg tgcttgattg ygatggtcat ttcccaccgr taaggttgga ataacaatat 240
ttgttgaaat tttaagtcgc tttaacttag aaatgtggtt ctagcaagtg ttaatttacc  300
ttcctttgac aattcatata atatttaaga ttgctaatga atgagaaaca aagtactttc  360
gttttgcatt tttttttcac aagaagtcaa agaacctttt t                      401

<210> SEQ ID NO 387
<211> LENGTH: 28
<212> TYPE: DNA
<213> ORGANISM: Glycine max

<400> SEQUENCE: 387
cccttccaat gaaataaagc acttggat                                    28

<210> SEQ ID NO 388
<211> LENGTH: 44
<212> TYPE: DNA
<213> ORGANISM: Artificial Sequence
<220> FEATURE:
<223> OTHER INFORMATION: S17156-001 Probe1

<400> SEQUENCE: 388
gaaggtgacc aagttcatgc tcaacaacta attgaccctg cagg                  44

<210> SEQ ID NO 389
<211> LENGTH: 43
<212> TYPE: DNA
<213> ORGANISM: Artificial Sequence
<220> FEATURE:
<223> OTHER INFORMATION: S17156-001 Probe2

<400> SEQUENCE: 389

```
gaaggtcgga gtcaacggat taacaactaa ttgaccctgc agg              43
```

<210> SEQ ID NO 390
<211> LENGTH: 401
<212> TYPE: DNA
<213> ORGANISM: Glycine max

<400> SEQUENCE: 390

```
ggttatttct actaaagttc tcgatctaac ggcttattta atttttatt aggaaaggga    60
ggacaaattc atttcaagaa agctataatt ttatttgttg accatcatta aagaaaaga   120
aaaattaagg catactaaat ttacaattta attaaggaaa aactcaagaa tgcccttcca   180
atgaaataaa gcacttggat rcctgcaggg tcaattagtt gttgaaatca gaaraacatt   240
ctgaaagcat caacaacttt ctcaggcctg tcaaaartac aaagggtata ttcttaagag   300
gttgaacaaa tcattttact attcactgaa atcctatgtt aactaaagtt acttaccagt   360
cctcttgtgg catatgacca gctccttcta tcaatttaag c                      401
```

<210> SEQ ID NO 391
<211> LENGTH: 27
<212> TYPE: DNA
<213> ORGANISM: Glycine max

<400> SEQUENCE: 391

```
tycagcccaa caaatctcaa atgggat                                       27
```

<210> SEQ ID NO 392
<211> LENGTH: 41
<212> TYPE: DNA
<213> ORGANISM: Artificial Sequence
<220> FEATURE:
<223> OTHER INFORMATION: S17159-001 Probe1

<400> SEQUENCE: 392

```
gaaggtgacc aagttcatgc tggaagacac gtggtccacc t                       41
```

<210> SEQ ID NO 393
<211> LENGTH: 41
<212> TYPE: DNA
<213> ORGANISM: Artificial Sequence
<220> FEATURE:
<223> OTHER INFORMATION: S17159-001 Probe2

<400> SEQUENCE: 393

```
gaaggtcgga gtcaacggat tggaagacac gtggtccacc c                       41
```

<210> SEQ ID NO 394
<211> LENGTH: 401
<212> TYPE: DNA
<213> ORGANISM: Glycine max

<400> SEQUENCE: 394

```
aaattagtga aakaaatctt attttaaaga aggtagatgt atatatgcgt acgtgtaccg    60
acattcacaa gcaattaatt caaatcaata attgaaataa cgtggggaag tgctcttatg   120
tttttttgaat aacattgaaa agaaacagcg gcaatttaaa cttyaaagtc tccagccyaa   180
caaatctcaa atgggatcat rgtggaccac cgtgtcttcc asaatataga rtgttgctag   240
gtgcacccar cattctttaa aaatgayaaa attatccctg yyaatttctc cccttacctt   300
acggatcaaa ttgatccgta aaatacttac ggatcaactt gatccgtaag gdatattttt   360
gtcttttcgt ggttagtgct rgatgcacca gcaataatac t                      401
```

```
<210> SEQ ID NO 395
<211> LENGTH: 20
<212> TYPE: DNA
<213> ORGANISM: Glycine max

<400> SEQUENCE: 395
cccttgaaag acgaccaaaa                                                    20

<210> SEQ ID NO 396
<211> LENGTH: 20
<212> TYPE: DNA
<213> ORGANISM: Glycine max

<400> SEQUENCE: 396
acttatccgc agccgtacac                                                    20

<210> SEQ ID NO 397
<211> LENGTH: 17
<212> TYPE: DNA
<213> ORGANISM: Artificial Sequence
<220> FEATURE:
<223> OTHER INFORMATION: S08590-1 Probe1

<400> SEQUENCE: 397
cagatcagtt gtcattt                                                       17

<210> SEQ ID NO 398
<211> LENGTH: 16
<212> TYPE: DNA
<213> ORGANISM: Artificial Sequence
<220> FEATURE:
<223> OTHER INFORMATION: S08590-1 Probe2

<400> SEQUENCE: 398
cagatcggtt gtcatt                                                        16

<210> SEQ ID NO 399
<211> LENGTH: 401
<212> TYPE: DNA
<213> ORGANISM: Glycine max

<400> SEQUENCE: 399
ctttcatgta agaagtcatt tgatattaac aatgaagtta tttatcttct cttgacgctg        60
atggactact tgtctatttc cagctatgaa gttatttatt aatttgactt ctcattaacg       120
cattttstgt tcctaattrg tttagaacaa ctaaagaccc ttgaaagacg accaaaattg       180
tttgtcttgt gttgcagatc rgttgtcatt tggcccgcgt gtacggctgc ggataagtta       240
tttatcgaaa taagtgtcag atcaaaggac gatctacgtc ccttaaaaat ttcaatgaca       300
acaaacacat tataagaatt tatttatatt ttaaattaag catcgccttt catcctaaca       360
aatgtatttt taacgcagat tattcgtcya taacattatt t                           401

<210> SEQ ID NO 400
<211> LENGTH: 25
<212> TYPE: DNA
<213> ORGANISM: Glycine max

<400> SEQUENCE: 400
cagagtgcct tgacgtagtg acata                                              25

<210> SEQ ID NO 401
```

```
<211> LENGTH: 50
<212> TYPE: DNA
<213> ORGANISM: Artificial Sequence
<220> FEATURE:
<223> OTHER INFORMATION: S17242-001 Probe1

<400> SEQUENCE: 401
gaaggtgacc aagttcatgc ttggggaata acatcgtgc tttataatta            50

<210> SEQ ID NO 402
<211> LENGTH: 49
<212> TYPE: DNA
<213> ORGANISM: Artificial Sequence
<220> FEATURE:
<223> OTHER INFORMATION: S17242-001 Probe2

<400> SEQUENCE: 402
gaaggtcgga gtcaacggat tgggaataa acatcgtgct ttataattc              49

<210> SEQ ID NO 403
<211> LENGTH: 401
<212> TYPE: DNA
<213> ORGANISM: Glycine max

<400> SEQUENCE: 403
gtatgaaaat gattagtgct gtgacctgtg gamttttcct aactaaatac atttctttca   60
caattgatga cgttacaaag aaagtgaact acaactaatg catataatgt gtctttgtat  120
gaccgtatcc aggcataaca aaaccattta aagttcaaga tacgcaatta cttggggaat  180
aaacatcgtg ctttataatt mttgttgtta tgtcactacg tcaaggcact ctgctatcac  240
gccattgtat tttaatttat cgcaataatc agtcttaaat gttttcgaaa ataagatatt  300
gttttatgat ataaattttt tgcactaaag tcgaataatg tctctttctt tgtaagcttt  360
cttgttattg ggcacatgta tgcgtttaca aggagaaaat g                     401

<210> SEQ ID NO 404
<211> LENGTH: 23
<212> TYPE: DNA
<213> ORGANISM: Glycine max

<400> SEQUENCE: 404
ccgcaaactg tagtacaaat caa                                          23

<210> SEQ ID NO 405
<211> LENGTH: 25
<212> TYPE: DNA
<213> ORGANISM: Glycine max

<400> SEQUENCE: 405
gggttgtaga aagtaacttg ggaag                                        25

<210> SEQ ID NO 406
<211> LENGTH: 16
<212> TYPE: DNA
<213> ORGANISM: Artificial Sequence
<220> FEATURE:
<223> OTHER INFORMATION: S17166-001 Probe1

<400> SEQUENCE: 406
caagacatgc agcaga                                                  16

<210> SEQ ID NO 407
<211> LENGTH: 15
```

```
<212> TYPE: DNA
<213> ORGANISM: Artificial Sequence
<220> FEATURE:
<223> OTHER INFORMATION: S17166-001 Probe2

<400> SEQUENCE: 407
caagacacgc agcag                                                          15

<210> SEQ ID NO 408
<211> LENGTH: 401
<212> TYPE: DNA
<213> ORGANISM: Glycine max

<400> SEQUENCE: 408
atgcatatgt gtgtgtgtgt ataaatgggt ttttaaaaaa tgttgtcaac aaataaaaaa         60
aaggtaattt cattgaattt tatattaagc taacaattta ttgctgcaat ttttattttg        120
gctcgatcat attaagctta attaagtccg caaactgtag tacaaatcaa tttggaccaa        180
cacatgtcct ccacaagaca ygcagcagaa gcccatttaa tcaaatgaca aaaggtaaat        240
gctaaataaa cttyccaagt tactttctac aaccccctttt cgttttgat ttacctttat        300 tccaaactya ccttttatct tcttcaactc cctttatagt tttattatat cabtcatggg        360
cacactccct cttctcacag tcgtaccagt catatatgca c                            401

<210> SEQ ID NO 409
<211> LENGTH: 27
<212> TYPE: DNA
<213> ORGANISM: Glycine max

<400> SEQUENCE: 409
gttttcacat gtaattttca aaacaaa                                             27

<210> SEQ ID NO 410
<211> LENGTH: 24
<212> TYPE: DNA
<213> ORGANISM: Glycine max

<400> SEQUENCE: 410
tgtcagtgat ggtgaaaatg atag                                                24

<210> SEQ ID NO 411
<211> LENGTH: 19
<212> TYPE: DNA
<213> ORGANISM: Artificial Sequence
<220> FEATURE:
<223> OTHER INFORMATION: S17167-001 Probe1

<400> SEQUENCE: 411
taactgtgct tttttaaaa                                                      19

<210> SEQ ID NO 412
<211> LENGTH: 17
<212> TYPE: DNA
<213> ORGANISM: Artificial Sequence
<220> FEATURE:
<223> OTHER INFORMATION: S17167-001 Probe2

<400> SEQUENCE: 412
taactgtgct cttttaa                                                        17

<210> SEQ ID NO 413
<211> LENGTH: 401
<212> TYPE: DNA
```

<213> ORGANISM: Glycine max

<400> SEQUENCE: 413

```
gaaattttaa ctaaatacat aagacttktt tagggtggtt ataagttttt tattttggt      60
tttcacatgt aattttcaaa acaaaacatt rtttgataaa gatagagttc aaataatttt    120
taatttaatt ttaaaatact tttacattca ttttttaaac taaaaaaaaa gatcttaaaa    180
tttgattttt agttttaaaa ragcacagtt accctacatt tgaaaatgac ccattttgtt    240
attgttacca ctattgttga yaccaccaac atcactatca ttttcaccat cactgacact    300
acaaccatca caaccaatat caccattatc attgtcaatc acaactatca tcaccacccg    360
ccattaacat tggcatcact gttgttatta ytgtcgtcat c                       401
```

<210> SEQ ID NO 414
<211> LENGTH: 26
<212> TYPE: DNA
<213> ORGANISM: Glycine max

<400> SEQUENCE: 414

```
cacttctgta aagagtcaac aagagg                                          26
```

<210> SEQ ID NO 415
<211> LENGTH: 24
<212> TYPE: DNA
<213> ORGANISM: Glycine max

<400> SEQUENCE: 415

```
tgaatacacc ttgagtccaa agaa                                            24
```

<210> SEQ ID NO 416
<211> LENGTH: 16
<212> TYPE: DNA
<213> ORGANISM: Artificial Sequence
<220> FEATURE:
<223> OTHER INFORMATION: S08539-1 Probe1

<400> SEQUENCE: 416

```
agagctttga agaatt                                                     16
```

<210> SEQ ID NO 417
<211> LENGTH: 18
<212> TYPE: DNA
<213> ORGANISM: Artificial Sequence
<220> FEATURE:
<223> OTHER INFORMATION: S08539-1 Probe2

<400> SEQUENCE: 417

```
tagagctttg aagagttt                                                   18
```

<210> SEQ ID NO 418
<211> LENGTH: 401
<212> TYPE: DNA
<213> ORGANISM: Glycine max
<220> FEATURE:
<221> NAME/KEY: misc_feature
<222> LOCATION: (66)..(66)
<223> OTHER INFORMATION: n is a, c, g, or t
<220> FEATURE:
<221> NAME/KEY: misc_feature
<222> LOCATION: (73)..(73)
<223> OTHER INFORMATION: n is a, c, g, or t

<400> SEQUENCE: 418

```
tgttaaatyt attttttta gttaaatata taaatactca ctcttattyt ttttcttgtr      60
```

```
taactntttt acnaatgtta tctttcactt htgtaaagag tcaacaagar gttatgcata    120
tttttcatga gagattaaca tgytttragt atcatgcaty caagatcawt grttgatcat    180
cattgttaga gctttgaaga rtttcttatt ytttggactc aargtgtatt caattcaata    240
atccgttcat tyaagattat ttttaaatat attttgatga tcataataca attacaaaac    300
caaracrcta aaaataatt tatttaaata ataaaaawaa tttatccaaa tgattyctaa     360
catatatgtt gatgatcaca atacaattgt aacacaagrt c                        401
```

<210> SEQ ID NO 419
<211> LENGTH: 30
<212> TYPE: DNA
<213> ORGANISM: Glycine max

<400> SEQUENCE: 419

```
gaattgatat ttcaaccatg gatgcatcat                                     30
```

<210> SEQ ID NO 420
<211> LENGTH: 45
<212> TYPE: DNA
<213> ORGANISM: Artificial Sequence
<220> FEATURE:
<223> OTHER INFORMATION: S17178-001 Probe1

<400> SEQUENCE: 420

```
gaaggtgacc aagttcatgc taccaccatt cggctaaagt caatc                    45
```

<210> SEQ ID NO 421
<211> LENGTH: 46
<212> TYPE: DNA
<213> ORGANISM: Artificial Sequence
<220> FEATURE:
<223> OTHER INFORMATION: S17178-001 Probe2

<400> SEQUENCE: 421

```
gaaggtcgga gtcaacggat tcaccaccat tcggctaaag tcaatt                   46
```

<210> SEQ ID NO 422
<211> LENGTH: 401
<212> TYPE: DNA
<213> ORGANISM: Glycine max

<400> SEQUENCE: 422

```
atcgcattta gtgttccttt gccatcgtta atgaagtttt ccagtagtgy tgcttattcg    60
ttttcctttt tgggaaatt tttkataata tgtccatwga atcctyaaca cttgcaaatt     120
agataaaggc ctccatactc aacattgaat ctatgattgt gaaaccaaac ctgtcccacc    180
accattcggc taaagtcaat yttttatacac accttgacwa actttttta tgatgcatcc    240 atggttgaaa tatcaattct cayggggtcgt tgttctgctg aagctaaagc tacaagaaca    300
ctttcatcat aatactctaa ctctaaaaac gagatcttta ccaaactaa ggtattgtta    360 accttcatat tcaatggttt gaaatccaac gaccgtagtc t                        401
```

<210> SEQ ID NO 423
<211> LENGTH: 29
<212> TYPE: DNA
<213> ORGANISM: Glycine max

<400> SEQUENCE: 423

```
ccagtttact tagttaggtg cccaaatta                                      29
```

<210> SEQ ID NO 424
<211> LENGTH: 54
<212> TYPE: DNA
<213> ORGANISM: Artificial Sequence
<220> FEATURE:
<223> OTHER INFORMATION: S17179-001 Probe1

<400> SEQUENCE: 424
gaaggtgacc aagttcatgc taaaaatatt ttctaactct aaaagcaaac tgga    54

<210> SEQ ID NO 425
<211> LENGTH: 51
<212> TYPE: DNA
<213> ORGANISM: Artificial Sequence
<220> FEATURE:
<223> OTHER INFORMATION: S17179-001 Probe2

<400> SEQUENCE: 425
gaaggtcgga gtcaacggat taatattttc taactctaaa agcaaactgg g    51

<210> SEQ ID NO 426
<211> LENGTH: 401
<212> TYPE: DNA
<213> ORGANISM: Glycine max
<220> FEATURE:
<221> NAME/KEY: misc_feature
<222> LOCATION: (367)..(367)
<223> OTHER INFORMATION: n is a, c, g, or t

<400> SEQUENCE: 426
agggaatatg catgataacg aagcaggact cgakcatttt cttcttcttg gtcaacatat    60
atatggggcc tagctaatta acttcttaaa ttaattagat tatgtctaca aatttatttc   120
aattgtakat ttawattaaa aaatcatttt tsaatcaagt tcaaattaaa aaatatttc    180 taactctaaa agcaaactgg racataattt gggcacctaa ctaagtaaac tgggttagtg   240
aggtttatct caycgatgtg ggygtatttt tttgyaataa gtttcatttt tggcttattk   300
ttcaataata tagaaaaaaa tgtgatacga taaattattt ttggtaatat ttaacccaac   360 tttttttngtt tttgtttttt ttccttaaac actctttatg t    401

<210> SEQ ID NO 427
<211> LENGTH: 30
<212> TYPE: DNA
<213> ORGANISM: Glycine max

<400> SEQUENCE: 427
cagtgcattt cccatagaaa gttatttgtt    30

<210> SEQ ID NO 428
<211> LENGTH: 51
<212> TYPE: DNA
<213> ORGANISM: Artificial Sequence
<220> FEATURE:
<223> OTHER INFORMATION: S17180-001 Probe1

<400> SEQUENCE: 428
gaaggtgacc aagttcatgc tgaaatgata aaacctagta agctttcagt t    51

<210> SEQ ID NO 429
<211> LENGTH: 50
<212> TYPE: DNA
<213> ORGANISM: Artificial Sequence
<220> FEATURE:
<223> OTHER INFORMATION: S17180-001 Probe2

<400> SEQUENCE: 429

```
gaaggtcgga gtcaacggat taaatgataa aacctagtaa gctttcagtg            50
```

<210> SEQ ID NO 430
<211> LENGTH: 401
<212> TYPE: DNA
<213> ORGANISM: Glycine max

<400> SEQUENCE: 430

```
tatacagata ctactcattt ttaactttaa ttagaaatag tatcaaaacc acgtattaaa            60
ctgtatccaa gttatctttt taagaaatta ttcgttttta tttggtttgt taactagtac           120
tattaatttt gttcagtgca tttcccatag aaagttattt gttctttcta ttttgaattt           180
gattgcaaga tattcaactt mactgaaagc ttactaggtt ttatcatttc ttctagtttt           240
attatacaaa tctttataat acttttttrca aktttttttt ttctcatttt atcctatctt           300
gtctcagatt tttttcttat ttttctcaca ttgtaakaat tgtaaaaaaa gaaaggcgta           360
ctttactcag cgcaaakaaa ttaatcatta attcattata g                              401
```

<210> SEQ ID NO 431
<211> LENGTH: 30
<212> TYPE: DNA
<213> ORGANISM: Glycine max

<400> SEQUENCE: 431

```
gggccaattt tgtattacat cttccagaa                                              30
```

<210> SEQ ID NO 432
<211> LENGTH: 51
<212> TYPE: DNA
<213> ORGANISM: Artificial Sequence
<220> FEATURE:
<223> OTHER INFORMATION: S17181-001 Probe1

<400> SEQUENCE: 432

```
gaaggtgacc aagttcatgc tgtaatcact aaaattacac acttaaatta c                    51
```

<210> SEQ ID NO 433
<211> LENGTH: 51
<212> TYPE: DNA
<213> ORGANISM: Artificial Sequence
<220> FEATURE:
<223> OTHER INFORMATION: S17181-001 Probe2

<400> SEQUENCE: 433

```
gaaggtcgga gtcaacggat tgtaatcact aaaattacac acttaaatta g                    51
```

<210> SEQ ID NO 434
<211> LENGTH: 401
<212> TYPE: DNA
<213> ORGANISM: Glycine max

<400> SEQUENCE: 434

```
tattattagg cttttcacat ttaaggactg gtaaaaatrt gactagttga ctgatattag            60
tgtattgtta tttcttatct aattttttat atgyaatttt gaaatttata ttgatacact           120
cacatatatc ccakcatatc gattattgat ataccgtatc actatttata kgtaatcact           180
aaaattacac acttaaatta scactaactt tagrgcacat tattttctgg aaagatgtaa           240
tacaaaattg gcccattagc tcttttgagt tttgacccta aaccttaaac acattccgtt           300
```

```
tctgtatagt ctgtggtcta tgattttgat gtkttcattt gttttatgtg caactaatat    360
taaacaaaaa cacttgaaaa tcgataagca cagaaggtat c                        401
```

<210> SEQ ID NO 435
<211> LENGTH: 29
<212> TYPE: DNA
<213> ORGANISM: Glycine max

<400> SEQUENCE: 435

```
ctcagatata catagatgag aggtgacaa                                       29
```

<210> SEQ ID NO 436
<211> LENGTH: 53
<212> TYPE: DNA
<213> ORGANISM: Artificial Sequence
<220> FEATURE:
<223> OTHER INFORMATION: S17182-001 Probe1

<400> SEQUENCE: 436

```
gaaggtgacc aagttcatgc tgtaataggt cataaatgtt gatggaatat tct           53
```

<210> SEQ ID NO 437
<211> LENGTH: 53
<212> TYPE: DNA
<213> ORGANISM: Artificial Sequence
<220> FEATURE:
<223> OTHER INFORMATION: S17182-001 Probe2

<400> SEQUENCE: 437

```
gaaggtcgga gtcaacggat tgtaataggt cataaatgtt gatggaatat tca           53
```

<210> SEQ ID NO 438
<211> LENGTH: 401
<212> TYPE: DNA
<213> ORGANISM: Glycine max

<400> SEQUENCE: 438

```
aaaattaatt ggtgaaccat atatcatctc tagaaattat atttagaaag accaaactca    60
tcctcatgct cctgaagaag aacagaaaga gctttggtta tctcttctgc tgccggaata    120
aactaggttt ggagctctac catagctttg gactcagata tacatagatg agaggtgaca    180
agtgaaaaca ccctatttta wgaatattcc atcaacattt atgacctatt acacttacat    240 atctctttt tctctctttc tctaagcmtt ggatagcatg catgcatgga gtggtcaatg    300
caacattttc ctataatatt gttacatctt tatctcaaac aacctttgta gcaatgttcc    360
tataaataac ccctgtctct tcaactctca cagtgacttt g                        401
```

<210> SEQ ID NO 439
<211> LENGTH: 27
<212> TYPE: DNA
<213> ORGANISM: Glycine max

<400> SEQUENCE: 439

```
atrcgtggcc accatttacc tgtatta                                         27
```

<210> SEQ ID NO 440
<211> LENGTH: 42
<212> TYPE: DNA
<213> ORGANISM: Artificial Sequence
<220> FEATURE:
<223> OTHER INFORMATION: S17183-001 Probe1

<400> SEQUENCE: 440

```
gaaggtgacc aagttcatgc tgatcgtgcg gtggatgtga ag              42
```

<210> SEQ ID NO 441
<211> LENGTH: 43
<212> TYPE: DNA
<213> ORGANISM: Artificial Sequence
<220> FEATURE:
<223> OTHER INFORMATION: S17183-001 Probe2

<400> SEQUENCE: 441

```
gaaggtcgga gtcaacggat tgatcgtgc ggtggatgtg aat              43
```

<210> SEQ ID NO 442
<211> LENGTH: 401
<212> TYPE: DNA
<213> ORGANISM: Glycine max

<400> SEQUENCE: 442

```
aaaaacttat aaggtatttt tattatttaa atgaktaata ccaccgactt wggcataatt    60
acatgactaa ttttgccgtt acttgaaatg aagacgagag aacttatagc gtggaatccg   120
tgggagcaca atgtttgtgg ggcatgggag atctggagcc gttcattgac gatgtggttt   180
gatcgtgcgg tggatgtgaa ktgccgacag gtaatacagg taaatggtgg ccacghatgc   240
atgtaaaaaa atgaatgaag tttatctgtt tatacattga atgatgaaaa tggtggtgga   300
ggaagtctta ttcttcttcg gttggtgggt cccmcttaga ttttggttga ggtgrcacca   360
tctttgaaaa gagatttcgg aagatagcta gaataagtga a                      401
```

<210> SEQ ID NO 443
<211> LENGTH: 26
<212> TYPE: DNA
<213> ORGANISM: Glycine max

<400> SEQUENCE: 443

```
attttccaga ctattgcctt tacctt                                26
```

<210> SEQ ID NO 444
<211> LENGTH: 28
<212> TYPE: DNA
<213> ORGANISM: Glycine max

<400> SEQUENCE: 444

```
agaatacttg actgtatagg atgcaaac                              28
```

<210> SEQ ID NO 445
<211> LENGTH: 15
<212> TYPE: DNA
<213> ORGANISM: Artificial Sequence
<220> FEATURE:
<223> OTHER INFORMATION: S02780-1 Probe1

<400> SEQUENCE: 445

```
actctggata acctg                                            15
```

<210> SEQ ID NO 446
<211> LENGTH: 15
<212> TYPE: DNA
<213> ORGANISM: Artificial Sequence
<220> FEATURE:
<223> OTHER INFORMATION: S02780-1 Probe2

<400> SEQUENCE: 446

```
actctgggta acctg                                               15

<210> SEQ ID NO 447
<211> LENGTH: 401
<212> TYPE: DNA
<213> ORGANISM: Glycine max

<400> SEQUENCE: 447
ggcatggaag ggctacattt tctgttcttc tttttcaggt tcctttgtaa cttaccatct    60
atctagaaac tgcaggattc tcttgtaaaa taaatatta aatgatataa tacttgagat    120
atgtagttgg ctaaayttca tcttatatga ggcatttgct tcaattttcc agactattgc   180
ctttaccttc tagactctgg rtaacctgaa ctgcatatcm tatagggca aaagtatgtt    240 attttgtcag catataaaca tgtttgcatc ctatacagtc aagtattcta cacagatact   300
atagaaagta gaaagaatag tggtrctttt cacttgtttc tgttgaaaac tgaatacaaa   360
gatatagaga gagtagagag aaaagggaga taaggtttct c                      401

<210> SEQ ID NO 448
<211> LENGTH: 20
<212> TYPE: DNA
<213> ORGANISM: Glycine max

<400> SEQUENCE: 448
cctcctcctc aaactgttgc                                          20

<210> SEQ ID NO 449
<211> LENGTH: 20
<212> TYPE: DNA
<213> ORGANISM: Glycine max

<400> SEQUENCE: 449
gtggcaaagt gcgaacaata                                          20

<210> SEQ ID NO 450
<211> LENGTH: 14
<212> TYPE: DNA
<213> ORGANISM: Artificial Sequence
<220> FEATURE:
<223> OTHER INFORMATION: S12107-1 Probe1

<400> SEQUENCE: 450
caatcggctc catc                                                14

<210> SEQ ID NO 451
<211> LENGTH: 14
<212> TYPE: DNA
<213> ORGANISM: Artificial Sequence
<220> FEATURE:
<223> OTHER INFORMATION: S12107-1 Probe2

<400> SEQUENCE: 451
caatcggctc cctc                                                14

<210> SEQ ID NO 452
<211> LENGTH: 401
<212> TYPE: DNA
<213> ORGANISM: Glycine max
<220> FEATURE:
<221> NAME/KEY: misc_feature
<222> LOCATION: (380)..(380)
<223> OTHER INFORMATION: n is a, c, g, or t

<400> SEQUENCE: 452
```

```
gagaaggtga taataataaa tatgaaaatg acttgagatt ytgactcttg actcctaacc        60
aaaatttkaa agcttttta cacagggagt tccactttga attccccatc cttgaaagaa       120
gtggggttca ccmaatgcta cagcacgaaa cttttccatc ttggtgrcaa agtgcgaaca       180
atattgaagg tgacaataga kggagycgat tgggaaggtg atataaattc tgcgcccatg       240
caacagtttg aggaggaggc agcctgagtk agtttaattt ggtgacaatt cccctcgact       300
tgtatgtaag tacatacatt gataattatt tctcatggac atgcaattaa tatatgctga       360
tcaactgcta ctaactgagn gagagaaggc attaaatatc t                           401
```

<210> SEQ ID NO 453
<211> LENGTH: 32
<212> TYPE: DNA
<213> ORGANISM: Glycine max

<400> SEQUENCE: 453

```
tagaataatc actacaataa cagatgatct tg                                      32
```

<210> SEQ ID NO 454
<211> LENGTH: 24
<212> TYPE: DNA
<213> ORGANISM: Glycine max

<400> SEQUENCE: 454

```
cattacatgc ataacctctc atca                                               24
```

<210> SEQ ID NO 455
<211> LENGTH: 19
<212> TYPE: DNA
<213> ORGANISM: Artificial Sequence
<220> FEATURE:
<223> OTHER INFORMATION: S03624-1 Probe1

<400> SEQUENCE: 455

```
agcatcatta gtgtcacat                                                     19
```

<210> SEQ ID NO 456
<211> LENGTH: 19
<212> TYPE: DNA
<213> ORGANISM: Artificial Sequence
<220> FEATURE:
<223> OTHER INFORMATION: S03624-1 Probe2

<400> SEQUENCE: 456

```
agcatcatta gtgccacat                                                     19
```

<210> SEQ ID NO 457
<211> LENGTH: 401
<212> TYPE: DNA
<213> ORGANISM: Glycine max
<220> FEATURE:
<221> NAME/KEY: misc_feature
<222> LOCATION: (19)..(19)
<223> OTHER INFORMATION: n is a, c, g, or t

<400> SEQUENCE: 457

```
ctcttggtgc aaaaaaawnt acactataga aatcatggta ggtatgamtt ttaaggtagt        60
tattgtacag gccaataaac ttaccatcga tgtatagact atagackatt ttctctttat       120
atatgagctg tttatccata ctttttttc tcaaaaacat tacatgcata acctctcatc       180
atgtaatcat ttaatatgtg rcactaatga tgctaacttg agagaaattt acctctaatc       240
```

```
ttatttgcag atgcatctac ttcttcatgc tccaccgcaa gatcatctgt tattgtagtg    300
attattctaa tctcagggca atcatcttta caagaaacat caagactatc tgcttcttct    360
ggtcctaact gttcatcccg ttcagaagaa taatgaatta a                        401
```

<210> SEQ ID NO 458
<211> LENGTH: 29
<212> TYPE: DNA
<213> ORGANISM: Glycine max

<400> SEQUENCE: 458

```
ggagtgtact tctttatgaa aaacggtga                                       29
```

<210> SEQ ID NO 459
<211> LENGTH: 28
<212> TYPE: DNA
<213> ORGANISM: Glycine max

<400> SEQUENCE: 459

```
gtgtcgggcc actaattttg gagccttt                                        28
```

<210> SEQ ID NO 460
<211> LENGTH: 17
<212> TYPE: DNA
<213> ORGANISM: Artificial Sequence
<220> FEATURE:
<223> OTHER INFORMATION: S01953-1 Probe1

<400> SEQUENCE: 460

```
ttccttcttc acttgat                                                    17
```

<210> SEQ ID NO 461
<211> LENGTH: 16
<212> TYPE: DNA
<213> ORGANISM: Artificial Sequence
<220> FEATURE:
<223> OTHER INFORMATION: S01953-1 Probe2

<400> SEQUENCE: 461

```
tccttctcca cttgat                                                     16
```

<210> SEQ ID NO 462
<211> LENGTH: 401
<212> TYPE: DNA
<213> ORGANISM: Glycine max

<400> SEQUENCE: 462

```
ttattgaaaa atatagactt attccgaaag tatatctcca atwctgtgaa tcatagttcc     60
agaaatacat ttctagaata gatatatgta attctggaaa gacatttcca aaaagcaaaa    120
ggagtgtact tctttatgaa aaacggtgaa gggtatgagg gtgtdcttag gaaactggtg    180
taaatatcaa aattccttct ycacttkatt gattaaaaaa gaggcacaaa tcaaagcaac    240
aaaggctcca aaattagtgg cccgacacga tagataaaag ggaattgcta tatccagttc    300
ctctttttgc taatacactc ccatttaat ttttattttc aaaagtaccc ctaataaata    360
cactccctgt accatgacat catcatcatc caacctacga g                        401
```

<210> SEQ ID NO 463
<211> LENGTH: 36
<212> TYPE: DNA
<213> ORGANISM: Glycine max

<400> SEQUENCE: 463

```
actgattcaa gatacgatca agtttccttz tcattt                              36
```

<210> SEQ ID NO 464
<211> LENGTH: 31
<212> TYPE: DNA
<213> ORGANISM: Glycine max

<400> SEQUENCE: 464

```
ttggttttgg tgaataactg gaaaagtgtg t                                   31
```

<210> SEQ ID NO 465
<211> LENGTH: 16
<212> TYPE: DNA
<213> ORGANISM: Artificial Sequence
<220> FEATURE:
<223> OTHER INFORMATION: S00111-1 Probe1

<400> SEQUENCE: 465

```
cctaattgcg tttacc                                                    16
```

<210> SEQ ID NO 466
<211> LENGTH: 17
<212> TYPE: DNA
<213> ORGANISM: Artificial Sequence
<220> FEATURE:
<223> OTHER INFORMATION: S00111-1 Probe2

<400> SEQUENCE: 466

```
cctaattacg tttaccc                                                   17
```

<210> SEQ ID NO 467
<211> LENGTH: 401
<212> TYPE: DNA
<213> ORGANISM: Glycine max

<400> SEQUENCE: 467

```
tttggcccaa tccaatcctc ataatcaacc tctctctctg actgttcact ctgtgtttgg    60
aggtggaaac ttagggtatg atttctgatt ccccttcctt ctcgctcgtt ctctgcttta   120
atccatcaac tatccttctw actcatattt cttcactgat tcaagatacg atcaagtttc   180
cttatcattt gctcctaatt rcgtttaccc tatacacact tttccagtta ttcaccraaa   240
ccaacaaata acaaatttca ggttgttgga gaaattgttc tgttgggggg ataygatgtc   300
gatggagaag gaagcttcaa gctccacacc tacgcgcaaa ttgtcgtgca ctgcatgctt   360
cgacgctgtc tatttctgct actgtaatac ccattgccct a                      401
```

<210> SEQ ID NO 468
<211> LENGTH: 26
<212> TYPE: DNA
<213> ORGANISM: Glycine max

<400> SEQUENCE: 468

```
cattcaccat ttatgaattt tgatcc                                         26
```

<210> SEQ ID NO 469
<211> LENGTH: 24
<212> TYPE: DNA
<213> ORGANISM: Glycine max

<400> SEQUENCE: 469

```
aaatgaaaac ccagaataat gtgc                                           24
```

```
<210> SEQ ID NO 470
<211> LENGTH: 16
<212> TYPE: DNA
<213> ORGANISM: Artificial Sequence
<220> FEATURE:
<223> OTHER INFORMATION: S04180-1 Probe1

<400> SEQUENCE: 470
cattgacact gttcct                                                       16

<210> SEQ ID NO 471
<211> LENGTH: 15
<212> TYPE: DNA
<213> ORGANISM: Artificial Sequence
<220> FEATURE:
<223> OTHER INFORMATION: S04180-1 Probe2

<400> SEQUENCE: 471
cattgacgct gttcc                                                        15

<210> SEQ ID NO 472
<211> LENGTH: 401
<212> TYPE: DNA
<213> ORGANISM: Glycine max

<400> SEQUENCE: 472
gatgataaaa cttggggaga attttgtcaa atcctcccca gcgcatttct tagtccatgc        60
tagcagattt actttttttt ttttccattt cttctggttg tgtaattcag ggattaatyg       120
ataattagac gacatgatta tgtaaatata tgtgcattca ccatttatga attttgatcc       180
ttatgtagtc ttacattgac rctgttcctt tctctwtata attgtggcac attattctgg      240
gttttcattt ttcagtattt gatttctctc wacatcatgc actgagcacc tgcgttaggc      300
tgaaagaaaa taaattaata atgttttgat tcataamcta cagaattcaa gctttccttt      360
agtatyaact tattgagtag ctaatggcma aattggaatt g                           401

<210> SEQ ID NO 473
<211> LENGTH: 32
<212> TYPE: DNA
<213> ORGANISM: Glycine max

<400> SEQUENCE: 473
atcccttgct ttaactagat tgttattcat gt                                     32

<210> SEQ ID NO 474
<211> LENGTH: 29
<212> TYPE: DNA
<213> ORGANISM: Glycine max

<400> SEQUENCE: 474
atgcactgga ttgtgaagag aatataagc                                         29

<210> SEQ ID NO 475
<211> LENGTH: 17
<212> TYPE: DNA
<213> ORGANISM: Artificial Sequence
<220> FEATURE:
<223> OTHER INFORMATION: S01008-1 Probe1

<400> SEQUENCE: 475
caattcctct gtaagtc                                                      17
```

```
<210> SEQ ID NO 476
<211> LENGTH: 17
<212> TYPE: DNA
<213> ORGANISM: Artificial Sequence
<220> FEATURE:
<223> OTHER INFORMATION: S01008-1 Probe2

<400> SEQUENCE: 476
caattgctct gtaagtc                                                   17

<210> SEQ ID NO 477
<211> LENGTH: 401
<212> TYPE: DNA
<213> ORGANISM: Glycine max

<400> SEQUENCE: 477
tatgtcamct tcaccttggg cagraaagaa attccgtact tggacttaaa gaattttcat    60
gttaagctat aacaatcaga gaaagatatt aatgaagcag caagcacata atatggagat   120
atgtgagttg caccttcaat cttggaggac aaatcatgca ctggattgtg aagagaatat   180
aagcatatag acttacagwg saattgttac aygtagcaaa actacatgaa taacaatcta   240
gttaaagcaa gggatgcata ctaacaaaca tcaaactctt atcacctcat ctagtcccac   300
ggtggatcta gtttgaaaca tgtaagcagt cttaaagcaa aatagcaggc atatsgtatc   360
tatctcaaac agaagtggat akaacagtaa accacatgcc a                       401

<210> SEQ ID NO 478
<211> LENGTH: 20
<212> TYPE: DNA
<213> ORGANISM: Glycine max

<400> SEQUENCE: 478
ggttcgaggg ttgtgtatcc                                                20

<210> SEQ ID NO 479
<211> LENGTH: 20
<212> TYPE: DNA
<213> ORGANISM: Glycine max

<400> SEQUENCE: 479
gattgcaccc atatcgacct                                                20

<210> SEQ ID NO 480
<211> LENGTH: 18
<212> TYPE: DNA
<213> ORGANISM: Artificial Sequence
<220> FEATURE:
<223> OTHER INFORMATION: S12862-1 Probe1

<400> SEQUENCE: 480
catttatcag attcgatc                                                  18

<210> SEQ ID NO 481
<211> LENGTH: 17
<212> TYPE: DNA
<213> ORGANISM: Artificial Sequence
<220> FEATURE:
<223> OTHER INFORMATION: S12862-1 Probe2

<400> SEQUENCE: 481
acatttatcg gattcga                                                   17

<210> SEQ ID NO 482
```

```
<211> LENGTH: 401
<212> TYPE: DNA
<213> ORGANISM: Glycine max

<400> SEQUENCE: 482
gggacctaat ttgaaacatt caagtaaaat atattgttta atctacctat tacatcaagg      60
tgatgacctt tttaacctaa cctactactc acatcctcac caatattcaa ggattgagtc     120
attatgacwt atcaatatga tacacgattg cacccatatc gaccttattg tgtgttccat     180
actctgaata tgatcgaatc ygataaatgt tcatcgaaac aaccggatma attacagctt     240
gaggatacac aaccctcgaa ccttaagtat aatgtacgta aaggctaagg cttgaggatc     300
gggttasaat ccgagatgta attcattttc gttttagttc atgttgactg atacacatgt     360
catcctgcac ttgtcacatg gggtgtccta cgtggtttac t                        401

<210> SEQ ID NO 483
<211> LENGTH: 24
<212> TYPE: DNA
<213> ORGANISM: Glycine max

<400> SEQUENCE: 483
cacacgttaa aactcttgtt cagc                                            24

<210> SEQ ID NO 484
<211> LENGTH: 28
<212> TYPE: DNA
<213> ORGANISM: Glycine max

<400> SEQUENCE: 484
tcctagaata aatatgatcc cttctcat                                        28

<210> SEQ ID NO 485
<211> LENGTH: 16
<212> TYPE: DNA
<213> ORGANISM: Artificial Sequence
<220> FEATURE:
<223> OTHER INFORMATION: S12867-1 Probe1

<400> SEQUENCE: 485
accacatgta actatt                                                     16

<210> SEQ ID NO 486
<211> LENGTH: 16
<212> TYPE: DNA
<213> ORGANISM: Artificial Sequence
<220> FEATURE:
<223> OTHER INFORMATION: S12867-1 Probe2

<400> SEQUENCE: 486
accacatgta actgtt                                                     16

<210> SEQ ID NO 487
<211> LENGTH: 401
<212> TYPE: DNA
<213> ORGANISM: Glycine max
<220> FEATURE:
<221> NAME/KEY: misc_feature
<222> LOCATION: (19)..(19)
<223> OTHER INFORMATION: n is a, c, g, or t

<400> SEQUENCE: 487
attgtaatat aattgaaana aaacatgcat tcatgatatg tattaccggc attccaacca      60
tggcgcgcgg atgatgaaaa atggttgtaa cttcaatcag acttgtattc acaattaagc     120
```

```
aaaactgaaa cccaaacaca cgttaaaact cttgttcagc tcgagcttat arcattamga    180
gatcatgacc acatgtaact rttattataa cacacacata cacacatgag aagggatcat    240
atttattcta ggatcaaata tacatgtgtg ggaccacttg aacacaaagt tatgtagart    300
agttgtttca tgccattgct aatcaggact tctcactgcc aatctatgtg tctcattctc    360
tctaatmtct ctgtcatttt gtgtctcatt cactaggatg a                        401
```

<210> SEQ ID NO 488
<211> LENGTH: 20
<212> TYPE: DNA
<213> ORGANISM: Glycine max

<400> SEQUENCE: 488

```
atacccagca gcagtcacca                                                 20
```

<210> SEQ ID NO 489
<211> LENGTH: 20
<212> TYPE: DNA
<213> ORGANISM: Glycine max

<400> SEQUENCE: 489

```
ttgtgtggcc ttacctttca                                                 20
```

<210> SEQ ID NO 490
<211> LENGTH: 17
<212> TYPE: DNA
<213> ORGANISM: Artificial Sequence
<220> FEATURE:
<223> OTHER INFORMATION: S04966-1 Probe1

<400> SEQUENCE: 490

```
catttgggta tgctgtg                                                    17
```

<210> SEQ ID NO 491
<211> LENGTH: 17
<212> TYPE: DNA
<213> ORGANISM: Artificial Sequence
<220> FEATURE:
<223> OTHER INFORMATION: S04966-1 Probe2

<400> SEQUENCE: 491

```
catttgggta tgcagtg                                                    17
```

<210> SEQ ID NO 492
<211> LENGTH: 401
<212> TYPE: DNA
<213> ORGANISM: Glycine max

<400> SEQUENCE: 492

```
ctcatcacag catgcttatg gcgttgtcac acwaaagcat tgaagataga tgcagataag    60
gatgttcgaa tgatggtcgc cgtcaacgca cgtgctaagt tcaatcctcc tttacctgtt    120
ggttattacg gtaatgccat tgcataccca gcagcagtca ccacagcagg gaagctttgt    180
ggaaatccat ttgggtatgc wgtggaatta ataaataaag tgaaaggtaa ggccacacaa    240
gagtawatgc attctgtggc agatctattg gctattaagg gacgtacat accaagaatg     300 gtgaggtctc ttactgtgtc agatttgaga ggttttgatc ccagacaaat tgatttggg    360 tggggccatg ctctctatgc tggaccagct caaggaggcc t                        401
```

<210> SEQ ID NO 493

```
<211> LENGTH: 21
<212> TYPE: DNA
<213> ORGANISM: Glycine max

<400> SEQUENCE: 493
tttgatgcaa gatctgtcga a                                              21

<210> SEQ ID NO 494
<211> LENGTH: 21
<212> TYPE: DNA
<213> ORGANISM: Glycine max

<400> SEQUENCE: 494
agccggttta cttggaatgt t                                              21

<210> SEQ ID NO 495
<211> LENGTH: 14
<212> TYPE: DNA
<213> ORGANISM: Artificial Sequence
<220> FEATURE:
<223> OTHER INFORMATION: S10631-1 Probe1

<400> SEQUENCE: 495
ccaactcaga tctt                                                      14

<210> SEQ ID NO 496
<211> LENGTH: 14
<212> TYPE: DNA
<213> ORGANISM: Artificial Sequence
<220> FEATURE:
<223> OTHER INFORMATION: S10631-1 Probe2

<400> SEQUENCE: 496
ccaactcgga tctt                                                      14

<210> SEQ ID NO 497
<211> LENGTH: 401
<212> TYPE: DNA
<213> ORGANISM: Glycine max

<400> SEQUENCE: 497
aaccgttatg gttggggatc gttgctacca aaaccaaaat ctcgggacgg atcaatgtcc    60
caatgcttgg tatgtctgat gccactttt gattctatgt ctcctcaatt ttttttttct   120
gattccgtct atgattgyta gattagatca aaagaattag ccggtttact tggaatgttt   180
gaatcatttc taataagatc ygagttggaa gaaaagacac atgtctagaa attcgacaga   240
tcttgcatca aatagaaggg aaaataatta atcattttca taatttttt tagtatttac    300 gtcctaatta gtagtcaata tgataattct accaatgagg tttataggtc atgtaagtaa   360
ctgtttatta ttcagaaaaa taggaatacr taacataaaa t                       401

<210> SEQ ID NO 498
<211> LENGTH: 22
<212> TYPE: DNA
<213> ORGANISM: Glycine max

<400> SEQUENCE: 498
tgaagcaact aggaaagctg aa                                             22

<210> SEQ ID NO 499
<211> LENGTH: 20
<212> TYPE: DNA
<213> ORGANISM: Glycine max
```

```
<400> SEQUENCE: 499
acgacccaat ttgcttgtct                                                   20

<210> SEQ ID NO 500
<211> LENGTH: 16
<212> TYPE: DNA
<213> ORGANISM: Artificial Sequence
<220> FEATURE:
<223> OTHER INFORMATION: S01574-1 Probe1

<400> SEQUENCE: 500
aaggcatctt tatctc                                                       16

<210> SEQ ID NO 501
<211> LENGTH: 15
<212> TYPE: DNA
<213> ORGANISM: Artificial Sequence
<220> FEATURE:
<223> OTHER INFORMATION: S01574-1 Probe2

<400> SEQUENCE: 501
aaggcatcgt tatct                                                        15

<210> SEQ ID NO 502
<211> LENGTH: 401
<212> TYPE: DNA
<213> ORGANISM: Glycine max

<400> SEQUENCE: 502
atcataatta ttgcaaaaac aatatctggt ctagtgtggg ctagataaat aagttttccc       60
tatcrgtctt tgatatcaag cctatttgag ctctcccatt cctatccaat gattttgctt      120
gatgagctct ccatatgttt tacgacccaa tttgcttgtc tctctaagaa gatmaatggc      180
atattttctt tgagagataa mgatgccttt tttggagcag gcaacttcta ttttcaggat      240
ttttttcagc tttcctagtt gcttcatttc aaattgagtt gtcaaccttt cccttaggat      300
ttgttttcaa cttcatcatt tcctgcaaca acatatcat ctacttagac caaaaggatt       360
gccaatttac ctgtctgaaa atgctttata gagtgtggtc a                          401

<210> SEQ ID NO 503
<211> LENGTH: 19
<212> TYPE: DNA
<213> ORGANISM: Glycine max

<400> SEQUENCE: 503
cactacagcc tcccgtgct                                                    19

<210> SEQ ID NO 504
<211> LENGTH: 23
<212> TYPE: DNA
<213> ORGANISM: Glycine max

<400> SEQUENCE: 504
cctctgaaga atagcttcca ctg                                               23

<210> SEQ ID NO 505
<211> LENGTH: 18
<212> TYPE: DNA
<213> ORGANISM: Artificial Sequence
<220> FEATURE:
<223> OTHER INFORMATION: S16594-001 Probe1
```

<400> SEQUENCE: 505
catgtcttat gtaaatat					18

<210> SEQ ID NO 506
<211> LENGTH: 17
<212> TYPE: DNA
<213> ORGANISM: Artificial Sequence
<220> FEATURE:
<223> OTHER INFORMATION: S16594-001 Probe2

<400> SEQUENCE: 506
catgtcttat gaaaata					17

<210> SEQ ID NO 507
<211> LENGTH: 401
<212> TYPE: DNA
<213> ORGANISM: Glycine max

<400> SEQUENCE: 507
cagaggttga atggagaatt tgcaccattt gggaagctgc ttatggcctg attcctacaa		60 gttcctcagc tgttgatctt ccggaaatta tagttgcaac cccactacag cctcccgtgc		120 tgtcatggaa tttgtacata ccctattga aggtcctgga atatcttcct cgtggaagcc		180 catcagaggc atgtcttatg waaatatttg ctgctacagt ggaagctatt cttcagagga		240 catttccacc tgagtccact agagaacaaa acagaaaatc aaaataccta gctggcatag		300 gctttggctc tgcctcaaaa aacctggccg tggcagaact tcgtacaatg gttcattcac		360 tcttcttaga atcatgtgca tctgtagagc ttgcttcacg c				401

<210> SEQ ID NO 508
<211> LENGTH: 22
<212> TYPE: DNA
<213> ORGANISM: Glycine max

<400> SEQUENCE: 508
acatatcgaa gtgcaaatac gg				22

<210> SEQ ID NO 509
<211> LENGTH: 22
<212> TYPE: DNA
<213> ORGANISM: Glycine max

<400> SEQUENCE: 509
tcgacttgaa atggaaactg aa				22

<210> SEQ ID NO 510
<211> LENGTH: 19
<212> TYPE: DNA
<213> ORGANISM: Artificial Sequence
<220> FEATURE:
<223> OTHER INFORMATION: S02777-1 Probe1

<400> SEQUENCE: 510
ttgttatctt ccactttag					19

<210> SEQ ID NO 511
<211> LENGTH: 18
<212> TYPE: DNA
<213> ORGANISM: Artificial Sequence
<220> FEATURE:
<223> OTHER INFORMATION: S02777-1 Probe2

<400> SEQUENCE: 511

```
ttgttatctt ccgcttta                                                    18

<210> SEQ ID NO 512
<211> LENGTH: 401
<212> TYPE: DNA
<213> ORGANISM: Glycine max

<400> SEQUENCE: 512
ctttgaaaat ataaagtaaa atatttttat gtgaatctat atatataaaa tctaatatca      60
cattcacacc ckaaaattta tctcatgcga acatgcttac aaaagcattg aattggaaam    120
aaacatatcg aagtgcaaat acggtatatc atactaaata tcagttatat ttccttaatt    180
ttaaaagttt gttatcttcc rctttagact atatattcat cattttccaa aatttcagtt    240
tccatttcaa gtcgagtttg attcaattca gctgtttagc gatdttgaag tggaaacagt    300
cagtagattt agtgtactga tgaggttgaa cacaagttag gatattactg tcttgcatgt    360
gaatttgttg gtcaattaca cttgcttcca ttcacwaaat t                        401
```